United States Patent
Abreu

(10) Patent No.: US 11,497,405 B2
(45) Date of Patent: Nov. 15, 2022

(54) METHOD AND APPARATUS FOR BIOLOGICAL EVALUATION

(71) Applicant: Brain Tunnelgenix Technologies Corp., Aventura, FL (US)

(72) Inventor: Marcio Marc Abreu, Aventura, FL (US)

(73) Assignee: Brain Tunnelgenix Technologies Corp., Aventura, FL (US)

( * ) Notice: Subject to any disclaimer, the term of this patent is extended or adjusted under 35 U.S.C. 154(b) by 499 days.

(21) Appl. No.: 15/869,495

(22) Filed: Jan. 12, 2018

(65) Prior Publication Data

US 2018/0206730 A1     Jul. 26, 2018

Related U.S. Application Data

(63) Continuation of application No. 14/512,421, filed on Oct. 11, 2014, now abandoned.
(Continued)

(51) Int. Cl.
*A61B 5/01*     (2006.01)
*A61F 7/00*     (2006.01)
(Continued)

(52) U.S. Cl.
CPC .............. *A61B 5/01* (2013.01); *A61B 5/002* (2013.01); *A61B 5/4812* (2013.01);
(Continued)

(58) Field of Classification Search
CPC ...... A61F 2007/0093; A61F 2007/0096; A61F 2007/0063; A61F 2007/0054;
(Continued)

(56) References Cited

U.S. PATENT DOCUMENTS

| 3,463,885 A | 8/1969 | Upton |
| 3,531,642 A | 9/1970 | Barnes et al. |

(Continued)

FOREIGN PATENT DOCUMENTS

| CN | 2398565 Y | 9/2000 |
| CN | 2446955 Y | 9/2001 |

(Continued)

OTHER PUBLICATIONS

Waknine, Y. "FDA Clears World's First Noninvasive Continuous Temperature Monitoring System" Medscape Medical News © 2010 WebMD, LLC <https://www.medscape.com/viewarticle/728490>. (Year: 2010).*

(Continued)

*Primary Examiner* — David J. McCrosky
(74) *Attorney, Agent, or Firm* — Studebaker & Brackett PC

(57) ABSTRACT

A medical device for monitoring biological parameters through an Abreu Brain Thermal Tunnel (ABTT) is provided. By monitoring and analyzing the temperature of the ABTT, it is possible to diagnosis changes in a patient or subject under a variety of conditions, including predicting the course of medical conditions. Furthermore, since the ABTT is predictive, analysis of the ABTT may be used to control mechanisms for safety when an impending medical condition makes such operation hazardous.

8 Claims, 66 Drawing Sheets

Related U.S. Application Data

(60) Provisional application No. 61/889,561, filed on Oct. 11, 2013.

(51) Int. Cl.
*A61B 5/00* (2006.01)
*A61F 7/12* (2006.01)

(52) U.S. Cl.
CPC ............ *A61B 5/6819* (2013.01); *A61B 5/746* (2013.01); *A61F 7/00* (2013.01); *A61B 5/4064* (2013.01); *A61B 5/4809* (2013.01); *A61B 5/7275* (2013.01); *A61F 2007/0056* (2013.01); *A61F 2007/0063* (2013.01); *A61F 2007/0069* (2013.01); *A61F 2007/0093* (2013.01); *A61F 2007/0096* (2013.01); *A61F 2007/126* (2013.01)

(58) Field of Classification Search
CPC ...... A61F 2007/0075; A61F 2007/0007; A61F 2007/0059; A61F 2007/0071; A61F 2007/0076; A61F 2007/0094; A61F 2007/0228; A61F 2007/108; A61F 2007/0056; A61F 2007/0069; A61F 2007/126; A61F 7/00; A61F 2007/0036; A61F 2007/0037; A61F 2007/0045; A61F 2007/0046; A61F 2007/0047; A61F 2007/0086; A61F 7/007; A61B 5/01; A61B 5/002; A61B 5/4812; A61B 5/746; A61B 5/4064; A61B 5/4809; A61B 5/7275

See application file for complete search history.

(56) References Cited

U.S. PATENT DOCUMENTS

| | | |
|---|---|---|
| 3,545,260 A | 12/1970 | Lichtenstein et al. |
| 3,585,849 A | 6/1971 | Grolman |
| 3,626,757 A | 12/1971 | Benzinger |
| 3,724,263 A | 4/1973 | Rose et al. |
| 3,769,961 A | 11/1973 | Fatt et al. |
| 3,897,272 A | 7/1975 | Medlar |
| 3,897,790 A | 8/1975 | Magilton et al. |
| 3,963,019 A | 6/1976 | Quandt |
| 4,186,184 A | 1/1980 | Zaffaroni |
| 4,231,052 A | 10/1980 | Day et al. |
| 4,297,685 A | 10/1981 | Brainard, II |
| 4,305,399 A | 12/1981 | Beale |
| 4,312,358 A | 1/1982 | Barney |
| 4,321,261 A | 3/1982 | Ellis et al. |
| 4,330,299 A | 5/1982 | Cerami |
| 4,331,161 A | 8/1982 | Patel |
| 4,344,315 A | 8/1982 | Moxon et al. |
| 4,344,438 A | 8/1982 | Schultz |
| 4,386,831 A | 6/1983 | Grounauer |
| 4,407,777 A * | 10/1983 | Wilkinson ............ A61M 1/325 422/46 |
| 4,444,990 A | 4/1984 | Viillar |
| 4,485,820 A | 12/1984 | Flower |
| 4,488,558 A | 12/1984 | Simbruner et al. |
| 4,595,020 A | 6/1986 | Palti |
| 4,597,392 A | 7/1986 | Opitz et al. |
| 4,628,938 A | 12/1986 | Lee |
| 4,629,424 A | 12/1986 | Lauks et al. |
| 4,771,792 A | 9/1988 | Seale |
| 4,784,149 A | 11/1988 | Berman et al. |
| 4,830,014 A | 5/1989 | Goodman et al. |
| 4,846,196 A | 7/1989 | Wiksell et al. |
| 4,860,755 A | 8/1989 | Erath |
| 4,922,913 A | 5/1990 | Waters, Jr. et al. |
| 4,944,303 A | 7/1990 | Katsuragi |
| 4,947,849 A | 8/1990 | Takahashi et al. |
| 4,951,671 A | 8/1990 | Coan |
| 4,979,831 A | 12/1990 | Schertz et al. |
| 5,005,577 A | 4/1991 | Frenkel |
| 5,046,482 A | 9/1991 | Everest |
| 5,062,432 A | 11/1991 | James et al. |
| 5,076,274 A | 12/1991 | Matsumoto |
| 5,109,852 A | 5/1992 | Kaye et al. |
| 5,115,815 A | 5/1992 | Hansen |
| 5,148,807 A | 9/1992 | Hsu |
| 5,165,409 A | 11/1992 | Coan |
| 5,179,953 A | 1/1993 | Kursar |
| 5,183,044 A | 2/1993 | Nishio et al. |
| 5,190,039 A | 3/1993 | Takeuchi et al. |
| 5,209,231 A | 5/1993 | Cote et al. |
| 5,217,015 A | 6/1993 | Kaye et al. |
| 5,222,495 A | 6/1993 | Clarke et al. |
| 5,222,809 A | 6/1993 | Ehrenkranz |
| 5,246,867 A | 9/1993 | Lakowicz et al. |
| 5,251,627 A | 10/1993 | Morris |
| 5,255,979 A | 10/1993 | Ferrari |
| 5,295,495 A | 3/1994 | Maddess |
| 5,297,554 A | 3/1994 | Glynn et al. |
| 5,341,805 A | 8/1994 | Stavridi et al. |
| 5,342,283 A | 8/1994 | Good |
| 5,342,789 A | 8/1994 | Chick et al. |
| 5,352,411 A | 10/1994 | Khuri |
| 5,356,780 A | 10/1994 | Robinson et al. |
| 5,375,595 A | 12/1994 | Sinha et al. |
| 5,383,452 A | 1/1995 | Buchert |
| 5,433,197 A | 7/1995 | Stark |
| 5,435,307 A | 7/1995 | Friauf et al. |
| 5,441,476 A | 8/1995 | Kitado et al. |
| 5,503,770 A | 4/1996 | James et al. |
| 5,522,662 A | 6/1996 | Shiokawa |
| 5,636,635 A | 6/1997 | Massie et al. |
| 5,653,239 A | 8/1997 | Pompei et al. |
| 5,664,578 A | 9/1997 | Boczan |
| 5,673,692 A | 10/1997 | Schulze et al. |
| 5,711,915 A | 1/1998 | Siegmund et al. |
| 5,770,149 A * | 6/1998 | Raible ................. A61M 1/1629 422/46 |
| 5,796,341 A | 8/1998 | Stratiotis |
| 5,813,982 A | 9/1998 | Baratta |
| 5,817,008 A | 10/1998 | Rafert et al. |
| 5,820,557 A | 10/1998 | Hattori et al. |
| 5,830,139 A | 11/1998 | Abreu |
| 5,833,633 A | 11/1998 | Sarvazyan |
| 5,854,078 A | 12/1998 | Asher et al. |
| 5,860,934 A | 1/1999 | Sarvazyan |
| 5,862,803 A | 1/1999 | Besson et al. |
| 5,898,004 A | 4/1999 | Asher et al. |
| 5,984,880 A | 11/1999 | Lander et al. |
| 5,994,701 A | 11/1999 | Tsuchimoto et al. |
| 6,011,984 A | 1/2000 | Van Antwerp et al. |
| 6,028,323 A | 2/2000 | Liu |
| 6,040,194 A | 3/2000 | Chick et al. |
| 6,042,266 A | 3/2000 | Cheslock et al. |
| 6,047,203 A | 4/2000 | Sackner et al. |
| 6,072,180 A | 6/2000 | Kramer et al. |
| 6,113,237 A | 9/2000 | Ober |
| 6,120,460 A | 9/2000 | Abreu |
| 6,123,668 A | 9/2000 | Abreu |
| 6,126,595 A | 10/2000 | Amano et al. |
| 6,135,968 A | 10/2000 | Brounstein |
| 6,152,875 A | 11/2000 | Hakamata |
| 6,178,346 B1 | 1/2001 | Amundson et al. |
| 6,181,957 B1 | 1/2001 | Lambert et al. |
| 6,187,599 B1 | 2/2001 | Asher et al. |
| 6,196,714 B1 | 3/2001 | Bellifemine et al. |
| 6,197,534 B1 | 3/2001 | Lakowicz et al. |
| 6,197,928 B1 | 3/2001 | Tsien et al. |
| 6,203,193 B1 | 3/2001 | Egawa |
| 6,213,943 B1 | 4/2001 | Abreu |
| 6,256,522 B1 | 7/2001 | Schultz |
| 6,290,140 B1 | 9/2001 | Pesko |
| 6,290,658 B1 | 9/2001 | Kolich |
| 6,292,685 B1 | 9/2001 | Pompei |
| 6,300,871 B1 | 10/2001 | Irwin et al. |
| 6,312,393 B1 | 11/2001 | Abreu |
| 6,319,540 B1 | 11/2001 | Van Antwerp et al. |

(56) References Cited

U.S. PATENT DOCUMENTS

| | | | |
|---|---|---|---|
| 6,385,473 B1 | 5/2002 | Haines et al. | |
| 6,385,474 B1 | 5/2002 | Rather et al. | |
| 6,423,001 B1 | 7/2002 | Abreu | |
| 6,432,050 B1 | 8/2002 | Porat et al. | |
| 6,470,893 B1 | 10/2002 | Boesen | |
| 6,529,617 B1 | 3/2003 | Prokoski | |
| 6,536,945 B2 | 3/2003 | Rolston | |
| 6,542,081 B2 | 4/2003 | Torch | |
| 6,543,933 B2 | 4/2003 | Stergiopoulos et al. | |
| 6,544,193 B2 | 4/2003 | Abreu | |
| 6,681,127 B2 | 1/2004 | March | |
| 6,702,783 B1* | 3/2004 | Dae | A61F 7/12 604/103.01 |
| 6,731,976 B2 | 5/2004 | Penn et al. | |
| 6,789,901 B1 | 9/2004 | Kormos | |
| 6,791,087 B1 | 9/2004 | Okumura | |
| 6,846,106 B1 | 1/2005 | Chen et al. | |
| 7,004,910 B2* | 2/2006 | Lindsey | G01K 1/024 128/903 |
| 7,187,960 B2 | 3/2007 | Abreu | |
| 7,340,293 B2 | 3/2008 | McQuilkin | |
| 7,346,386 B2 | 3/2008 | Pompei | |
| 7,515,054 B2 | 4/2009 | Torch | |
| 7,597,668 B2 | 10/2009 | Yarden | |
| 7,621,877 B2 | 11/2009 | Schnall | |
| 7,689,437 B1 | 3/2010 | Teller et al. | |
| 7,756,559 B2 | 7/2010 | Abreu | |
| 7,787,938 B2 | 8/2010 | Pompei | |
| 7,837,623 B2 | 11/2010 | Aubry et al. | |
| 8,103,071 B2 | 1/2012 | Schnell et al. | |
| 8,172,459 B2 | 5/2012 | Abreu | |
| 8,328,420 B2 | 12/2012 | Abreu | |
| 8,500,271 B2 | 8/2013 | Howell et al. | |
| 8,527,022 B1 | 9/2013 | Lash et al. | |
| 8,721,562 B2 | 5/2014 | Abreu | |
| 8,834,020 B2 | 9/2014 | Abreu | |
| 8,849,379 B2 | 9/2014 | Abreu | |
| 9,007,220 B2 | 4/2015 | Johns et al. | |
| 9,345,614 B2* | 5/2016 | Schaefer | A61F 7/00 |
| 2001/0028309 A1 | 10/2001 | Torch | |
| 2002/0026119 A1 | 2/2002 | Pompei | |
| 2002/0035340 A1 | 3/2002 | Fraden et al. | |
| 2002/0049374 A1 | 4/2002 | Abreu | |
| 2002/0049389 A1 | 4/2002 | Abreu | |
| 2002/0068876 A1 | 6/2002 | Pompei et al. | |
| 2002/0111657 A1 | 8/2002 | Dae et al. | |
| 2002/0126731 A1 | 9/2002 | Stergiopoulos et al. | |
| 2003/0055473 A1 | 3/2003 | Ramsden et al. | |
| 2003/0060863 A1 | 3/2003 | Dobak, III | |
| 2003/0067958 A1 | 4/2003 | Jang | |
| 2003/0108223 A1 | 6/2003 | Prokoski | |
| 2003/0111605 A1 | 6/2003 | Sato et al. | |
| 2003/0179094 A1 | 9/2003 | Abreu | |
| 2003/0210146 A1 | 11/2003 | Tseng | |
| 2003/0212340 A1 | 11/2003 | Lussier et al. | |
| 2004/0039298 A1 | 2/2004 | Abreu | |
| 2004/0059212 A1 | 3/2004 | Abreu | |
| 2004/0076316 A1 | 4/2004 | Fauci | |
| 2004/0082862 A1 | 4/2004 | Chance | |
| 2004/0125996 A1 | 7/2004 | Eddowes et al. | |
| 2004/0152991 A1 | 8/2004 | Pompei | |
| 2004/0154550 A1 | 8/2004 | McQuilkin | |
| 2004/0170216 A1 | 9/2004 | Russak et al. | |
| 2004/0210159 A1 | 10/2004 | Kibar | |
| 2004/0242976 A1* | 12/2004 | Abreu | A61B 5/02416 600/315 |
| 2004/0246548 A1 | 12/2004 | Papuchon et al. | |
| 2005/0250996 A1 | 11/2005 | Shirai et al. | |
| 2006/0122473 A1 | 6/2006 | Kill et al. | |
| 2006/0215728 A1 | 9/2006 | Jang | |
| 2006/0264726 A1 | 11/2006 | Manheimer et al. | |
| 2007/0055171 A1 | 3/2007 | Fraden | |
| 2007/0219434 A1 | 9/2007 | Abreu | |
| 2008/0043809 A1 | 2/2008 | Herbert | |
| 2008/0200830 A1 | 8/2008 | Pompei | |
| 2008/0214949 A1 | 9/2008 | Stivoric et al. | |
| 2008/0260225 A1 | 10/2008 | Szu | |
| 2009/0105560 A1 | 4/2009 | Solomon | |
| 2009/0105605 A1 | 4/2009 | Abreu | |
| 2009/0157056 A1 | 6/2009 | Ferren et al. | |
| 2010/0010552 A1 | 1/2010 | Wilson et al. | |
| 2010/0022909 A1 | 1/2010 | Padiy | |
| 2010/0113894 A1 | 5/2010 | Padiy | |
| 2010/0204765 A1 | 8/2010 | Hall et al. | |
| 2011/0024626 A1 | 2/2011 | O'Donnell et al. | |
| 2011/0040161 A1 | 2/2011 | Abreu | |
| 2011/0077546 A1 | 3/2011 | Fabian | |
| 2011/0092822 A1 | 4/2011 | Pompei | |
| 2011/0125238 A1 | 5/2011 | Nofzinger | |
| 2012/0031405 A1 | 2/2012 | Geist et al. | |
| 2012/0136285 A1 | 5/2012 | Korb et al. | |
| 2013/0124039 A1 | 5/2013 | Abreu | |
| 2013/0215928 A1 | 8/2013 | Bellifemine | |
| 2013/0292571 A1 | 11/2013 | Mukherjee et al. | |
| 2014/0135879 A1* | 5/2014 | Flint | A61F 7/00 607/106 |

FOREIGN PATENT DOCUMENTS

| | | |
|---|---|---|
| CN | 1328432 A | 12/2001 |
| DE | 4433104 C1 | 5/1996 |
| EP | 0236028 A2 | 9/1987 |
| EP | 0411121 A2 | 2/1991 |
| EP | 2 120 681 B1 | 7/2011 |
| EP | 1 951 110 B1 | 10/2012 |
| GB | 2396421 A | 6/2004 |
| JP | S61-48369 A | 3/1986 |
| JP | 5-3873 | 1/1993 |
| JP | H05-3873 A | 1/1993 |
| JP | H07-174395 A | 7/1995 |
| JP | H10-075934 A | 3/1998 |
| JP | H10-239158 A | 9/1998 |
| JP | H11-164826 A | 6/1999 |
| JP | 2001-500394 A | 1/2001 |
| JP | 2001/031151 A | 2/2001 |
| JP | 2002-525132 A | 8/2002 |
| JP | 2004-092918 A | 3/2004 |
| JP | 3885024 B2 | 2/2007 |
| JP | 2010-127520 A | 6/2010 |
| JP | 2010-133692 A | 6/2010 |
| JP | 2010-201001 A | 9/2010 |
| WO | 93/01745 A1 | 2/1993 |
| WO | 97/19188 A1 | 5/1997 |
| WO | 98/22820 A1 | 5/1998 |
| WO | 99/51142 A2 | 10/1999 |
| WO | 00/10007 A2 | 2/2000 |
| WO | 00/13580 A1 | 3/2000 |
| WO | 00/16051 A1 | 3/2000 |
| WO | 00/16099 A1 | 3/2000 |
| WO | 00/18237 A1 | 4/2000 |
| WO | 20000025662 A1 | 5/2000 |
| WO | 00/64492 A1 | 11/2000 |
| WO | 02/03855 A1 | 1/2002 |
| WO | 02/28271 A2 | 4/2002 |
| WO | 02/067688 A1 | 9/2002 |
| WO | 2005/015163 A2 | 2/2005 |
| WO | 2010-042738 A2 | 4/2010 |
| WO | 2010/105045 A2 | 9/2010 |

OTHER PUBLICATIONS

PR Newswire "BTT Corp Announces Its Research System Is Available for Pre-Order" 2017 <https://www.prnewswire.com/news-releases/btt-corp-announces-its-research-system-is-available-for-pre-order-300495576.html>. (Year: 2017).*

RCA Technical Notes, Contact Lens Tonometer by Robert E. Morey, RCA TN No. 602, dated Dec. 1964, 2 pages.

Ophthal. Physiol. Opt., 1989, vol. 9, April, Research Note, Multiple Applications of the NCT: An Assessment of Instrument's Effect on IOP by G.E. Russell and J.P.G. Bergmanson, pp. 212-214.

(56) References Cited

OTHER PUBLICATIONS

Arch Ophthalmol—vol. 97, Mar. 1979, The Pneumatonograph—A Laboratory Study, by Robert A. Moses, M.D. and Walter J. Grodzki Jr., D.D.S., pp. 547-552.
IEEE Transactions on bio-Medical Engineering, vol. BME-14, No. 2, Apr. 1967, Miniature Passive Pressure Transensor for Implanting in the Eye, by C.C. Collins, pp. 74-83.
Trans. Amer. Acad. of O. & O., Jan-Feb. 1957, Tonometer Calibration, An Attempt to Remove Discrepancies Found in the 1954 Calibration Scale for Schiotz Tonometers by Jonas S. Friedenwald, M.D., pp. 108-123.
Investigative Ophthalmology, Feb. 1962, The Relationship Between Pressure and Volume Changes in Living and Dead Rabbit Eyes, by John E. Eisenlohr and Maurice E. Langham, pp. 63-77.
Investigative Ophthalmology, Sep. 1971, vol. 10, No. 9, Theory and Calibration of the Schiotz Tonometer VII. Experimental Results of Tonometric Measurements: Scale Reading Versus Indentation Volume, by Robert A. Moses and Walter J. Grodzki, pp. 716-723.
The British Journal of Ophthalmology, Jun. 1920, Communications-Tonometry, by HJ. Schiötz, pp. 249-261.
American Journal of Opthalmology, vol. 20, No. 10, Oct. 1937, Contribution to the Theory and Practice of Tonometry by Jonas S. Friedenwald, M.D., pp. 985-1024.
Ophthalmologica vol. 150, No. 5, (1965), Rheology of the Human Sclera, Unifying Formulation of Ocular Rigidity, by W.K. McEwen and Roger St. Helen, pp. 321-346.
A.M.A. Archives of Ophthalmology, vol. 57, Apr. 1957, Tonometer Calibration, by Earle H. McBain, M.D., pp. 520-531.
The Photonics Dictionary, 1996 Book 4, 42nd Edition, pp. D-24, D153.
Manual of Skin Diseases, Fifth Edition, Gordon C. Sauer, MD., 1985, pp. 204, 373.
FM-2 Fluorotron™ Master Ocular Fluorophotometer, 1994 OcuMetrics, Inc.
Textbook of Biochemistry With Clinical Correlations, Second Edition, Thomas M. Devlin, Ph.D., 1986, pp. 118, 139.
Physical Optics, Third Revised Edition, Robert W. Wood, 1961, pp. 650-651.
Examiner's First Report; issued by the Australian Government, IP Australia dated Dec. 18, 2008, which corresponds to Australian Patent Application No. 2004263812.
Examiner's First Report; issued by the Australian Government, IP Australia dated Mar. 10, 2010, which corresponds to Australian Patent Application No. 2009212808.
Examiner's First Report; issued by the Australian Government, IP Australia dated Feb. 19, 2010, which corresponds to Australian Patent Application No. 2009212861.
Examiner's First Report; issued by the Australian Government, IP Australia dated Nov. 4, 2013, which corresponds to Australian Patent Application No. 2012247045.
Office Action issued by the Canadian Intellectual Property Office dated May 3, 2012, which corresponds to Canadian Patent Application No. 2,517,869.
English translation of a First Office Action and Search Report; issued by the State Intellectual Property Office of the People's Republic of China dated Jul. 21, 2014, which corresponds to Chinese Patent Application No. 201310097177.3.
English translation of a First Office Action and Search Report; issued by the State Intellectual Property Office of the People's Republic of China dated Jul. 22, 2014, which corresponds to Chinese Patent Application No. 201310097142.X.
Supplementary European Search Report; issued by the European Patent Office dated Oct. 17, 2008, which corresponds to European Patent Application No. 04785841.0-1265.
"Communication pursuant to Article 94(3) EPC," issued by the European Patent Office dated Jan. 27, 2009, which corresponds to European Patent Application No. 04785841.0-1265.
"Communication pursuant to Article 94(3) EPC," issued by the European Patent Office dated Sep. 12, 2013, which corresponds to European Patent Application No. 04785841.0-1657.
English Translation of Relevant Portion of Office Action; issued by the State of Israel Department of Justice, Patent Office dated Jul. 3, 2013, which corresponds to Israeli Patent Application No. 1704896.
English translation of Notification of Reasons for Refusal; issued by the Japanese Patent Office dated Jun. 11, 2009, which corresponds to Japanese Patent Application No. 2006-508817.
English translation of Notification of Reasons for Refusal; issued by the Japanese Patent Office dated Jan. 12, 2010, which corresponds to Japanese Patent Application No. 2006-508817.
Summarized English Translation of Office Action; issued by the Institute Mexicano de la Propiedad Industrial dated Jul. 1, 2008, which corresponds to Mexican National Phase Patent Application No. PA/a/2005/009159.
Office Action; issued by the Institute Mexicano de la Propiedad Industrial dated Sep. 25, 2009, which corresponds to Mexican National Phase Patent Application No. PA/a/2005/009159.
International Search Report & Written Opinion; PCT/US2004/005496; dated May 6, 2005.
English translation of an Office Action; issued by the Japanese Patent Office dated Jan. 22, 2009, which corresponds to Japanese Patent Application No. 2004-515642.
English translation of an Office Action; issued by the National Institute of Industrial Property dated Jul. 1, 2013, which corresponds to Brazilian Patent Application PI0309578-9.
English translation of an Office Action; issued by the National Institute of Industrial Property, which corresponds to Brazilian Patent Application PI0309578-9.
English translation of the "First Office Action," and "Search Report," issued by the State Intellectual Property Office of the People's Republic of China dated Jun. 4, 2014, which corresponds to Chinese Application No. 201210361917.5.
"Communication pursuant to Article 94(3) EPC," issued by the European Patent Office dated Jan. 27, 2009, which corresponds to European Patent Application No. 03 754 363.4-1265.
Second "Communication pursuant to Article 94(3) EPC," issued by the European Patent Office dated Sep. 13, 2013, which corresponds to European Patent Application No. 03 754 363.4-1657.
Third "Communication pursuant to Article 94(3) EPC," issued by the European Patent Office dated Mar. 4, 2014, which corresponds to European Patent Application No. 03 754 363.4-1657.
Fourth "Communication pursuant to Article 94(3) EPC," issued by the European Patent Office dated Sep. 24, 2014, which corresponds to European Patent Application No. 03 754 363.4-1657.
English translation of an Office Action; issued by the State of Israel Department of Justice, Patent Office dated Nov. 26, 2008, which corresponds to Israeli Patent Application No. 164685.
English translation of an Office Action; issued by the Korean Intellectual Property Office dated Dec. 26, 2011, which corresponds to Korean Patent Application No. 10-2010-7018173.
International Search Report; PCT/US03/12382; dated May 13, 2005.
International Search Report; PCT/US2006/041238; dated Aug. 31, 2007.
Office Action issued by the Canadian Intellectual Property Office dated Aug. 2, 2011, which corresponds to Canadian Patent Application No. 2,627,278.
Second Office Action issued by the Canadian Intellectual Property Office dated Mar. 14, 2012, which corresponds to Canadian Patent Application No. 2,627,278.
"Communication pursuant to Particle 94(3) EPC," issued by the European Patent Office dated May 13, 2011, which corresponds to European Patent Application No. 06 826 452.2-2319.
English translation of an Office Action; issued by the State of Israel Department of Justice, Patent Office dated Jun. 23, 2011, which corresponds to Israeli Patent Application No. 191039.
Examiner's First Report; issued by the Australian Government, IP Australia dated Jan. 13, 2012, which corresponds to Australian Patent Application No. 2011202015.
Patent Examination Report No. 1; issued by the Australian Government, IP Australia dated Dec. 13, 2013, which corresponds to Australian Patent Application No. 2012203667.

(56) References Cited

OTHER PUBLICATIONS

Office Action and Examination Search Report issued by the Canadian Intellectual Property Office dated Mar. 26, 2015, which corresponds to Canadian Patent Application No. 2,627,278.
International Search Report; PCTUS2015/010873; dated Apr. 10, 2015.
English translation of an Unfavorable Technical Opinion; issued by the National Institute of Industrial Property, which corresponds to Brazilian Patent Application BR122013001249-4.
Examiner's First Report; issued by the Australian Government, IP Australia dated Apr. 21, 2009, which corresponds to Australian Patent Application No. 2006306422.
Examiner's Report No. 2; issued by the Australian Government, IP Australia dated Nov. 10, 2010, which corresponds to Australian Patent Application No. 2006306422.
English translation of an Office Action; issued by the Korean Intellectual Property Office dated Jun. 21, 2013, which corresponds to Korean Patent Application No. 10-2008-7012335.
English translation of an Office Action; issued by the Japanese Patent Office dated Nov. 17, 2011, which corresponds to Japanese Patent Application No. 2008-537828.
English translation of a Second Office Action; issued by the Japanese Patent Office dated Nov. 13, 2012, which corresponds to Japanese Patent Application No. 2008-537828.
English translation of a Third Office Action; issued by the Japanese Patent Office dated Nov. 26, 2013, which corresponds to Japanese Patent Application No. 2008-537828.
Overton, Staci. "Brain Temperature Tunnel Discovered." Medical Breakthroughs Reported by Ivanhoe, Jun. 2, 2003.
International Search Report; PCT/US2014/060199; dated Jan. 8, 2015.
International Search Report; PCT/US2014/060201; dated Mar. 3, 2015.
Dittmar, A. et al., A Non Invasive Wearable Sensor for the Measurement of Brain Temperature. Proceedings of the 28th IEEE EMBS Annual International Conference. Aug. 30-Sep. 3, 2006. pp. 900-902, New York City, USA.
Notification of Transmittal of International Preliminary Report on Patentability (Chapter II); PCT/US2014/060199; dated Oct. 1, 2015.
International Preliminary Report on Patentability (Chapter I) and Written Opinion of the International Searching Authority; PCT/US2014/060201 dated Apr. 12, 2016.
Communication issued by the EPO in corresponding EP Patent Appln. No. 14851818.3-1657 dated May 19, 2017; 15pp.
First Examination Report issued by the Australian Patent Office dated May 10, 2018 in corresponding Australian Patent Application No. 2016201025; 6pp.
Extended European Search Report (EESR) issued in corresponding European application No. 14851818.6-1657 dated Nov. 7, 2017; 18pp.
Examination report issued in corresponding Australian application No. 2016247223 dated Mar. 2, 2018; 5pp.
Redeker, N S et al: "Sleep patterns in women after coronary artery bypass surgery", Applied Nursing Rese, N.B. Saunders, Amsterdam, NL, vol. 9, No. 3, Aug. 1, 1996, pp. 115-122.
Pierro, Michele L et al: "Relative phase of oscillations of cerebral oxy-hemoglobin and deoxy-hemoglobin concentrations during sleep", Photonic Therapeutics and Diagnostics VIII, SPIE, 1000 20th St. Bellingham WA 98225-6705 USA, vol. 8207, No. 1, Feb. 3, 2012, pp. 1-81.

* cited by examiner

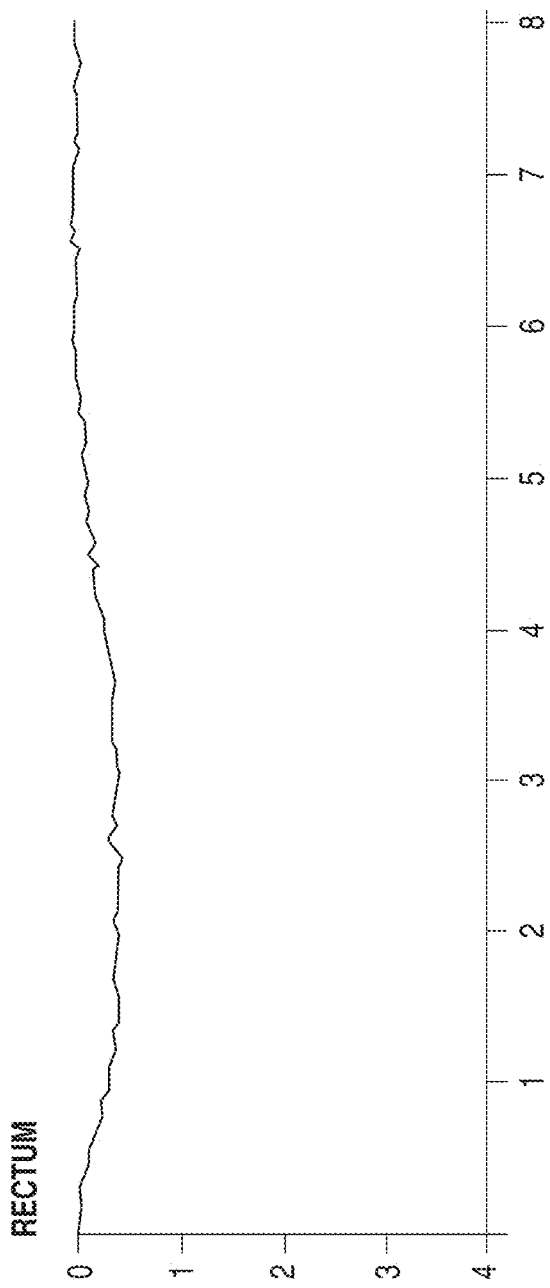

FIG. 30
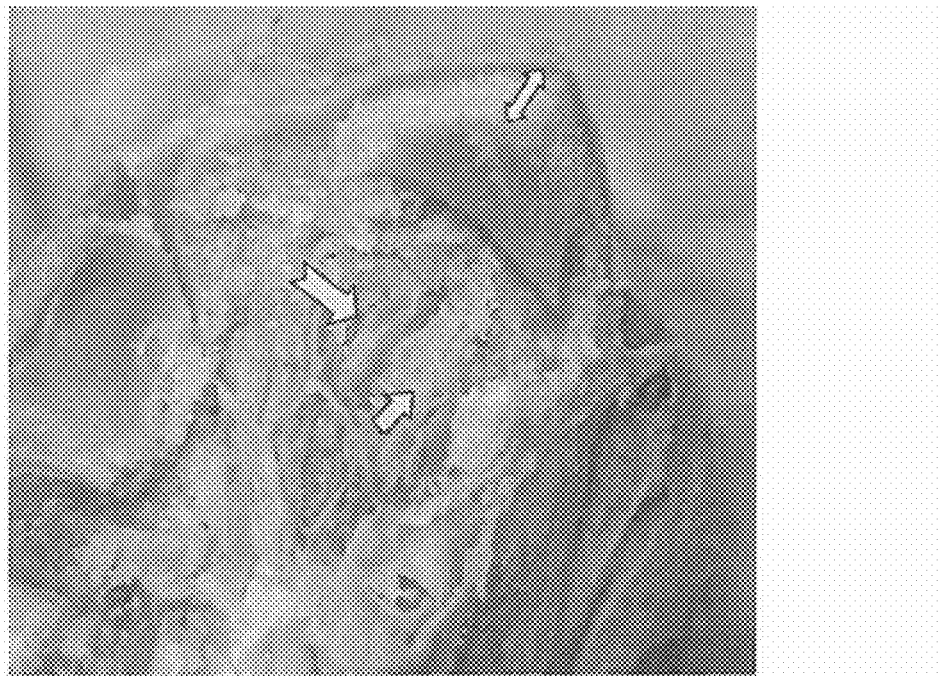
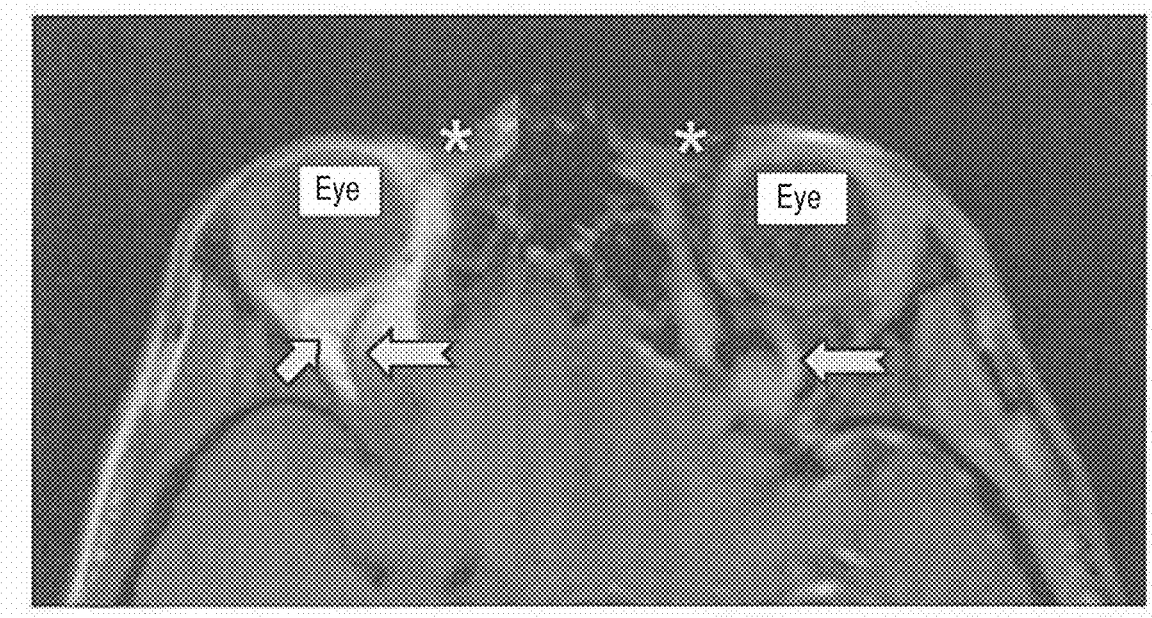
FIG. 32

Total Electrical Isolation between Appliance Circuitry & Earth Ground and the Medical Grade Module

METHOD AND APPARATUS FOR BIOLOGICAL EVALUATION

CROSS-REFERENCE TO RELATED APPLICATIONS

This application is a continuation application of U.S. patent application Ser. No. 14/512,421, filed on Oct. 11, 2014 which claims the benefit of priority to U.S. Provisional Patent Application No. 61/889,561, filed on Oct. 11, 2013, which are hereby incorporated by reference in their entirety.

TECHNICAL FIELD

This disclosure relates to a medical device for monitoring biological parameters.

BACKGROUND

Diagnostics for measuring and monitoring an array of biological parameters exist. Among the many biological parameters that can be measured are pulse, blood pressure, heart function (EKG), brain function (EEG), temperature, etc.

SUMMARY

This disclosure provides a system for cooling a human, comprising a temperature sensor, a cooling apparatus, at least one of an alarm and a display, and a controller. The temperature sensor is configured to transmit a signal representative of temperature positioned on skin of the human on, over, or adjacent the brain thermal tunnel terminus. The cooling apparatus is positioned to provide cooling to the human. The controller is configured to receive the temperature signal, to determine from the temperature signal a first temperature representative of an uncooled condition of the human, to determine when the temperature signal is indicative of a second temperature that is at least one degree Celsius less than the first temperature, and to transmit a signal to at least one of the alarm and the display to present an indication that the second temperature has been reached.

This disclosure also provides a system for modifying a core temperature for a human, comprising a temperature sensor, a temperature modifying apparatus, at least one of an alarm and a display, and a controller. The temperature sensor is positioned and configured to transmit a signal representative of temperature of skin of the human on, over, or adjacent the brain thermal tunnel terminus. The temperature modifying apparatus is positioned to provide temperature modification for the human. The controller is configured to receive the temperature signal, to determine from the temperature signal a first temperature representative of a baseline condition of the human, to determine when the temperature signal is indicative of a second temperature that is at least 0.5 degrees Celsius different from the first temperature, and to transmit a signal to at least one of the alarm and the display to present an indication that the second temperature has been reached.

This disclosure also provides a system for analyzing the brain thermal tunnel temperature of a human, the system comprising a temperature sensor and a controller. The temperature sensor is positioned and configured to transmit a signal representative of temperature positioned on skin of the human on, adjacent, or over the brain thermal tunnel. The controller is positioned to receive the temperature signal and configured to provide a frequency analysis of the temperature signal, the frequency analysis having a plurality of frequency peaks. The controller is configured to determine from an amplitude of each frequency peak a slope, and the controller is configured to determine when the slope exceeds a predetermined non-zero slope indicative of a medical condition in the human.

This disclosure also provides a system for analyzing the brain thermal tunnel temperature of a human, the system comprising a temperature sensor and a controller. The temperature sensor is positioned and configured to transmit a signal representative of temperature on skin of the human on, over, or adjacent the brain thermal tunnel terminus. The controller is positioned to receive the temperature signal and configured to provide a frequency analysis of the temperature signal, the frequency analysis having a plurality of frequency peaks. The controller is configured to determine when the average spacing of the plurality of frequency peaks in a predetermined frequency range exceeds a predetermined spacing indicative of a medical condition in the human.

This disclosure also provides a system for detecting a sleep condition of a human, comprising a temperature sensor and a controller. The temperature sensor is positioned and configured to transmit a signal representative of temperature on skin of the human on, over, or adjacent the brain thermal tunnel terminus. The controller is configured to receive the temperature signal, to determine from the temperature signal a temperature decline of at least 0.2° C. in a period of one minute, so as to identify a sleep condition when the temperature decline of 0.2° C. in a period of one minute occurs.

This disclosure also provides a method of detecting a sleep condition of a human, comprising measuring the temperature of skin of the human on, over, or adjacent the brain thermal tunnel terminus; and identifying a sleep condition by identifying a temperature decline of at least 0.2° C. in a period of one minute.

This disclosure also provides a temperature measuring apparatus, comprising a temperature sensor, at least one indicator having a variable output, and a controller. The temperature sensor is configured to measure temperature and to transmit a signal representing the measured temperature to a controller. The controller is configured to receive the temperature signal, to identify a peak temperature in a predetermined region of a human or animal subject, and to vary the indicator in proportion to the measured temperature in comparison to the peak temperature.

This disclosure also provides a temperature measuring apparatus, comprising a skin contact temperature sensor, a plurality of indictors, and a controller. The skin contact temperature sensor is configured to measure temperature and to transmit a signal representing the measured temperature to a controller. The controller is configured to receive the temperature signal, to identify a peak temperature in a predetermined region of a human or animal subject, and to vary the plurality of indicators to indicate a direction towards or away from the peak temperature.

Advantages and features of the embodiments of this disclosure will become more apparent from the following detailed description of exemplary embodiments when viewed in conjunction with the accompanying drawings.

BRIEF DESCRIPTION OF THE DRAWINGS

FIGS. 17A-G are graphs showing a relationship between temperatures measured in various locations including on the skin adjacent to, over, or on the ABTT terminus during a sleep cycle of the same subject.

FIG. 30 is a view of a cut of a human cranium showing the frontal bone and superior ophthalmic vein (SOV).

FIG. 32 is a weighted radiograph showing portions of the SOV in a human.

DETAILED DESCRIPTION

Figure 1:
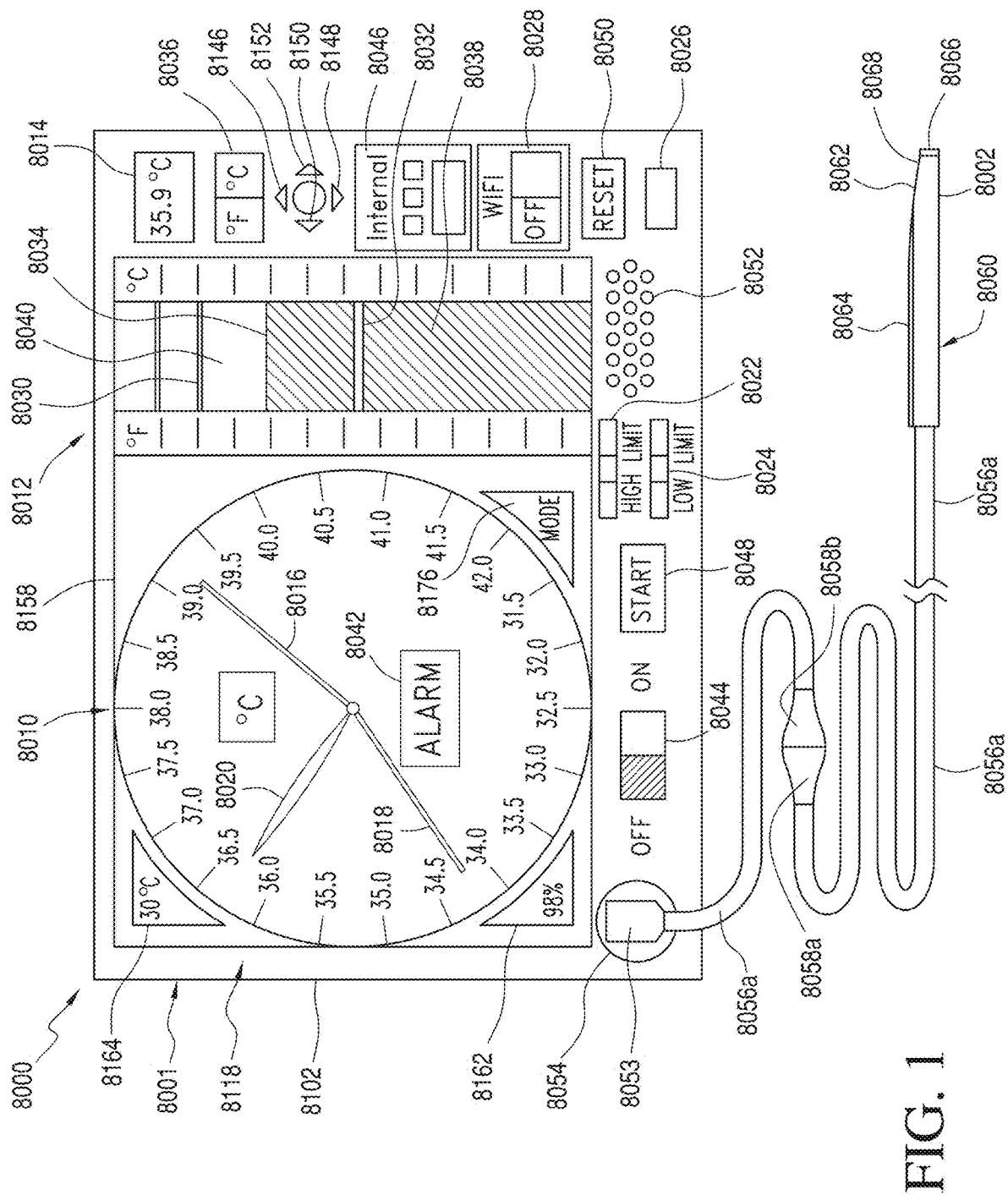
FIG. 1 is simplified view of an Abreu Brain Thermal Tunnel (ABTT) system display and temperature sensor of an Abreu Brain Thermal Tunnel (ABTT) monitoring system in accordance with an exemplary embodiment of the present disclosure, showing display of temperature in multiple formats and the controls of the ABTT monitoring system.

The present disclosure provides a medical device for monitoring biological parameters through an Abreu Brain Thermal Tunnel (ABTT), which was previously described as a brain temperature tunnel, and which is described in more detail in U.S. Pat. Nos. 7,187,960, 8,172,459, 8,328,420, 8,721,562, 8,834,020, and 8,849,389, incorporated herein by reference in its entirety. Contrary to previous disclosures, the Applicant of this current disclosure recognized that the structure was not a brain temperature tunnel, but indeed a brain thermal tunnel, in which measurement of temperature is only one feature among many, including brain thermal patterns (which are subject of this disclosure), and that this newly identified and characterized Brain Thermal Tunnel is part of a complex thermodynamic system and includes, by way of illustration, an intra-brain thermodynamic subsystem, a brain-heart thermodynamic subsystem, a brain-hormonal thermodynamic subsystem, and brain-environment subsystem, all of which are objects of the present disclosure.

General Discussion of the ABTT

The ABTT comprises a continuous, direct, and undisturbed connection between a thermal energy source within a human brain and an external point on the facial skin at the end of the tunnel. The physical and physiological events at one end of the tunnel are reproduced at the opposite end. The ABTT allows direct thermal energy transfer through the tunnel without interference by heat absorbing elements. The source of the thermal heat in the brain is the region of the brain that is a control center for involuntary functions of the body. More specifically, the ABTT terminates adjacent to the hypothalamus. The recipient of the thermal heat is four veins that converge to an ABTT "target area" or "terminus," which is at the facial end of the ABTT. The target area measures about 11 mm in diameter, measured from the medial corner of the eye at the medial canthal tendon and the lacrimal or tear puctum and extending superiorly for about 6 mm, and then extending into the upper eyelid in a horn-like projection for another 22 mm. Applicant recognized that blood flow in the ABTT is minimal or stagnant, and, in contrast with other portions of the circulatory system, is bi-directional. Furthermore, Applicant recognized that temperature in the area of the hypothalamus was, contrary to conditions in other portions of the body where temperature is measured, constantly varying. Applicant also recognized that the area of the brain around the hypothalamus has specialized thermodynamics. Still further, Applicant determined that the variation in thermal status presented substantial potential for monitoring the condition of a person because of the speed of temperature variation was indicative of the performance and condition of the body. However, considering that the potential for the ABTT is presently unappreciated, equipment for monitoring the ABTT is presently unavailable. Accordingly, the present disclosure presents configurations for monitoring the facial terminus or end of the ABTT, and for precisely measuring brain temperature and thermal milieu.

The ABTT is located in a crowded anatomic area. Therefore, the positioning of an apparatus to gather data from the ABTT requires special geometry for direct contact with the ABTT target area and for optimal thermal transfer, and for non-contact capturing of thermal energy from the area. Four facial veins converge at the ABTT target area: frontal, superior palpebral, supraorbital, and angular/facial. The angular/facial vein extends from the ABTT target area, running alongside the nose, and then extending toward the cheek; the superior palpebral vein extends from the ABTT target area to run along the eyebrow; and the frontal and supraorbital veins extend from the ABTT target area to run upwardly across the forehead. The ABTT target area is the only location where four veins converge, connecting the center of the brain to the skin. Additionally, the ABTT target area has special vasculature and is the only skin area in which a direct branch of the cerebral vasculature is superficially located and covered by a thin skin without or in the absence of a fat layer. The main trunk of the terminal branch of the superior ophthalmic vein is located right at the ABTT target area and just above the medial canthal tendon supplied by the medial palpebral artery and supra-orbital vein. The ABTT target area on the skin, supplied by a terminal and superficial blood vessel ending in a particular area without fat and void of thermoregulatory arteriovenous shunts, provides a superficial source of undisturbed biological signals including brain temperature, heart rate, blood pressure, blood flow, oxygen levels and oxygen saturation, and body chemistry such as glucose level, and the like, besides carbon dioxide and other gases.

The present disclosure provides answers to apparent meso-skeletal, venous, and arterial flaws, and aberrations that endanger life, and includes multiple apparatus and methods for measuring, decoding, and analyzing signals from not only the ABTT, but also all associated neural, vascular, and hormonal links including the aberrations. Why is the brain protected with a thick skull, but leaves a hole that is covered by the thinnest, fat-free skin? Why does the tunnel contain a valveless vein that courses along a transverse axis and facilitates spread of infection (including acne) from the "death triangle" of the face to the cavernous sinus (CS), potentially killing the otherwise young and healthy by CS thrombosis and infection? Why encircle this vein with fat, have it course without an artery and carry deoxygenated blood to an oxygen-demanding organ? Why have the cerebral venous (CV) system carry waste products/metabolite-laden blood to a stagnant pool adjacent to the brain (CS)? A potential intracranial fatal relationship also occurs with the arterial system; the ICA makes a sigmoidal turn through the CS. Why predispose to carotid-cavernous fistula and potentially fatal cerebral hemorrhage by combining two dissimilar pressure structures (artery-vein) and why cause turbulence, with an S-shaped vessel, that may damage blood cells and vessel wall?

When viewed from a matter (structure, blood flow) standpoint, the aforementioned configurations appear to be morphological and physiological aberrancies at best and lethal flaws at worst. However, the information provided in the present disclosure showed that the aberrancies and ABTT should be viewed from thermal and electromagnetic perspectives. The answer to the question revealed herein is thermodynamics. As shown by dissection, fat arrangement in the ABTT enables non-dissipated transmission of thermal energy between brain and surface; this insulated configuration is even more significant as low velocity blood in the superior ophthalmic vein (SOV) facilitates thermal exchange with surrounding tissues, thereby eliminating the thermal integrity of the passage. Thermodynamics also explains the large-sized vein and slow moving venous blood (since these provide optimal thermal carrying capabilities) and the lack of a parallel artery (since this configuration avoids counter-current heat exchange in the ABTT). SOV and the cerebral venous system as shown herein play a role in the context of thermal information, regulation, and/or exchange systems.

Thermodynamics also elucidates arterial "aberrancies." Thermal exchange between CS and arterial blood coursing rapidly through a straight vessel would be minimal. However, Applicant recognized that the S-geometry of ICA as it courses through CS increases surface area in contact with CS, decreases blood velocity, and changes flow from laminar to turbulent (high Reynolds number); the combination promotes efficient thermal transfer across the ICA wall. When those thermodynamic factors are accounted for, Applicant further recognized that the potentially enhanced thermal transfer ICA-CS justifies the S-geometry and combining dissimilar pressure structures and arterial-venous blood into one structure.

In FIGS. 30-56, markers of the anatomic structures are as follows: double arrow=frontal bone; short arrow with straight end=orbital fat; arrow with angled end=Superior Ophthalmic Vein (SOV); asterisks=ABTT exit on skin; triangle=cavernous sinus (CS); long arrow with straight end=internal carotid artery (ICA); and angled arrow head=cerebral vein (CV, superficial middle cerebral vein (SMCV).

In the present disclosure, Applicant also reveals a previously unappreciated peri-hypothalamic triunal thermo-sensory/regulatory system, which is the object of various embodiments in this disclosure, as shown in FIGS. 30-56. Referring to FIG. 38, an axial view of a human cranium 8410 reveals that input from the SOV 8412 (in the ABTT), CV and ICA (three individualized medium, but of same thermal energetic nature) provides three respective thermal inputs to a summing junction like arrangement (the CS). Triunal arrangement provides dynamic thermal integration among the components, allowing the brain to anticipate thermal changes and make adjustments (centrally and/or peripherally) to maintain an optimal thermal zone, and all of those previously unknown signals essential for life and health are decoded and analyzed by the inventions of this disclosure. The CS also has intimate contact with the brain and encompasses the trigeminal nerve (e.g., see FIG. 35), whose thermo-sensory role is evidenced by being the afferent limb of the diving reflex. The tunnel is in continuity with the hypothalamus and with the endocrine system via hypothalamo-hypophyseal hormones (e.g., see FIG. 33), and other embodiments extracted and deciphered the neuroendocrine signals. The ABTT and its continuum with neuroendocrine system allows thermal regulation and/or sensation, with the previously unknown signals generated being extracted and decoded by the inventions of the present disclosure, with the process of apparatus and methods disclosed herein facilitated by: trabecula in the CS channeling blood and hence thermal energy among CS and triunal components; sphincters regulating flow to neighboring sinuses; and bidirectional flow via SOV.

In addition to thermal communication, apparatus and methods of the present disclosure identified and decoded light transmission via this energy path, including phototransduction, by the proximity of the ABTT terminus to the suprachiasmatic nucleus in the brain as well as the unexpected presence of photoreceptors in the hypothalamus. The apparatus and methods disclosed herein identified, decoded and analyzed: (i) unknown brain/core thermal discordance; (ii) unknown brain signals from heat exposure, exercise, surgery; (iii) unknown cerebral neuronal activity, (iv) unknown brain signals from sleep, awakening, arousal, seizures; (v) unknown heat generated by human thought; (vi) unknown spectral and fractal patterns that characterize cerebral thermodynamics; and (vii) unknown brain oscillatory signals. The present disclosure transforms temperature from a non-cerebral dichotomous (febrile/afebrile) variable into a brain oscillating signal for monitoring anesthesia/surgery, behavior/cognition, exercise, fever/pyrogens, heatstroke, hypothermia, ovulation, and populations threatened by bioterrorism, pandemics, and heat waves while providing a tool for reducing livestock carbon footprint. The embodiments provide thermo-diagnostic information and/or information on mis-folded proteins including Alzheimer's, Parkinson's, multiple sclerosis, and diabetes. The cerebral bidirectional energy path disclosed herein allowed embodiments that can impact the brain from an external signal, input, or stimulus for diagnosing and treating various conditions and disorders.

The present disclosure examined the limited arrays of fat within the cranium from a new thermal energy perspective, distinct from the established role of fat in limiting heat transmission between core and surface. Usually fat is discarded during dissections. However, in light of its low thermoconductivity (k) [k=0.00004 Kcal/(s·N·C)] (6), this fat was the prime target of the macroscopic and microscopic search of this disclosure for low-k tissue configured as a thermally transmissive path.

Figure 31:
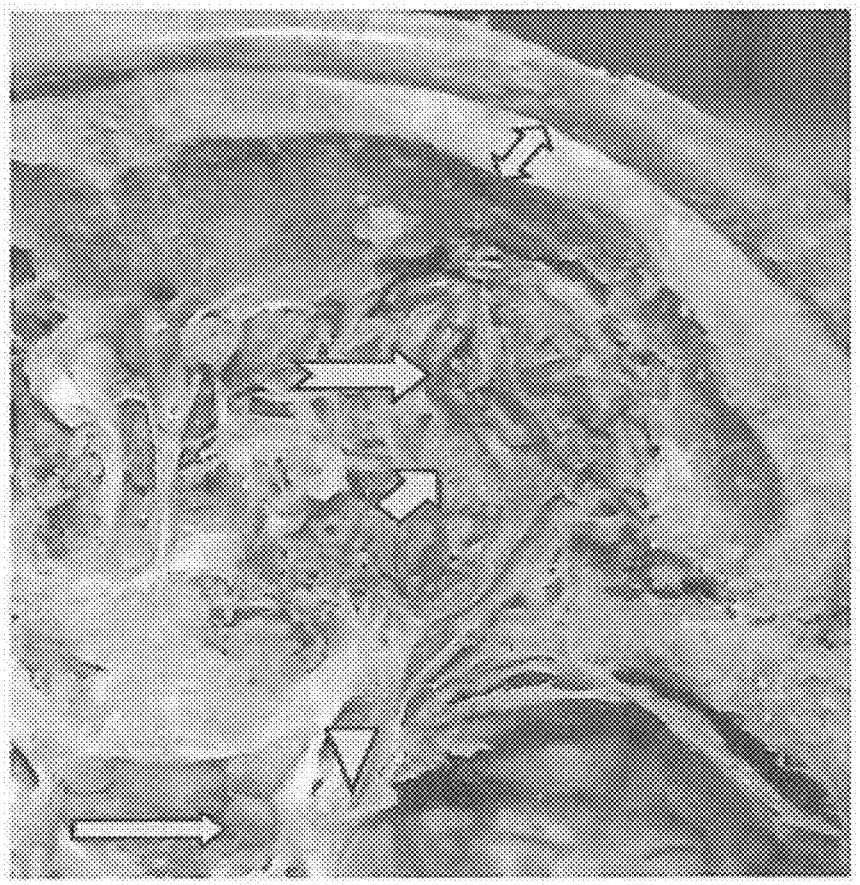
FIG. 31 is another view of a cut of a human cranium showing the frontal bone and SOV.

Especially since there is no fat in the cranial cavity and the brain does not use fatty acids as energy source, Applicant was intrigued by large orbital fat pads (OFP, the predominant nonocular tissue within the orbit; e.g., see FIGS. 30, 31, and 32). Prior to the present report, a disputed mechanical function (support/sliding/shock absorption) was considered to be the major benefit of orbital fat; however, analysis by the Applicant showed that fat, (the tissue with the lowest thermo-conductivity) encircles (insulates) a path between brain and surface, and research and experimentation disclosed herein showed that this unknown path in the prior art has a specialized thermal and electromagnetic function, besides ultrasonic. Being the only fat-encircled path in the body, this conduit constitutes a previously unappreciated means of brain thermal transmission, wherein the low-k wall precludes heat exchange along its course. By combining the lowest-k tissue (fat) with the high heat capacity tissue present in a key component (blood) of the ABTT, the thermodynamics for thermal transmission in the tunnel are optimized. Thermodynamic function of this fat is further supported by its thermo-mechanics: because orbital fat has a much lower viscous shear modulus than other body fat, minimal energy is dissipated within it, more effectively preserving the thermal representation of heat within the path disclosed herein.

To further support that this fat-enclosed path revealed herein constitutes a tunnel for undisturbed brain↔surface thermal transmission was support by three additional experimental evidence and analysis disclosed by the present disclosure: 1) the contents of the tunnel suitable for undisturbed thermal energy transfer; 2) the internal end of the tunnel is configured for thermal energy transfer to/from brain; and 3) the peripheral end of the tunnel is configured for thermal energy transfer to/from body surface.

The thermodynamic configuration disclosed by the present disclosure is verified by what passes through and what does not pass through the tunnel. The insulated horizontal path-contains an optimal thermal energy carrier, slowly moving blood in a uniquely valveless and large vein, the SOV; coursing between the superomedial orbit (and the eyelid) and the cavernous sinus (CS) (e.g., see FIGS. 33, 34, 36, and 39). In contrast to traditional role of vasculature to exchange thermal energy along its course, fat encircling the SOV prevents heat exchange with surrounding tissues. In addition, the SOV runs basically without an accompanying artery that would promote countercurrent heat exchange.

Figure 33:
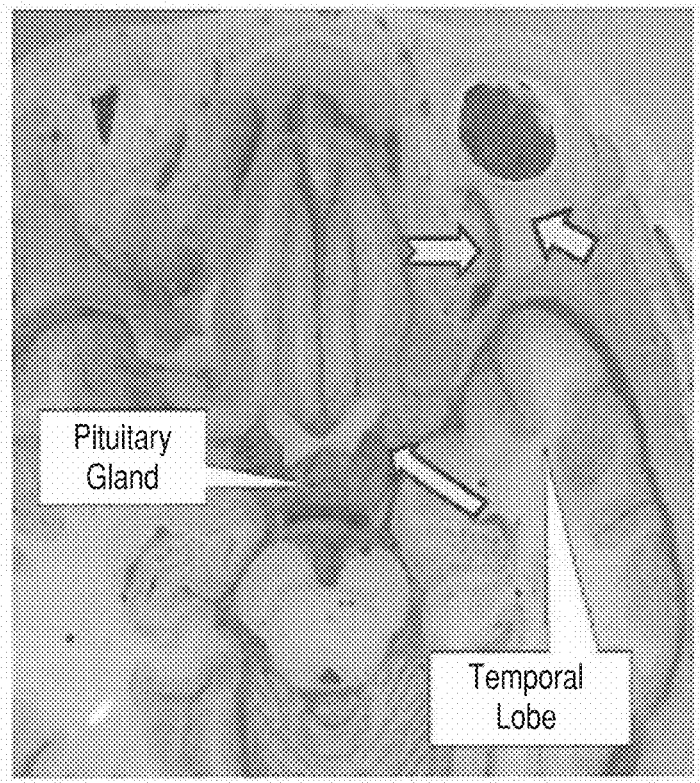
FIG. 33 is an axial cut of a human cranium showing orbital fat surrounding the SOV.
Figure 34:
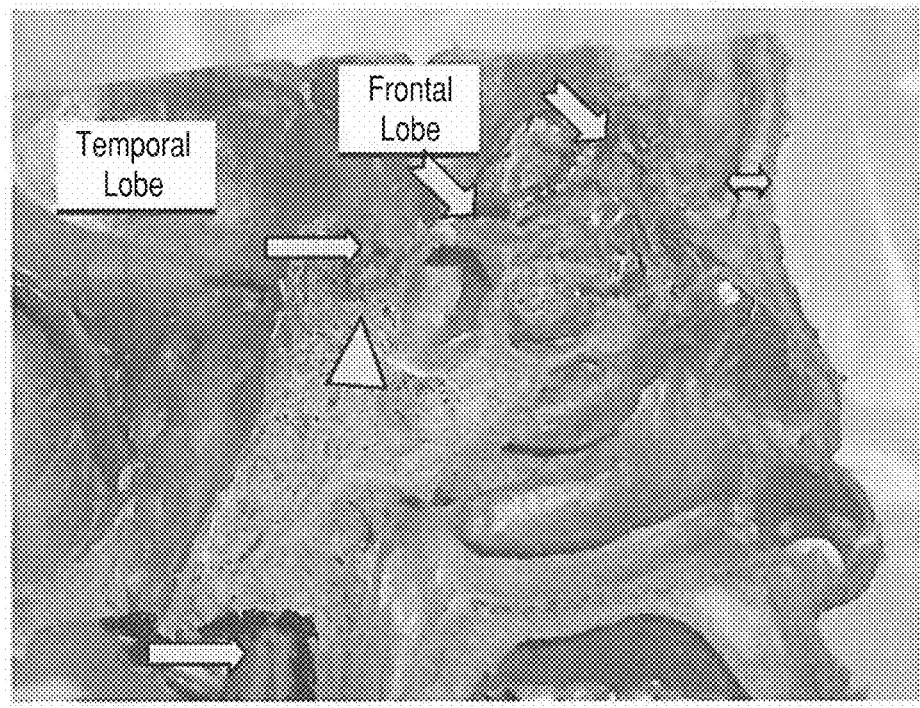
FIG. 34 is a parasagittal cut of a human cranium showing a cavernous sinus (CS), ostial framework, and tunnel configuration of the ABTT.
Figure 36:
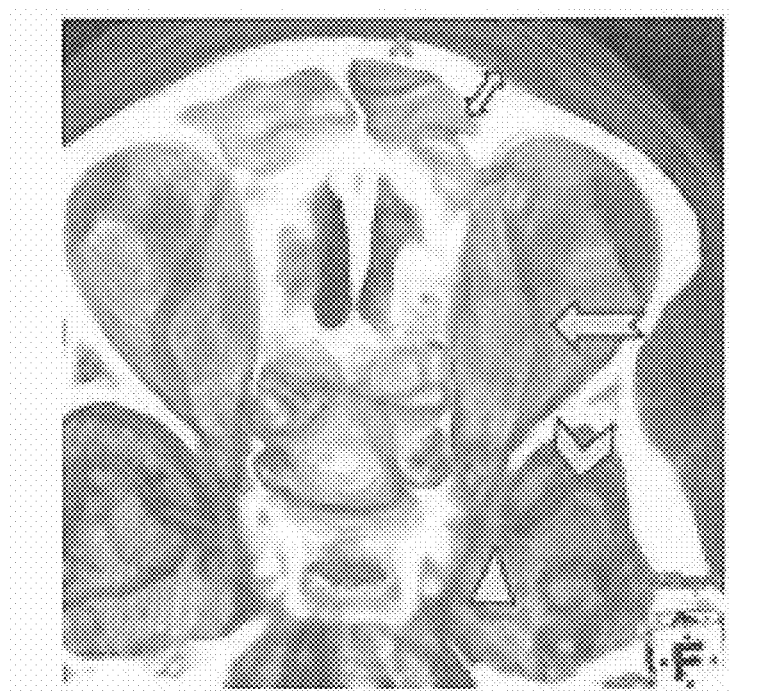
FIG. 36 is volumetric CT reconstruction showing cross-section of orbits and frontal bone, with SOV and cerebral vein in a human cranium.
Figure 37:
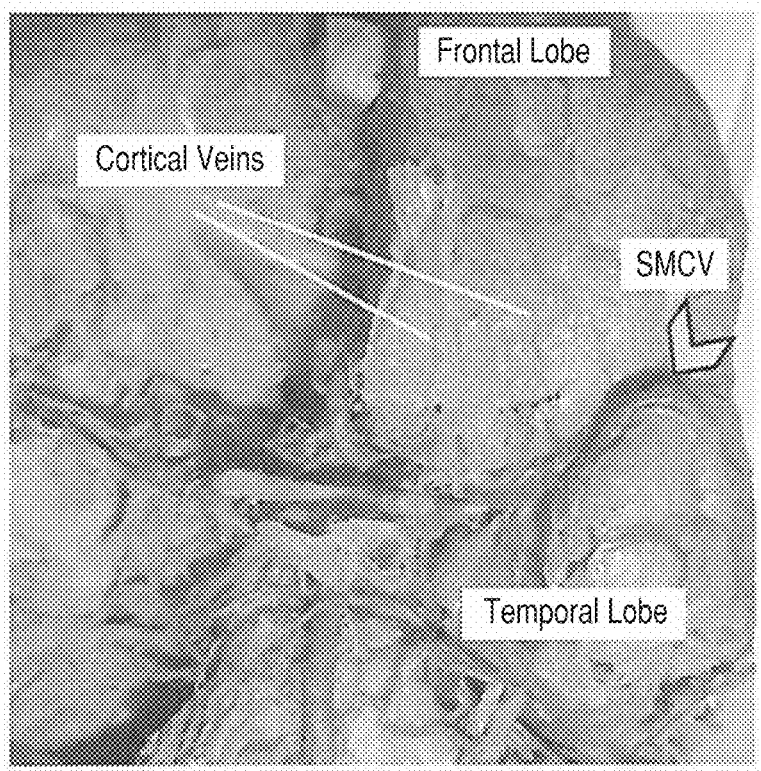
FIG. 37 is a view of rich cerebral venous drainage to the CS by superficial middle cerebral vein (SMCV) and cortical veins in a human cranium.
Figure 38:
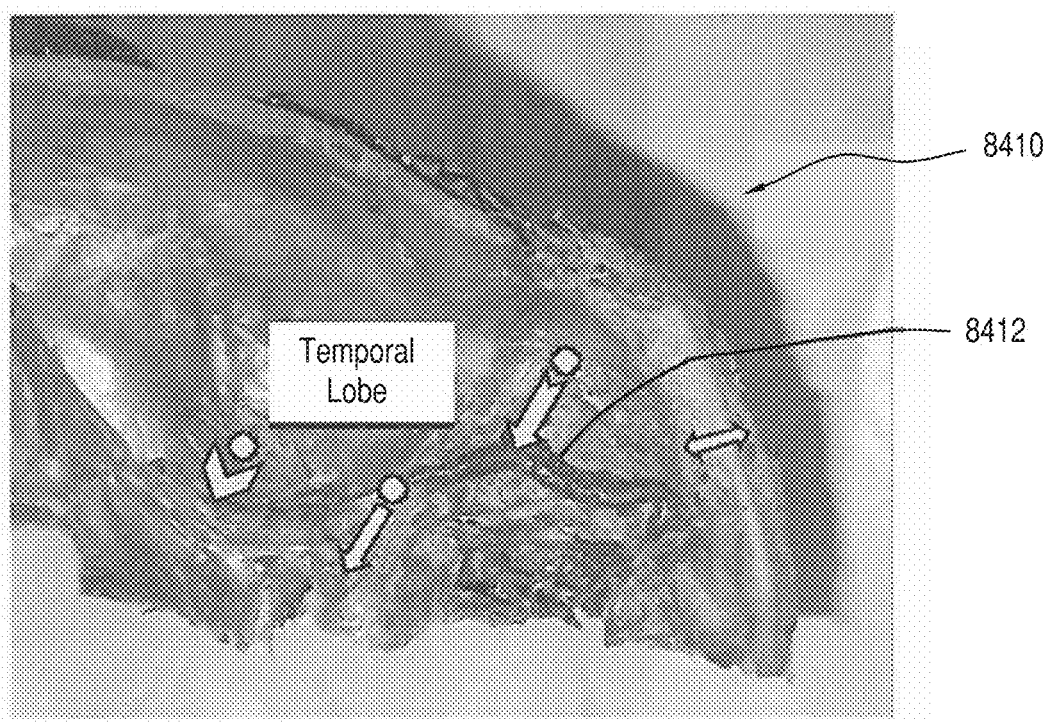
FIG. 38 is an axial cut of a human cranium showing components of a triunal thermal information arrangement from the ABTT.
Figure 39:
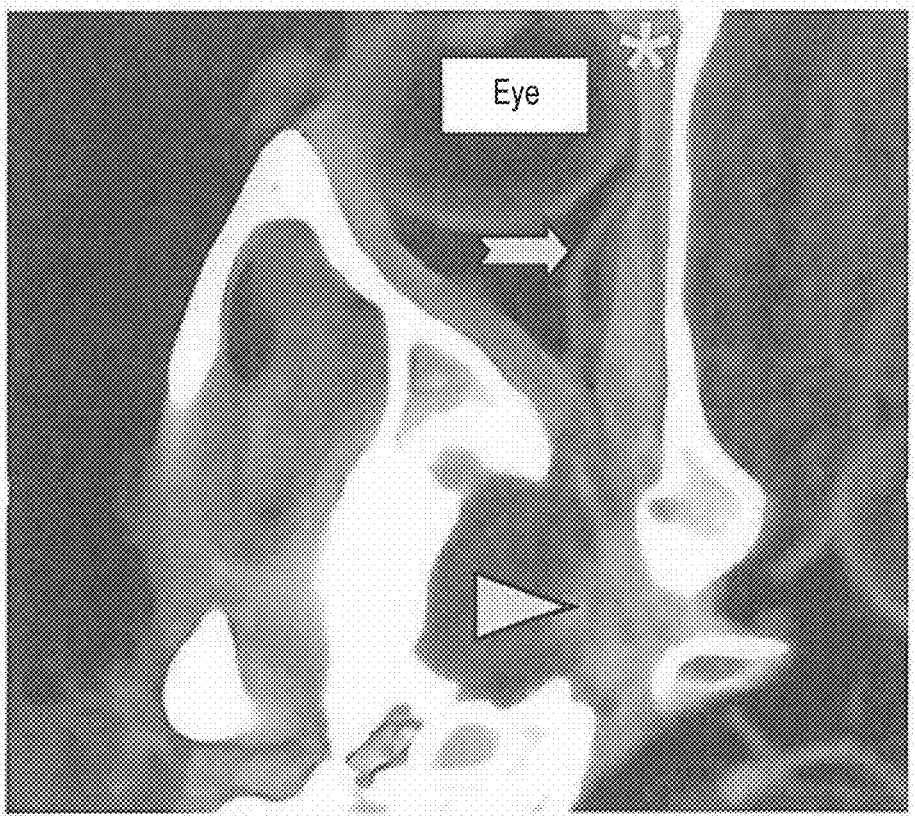
FIG. 39 is a reconstructed image via multi-slice tomography, with a specific window for vessels in a human, illustrating the direct path that characterizes the architecture of the SOV within the ABTT between the SMO and the CS.
Figure 40:
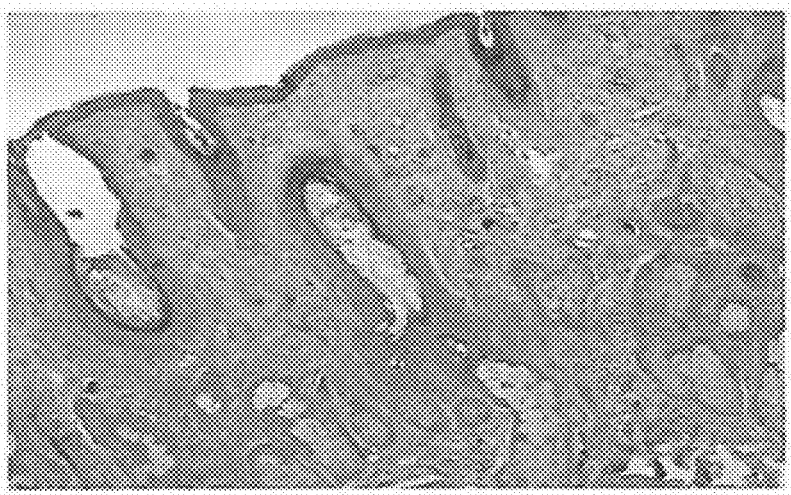
FIG. 40 is a photomicrograph of a human forehead skin specimen showing the epidermis.
Figure 42:
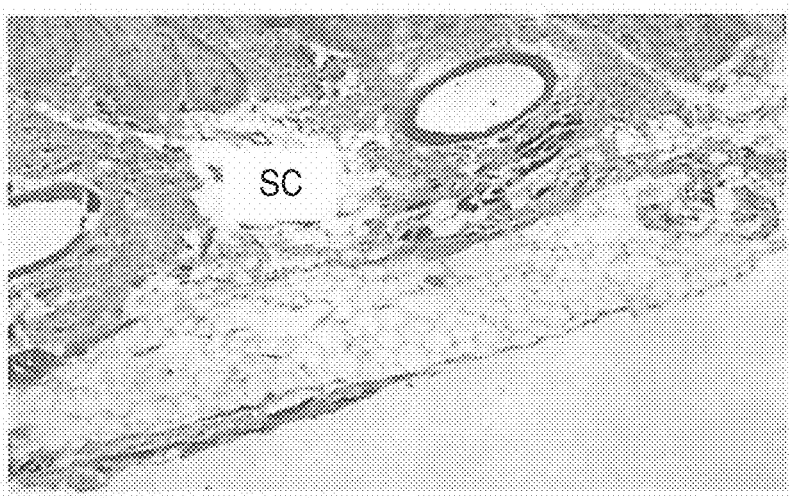
FIG. 42 is a photomicrograph of a human forehead skin specimen showing subcutaneous (SC) fat.
Figure 41:
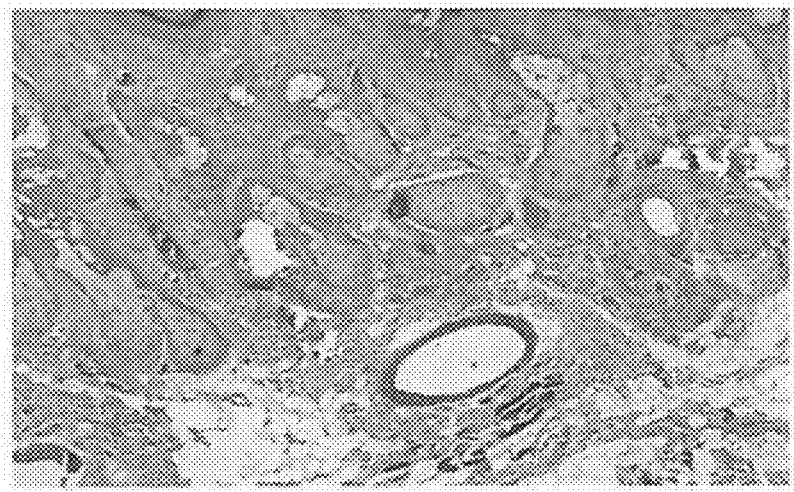
FIG. 41 is a photomicrograph of a human forehead skin specimen showing the dermis.
Figure 43:
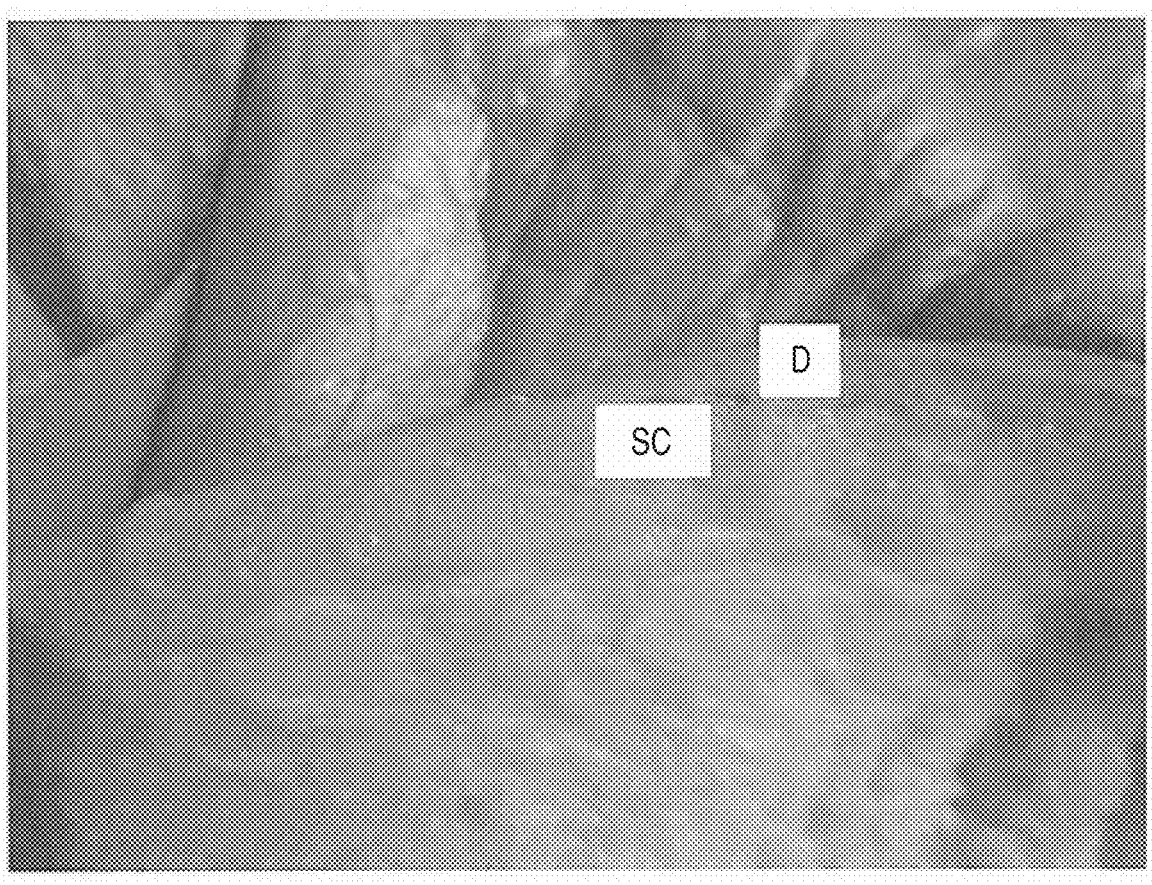
FIG. 43 is a cross section of a human cadaver's axilla showing thick dermis and subcutaneous fat (SC).
Figure 44:
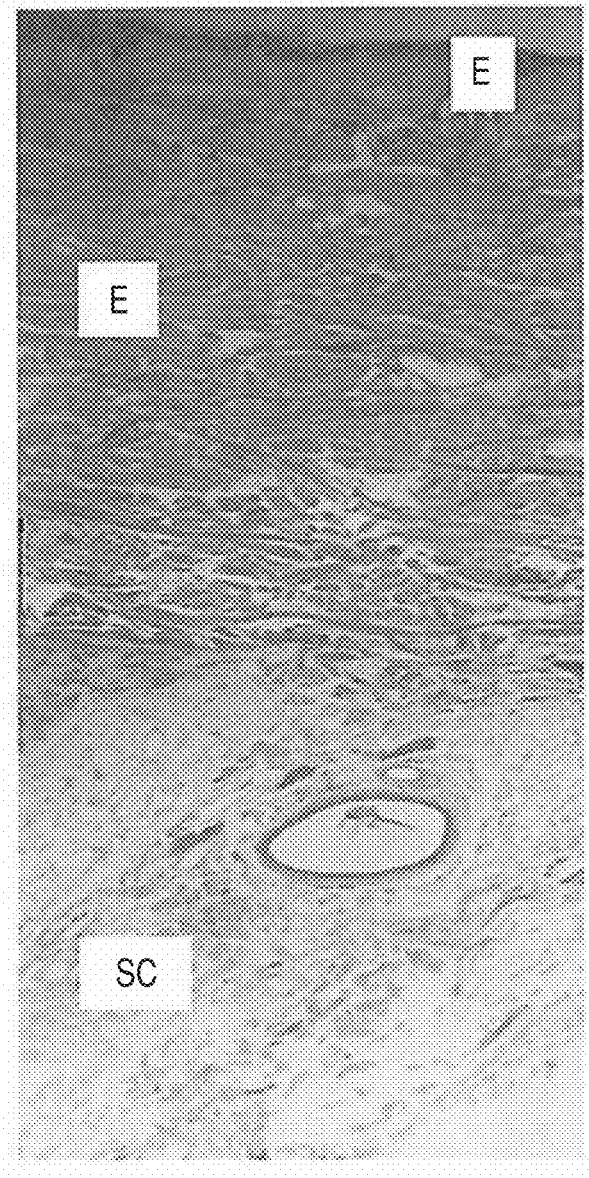
FIG. 44 is a micrograph of human neck skin showing thick dermis and thick SC fat.
Figure 45:
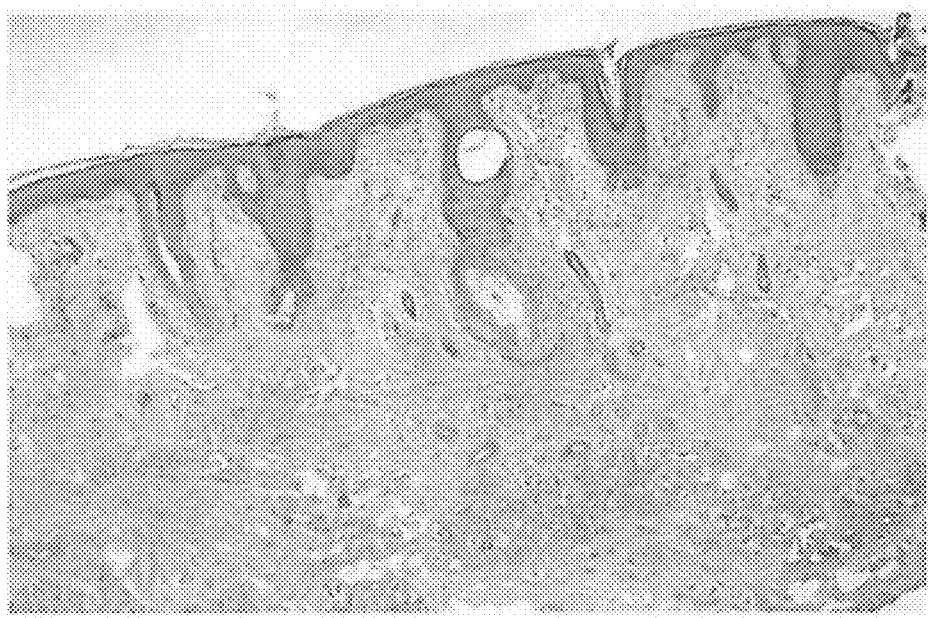
FIG. 45 is a photomicrograph of an ABTT skin specimen from a human cadaver showing the thin dermis and absence of SC fat in this area.
Figure 46:
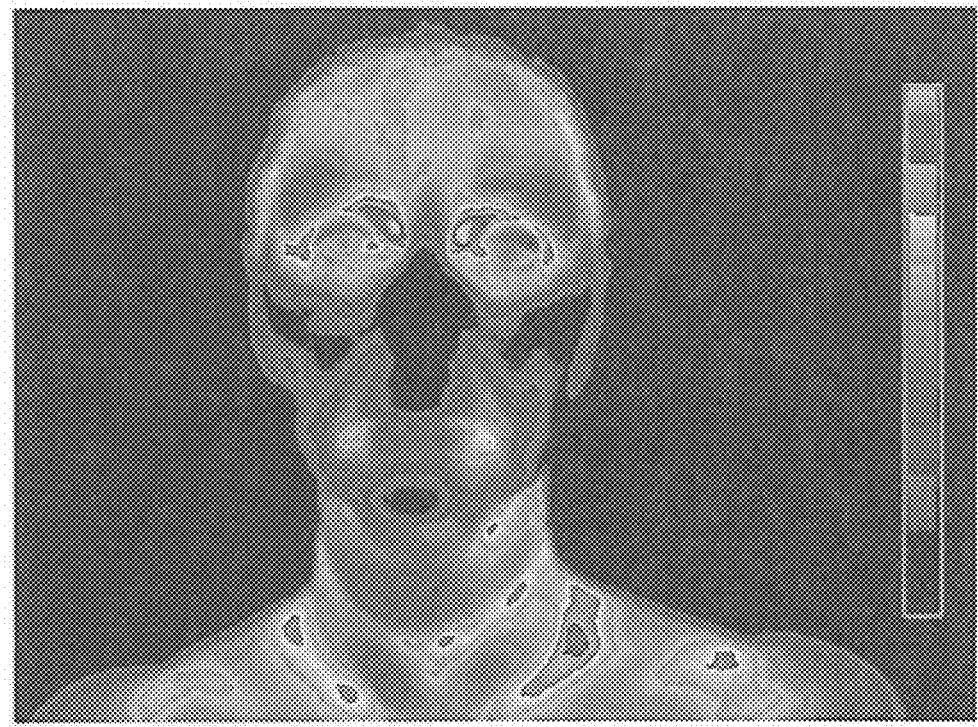
FIG. 46 is a thermographic image of a human face demonstrating high infrared (IR) emission at the ABTT in a 60 year old.
Figure 47:
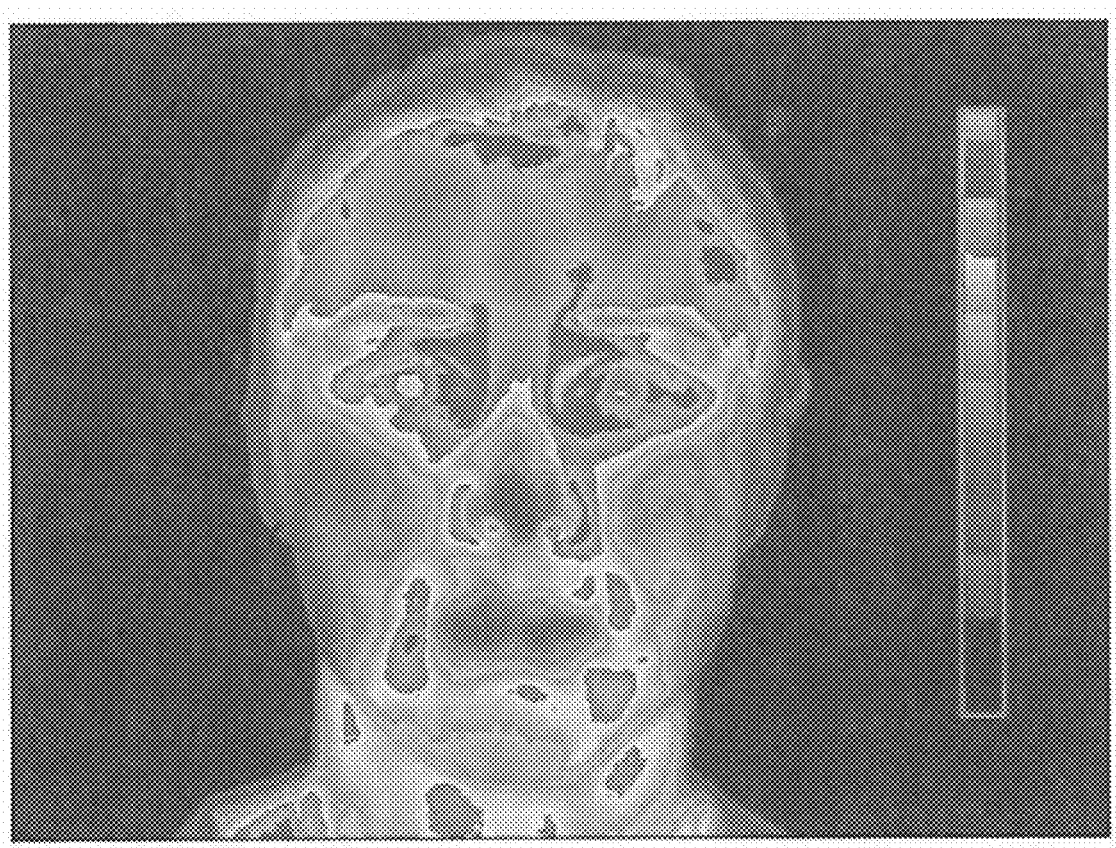
FIG. 47 is another thermographic image of a human face of a 35 year old showing the low and variable IR emission of the forehead and other facial features.
Figure 48:
FIG. 48 is another thermographic image of a human face of a 48 year old showing that even the forehead region overlying the superficial temporal artery has much lower thermal emission than the ABTT.
Figure 49:
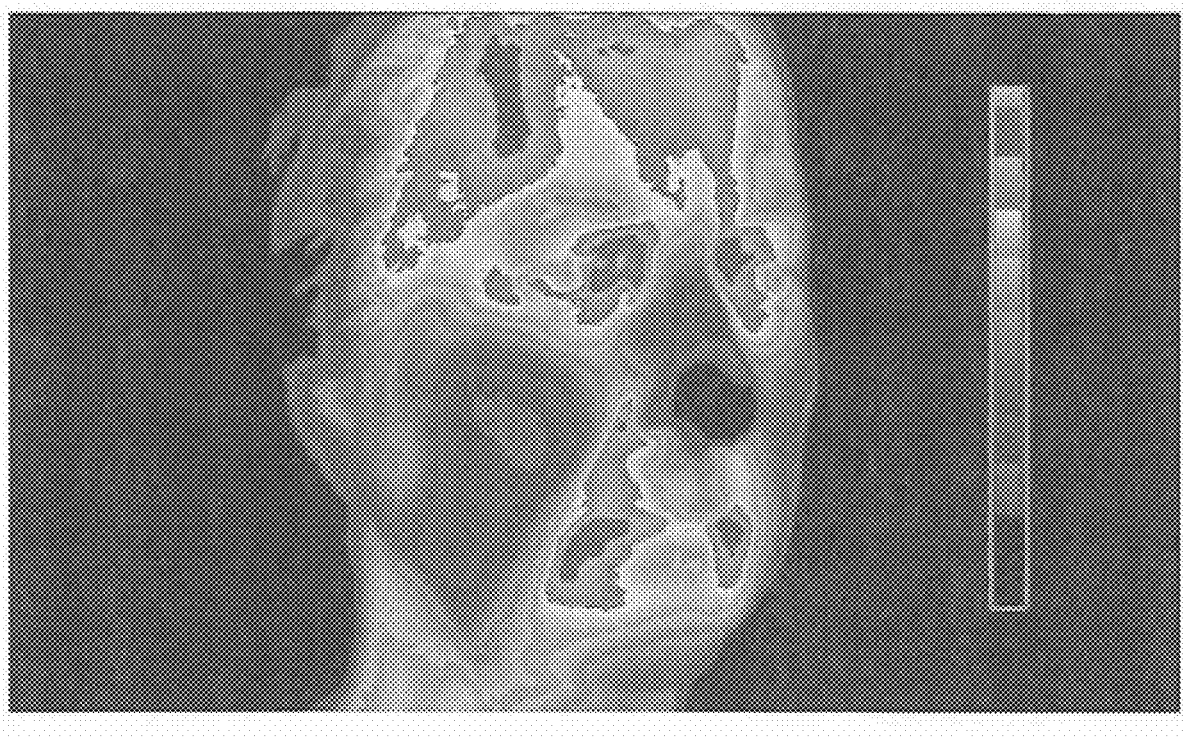
FIG. 49 is a thermographic image of a human face at an angle, focusing on the area of the superficial temporal area, showing low thermal emission as compared to the ABTT.
Figure 50:
FIG. 50 is a human cadaver head specimen showing the superficial temporal artery.
Figure 51:
FIG. 51 is a human cadaver head specimen showing rich facial arterial and venous networks.
Figure 52:
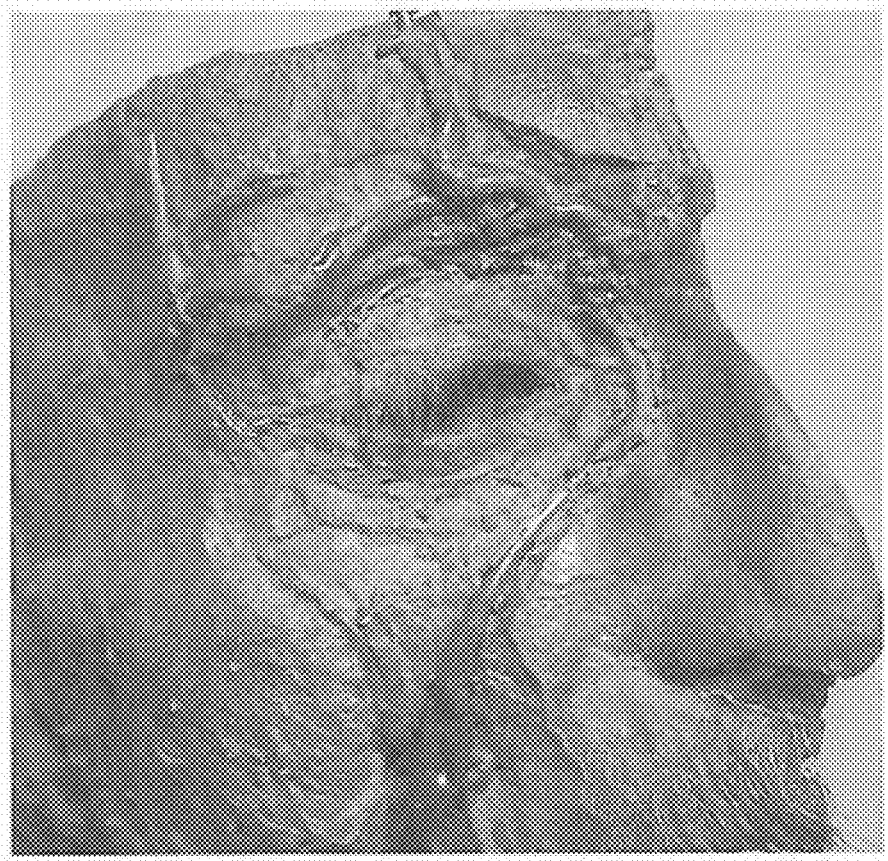
FIG. 52 is a human cadaver head specimen delineating the course of the superior palpebral vein (SP) just beneath the skin as it converges with the frontal (Fr), supraorbital (SOR) and facial/angular (Fa/A) veins to form the SOV in the skin adjacent to or on the superomedial orbit (SMO).
Figure 53:
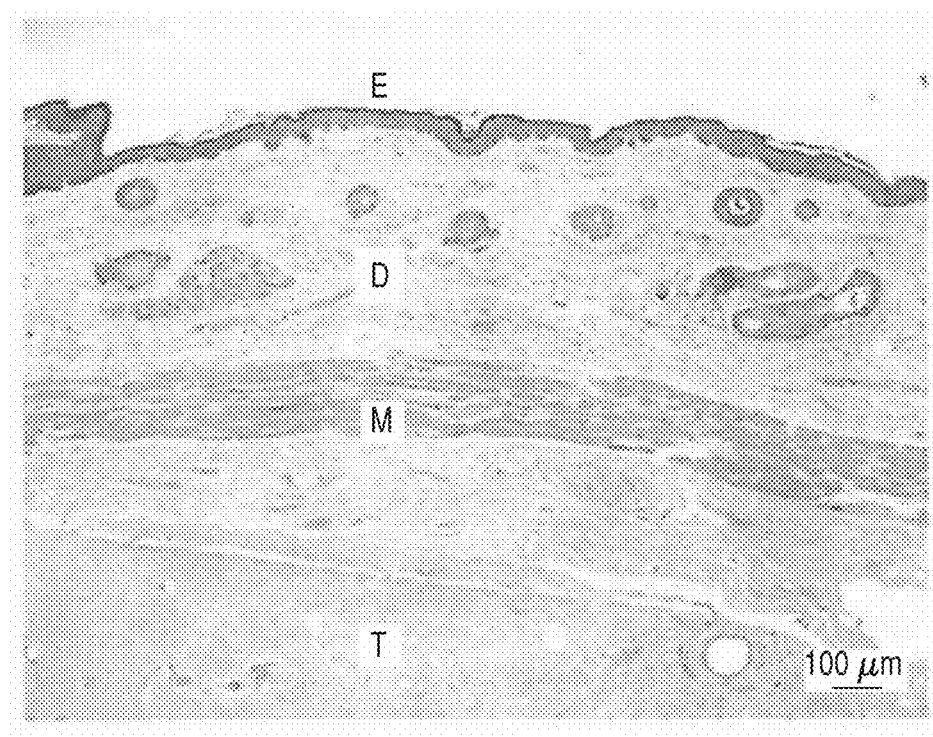
FIG. 53 is a section of human skin showing the histology of the superior palpebral region.
Figure 55:
FIG. 55 is a thermal image of a face of a cat showing IR emission via the left ITP.
Figure 54:
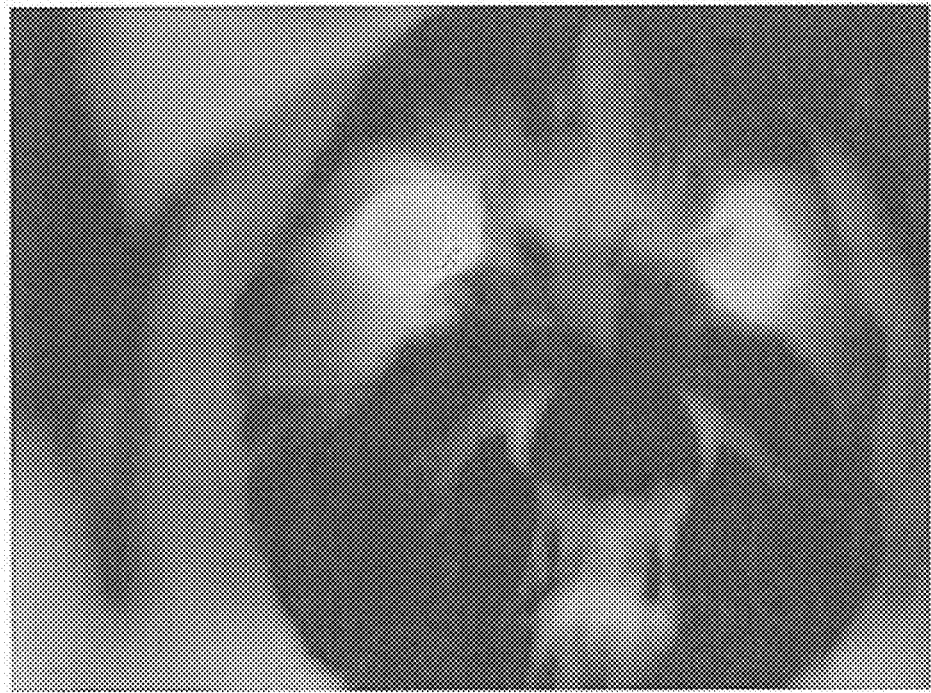
FIG. 54 is a thermal image of a face of a dog showing IR emission via the right ITP and its corona.
Figure 56:
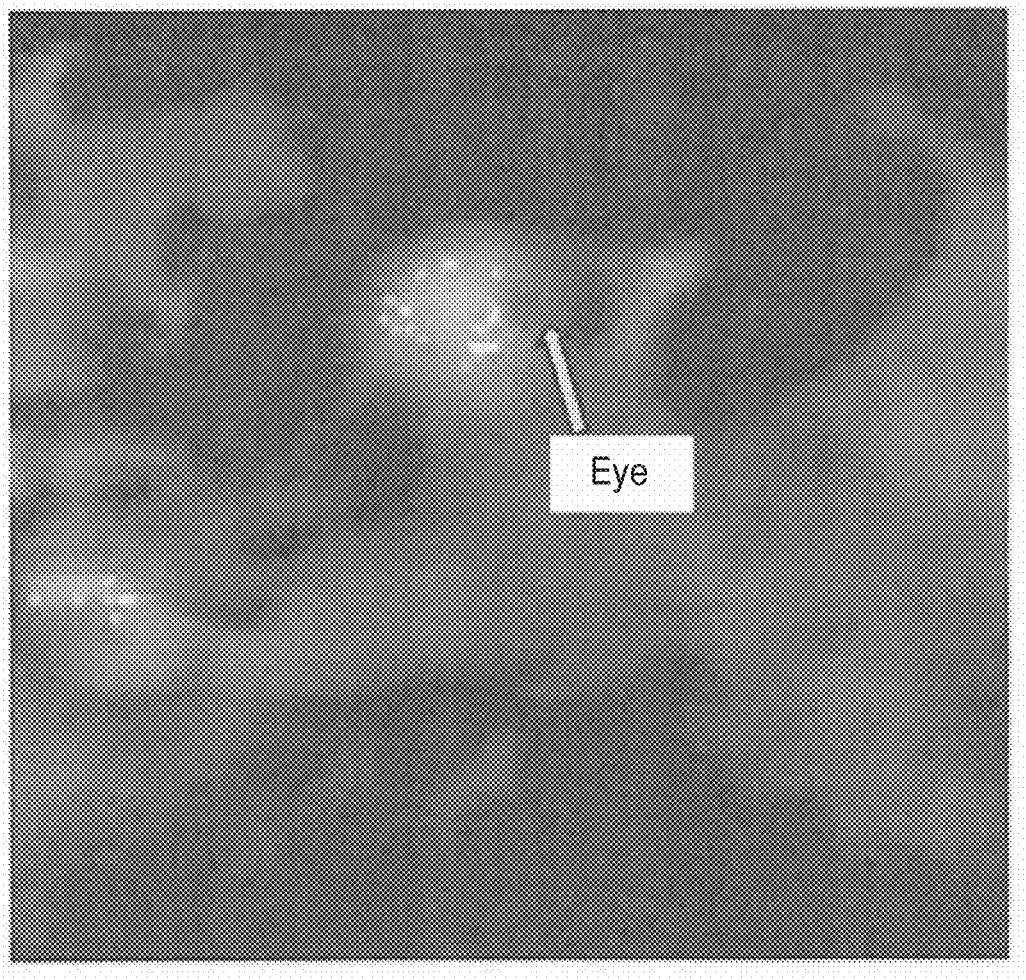
FIG. 56 is a thermal image of a bovine showing high intensity IR emission only from the ITP and inside the oral cavity.

At its intracranial terminus, the ABTT continues until the SOV passes through the superior orbital fissure to terminate at the CS (e.g., see FIGS. 33, 36, and 37). The thermal energy within the tunnel is transmitted in an undisturbed fashion from/to the CS and neighboring brain (e.g., see FIGS. 30, 31, and 32). At the CS, blood transported via the SOV is in thermal continuity not only with neighboring regions of the brain (e.g., see FIGS. 36 and 37) but also the ICA (e.g., see FIGS. 33, 36, and 37), which passes through the CS (e.g., see FIGS. 38, 39, and 40-42), show that, in addition, the CS receives cerebral veins (CV) providing thermal communication with brain; and the trigeminal nerve courses through the CS lateral wall (e.g., see FIG. 37).

The aforementioned low-k walled path (ABTT) provide insulated heat convection (conduction) through the orbit, and thereby facilitates thermal exchange with facial blood, which is subject of an apparatus and method of the present disclosure. The ABTT disclosed herein prevents dissipation of thermal gradients during passage of the SOV within the orbit.

However, the path from the brain alone would not enable totally undisturbed brain↔surface transmission. Without a high-k external terminus, direct (e.g., radiant) transfer of thermal energy at the body surface would be prevented by the cranium's seemingly omnipresent adipose and skeletal wall. This not only would preclude surface measurement of brain temperature but also impede effective brain↔surface thermal communication and heat dissipation. Other sites, including forehead (FH) (see, e.g., FIGS. 40-42), axilla (see FIG. 43), and neck (see FIG. 44), have thick layers of subcutaneous (SC) fat and thick dermis; these have low k values [k=0.00004 Kcal/(s·N·C) and k=0.00009 Kcal/(s·N·C) respectively], thereby creating a barrier for transferring thermal energy through the body surface. In addition, these regions show marked inter-subject variability (see Table 1), further compromising reliable transmission of thermal signals to/from the body. Hence, the importance of present disclosure identifying and revealing a remarkable thermo-physical property of skin overlying the external ABTT terminus and eyelid skin, and associated area underneath the brow ridge; which was identified as a specialized high-k area. Macroscopic and microscopic analysis revealed that this specialized skin is free of fat and has uniquely thin dermis, with a paucity of surface vessels (e.g., see FIGS. 40 and 45, and Table 1). Fat and dermis have small k values; numerator of heat dissipation equation is largely dependent on k and denominator on thickness. Thus, minimal dermal thickness, combined with lack of fat maximizes k of skin overlying BTT. The histologic specimens revealed in this disclosure showed that the skin overlying the tunnel is uniquely configured for virtually direct thermal exchange with the environment. Moreover, in contrast to varying thickness at other sites throughout the body, this newly identified unique high-k histology at the facial terminus of the tunnel was consistent among cadavers (Table 1).

Multiple embodiments that decoded brain information are disclosed in the present disclosure. Embodiments also extract and deciphered thermal and electromagnetic transmission between brain and this newly identified high-k skin surface. Cerebral information previously unknown was recognized, decoded, and analyzed in both humans and animals by the various embodiments disclosed herein. The disclosure includes apparatus and methods for capturing and coding thermal emission via the ABTT. Other embodiments altered cerebral neuronal activity and/or inducing brain/core discordance in humans and animals, with the brain information generated being decoded and analyzed.

The present disclosure also discloses a tunnel-enabled thermo-sensory and thermo-regulatory triunal configuration, which is an object of various embodiments shown herein. This disclosure further recognized and decoded light emission from the ABTT and showed that works as black body radiant. The thermodynamic configuration described herein unearthed the development of apparatus and methods to measure or alter thermal transmission by acting on a link between neural (and brain), and vascular systems.

Table 1 provides the thickness (in microns) of the layers of skin and fat. The two BTT skin specimens were the only areas with the same dermis thickness and no SC fat.

TABLE 1

Thickness of histologic specimens.

| Tissue | Axilla | Neck | Forehead(1) | Forehead(2) | BTT(1) | BTT(2) |
|---|---|---|---|---|---|---|
| Epidermis | ~70 | ~70 | ~70 | ~70 | ~70 | ~70 |
| Dermis | 2000 | 2700 | 1900 | 2300 | 1100 | 1100 |
| Fat | 5000-10000 | 2200 | 2400 | 1200 | 0 | 0 |

The Brain Thermal Tunnel Background

Applicant's studies of brain and cerebral thermodynamics showed a hidden and encrypted phenomenal system in the brain, referred herein as the Abreu Brain Thermal Tunnel (ABTT), and also as the less precise Abreu Brain Temperature Tunnel. Applicant reveals that fat distribution in the cranium and associated brain structures creates a thermodynamic configuration for brain thermal transfer in humans and animals, which is the subject of various inventions in the present disclosure, including the apparatus and methods described herein.

The present disclosure capitalizes on new information from a new understanding of the ABTT and how it functions, from which Applicant recognized certain characteristics amenable to measurement and analysis that lead to improved diagnostics of human subjects and animals. Moreover, in the present disclosure, Applicant reveals a hitherto unappreciated distinction in the brain path of humans and animals, which is reflected in the apparatus and methods for humans and animals disclosed herein.

The inventions of the present disclosure also extract from the cerebral thermodynamic configuration revealed herein a useful signal that, by being decoded by the apparatus and methods of the present disclosure, provide information that, prior to the inventions of the present disclosure, was previously only available to the brain. With the apparatus and methods disclosed herein the information is decoded and analyzed so as to be available for the benefit of humanity through the diagnosis of diseases, analysis of non-disease human biology, the treatment of diseases, and the cure of maladies.

The present inventions decode signals from the brain that contains information previously unknown and unavailable in the current body of knowledge of the world. With the inventions of the present disclosure, it is possible to decode information that reveals a brain thermal or thermodynamic communication and exchange system, which provides early diagnosis of myriad pathologic and physiologic conditions, the ability to treat diseases, and potentially even to extend longevity, which may enable humans to reach the age of 120 years in full vitality. Applicant's research shows that thermodynamics is the basis for, and the main form of communication in, the brain, but this communication information was unknown prior to this disclosure, and the information is encrypted. The apparatus and methods of the present disclosure reveals information that was previously privy to the brain only, and that information is related to keeping the body functioning and enabling humans and animals to remain alive and well. Applicant's research further showed that the body as a whole, and more specifically the structure of the cranium and brain, is designed with the purpose of this thermodynamic configuration generating signals for brain function and preservation of life, to the extreme that the brain and body jeopardize life itself for the sake of brain thermodynamic communication.

The ABTT also explains aberrancies in the body and brain, even lethal aberrancies, and the present disclosure shows how to use those aberrancies to preserve life, with the apparatus and methods showing how to extract and decode the signals ranging from heart-brain thermodynamic structures to intra-brain thermodynamic information and configuration. The coded information that was previously a privilege of the brain is only now being decoded with the present inventions for the benefit of humanity and reduction of human suffering.

The inventions of the present disclosure work to assist the brain in performing its function in an optimized manner, and by knowing the way the brain communicates and functions the inventions of the present disclosure assist the brain in times in which brain reserves are exhausted, or when the aging brain no longer can function adequately, the inventions of the present disclosure provide the means and support needed to enhance and restore brain function, ranging from the use of electromagnetic means (all wavelengths in the spectrum) and ultrasound to pharmacological means. The inventions of the present disclosure also provide apparatus and methods that allow the brain to fight diseases. Other associated means (including pharmacological and drugs) assist the brain, but the central point is the brain, such brain function being enabled and facilitated by the devices, systems, methods, and drug delivery systems disclosed herein. By way of illustration, but not of limitation, in some embodiments the current disclosure provides the extra "troops" that are missing in the brain (due to disease or other conditions including genetic conditions), said troops being thermodynamic and thermal means that, added to any available natural brain means, enables the brain and associated body to fight a variety of conditions and diseases ranging from infections to cancer, and even altered genetics. Embodiments of the inventions of the present disclosure decode the brain thermal transfer signals present in the ABTT, and provide the extra "troops" needed to restore brain function and to protect the body.

A fat-based thermoconductive configuration revealed herein in the ABTT allowed creation of apparatus and methods that revealed brain thermal transfer mechanisms, said apparatus and methods provide codes and patterns associated with cerebral neuronal activity and delineation of said activity. Viewed herein from macroscopic/microscopic thermodynamic perspectives, the path between cavernous sinus and uniquely thermoconductive orbital and eyelid skin provides the basic structure of the ABTT, allowing the apparatus and methods disclosed herein to overcome the body's natural thermal barrier. ABTT generated the highest radiant surface and the inventions of the current disclosure decoded the light emission that contains vital information only previously available to the brain itself. The apparatus and methods described herein transformed a non-cerebral dichotomy (febrile/afebrile) into continuous oscillatory cerebral signals providing spectral-domain thermal characterization of REM sleep (Rapid Eye Movement phase of sleep) with identification of the frequency band (0.01 Hz; see FIG. 21), heat-stress fractal patterns in animals, and even thermodynamic patterns of human thinking.

The inventions of the present disclosure helped to identify and decode brain (ABTT)/core discordance in anesthesia, surgery, exercise, seizures, arousal, and sleep reaching even 5.6° C. Apparatus and methods of the present disclosure provide means for monitoring psychological, physiological, and pathophysiological processes, in addition to providing means for monitoring public health such as pandemics, agro-terrorism, and heat waves. The inventions of the present disclosure also helped to identify and decode thermal milieu for protein folding and triunal thermoregulatory/sensory morphologies that contains signals essential to survival.

The apparatus and methods provided herein include the means to decode signals in the sick (with fever) to robust (with heatstroke), including: (i) psychological assessment by the apparatus deciphering codes associated with aggressive behavior, depression, emotions, illicit drug use, interpersonal behavior, neurocognitive dysfunction, and sexual behavior; (ii) physiological assessment by the apparatus deciphering codes associated with longevity, fatigue, sleep, pre-ovulation and ovulation, hydration status, electrochemical and electrolytic status, and sexual activity and pleasure; (iii) pathophysiological assessment by the apparatus deciphering codes associated with hormonal disorders, neurological disorders, vascular and cardiac disorders, respiratory disorders, infectious disorders, metabolic disorders, cancer, coma, sudden infant death syndrome, brain trauma, foot-and-mouth disease, and protein folding in a variety of disorders including, but not limited to Alzheimer's Disease, Parkinson's disease, diabetes, Huntington's disease, amyotrophic lateral sclerosis, and multiple sclerosis; and (iv) treatment of disorders by the apparatus deciphering codes associated with therapy of various diseases, and by way of illustration, but not of limitation, treatment ranging from cancer to neurologic diseases and from stroke to coma and sleep disorders. Apparatus and methods of the current disclosure, by deciphering and documenting cerebral thermal milieu, allow understanding psychological, physiologic, and pathophysiologic processes, with creation of inventions for detecting and treating protein mis-folding, abnormal enzymatic reactions, and altered circadian rhythms.

Prior art has not been able to achieve any of the objects of the present disclosure because among the many limitations and drawbacks of the prior art, the sites where measurement is taken is not suitable for or capable of generating adequate signals. For example, skin throughout the body (except in the ABTT) is structured for thermal insulation, not thermal transmission. Other prior art means involve invasion of organs, but such organs used as a source of thermal information are not structured for delivering thermal signals, being structured for hearing (ear thermometer), breathing (nasal thermometers), ingestion (oral and esophageal thermometers), and excretion (rectal and bladder thermometers). All of the aforementioned sites contain components and/or contents that impede measurements. Limitations of the prior art prevent adequately answering a simple question: "Does an individual (human or animal) have fever?" as one site indicates normothermia and another simultaneously indicates fever. Even children in intensive care are not spared, with practitioners pleading: "Can there be a standard for temperature measurement . . . ?"

Applicant examined tissues from a physics perspective, shifting from seeing tissues solely as matter to viewing tissues, macro- and microscopically, as components of thermodynamic systems. Applicant searched for low thermoconductivity tissues, viewing insulation as an indicator of a conductor of thermal energy within the cranium. This formerly hypothetical thermal conductor would require a pathway encircled by fat, the lowest thermoconductivity tissue at 0.00004 Kcal/(s·N·C). Dissections revealed the orbital fat pad to be uniquely configured as an insulated thermal tunnel, surrounding the superior ophthalmic vein (SOV) (e.g., see FIGS. 30-34) as it courses from the supero or superior medial orbit (SMO) to join the cavernous sinus (CS) (e.g., see FIGS. 31, 35, and 39), thereby enabling insulated intracranial thermal transfer without dissipation to surrounding tissues. The heretofore unappreciated fat-lined thermal conduit was coined ABTT, and the thermodynamic function of the tunnel (and of the SOV) was suggested by its fat encasement, valveless construction of the vein, transverse course of blood toward the brain (rather than flowing towards the heart), slow moving deoxygenated blood, and lack of arterial counterpart.

The CS (e.g., see FIGS. 31, 34-36, and 39) receives flow from the SOV and cerebral veins (mainly superficial middle cerebral vein draining brain cortex) (e.g., see FIGS. 36 and 37); interfaces with internal carotid arteries (ICA) (carrying blood at core temperature) (e.g., see FIGS. 31, 33-36, and 38); and is separated by a thin dura mater from the temporal lobe (e.g., see FIGS. 33 and 37). FIG. 38 identifies vascular components, which were identified by the Applicant as a previously unappreciated triunal thermodynamic information system. CS-hypothalamus venous networks were identified as conduits for hormone delivery; and the present disclosure recognized these conduits completing a thermal continuum involving hypothalamus, brain cortex, CS, Intracranial Arteries (ICA), and SOV, which contain information and codes which were identified and deciphered by the apparatus and methods of the present disclosure.

Cerebral venous blood (e.g., see FIGS. 36 and 37), which represents cerebral heat production draining to the CS, provides the encrypted brain thermal message, which is decoded and measured by the inventions of the present disclosure. The SOV (within the ABTT) terminates directly underneath skin with specialized thermoconductive histology or morphology that allows surface detection of this thermal message from the brain. In contrast to skin over the ABTT, the body is covered by low thermoconductivity layers comprised of thick and variable dermis (labelled D in FIGS. 30-56) [conductivity of 0.00009 Kcal/(s·N·C)] and subcutaneous (SC) fat (which has the thermoconductivity of oak), exemplified herein by specimens from FH (e.g., see FIGS. 40-42), axilla (e.g., see FIG. 43) and neck (e.g., see FIG. 44). This "thermal insulatory wall," which has been the site of measurements in the prior art, prevents skin measurement of brain (or core) temperature. Further, correction factors are not feasible due to variations (see Table 1) in insulatory layers among individuals, variations of fat according to location on same individuals, and variations of fat over time. In sharp contrast, unique high-thermoconductivity skin overlies the ABTT (between eyebrow and eye) and the eyelid area. Specimens show that ABTT skin is fat-free and has the thinnest dermis (e.g., see FIG. 45). Combined atypical absence of fat (at ABTT surface) with atypical presence of fat (lining ABTT) creates a fat architecture and brain-surface thermal pathway with consistent and optimal thermal codes associated with brain thermal transfer and emission, that are captured and decoded by inventions of the present disclosure.

Table 1 provides measurements of the thickness of fat and dermis in the axillary (armpit), neck, forehead, and the skin adjacent to, over, or on the ABTT terminus. The measurements were from dissections performed on cadavers fixed in 4% formaldehyde. Fragments of skin and underlying tissue from the SMO and eyelid, forehead, neck, and axilla, were embedded in paraffin, sectioned, and stained with HE (hematoxylin and eosin stain) and Masson's trichrome. Dissection was performed to expose the anatomy underneath the SMO and its continuity to the brain. Photomicrographs were obtained and histomorphometry performed.

The results show that the axillary, neck, and forehead had palisades of fat and thick dermis, both of variable thickness (measured in micrometers in Table 1). In contrast, SMO and eyelid skin over the ABTT of all cadavers showed no fat and a commonly thin dermis. Gross anatomic dissection confirmed that this thin, fat-free skin was directly over the aforementioned brain thermal tunnel, which is consistent with thermograph documentation that infrared radiation from this region exceeds that of all other sites on the face and forehead, and the remainder of a human body.

All sites other than the SMO and superior medial eyelid used for surface thermometry must overcome a thick insulatory wall, including fat with the thermal conductivity comparable to oak at 0.00004 Kcal/(s·N·C). The thicknesses shown herein accounts in large part for differences and variability in temperature found among non-SMO surface sites, e.g., the axillary, forehead, and neck, including corresponding forehead sites on different cadavers. Application of an offset to adjust for the insulating nature of fat and dermis is complicated by variations in insulatory layers among individuals, among sites on the same individual, and over time at the same site on the same individual. The differences and inconsistencies due to this variable thermal wall are critical not only for quality patient care, but also for documentation and adherence to monitoring guidelines and requirements (e.g., Surgical Care Improvement Program or SCIP) in different perioperative locations (e.g., operating room, Intensive Care Unit or ICU).

Exemplary Medical Devices

The medical devices disclosed herein may include a modular configuration, including an electrically isolated microprocessor based system, which may be described as an Interface Module System (ISM), which interfaces with a sensor and a computing device, such as an external computer, tablet, cell phone, watch, eyeglasses, or the like, with the ISM providing signals to a second module that includes a personal computer (e.g., a computer with a Windows operating system; a computer with a Macintosh operating system; a computer with a Linux operating system, a computer with Android operating system, any electronic device with computing capabilities, and the like). The personal computer hosts software configured to analyze the signals provided by the sensor to determine a condition of a biological activity, such as brain function, illness, organ function, etc.

Description of an Exemplary ABTT Monitor System

An exemplary embodiment ABTT monitoring system 8000 is shown in FIG. 1. Though the term ABTT monitoring system is used throughout, the ABTT monitoring system is for measuring skin temperature, with particular value on measuring skin temperature at a skin location at the ABTT terminus, with said skin temperature uniquely representing the internal temperature of the body (and of the brain), as described herein. Thus, a more complete name for system 8000 is Brain Thermal Tunnel Skin Temperature Monitor, which, for the sake of convenience, is described as ABTT (Abreu Brain Thermal Tunnel) monitoring system 8000 or Skin Temperature Monitoring (STM) system 8000. ABTT monitoring system 8000 is configured to include at least one sensor, a display, transitory and non-transitory memory, and appropriately configured processes to operate ABTT monitoring system 8000 to monitor and record at least one biological parameter, which may include heart rate, blood pressure, oxygen, temperature, and concentration of molecules such as glucose, cholesterol, and the like. As described further herein, ABTT monitoring system 8000 is configured to provide continuous monitoring and non-continuous or spot-check monitoring one or more biological parameters for clinical use, e.g., medical office, clinic, medical laboratory, urgent care, emergency room, hospital, etc.; mobile use, e.g., ambulance, fire rescue vehicles, emergency and non-emergency medical flights, Emergency Medical Technicians (EMT's), etc.; office and factory, including nurses offices, First Responders having appropriate training, etc.; home use; and other uses where monitoring of biological parameters is beneficial, such as laboratories, and in academic environments. The list of uses presented herein is exemplary. The applicability of ABTT monitoring system 8000, or a system having features similar to ABTT monitoring system 8000, in any particular environment is determined by the need to monitor biological parameters. Thus, Applicant anticipates that a system having the features of ABTT monitoring system 8000 may be used in outer space, e.g., on a space station or in a vehicle intended for extraterrestrial travel; on and under water, e.g., in submarines, ocean-going vessels of all types, etc.; and in other environments where people travel, work, and live. Of course, the system may require modifications to operate in one or more of the aforementioned environments, but such modifications should be achievable in view of the present disclosure.

ABTT monitoring system 8000 may be configured to be an electrically isolated microprocessor-based interface providing temperature readings from the attached thermistor temperature sensor to an internal or external controller. Many aspects of the disclosure are described in terms of sequences of actions to be performed by elements of a computer system or other hardware capable of executing programmed instructions, for example, a general-purpose computer, special purpose computer, workstation, or other programmable data process apparatus. It will be recognized that in each of the embodiments, the various actions could be performed by specialized circuits (e.g., discrete logic gates interconnected to perform a specialized function), by program instructions (software), such as program modules, being executed by one or more processors (e.g., one or more microprocessors, a central processing unit (CPU) and/or application specific integrated circuit), or by a combination of both. For example, embodiments can be implemented in hardware, software, firmware, microcode, or any combination thereof. The instructions can be program code or code segments that perform necessary tasks and can be stored in a non-transitory machine-readable medium such as a storage medium or other storage(s). A code segment may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents.

The non-transitory machine-readable medium can additionally be considered to be embodied within any tangible form of computer readable carrier, such as solid-state memory, magnetic disk, and optical disk containing an appropriate set of computer instructions, such as program modules, and data structures that would cause a processor to carry out the techniques described herein. A computer-readable medium may include the following: an electrical connection having one or more wires, magnetic disk storage, magnetic cassettes, magnetic tape or other magnetic storage devices, a portable computer diskette, a random access memory (RAM), a read-only memory (ROM), an erasable programmable read-only memory (e.g., EPROM, EEPROM, or Flash memory), or any other tangible medium capable of storing information. It should be noted that the system of the present disclosure is illustrated and discussed herein as having various modules and units that perform particular functions.

It should be understood that these modules and units are merely described based on their function for clarity purposes, and do not necessarily represent specific hardware or software. In this regard, these modules, units and other components may be hardware and/or software implemented to substantially perform their particular functions explained herein. The various functions of the different components can be combined or segregated as hardware and/or software modules in any manner, and can be useful separately or in combination. Input/output or I/O devices or user interfaces including, but not limited to, keyboards, displays, pointing devices, and the like can be coupled to the system either directly or through intervening I/O controllers. Thus, the various aspects of the disclosure may be embodied in many different forms, and all such forms are contemplated to be within the scope of the disclosure.

Figure 2:
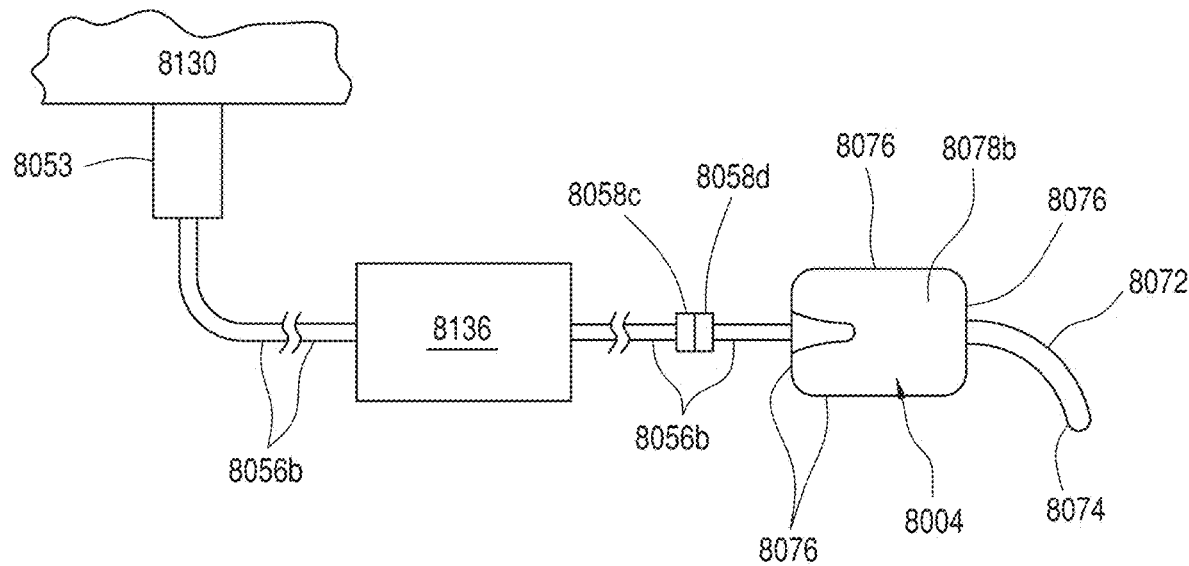
FIG. 2 is a view of an interface module, a temperature sensor, and connection elements compatible with the ABTT monitoring system of FIG. 1 or an external computer, in accordance with a first exemplary embodiment of the present disclosure.
Figure 3:
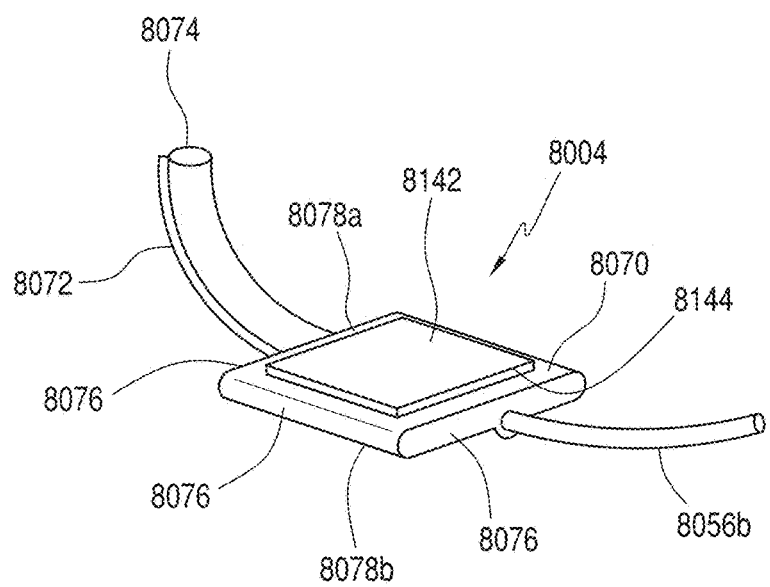
FIG. 3 is a perspective view of the temperature sensor of FIG. 2.
Figure 4:
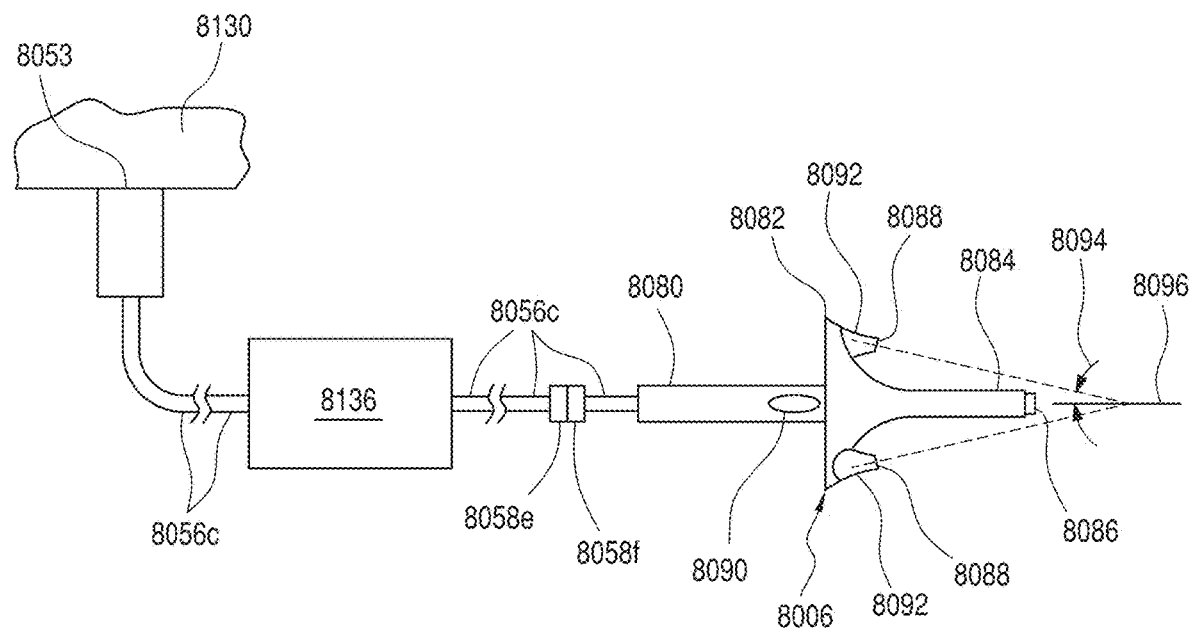
FIG. 4 is a view of an interface module, a temperature sensor, and connection elements compatible with the ABTT monitoring system of FIG. 1 or an external computer, in accordance with a second exemplary embodiment of the present disclosure.
Figure 5:
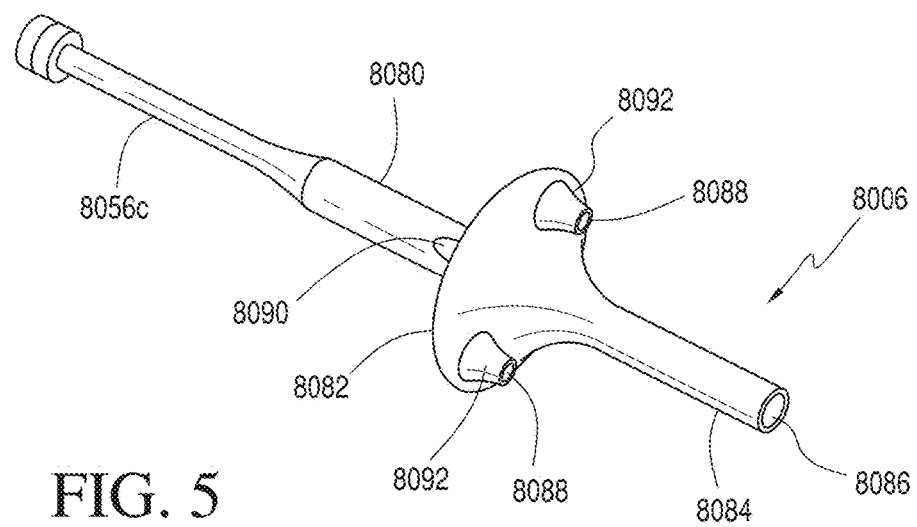
FIG. 5 is a perspective view of the temperature sensor of FIG. 4.
Figure 6:
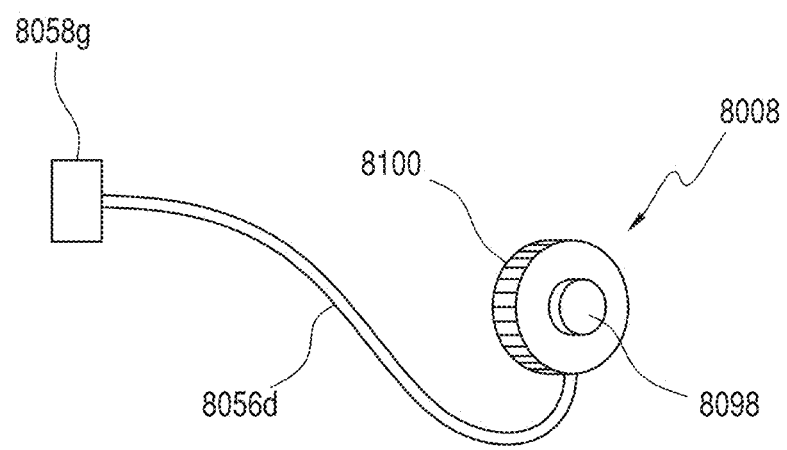
FIG. 6 is a perspective view of a temperature sensor in accordance with a third exemplary embodiment of the present disclosure that is compatible with the ABTT monitoring system of FIG. 1.

By way of illustration, but not of limitation, ABTT monitoring system 8000 is a single channel electronic instrument intended principally for sensing and monitoring patient temperature. However, it should be understood that a multi-channel system with multiple sensors and detectors for monitoring various biological parameters is within the scope of the disclosure. ABTT monitoring system 8000 includes a temperature sensor, such as the temperature sensors shown in FIGS. 1-5. The temperature sensors may be entirely disposable to reduce the need for sterilizing sensitive equipment prior to reuse, may include removable portions that are disposable, or may be configured to be reusable and sterilized without damage. A temperature sensor or probe 8002 shown in FIG. 1 in accordance with an exemplary embodiment of the present disclosure is configured in a rod or pen-like shape with a relatively narrow tip to contact the ABTT facial terminus easily. FIGS. 2 and 3 show a temperature sensor 8004 in accordance with another exemplary embodiment of the present disclosure. Temperature sensor 8004 is configured to have a supporting portion and/or adhesive surface to be positioned on a forehead and retained in position with a suitable adhesive, surgical tape, a head band, hat, or other retention device such that the sensor portion, described in more detail herein, is positioned on the skin adjacent to, over, or on the ABTT; i.e., the ABTT terminus. FIGS. 4 and 5 show yet another exemplary embodiment temperature sensor 8006 that is similar to the pen temperature sensor of FIG. 1 with additional features, described further herein. FIG. 6 shows a further exemplary embodiment temperature sensor 8008 that is suitable for manual use or may be incorporated into another item, such as a wearable frame similar to the frame for eyeglasses, a monocle, or other items intended to be positioned on or near the face that can provide support for temperature sensor 8008. Temperature sensor 8008 is described in more detail further herein. While any one of these temperature sensors may be considered to be disposable, the configuration of FIGS. 2 and 3 is specifically configured for one-time, one-patient, or disposable use after a period from minutes to days, and even weeks. Furthermore, any temperature sensor described herein may alternatively be described as a Skin Temperature Probe (STP). Thus, temperature sensors 8002, 8004, 8006, 8008, any other temperature sensor referenced herein, or any other temperature sensor, may also be described as an STP, for example, STP 8002, 8004, 8006, and 8008. It should be understood that any sensor or detector, including, but not limited to, blood pressure and pressure sensors, heart rate, oximetry and oxygen, carbon dioxide, and any other blood gas, and analyses of blood, such as glucose, cholesterol and the like, can be used in place of sensors 8002, 8004, 8006, and 8008.

Returning to FIG. 1, ABTT monitoring system 8000 may include a display unit 8001 that includes multiple features to enable efficient and effective use in a variety of environments. ABTT monitoring system 3000 can monitor various biological parameters simultaneously and may include, by not by way of limitation, displays for temperature, hear rate, EKG, respiratory rate, blood pressure, oxygen level, and oxygen saturation. For example, ABTT monitoring system 8000 may include one or more temperature displays and gauges, such as an analog dial or circular gauge or display 8010, a bar-type gauge or display 8012, and a digital display or output 8014. Each of the displays may include high and low limit alarm points that can be set and displayed on at least dial display 8010 and bar display 8012.

Analog dial gauge or display 8010 includes a pointer 8020 to indicate the temperature received from an associated temperature sensor by pointing to a value near a periphery of the gauge or display. The display may include a single unit of measure, such as Celsius, or may present more than one unit of measure. System display 8001 may include a "units" switch 8036 to select which unit(s) is or are displayed on dial gauge or display 8010. As shown in FIG. 1, high and low limits may be established that may be in the form of a high limit pointer 8016 and a low limit point 8018, though such can be in other forms, depending on the type of display, such as tic marks. To enhance the ability to identify each pointer, high limit pointer 8016 may be in a first color, such as red or orange, low limit pointer 8018 may be in a second color, such as blue, and temperature pointer 8020 may be in a third color, which includes black and white.

To move the positions of high limit pointer 8016 and low limit point 8018, system display 8001 may include dedicated high and low limit set point switches, such as high limit set switch 8022 and low limit set switch 8024. Positioning of high limit pointer 8016 and low limit pointer 8018 may be accomplished by move the associated high limit set switch 8022 or the low limit set switch 8024 into the "−" or "+" positions shown in FIG. 1, with increments typically being predetermined, for example, 0.1 degree Celsius. Other methods of establishing the position of high limit pointer 8016 and low limit pointer 8018 may be used. For example, the positions of the pointers may be set by an external computer, tablet, cell phone, watch, eyeglasses, etc., via a USB port 8026 or by a Wi-Fi connection, which may be turned on or off via a Wi-Fi switch 8028. ABTT system display 8001 may also be adjusted by a mouse directly connected to ABTT system display 8001, either via port 8026, or wirelessly.

ABTT system display 8001 may further include an up arrow button 8146, a down arrow button 8148, a left arrow button 8150, a right arrow button 8152, and an enter button 8154. As described further herein, these buttons may assist in accessing expanded features of ABTT monitoring system 8000.

Similar to dial gauge or display 8010, bar gauge 8012 may include a high temperature limit indicator 8030, a low limit indicator 8032, and a temperature indicator 8034. Simultaneous displays of temperature in more than one type of unit, such as degrees Celsius and degrees Fahrenheit, may be provided. Alternatively, a single display of units may be provided, and units switch 8036 may be used to select the type of units displayed. As with dial gauge or display 8010, high temperature limit indicator 8030 may be in a first color, low limit indicator 8032 may be in a second color, and temperature 8034 may be in a third color, with the term color or temperature color including black and white. Temperature indicator 8034 may be associated with a bar portion 8038 that presents in a color different from an area 8040 adjacent bar portion 8038.

Digital display 8014 may also be configured to present temperature in more than one unit, or may present a single unit at a time that may be selected by units switch 8036. In order to present high and low limits, digital display 8014 may include flashing lights, changing colors, separate displayed indicators, and the like. Display 8014 also may include specialized LED (in the physical unit) or software-based specialized flashing light or lights that turn on and that are displayed on the display, and that warn about imminent danger or to guide a procedure.

In addition to the aforementioned controls and gauges or displays, ABTT system display 8001 may include elements. For example, system display 8001 may include an alarm display 8042 that flashes or changes colors when a high or low limit is reached, or when other predetermined conditions exist, such as a system fault or failure to receive a temperature signal. System display 8001 may also include an ON/OFF control or switch 8044, an interval portion 8046 with controls or switches and a display to set and display a temperature measurement interval or length of time, a START switch or control 8048 to control the start of a measurement interval or length of time, which may also act to control stop of the measurement interval or length of time, a RESET button, switch, or control 8050 to clear all controls or restore them to an unset or nominal position, and a speaker 8052 for providing audible alarms or other notifications.

System display 8001 may provide error conditions on an existing display portion, or may include a dedicated display portion. FIG. 7-10 show exemplary error conditions that may be displayed on, for example, digital display 8014.

Figure 7:
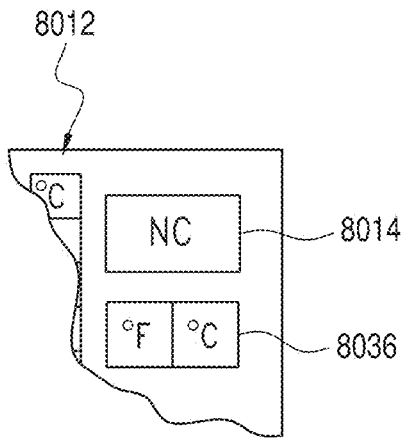
FIG. 7 is a view of a portion of the ABTT system display showing a first exemplary error condition of the ABTT monitoring system of FIG. 1.
Figure 8:
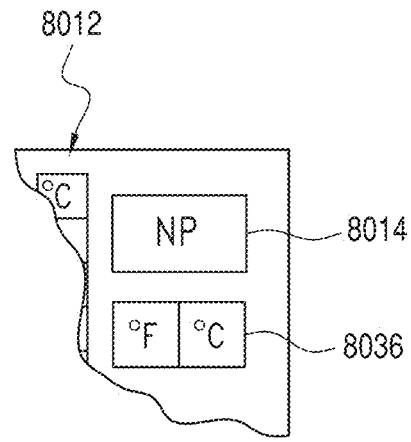
FIG. 8 is a view of a portion of the ABTT system display showing a second exemplary error condition of the ABTT monitoring system of FIG. 1.

FIG. 7 shows an indication "NC," which may be an indicator that a USB cable to an associated computer, tablet, or other device is disconnected. Note that this indication may be transitory since a computer, tablet, or external device is not required for ABTT monitoring system 8000 to function. However, an external device or an internal controller or processor and memory may be valuable to provide additional analysis capability of measurement information collected by an ABTT monitoring system 8000 temperature sensor. FIG. 8

FIG. 8 shows an indication "NP," which may be an indicator that a temperature sensor, such as temperature sensor 8002, 8004, 8006, or 8008, has become disconnected, is shorted, or has another malfunction.

Figure 9:
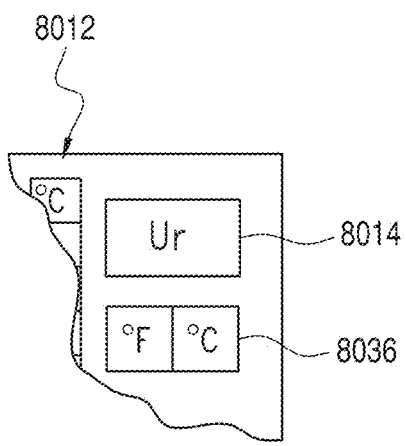
FIG. 9 is a view of a portion of the ABTT system display showing a third exemplary error condition of the ABTT monitoring system of FIG. 1.

FIG. 9 shows an indication "Ur," which may be an indication that a temperature probe is reading less than a predetermined lower limit, for example, 10 degrees Celsius, which may be an indication of a bad connection, a bad sensor, or extreme cold. Though not shown, display 8014 may also show an indication of "Or," which may be an indication that a temperature range is over a predetermined value, for example 45 degrees Celsius. Such an indication may be reached if there is moisture in the system, including the temperature sensor, an associated cable, or ABTT system display 8001, if there is an extreme ambient temperature condition, or if there is an extreme patient temperature. In the case of a malfunction, replacement of the cable or sensor, or other corrective action may be warranted.

Figure 10:
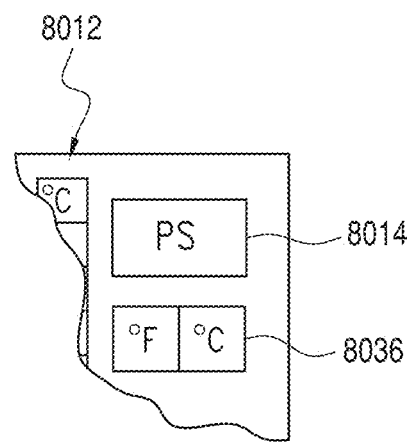
FIG. 10 is a view of a portion of the ABTT system display showing a fourth exemplary error condition of the ABTT monitoring system of FIG. 1.

FIG. 10 shows an indication of "PS," which means that an associated temperature sensor or probe may be shorted or otherwise damaged. Accordingly, the operator of ABTT monitoring system 8000 should replace the temperature sensor.

In any of the aforementioned condition, alarm tones or signals, including spoken alerts or warnings, can be enabled to warn of these conditions as well as operator set warning levels for patient temperature.

Returning to FIGS. 1-6, temperature sensors 8002, 8004, 8006, and 8008 are connected by a connector 8053 to ABTT system display 8001 by way of a port, connector, or connection 8054 located on ABTT system display 8001. However, it should be understood that wireless connection to a remote device is also within the scope of the disclosure. Maximum current available at port, connector, or connection 8054 in an exemplary embodiment is less than 500 micro amperes (0.000500). Alternatively, a temperature sensor may be connected wirelessly to ABTT system display 8001. Each temperature sensor may be connected by a cable or wire assembly 8056*a-d*, each of which may be identical, or may be different, depending on the needs of the individual temperature sensor. Because the temperature sensor may be disposable, cable connectors 8058*a-f* may be provided to define the disposable portion of a temperature sensor, or for other purposes, including ease of changing temperature sensors, re-routing of cables, etc.

Temperature sensor 8002 is designed for "spot" or instantaneous readings of the SMO site, as well as temperature measurements on any skin surface. Temperature sensor 8002 is configured to be disposable. However, temperature sensor 8002 may also be configured to be sterilized at high temperature or in a liquid such as alcohol. Temperature sensor 8002 includes a generally or substantially longitudinal body 8060 that includes a tapered portion 8062 and a main body or handle portion 8064. Cable 8056*a* enters and is physically retained in main body 8064 at a first end of temperature sensor 8002. In the exemplary embodiment of FIG. 1, a thermistor 8066 is positioned at a tip 8068 of tapered portion 2062 that is located at a second end of temperature sensor that is generally at the opposite end of temperature sensor 8002 from the first end, and thus opposite the entry point of cable 8056*a* into main body 8064. Because the diameter of the ABTT, which is approximately circular and has a rod or wand-type structure, is approximately 3-9 millimeters, in the exemplary embodiment thermistor 8066 is 5 millimeters in diameter or less, and in an exemplary embodiment, is 3 millimeters in diameter or less. In a further exemplary embodiment, thermistor 3066 has a convex surface for apposition with the skin at the ABTT tunnel terminus, which typically has a concave configuration. Additionally, to provide a frequency response comparable to the frequency response of the ABTT, in an exemplary embodiment thermistor 8066 has a frequency response of at least 20 Hz. However, in situations where precise tracking of temperature from the ABTT is unnecessary, such as when an average temperature is the measure sought, in an exemplary embodiment, the frequency response can be less than 20 Hz. In another exemplary embodiment, the frequency response may be 10 Hz or less, and more preferably, 1 Hz or less.

Temperature sensor or probe 8004, shown in FIGS. 2 and 3, is configured to be a low-cost disposable probe that may be used for continuous temperature monitoring at the SMO and eyelid site during surgery, critical care, and recovery, and for other situations requiring continuous temperature monitoring. Temperature sensor 8004 includes a plate-like or extended flat portion 8070, a curved finger portion 8072, and a thermistor 8074. In the exemplary embodiment of FIG. 3, cable 8056*b* enters flat portion 8070 from an edge or side 8076 of flat portion 8070, and curved finger portion 8072 extends from an opposite edge or side 8076 from the edge or side where cable 8056*b* enters flat portion 8070. Thermistor 8074, which may be identical to thermistor 8066, is positioned at an end of finger 8072 that is opposite the end of finger 8072 that extends from flat portion 8070. Flat portion 8070 further includes opposing face portions 8078*a* and 8078*b*. Finger 8072 may be flexible and movable into a plurality of positions to provide optimal contact between face 8078*a* and a forehead of a patient or subject and between thermistor 8074 and a subject's ABTT. Because of the large cross-sectional area of face 8078, and the natural oils in the forehead of many people, temperature sensor 8004 may remain in place for a length of time sufficient to measure temperature. Alternatively, temperature sensor may be retained by adhesive, surgical tape, or manual retention, such as by a hand or finger or an appliance, which may include headbands and hats.

Temperature sensor 8006, shown in FIGS. 4 and 5, includes a main body or handle 8080, a shield 8082, a probe 8084, a thermistor 8086 positioned on a tip or end portion of probe 8084 that is generally opposite the end of temperature sensor 8006 where cable 8056*c* enters main body or handle 8080, one or more LED's 8088, and an ON/OFF switch 8090 to control LED's 8088. As with temperature sensor 8002, temperature sensor 8006 is designed for "spot" or instantaneous readings of the SMO or eyelid site, as well as temperature measurements on any skin surface. Temperature sensor 8006 is configured to be disposable. However, temperature sensor 8006 may also be configured to be sterilized at high temperature or in a liquid such as alcohol.

LED's 8088 may be positioned in a protrusion 8092 extending from shield 8082 in a direction that is toward probe 8084. Each protrusion 8092 may be formed to direct the light output from LED's 8088 at an angle 8094 to a longitudinal axis 8096 of temperature sensor 8006 such that the light from LED's 8088 is configured to be directed slightly in front of thermistor 8086. The benefit of this configuration is that the light from LED's 8088 is configured to illuminate the ABTT area, enabling a user or operator to find the ABTT more easily in all ambient light conditions.

Temperature sensor 8008 is similar to temperature sensor 8004 in that it is intended for long-term use. Temperature sensor 8008 may be affixed directly to a subject or patient by adhesive or tape, or may be mounted, attached, or positioned to an appliance, such as a frame similar to eyeglass frames, a headband, a hat, or any head-mounted gear, thus holding the thermistor portion of temperature sensor 8008 to a patient or subject ABTT, though temperature sensor 8008 is suitable for measuring temperature in multiple locations on the body. Temperature sensor 8008 includes a thermistor 8098, which may be similar to the thermistors previously described herein, and an insulated backing pad 8100. Insulated pad 8100 may be attached to a mechanism (not shown) that provides a spring or other preload to keep thermistor 8098 in physical contact with a patient or subject's ABTT.

While the operating environments for temperature sensors are well understood, the following information is provided for guidance. Common components for the temperature sensors include the precision thermistor, and may include medical grade quick recovery polyurethane foam insulation, two layers of a white insulating foam, and adhesive backed structural insulating foam, and a protective sleeve covering the thermistor lead. All temperature sensors may incorporate a protected terminal connector. Thermistor wire leads 8056*a-d* are insulated with an insulating material. The thermistor is protected with an insulating coating. The final structure may be coated with another protective layer).

The support structure for the thermistor used in the sensors of FIGS. 1-6 may be identical, and may include a base of polyurethane, a double thermal barrier of disks, and a conformal coating.

Figure 11:
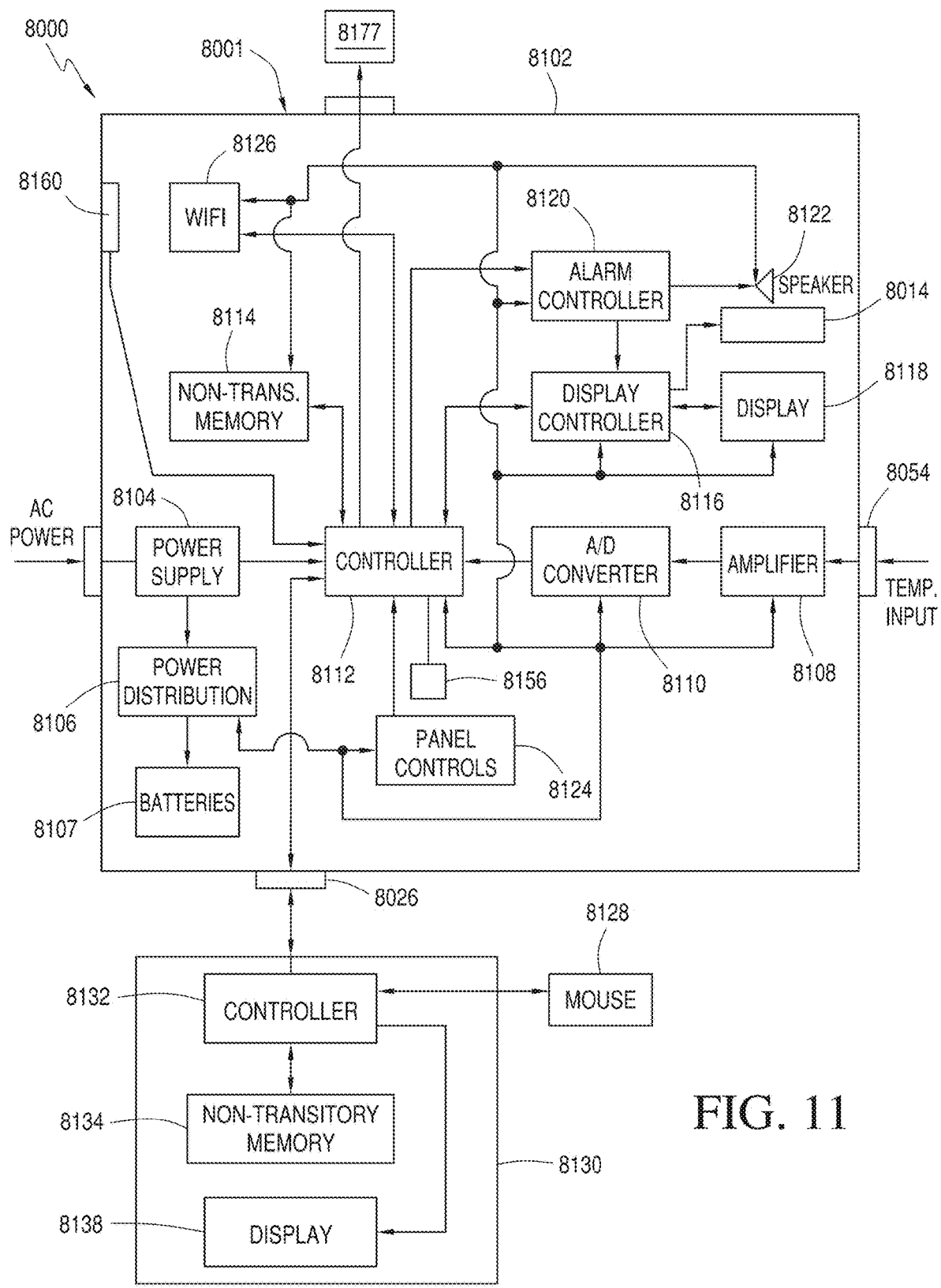
FIG. 11 is a block diagram of various hardware elements, units, and/or subsystems of the ABTT monitoring system of FIG. 1 in accordance with an exemplary embodiment of the present disclosure.

ABTT monitoring system 8000 includes a plurality of hardware elements, units, or subsystems that provide many of the functional capabilities of ABTT monitoring system 8000, an exemplary embodiment of which is shown in FIG. 11. The plurality of hardware elements, units, or subsystems may be at least partially included in a housing, casing, or enclosure 8102 of ABTT system display 8001. As noted from the description provided herein, while the term "ABTT system display" is used because of a primary function of display 8001, ABTT system display 8001 may be described in terms of one of its many other functions. For example, ABTT system display 8001 may also be described as ABTT system controller 8001, ABTT analyzer 8001, or ABTT alarm system 8001.

ABTT monitoring system 8000 may be configured to be an electrically isolated microprocessor-based interface providing temperature readings from the attached thermistor temperature sensor to an internal or external controller. It should be understood that other readings, including blood pressure, heart rate, respiratory rate, oximetry, oxygen, carbon dioxide, concentration of molecules (e.g. glucose), blood components, and the like, that use an electrically isolated microprocessor-based interface are within the scope of the disclosure.

ABTT monitoring system 8000 may derive its power from an external computer. The operating voltage range is between 4.7 volts and 5.3 volts, with a nominal current consumption at 5.0 volts of 190 ma. ABTT monitoring system 8000 may have two different ground separations to provide a power supply with two different isolated DC-to-DC power converters. These two DC-to-DC power converters may have UL recognition per UL 1577. Alternatively, ABTT system display 8001 may include a power supply 8104 that is configured to receive external power, which is typically AC power, and to generate at least one filtered DC power for the elements, units, or subsystems of ABTT system display 8001. Power supply 8104 may include an integral power distribution system, or may supply a separate power distribution system 8106. Power supply 8104 and power distribution system 8106 provide the power required by the various elements, units, or subsystems of ABTT system display 8001. As yet another alternative, ABTT monitoring system 8000 may include batteries 8107 that supply power to power distribution 8106. Because of the moderate power consumption of ABTT monitoring, either four standard AA alkaline or four AA NiMH cells are configured to power the STM for at least 24 hours. Because such power supplies and distribution systems are generally well understood in the art, they will not be described further herein.

Although any biological parameter can be monitored according to this present disclosure, by way of illustrating one particular biological signal being monitored, ABTT system display 8001 receives a signal representing temperature from a temperature sensor via port or connector 8054. To process the signal, ABTT system display 8001 may include an amplifier 8108, an analog-to-digital (A/D) converter 8110, and a system unit controller 8112. Amplifier 8108 receives the signal from the temperature sensor and increases the strength of the signal from the temperature sensor, and may also filter the signal to remove noise. The amplified signal is sent from amplifier 8108 to A/D converter 8110, where the signal is converted to a digital format that is provided to an input of ABTT system unit controller 8112. System unit controller 8112 performs a variety of functions within ABTT system 8000.

ABTT system display 8001 may further include a non-transient memory 8114, a display controller 8116, a display 8118, an alarm controller 8120, a speaker 8122, and a plurality of panel controls 8124.

Once in system unit controller 8112, the digital temperature signal may be stored in non-transitory memory 8114, which may be removable memory, for archival purposes or for later analysis. In an exemplary embodiment, up to approximately 24 hours of data may be stored in non-transitory memory 8114 for later analysis or download to an external computer. The digital temperature signal is also provided to display controller 8116, which may be integral to ABTT system unit controller 8112, or may be a separate controller, as shown in FIG. 11. Display controller 8116 formats the digital signal into a format suitable for display 8118, which presents a display for an operator, patient, medical professional or other user. Display 8118 may include a battery life display 8162 and an ambient temperature display 8164, described further herein. Additionally, display 8118 may be configured with a touch-sensitive screen, which permits operation of ABTT monitoring system 8000 from display 8118. If display 8118 includes a touch-sensitive screen, inputs from the touch-sensitive screen may be transmitted either directly to system unit controller 8112, or may be transmitted to system unit controller 8112 by way of display controller 8116.

Returning to system unit controller 8112, the temperature signal is analyzed to determine whether the received temperature is at or under a predetermined temperature level or at or over a predetermined temperature level. If the temperature is at or above predetermined levels or limits, a signal is transmitted to an alarm controller 8120, which suitably prepares the signal to be output to various devices for alarm-related functions. For example, the signal transmitted to alarm controller may be used to initiate an audible alarm, which may include tones, vocal warnings, etc., that are provided to speaker 8122. Alarm controller 8120 may also provide a suitable signal for display to display controller 8116 or other output, such as alarm display 8042, as well as a wireless signal to a remote device, including, but not limited to, a cell phone, tablet, external computer, watch, eyeglasses, and the like.

Panel controls 8124 may include, among other controls, high limit set switch 8022, low limit set switch 8024, Wi-Fi switch 8028, units switch 8036, ON/OFF switch 8044, set interval switches that are part of set interval portion 8046, and RESET button or switch 8050. The signals from various panel controls are provided to system unit controller 8112, which responds to the signals according to their source, and as described herein. As examples, system unit controller 8112 may receive signals from high limit set switch 8022 used to establish a high temperature limit, which is translated into a position of high limit pointer 8016 and/or high temperature limit indicator 8030, either in system unit controller 8112 or in display controller 8116. The signals received from other panel controls are also suitably processed by ABTT system unit controller 8112 and used to operate the various functions of ABTT monitoring system 8000.

ABTT system display 8001 may further include a Wi-Fi or other near field communication (NFC) device 8126. Wi-Fi device 8126 may be used to communicate with the temperature sensor, with an external computer, tablet, cell phone, watch, eyeglasses, or the like, or another properly enabled device.

USB port 8026 may be used to communicate with one or more external devices, such as a computer mouse 8128, an external computer, tablet, cell phone, watch, eyeglasses, or the like 8130, or an external non-transitory memory, which may be similar to a non-transitory memory 8134 included in external computing device 8130. External computer 8130 includes an external computer controller 8132 for performing various types of analysis on temperature signal data, non-transitory memory 8134, and a computer display 8138. Additionally, external computer 8130 may provide additional functionality to ABTT monitoring system 8000.

Because ABTT monitoring system 8000 includes non-transitory memory 8114 and system unit controller 8112, if the temperature sensor, such as temperature sensor 8002, is disconnected and later reconnected, any set points and limits are configured to remain where last set. If ABTT monitoring system 8000 is shut down and restarted—the set points are configured to default to predetermined or pre-programmed levels, such as 34.0° C. for the low limit and 38° C. for the high limit. As will be described further herein, tones may be used to help establish the position of the temperature sensor. These tones, alert alarms, and other functions of ABTT monitoring system 8000 are stored in non-transitory memory, such as non-transitory memory 8114, or non-transitory memory located in one or more of the controllers of ABTT monitoring system 8000, such as ABTT system unit controller 8112, display controller 8116, or alarm controller 8120. Various functions of ABTT monitoring system 8000 are enabled during startup of ABTT monitoring system 8000.

As described previously herein, the above-description is for an exemplary embodiment of ABTT monitoring system 8000. Additional exemplary features of ABTT monitoring system 8000 are provided in the following paragraphs.

Housing 8102 may be configured to be disinfected using medical alcohol (70% concentration) without damage;

Housing 8102 may be a conventional "off-the-shelf" component or a custom-designed housing. For cost reasons, a conventional off-the-shelf component is preferred.

Housing 8102 may be configured with a detachable IV pole clamp (not shown). The pole clamp may be used to assist in routing the cable for an associated temperature sensor or for other functions.

Housing 8102 may be configured to provide access to four standard AA batteries without disassembly of housing 8102.

The portion of housing 8102 that locates display 8118 is generally considered a front panel 8158.

Front panel 8158 may include input buttons for "Left" (left arrow button 8150), "Right" (right arrow button 8152), "Up" (up arrow button 8146), "Down" (down arrow button 8148), "Enter" (enter button 8154), "Reset" (reset button 8050), and "Power" (ON/OFF switch 8044).

The buttons on front panel 8118 of housing 8102 may be configured as capacitive touch sensors.

ABTT monitoring system 8000 may be configured to include an audible alarm, which is shown as speaker 8052 in an exemplary embodiment of this disclosure.

In an exemplary embodiment, the audible alarm produces tones from 100 Hz to 6200 Hz.

In an exemplary embodiment, the amplitude of audible alarm tones may be at least 60 dB-SPL at 3.0 kHz frequency.

In an exemplary embodiment, ABTT monitoring system 8000 is configured to operate for a minimum of 24 hours on four standard NiMH AA batteries or cells (not shown) or on four standard Alkaline AA batteries or cells.

In an exemplary embodiment, ABTT monitoring system 8000 is configured not to be damaged by the insertion of NiCad AA batteries or cells; i.e., ABTT monitoring system is configured to operate without damage on NiCad AA batteries or cells and installing such does not require damaging or disassembling ABTT monitoring system 8000. More specifically, housing 8102 includes access for permit the installation of four AA batteries (not shown). Such access may be through a fastener-free panel or may be through a panel secured by one or more fasteners the principal purpose of which is to provide access to a battery bay (not shown).

In an exemplary embodiment, ABTT monitoring system 8000 is configured to be powered by an off-the-shelf medical rated power adapter.

As previously described herein, ABTT monitoring system 8000 is configured to interface with an STP or temperature sensor, such as those described herein, or any other type of sensor.

In an exemplary embodiment, a temperature sensor of ABTT monitoring system 8000, such as temperature sensors 8002, 8004, 8006, or 8008, is configured with a conventional 1OK31AM thermistor.

In an exemplary embodiment, ABTT monitoring system 8000 is configured to allow no more than 2 μA of current to flow through the temperature sensor or STP over the normal temperature sensor or STP sensing range.

Safety

In an exemplary embodiment, ABTT monitoring system 8000 is configured to use low voltage and low current. Furthermore, contact between a patient or subject and voltage and current is prevented by design. Lastly, ABTT monitoring system 8000 is configured for low electromagnetic interference susceptibility.

Temperature Sensor

In an exemplary embodiment, ABTT monitoring system 8000 is configured with an ambient temperature sensor 8160. In an exemplary embodiment, ambient temperature sensor 8160 is configured to have a digital output. Alternatively, if ambient temperature sensor 8160 has an analog output, the output may be input to an A/D converter, such as A/D converter 8110. If an ambient temperature sensor is provided, in an exemplary embodiment ambient temperature sensor 8160 is configured with a resolution of at least 1.0 degree Celsius.

In an exemplary embodiment, ABTT system display 8001 and display 8118 is configured to have dimensions such that temperatures presented on display 8118 are of a size that a person with average eyesight can read the displayed temperature from 1 meter away. In another embodiment, ABTT system display 8001 is configured to conform to the readability requirements of ASTM E1112-00 section 4.4.2.2. In exemplary embodiments, display 8118 is configured with sufficient resolution to display a temperature graph with the desired temperature resolution.

In an exemplary embodiment, display 8118 is configured to have sufficient brightness to be visible in normal office, laboratory, and clinical environments, excepting direct illumination by high-intensity operating room lights or similar lights. To improve visibility in the presence of high-brightness or intensity lighting, housing 8102 may be configured to include a shield to reduce direct illumination of display 8118 by lights positioned vertically higher than ABTT monitoring system 8000.

In an exemplary embodiment, display 8118 is configured to be visible in darkened room conditions. Thus, in some embodiments display 8118 may include backlighting, side lighting, etc., to provide sufficient illumination to read display 8118. Included in such an embodiment may be appropriate lighting for bar graph or gauge 8012 and digital display 8014, if bar graph 8012 or digital display 8014 is provided separately from display 8118. For convenience of explanation, lighting may be described as "backlighting," but in the context of this application, backlighting refers to any apparatus used to illuminate the displays described herein.

In an exemplary embodiment, display 8118 is configured to allow control of display intensity.

In an exemplary embodiment, ABTT monitoring system 8000 includes non-volatile memory 8114 for storage of temperature and other system functions. Non-volatile memory 8114 may include sufficient data storage to store at least 24 hours of 1 to 15 second temperature sensor or STP temperature readings, display 8118 characteristics, and operational parameters, as required. Furthermore, in an exemplary embodiment, non-volatile memory is configured to provide sufficient read/write cycles to allow continuous operation for at least 10 years, and is configured to provide at least one megabyte of memory more than is required by initial program implementation. Given the current state-of-the-art in non-volatile memory, the read/write speeds and space needed for ABTT monitoring system 8000 are easily met by a number of conventional technologies at a price that is effectively free in consideration of the overall anticipated cost of ABTT monitoring system 8000. Thus, a memory margin of one megabyte may easily become one gigabyte with negligible cost increase.

In an exemplary embodiment, ABTT monitoring system 8000 includes an interface that is electronically isolated for use in the field and while connected to a patient with a temperature sensor or STP. The interface may be incorporated as part of amplifier 8108, as a part of ISM 8136, as part of another component, or as an entirely separate component.

In the exemplary embodiment, ABTT monitoring system 8000 includes at least one controller, such as system unit controller 8112. System unit controller 8112 is typically a commonly available conventional controller, though it may be a custom-made controller. It is preferable that all controllers used in conjunction with ABTT monitoring system 8000 be supported by readily available cost effective development tools. It is also preferable that system unit controller 8112 have either integral or separate non-volatile memory, such as non-volatile memory 8114. Non-volatile memory 8114 may be flash based program memory or other non-volatile memories.

In an exemplary embodiment, system unit controller 8112 may be reprogrammable, either via USB port 8026, or by a connector 8156 specifically for that purpose within housing 8102. Alternatively, connector 8156 may be accessible from an external location on housing 8102, for example, on a back panel of housing 8102 that is opposite front panel 8158. In an exemplary embodiment, program memory of system unit controller 8112 is sized such that no more than approximately 50% of program memory is used by the initial software implementation. Thus, program memory is configured to have capacity for updates and upgrades, enabling each ABTT monitoring system 8000 to have a relatively long useful life.

In an exemplary embodiment, ABTT monitoring system 8000 includes a watchdog timer (not shown). The watchdog timer may be stand alone or part of system unit controller 8112. In a typical embodiment, the watchdog timer is configured to be active all the time or full time. The watchdog timer is useful in associating temperature readings with particular times, which is useful in analyzing the temperature readings.

Interface System Module

ABTT monitoring system 8000 may include an Interface System Module (ISM) 8136, shown in at least FIGS. 2 and 4. Interface module 8136 may powered by −5V from an external computer. Interface module 8136 may draw approximately 175 mA while in operation or functioning. The chassis or housing of ISM 8136 may be grounded to a building electrical earth ground by way of the connection of external power to power supply 8104. This earth ground is carried to interface module 8136 by cable 8056*b* or 8056*c* in the "drain wire" and foil shield. If the external computer is powered by a two prong power plug, i.e., there is no earth ground, the foil shield in cable 8056*b* or 8056*c* is tied to the housing of an external computer controller 8130. A metal shield of port 8053 is totally isolated from the internal circuitry.

The circuit in interface module 8136 is double isolated from the power from an external computer or other external controller 8130 using approved power and port signal isolation circuitry. The earth ground stops at the shield of the port connector. Interface module 8136 is covered by a suitable plastic that prevents any direct connection to earth ground to anyone touching or holding the case. ISM 8136 provides much or all of the functionality of ABTT monitoring system 8000 when used in conjunction with an external computer, such as external computer 8130. Features of an exemplary embodiment of ISM 8136 may include:

Single chip port to asynchronous serial data transfer interface;
Fully integrated 1024 bit EEPROM storing device descriptors and CBUS I/O configuration;
Fully integrated port termination resistors;
Fully integrated clock generation and clock output selection;
128 byte receive buffer and 256 byte transmit buffer to allow for high data throughout;
Chip-ID feature;
Configurable CBUS I/O pins;
Transmit and receive LED drive signals;
Integrated level converter for port I/O;
Integrated +3.3V level converter for port I/O;
Fully integrated AVCC supply filtering—no external filtering required;
UART signal inversion option;
+3.3V (using external oscillator) to +5.25V (internal oscillator) Single Supply Operation;
Low operating and port suspended current;
Low bandwidth consumption;
UHC/OHCI/EHCI host controller compatible;
Post 2.0 Full Speed compatible;
−40° C. to 85° C. extended operating temperature range;
Available in compact lead-free 28 Pin SSOP and QFN-32 packages (both RoHS compliant);
Port Module Interface to RS232/RS422/RS485 Converters;
Cellular and Cordless phone data transfer cables and interfaces;
Interfacing MCU/PLD/FPGA based designs to port;
Audio and Low Bandwidth Video data transfer;
PDA to port data transfer;
MP3 Player Interface; Flash Card Reader and Writer;
Digital Camera Interface;
Hardware Modems;
Bar Code Readers;
Software and Hardware Encryption Dongles; and
Linear power regulators (LDO)—LT 1762—150 mA, Low Noise Micro-power Regulators.

Control and Software Elements:

While ABTT monitoring system 8000 may be configured with circuits that perform temperature analysis, software and/or firmware provide greater flexibility for operation of system 8000. Exemplary embodiments of the software are configured to perform an array of functions, as described herein. For simplicity, the software for ABTT monitoring system 8000 is described simply as system 8000 software.

In an exemplary embodiment, system 8000 software is configured to use watchdog timer.

In most exemplary embodiments, system 8000 software is configured to be implemented predominantly in a commonly used high level language.

In an exemplary embodiment, system 8000 software is configured to have a program setup mode. The program setup mode is configured to be entered on command, which may be from ABTT system display 8001, or from an external controller or computer, such as external computer 8130. The setup mode allows an option for selecting units, such as Celsius and Fahrenheit, high temperature and low temperature limits, and other adjustable parameters of ABTT monitoring system 8000, as opposed to physical switches and buttons on front panel 8158 of housing 8102. The program setup mode may be exited at any point with an appropriate command or command key, such as EXIT or END.

In an exemplary embodiment, the low temperature alarm level is adjustable between 29.0° C. and 38.0° C. in 0.1 degree increments. Also in an exemplary embodiment, the low temperature alarm level defaults to 34° C.

In an exemplary embodiment, the system 8000 software is configured to set the high temperature limit, which in an exemplary embodiment is adjustable between 35.0° C. and 40.0° C. in 0.1° C. increments. If the high temperature limit or level is reached, an alarm may sound, if sound is enabled, along with one or more visible indicators on front panel 8158 of ABTT system display 8001. In an exemplary embodiment, the high temperature limit or alarm level is configured to default to 38.5° C.

In an exemplary embodiment, system 8000 software is configured to allow setting of the amplitude or intensity of audible tones and alarms.

In an exemplary embodiment, system 8000 software is configured to set a conversion offset of ABTT monitoring system 8001, which in an exemplary embodiment is adjustable from −10.0° C. to 10.0° C. in 0.1° C. increments. Also in an exemplary embodiment, the conversion offset is configured to default to 0.0° C.

In an exemplary embodiment, system 8000 software is configured with a sensor placement mode. The sensor placement mode is entered on command, which may be from display 8118, from a switch or button on front panel 8158 of ABTT system display 8001, or from an external controller, such as external computer 8130. System 8000 software is configured to enter the sensor placement mode on command. In an exemplary embodiment, system 8000 software is configured to receive a temperature signal from a temperature sensor or probe every 250 milliseconds (ms). To conserve power, in an exemplary embodiment the system 8000 software may power the temperature sensor or probe for no more than 1 ms out of every 250 ms. The system 8000 software may be configured to acquire multiple readings from a temperature sensor or probe and to average those readings in the sensor placement mode. In an exemplary embodiment, system 8000 software may acquire and average sixteen readings from the temperature sensor or probe in the temperature placement mode. It should be apparent from the previously provided description herein that the system 8000 software is configured to display the temperature readings, averaged, instantaneous, or otherwise, in the selected display units, typically degrees Celsius or degrees Fahrenheit.

In an exemplary embodiment of the present disclosure, system 8000 software is configured to product a tone proportional to the temperature sensed on the temperature sensor or probe in the sensor placement mode. As a distinct indicator of low temperatures that would normally be considered out of range, an exemplary system 8000 software is configured to produce an audible tone of 150 Hz when the temperature signal from the temperature sensor or probe is at or below 30° C. Similarly, system 8000 software may be configured to produce an audible tone of 6000 Hz when the signal from the temperature sensor or probe is at or above 43° C. As with most modes of ABTT monitoring system 8000, system 8000 software is configured to leave the sensor placement mode upon command. Alternatively, system 8000 software may be configured to leave the sensor placement mode after three minutes.

Once the temperature sensor has been positioned or placed on the ABTT terminus, in an exemplary embodiment the system 8000 software enters an operational mode. In the operational mode, the system 8000 software is configured to receive a temperature reading at intervals, which by default may be once every 15 seconds. However, it should be understood that the reading interval can range from less than a second up to 60 seconds. To preserve system power for battery mode operation, system 8000 software may limit the time as which the temperature sensor is powered. In an exemplary embodiment, the system 8000 software may power the temperature sensor or probe in the operational mode for a maximum of 1 ms out of every 15 seconds.

In an exemplary embodiment, system 8000 software may acquire and average sixteen readings from the temperature sensor or probe in the operational mode. However, it should be understood that less than 16 readings is also within the scope of this disclosure. It should be apparent from the previously provided description herein that the system 8000 software is configured to display the temperature readings, averaged, instantaneous, or otherwise, in the selected display units, typically degrees Celsius or degrees Fahrenheit.

If ABTT monitoring system includes an ambient temperature sensor, such as temperature sensor 8160, in an exemplary embodiment, system 8000 software may be configured to read the temperature from ambient temperature sensor 8160 every 15 seconds. In another exemplary embodiment, ambient temperature may be read from temperature sensor 8160 in a range of 10 to 15 seconds. In a further exemplary embodiment, ambient temperature may be read from temperature sensor 8160 in a range of 5 to 10 seconds.

When ABTT monitoring system 8000 enters a battery powered mode, i.e., external power is not available to ABTT monitoring system 8000, the system 8000 software is configured to determine the remaining battery life periodically. In an exemplary embodiment, remaining battery life may be determined approximately once every 60 seconds.

As previously described herein, an exemplary embodiment ABTT monitoring system 8000 includes non-volatile memory. System 8000 software is configured to store each temperature sensor or probe temperature reading in non-volatile memory. However, ABTT monitoring system 8000 is not limited to storing temperature data in non-volatile memory, though such storage is preferable for making the data available for future analysis and reference purposes. In an exemplary embodiment, system 8000 software is configured to save the most recent 24 hours of temperature readings in non-volatile memory. However, ABTT monitoring system 8000 is not limited to 24 hours. In some embodiments, data may not be save in non-volatile memory at all. In other embodiments, data may be saved for days, weeks, or even longer, depending on the particular environment in which ABTT monitoring system 8000 is being used and the requirements of that environment. Data may also be saved in memory (not shown) housed in or co-located with temperature sensor 8002, 8004, 8006, or 8008.

As described herein, an exemplary embodiment ABTT monitoring system 8000 in accordance with the present disclosure includes a display 8118. System 8000 software is configured to display currently sensed temperature sensor or probe temperature in the selected display units, typically degrees Celsius, degrees Fahrenheit, or both. In an exemplary embodiment, display of temperature may be in 0.1 degree increments.

System 8000 software is also typically configured to display the ambient temperature, which may be on ambient temperature display 8164, received from ambient temperature sensor 8160 or from elsewhere, in the currently selected display units, though the units for the ambient temperature display may be selected independently of other temperature displays on ABTT system display 8001. If system 8000 software is configured to display ambient temperature, the resolution of the ambient temperature is at least 1 degree, with 0.1 degree being preferable.

In an exemplary embodiment, system 8000 software is configured to display the remaining battery life on display 8118. Such display may be on battery life display 8162.

As described herein, the displays of ABTT monitoring system 8000 may include backlighting, side lighting, or other lighting to enable reading of the various displays presented by ABTT system display 8001. To conserve power, system 8000 software is configured to turn off the backlight after a predetermined time after a new reading or alarm is displayed. Such a power saving mode may be a standard operating mode, or may be entered when a low battery condition is detected.

Alarms have been previously described herein. System 8000 software is configured to provide a visible alarm on ABTT system display 8001, such as by flashing the display, or presenting an alarm signal on a separate display, such as display 8042. Alarms may also be audible, and system 8000 software is configured to enable or disable audible alarms, prior to an alarm condition or after the alarm condition. If an alarm condition exists and audible tones are present, the audible tones may be disabled by pressing reset button 8050 once, which permits displayed alarms to continue. Pressing reset button 8050 a second time resets all displayed alarms to a non-alarm condition. When an audible alarm is enabled, such alarm may be by voice, which in an exemplary embodiment may present, for example, a vocal alarm indicating the precise nature of the alarm, such as: "Warning! Over-temperature condition detected"; "Warning! Under temperature condition detected"; "Fault detected. The temperature probe appears disconnected or malfunctioning"; etc. In another exemplary embodiment, the alarm may be an audible tone with a frequency of at least 3000 Hz. The alarm tone may be configured to alternate between a high tone and an off tone, or lower tone, or the alarm tone may be matched to a particular alarm condition.

If the system 8000 software detects that the temperature sensor or probe has reached or exceeded the high temperature limit, enabled alarms, display and audible, are configured to operate. Alarm display 8042 may alternate between "ALARM" and "HIGH TEMP," or other, similar indication, to indicate that the high temperature limit has been reached. Similarly, if the system 8000 software detects that the temperature sensor or probe has reached or fallen below the low temperature limit, enabled alarms, display and audible, are configured to operate. Alarm display 8042 may alternate between "ALARM" and "LOW TEMP," or other, similar indication, to indicate that the low temperature limit has been reached.

If system 8000 software detects a fault in ABTT monitoring system 8000 that prevents safe and accurate temperature readings from the temperature sensor, alarm display 8042 may alternate between "ALARM" and "ERR." Similarly, if battery life is 60 minutes or less, or there is a malfunction of the battery system, system 8000 software may display "ALARM" alternating with "BATT." If system 8000 software is able to present a temperature reading in any alarm condition, system 8000 software is configured to continue to do so even while presenting alarm indications.

ABTT monitoring system 8000 includes features to control the function of the various displays. In an exemplary embodiment, adjustment and memory of adjustment of display intensity, contrast, color balance and/or correction, size, position, sharpness, etc., may be provided, in addition to a reset button that restores all display-related settings to factory default settings.

Figure 13:
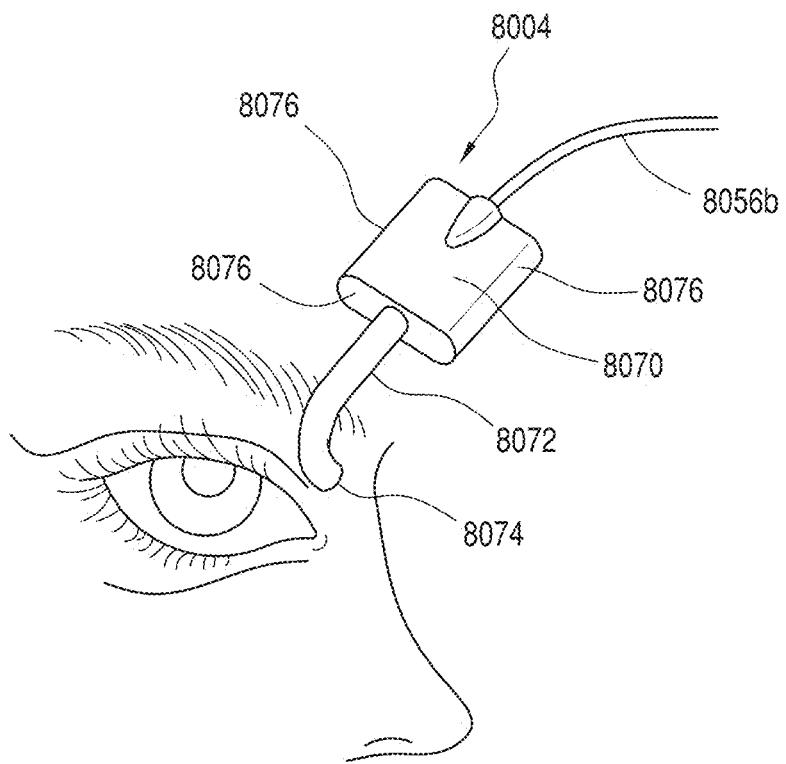
FIG. 13 shows the stylized human face of FIG. 12 with the temperature sensor of FIGS. 2 and 3 positioned to read the temperature of the ABTT.

In an exemplary embodiment, ABTT system display 8001 may include a graphing mode. Referring to FIGS. 1 and 13, ABTT system display 8001 may include a mode button 8176 that is either integral with display 8118, or a separate mechanical switch. By pressing mode button 8176, display 8118 switches between a plurality of display modes. One such display mode may be a graphing display, such as that shown in FIG. 13. In the graphing mode, system 8000 software presents a graphing display 8166 on system display 8118 that presents temperature over a time interval. Graphing display 8166 includes a horizontal scale 8168 displaying time and date, a vertical scale 8170 displaying temperature in the selected units. Display 8118 allows movement of time scale 8168 and temperature scale 8170 by using a mouse or contacting display 8118, and dragging the selected scale in the direction of desired change; i.e., left or right to change the position of the time scale and up or down to change the position of the temperature scale. Additionally, graphing display 8166 includes soft buttons that permit changing the scale of both time, time scale button 8172, and temperature, temperature scale button 8174. Each button includes a "+" or "−" to increase or zoom in, or decrease or zoom out from the present scale. In an exemplary embodiment, the fixed location for scale changes may be at the lower left corner of graphing display 8166. In another exemplary embodiment, the fixed location may be in the center of time scale 8168 and temperature scale 8170. However, graphing display 8166 may be configured to provide any location as a fixed point for changing scales, depending on the desires of an end user. Mode button 8176 may be pressed once more to change temperature scale 8170 from an absolute time scale displaying the current time and date and extending from there backward to a relative time scale with the present at 0 hours, and extending backward for the time limit permitted by stored data and the ability of graphing display 8166 to zoom out, or for temperature scale 8170 to be moved.

In an exemplary embodiment, system 8000 software is configured to display alarm events, such as alarm event 8178, on graphing display 8166. By selecting or touching alarm event 8178, time, date, and type of alarm is presented in a box (not shown) overlaid on graphing display 8166. The alarm information is hidden after a predetermined period, such as 3 seconds, but may also be hidden by clicking on the alarm information box while it is displayed.

In an exemplary embodiment, system 8000 software is organized as a software control loop. The software control loop is configured to place ABTT monitoring system 8000 in a low power state when no activities are pending. The software control loop is configured to be triggered by interrupt events. The software control loop is configured to call a display screen update routine on every iteration to provide updates for at least display 8118 and digital display 8014. The software control loop is configured to call port support on every iteration.

When a port is active, i.e., when data is available, the software control loop is configured to call the data transfer routine on every iteration. The software control loop is configured to call the touch switch routines every one tenth of a second; i.e., displayed or soft switches are read approximately every one tenth of a second. When any display screen, except a startup screen (not shown) or a probe setup screen (not shown), is active, the software control loop is configured to initiate a temperature read process every fifteen seconds. The temperature read process is defined as a process where power is provided to a temperature sensor or probe, unless power is already applied, and temperature is acquired over predetermined period for a predetermined number of readings.

During any process where temperature is read, including a mode where the ABTT is located and the temperature read process, when any display screen except the startup screen (not shown) or probe setup screen is active, the software control loop is configured to store the read temperature. In an exemplary embodiment, when the probe setup screen is active, the software control loop is configured to initiate the temperature read process every one quarter second.

The software control loop is configured to send stored patient temperature data when requested by the port host.

The software control loop is configured to call a battery monitor routine one per minute.

In an exemplary embodiment, system 8000 software is configured to use an interrupt based hardware timer to time STM events. The system 8000 software timer interrupt routine is configured to set flags indicating predetermined time intervals have passed. In exemplary embodiments, flags are set at one tenth second, one quarter second, one second, fifteen seconds, and one minute. In addition, the system 8000 software timer interrupt routine is configured to process timer subsystem timers.

As noted herein, ABTT monitor system 8000 includes one or more ports or connectors to interface with external devices, for example, external computer 8130. In order to communicate with such devices, in an exemplary embodiment system 8000 software is configured to include port background routines. Such port background routines are configured to be interrupt driven. Furthermore, port background routines are configured to handle all handshakes with external host devices. In addition, port background routines are configured to provide for data sent to the host device to be the system 8000 software control loop. Still further, port background routines are configured to send data from the system 8000 software control loop to the host device.

As described herein, ABTT monitoring system 8000 may include one or more soft buttons or switches, which are displayed buttons that are actuated by touch, proximity, mouse control, light pen, etc. In an exemplary embodiment, the system 8000 software is configured to read touch button values approximately every second, or less. To minimize power consumption and overly sensitive response, touch switch or touch button average values are updated every one reading when the touch button or switch is not touched. In an exemplary embodiment, if a touch button reading exceeds the touch button average for three consecutive readings, then system 8000 software is configured to consider a touch to have occurred. Conversely, if a touch button or touch switch reading is below the touch button average for three consecutive reading, the system 8000 software is configured to consider that a touch has not occurred.

As described herein, ABTT monitoring system 8000 may include a battery monitor. In an exemplary embodiment, the battery monitor of system 8000 software is configured to: check battery status once per minute; estimate remaining battery life; and to set a battery alarm flag when remaining battery life drops below 60 minutes. The battery alarm flag may then be used by system 8000 software to activate ABTT monitoring system 8000 alarms, including alarm display 8042 and the audible alarm.

Though ABTT monitoring system 8000 may include physical buttons, many or even all such buttons may be connected through the system 8000 software. Accordingly, this discussion incorporates mechanical and soft or displayed switches.

When ABTT monitoring system 8000 is in a power off state or condition, the power button or ON/OFF switch 8044, when the ON position is selected, is configured to connect power to ABTT monitoring system 8000 to operate system 8000 or turn system 8000 to a power on or operating condition, assuming a valid power source is available. Conversely, if ON/OFF switch 8044 is moved from the ON position to the OFF position, then power is removed from the internal devices, components, and elements of ABTT monitoring system 8000, and system 8000 assumes a power off condition.

For the following discussion of buttons and switches, the term "any button" generally refers to any button except the power button and as otherwise noted. Generally, ABTT monitoring system 8000 is configured such that pressing any button at any level causes an audible "click." This condition exists for mechanical switches and soft switches. Pressing any button while display 8118 is active and with any backlighting, side lighting, or front light inactive causes any such type of lighting to activate with no other action.

Temperature Read Process

Figure 15:
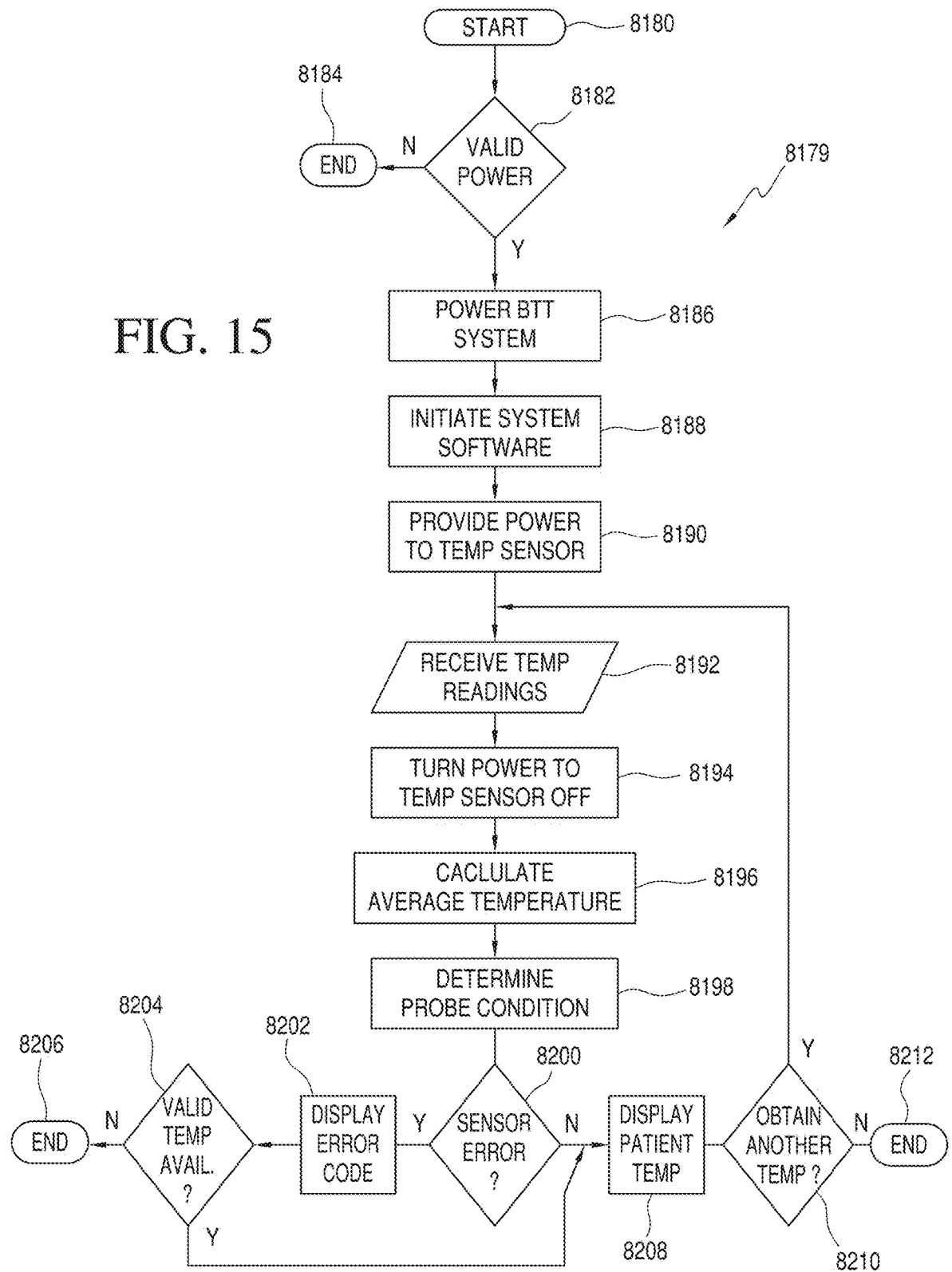
FIG. 15 shows a temperature read process in accordance with an exemplary embodiment of the present disclosure.

ABTT monitoring system 8000 is configured to include a temperature read process 8179, shown in FIG. 15. Temperature read process 8179, which may, in certain circumstances, also be described as a patient temperature read process 8179, is described in the following paragraphs.

At a start process 8180, ABTT monitoring system 8000 is set to an on or powered condition. Once power is provided to ABTT monitoring system 8000, all systems are set to factory default conditions or a previously set and saved condition, if such is provided. Included is resetting all storage to a zero or null condition, and all comparators to a null or zero condition. Control then passes from start process 8180 to a valid power decision process 8182.

In valid power decision process 8182, ABTT monitoring system 8000 determines that valid power is available. The determination of valid power may be made in power distribution hardware unit 8106. If valid power is available, then a valid power condition is determined, and power is automatically provided through power distribution 8106 to the systems, elements, and components of ABTT monitoring system 8000. If valid power is not available, control passes from valid power decision process 8182 to an end process 8184. In some embodiments, digital display 8014 may indicate NOPWR, indicating valid power is not available. If valid power is available, control passes from valid power decision process 8182 to a power ABTT monitoring system process 8186.

In process 8186, power is provided to various systems, components, and elements of ABTT monitoring system 8000, except for portions of ABTT monitoring system 8000 that are not yet required to be powered or are optionally operated. Such optional systems may include Wi-Fi or near field communication unit 8126 and the temperature sensor. Once power ABTT monitoring system process 8186 is complete, control passes from power ABTT monitoring system process 8186 to an initiate system software process 8188.

After power is provided to all portions of ABTT monitoring system 8000, controller 8112 begins operating and initiates system 8000 software to perform the functions of ABTT monitoring system 8000 in initiate system software process 8188. Once system 8000 software is operational, control passes from initiate system software process 8188 to a power temperature sensor process 8190.

In power temperature sensor process 8190, power is provided to the temperature sensor. Control then passes from process 8190 to a receive temperature readings process 8192.

In receive temperature sensor readings process 8192, controller 8112 receives a predetermined number of temperature readings from A/D converter 8110. In an exemplary embodiment, the number of temperature readings may be sixteen. Once the predetermined number of temperature readings has been received by controller 8112, control passes from receive temperature sensor readings process 8192 to a temperature sensor power off process 8194, where power to the temperature sensor is removed. Control then passes from process 8194 to an average temperature process 8196, where the average temperature is calculated from the predetermined number of readings. Control then passes from average temperature process 8196 to a determine temperature sensor or probe condition process 8198.

In process 8198, the average temperature is converted to a value using a translation table. The purpose of the translation table is to substitute a digital value for a measured probe condition. If the translated average reading is 0x0000, then process 8198 substitutes a PROBE_SHORTED value for the reading. If the translated average reading is 0xfff, then process 8198 substitutes a PROBE_OPEN value for the reading. If the translated average reading is below the lowest translation table value available, then process 8198 substitutes a PROBE_LOW value for the reading. If the translated average reading is above the highest translation table reading, then process 8198 substitutes a PROBE_HIGH value for the reading. Once probe condition process 8198 is complete, control passes from process 8198 to a sensor error decision process 8200.

If any error condition is returned from process 8198, then an error condition exists, and control passes from sensor error decision process 8200 to a display error code process 8202. In process 8202, an error is displayed, which may be, for example, on digital display 8014. Exemplary error codes are described herein. Once process 8202 is complete, control passes to a valid temperature available decision process 8204.

In valid temperature decision process 8204, a determination is made as to whether a valid temperature exists, such as a temperature below a lower limit, above, a lower limit, or other valid temperature, even in the presence of an error. If a valid temperature is not available, control passes to an end process 8206 and temperature read process 8179 ends. If a valid temperature is available, control passes to a display patient temperature process 8208, which is also where control passes from sensor error decision process 8200 if no sensor error condition exists.

In display patient temperature process 8208, the average temperature obtained from average temperature process 8196 is displayed on one or more portions of ABTT system display 8001, such as dial gauge 8010, bar graph or gauge 8012, and digital display 8014. Once the average temperature is displayed, control passes to a new temperature decision process 8210.

In new temperature decision process 8210, ABTT monitoring system determines whether another temperature is desired. Such a determination may be made automatically if a timeout situation has not occurred, or if temperature readings differentiate from ambient by a predetermined amount. If temperature read process 8179 determines that additional temperature readings are desired, control passes from new temperature decision process 8210 to receive temperature readings process 8192, described herein. Alternatively, if additional temperature readings no longer appear needed, then control passes from new temperature decision process 8210 to an end process 8212, where temperature read process 8179 ends.

Though temperature read process 8179 is described in terms of a power off condition of ABTT monitoring system 8000, as long as system 8000 remains on, controller 8112 periodically tests for the presence of a temperature sensor at predetermined intervals and for temperature changes that differentiate from ambient. If such changes are detected, temperature read process 8179 is initiated again, though temperature read process 8179 is configured to recognize that processes 8180 to 8188 have already been accomplished, thus control is configured to immediately pass to power temperature sensor process 8190, where temperature read process 8179 is configured to continue as previously described.

Ambient Temperature Read Process

In an exemplary embodiment, system 8000 software is configured to include an ambient temperature read process. Reading ambient temperature begins by turning power on to ambient temperature sensor 8160. Once ambient temperature sensor 8160 is properly powered, signals from ambient temperature sensor representing the ambient temperature are provided to system controller 8112. Once the ambient temperature is read, power to ambient temperature sensor 8160 is turned off.

Display Screens

Main Display Screen

The display screens described herein are one of the easiest and most useful ways to present data acquired by ABTT monitoring system 8000. In all discussions involving displays, it should be understood that while displayed functions are sometimes described in terms of the display, all display-related functions are driven by a controller, which includes system 8000 software. Accordingly, in most cases the described actions and features are the result of system 8000 software. When power is applied to ABTT monitoring system 8000, display 8118 is configured to initially display a startup screen while various system elements, including system 8000 software, such as a logo showing ABTT, for Abreu Brain Thermal Tunnel. This initial screen may also be configured to display a part number and version for the system 8000 software. After a period, which is determined by the time it takes to initialize all systems fully, the initial startup screen is replaced by a main display screen, such as that shown in FIG. 1 for display 8118. If the startup screen appears to be moving slowly to the main display screen, system 8000 software is configured such that touching any button, clicking on the display with a mouse pointer, or touching the screen causes a transition from the startup screen to the main display screen.

As shown in FIG. 1, where display 8118 presents an exemplary embodiment of the present disclosure, the main display screen is configured to numerically display the most recent patient or subject temperature. If no alarm condition exists, display 8118 is configured to display the main display screen and is configured to continuously present the most recent patient or subject temperature data. If an error condition exists, at least one of the displays presented on the front panel of ABTT system display 8001 presents an error code. In an exemplary embodiment presented herein, the error codes are display on digital display 8014. Such error codes may include temperature data with a value of PROBE_SHORTED, wherein at least one display is configured to present "PS" for the temperature data; temperature data with a value of PROBE_OPEN, wherein at least one display is configured to present "NP" for the temperature data; temperature data with a value of PROBE_LOW, wherein at least one display is configured to present "UR" for the temperature data; and temperature data with a value of PROBE_HIGH, wherein at least one display is configured to present "OR" for the temperature data. If a low patient temperature alarm exists, system 8000 software is configured to display on at least one display screen, at one second intervals, the word "Low," and the most recent patient temperature data. If a high patient temperature alarm exists, system 8000 software is configured to display on at least one display screen, at one second intervals, the word "High' and the most recent patient temperature data.

In an exemplary embodiment, the system 8000 software is configured so that the display of the most recent temperature data blinks when the display is being updated.

In an exemplary embodiment, while the main display screen is displayed, system 8000 software is configured to display the most recent patient temperature on the main display screen as a numerical value.

In the exemplary embodiments presented herein, patient or subject temperature is displayed in the currently selected unit of measure.

In an exemplary embodiment, while the main display screen is displayed, system 8000 software is configured to blink a low battery icon on the main display screen at one second intervals when a low battery alarm condition exists.

In an exemplary embodiment, while the main display screen is displayed, system 8000 software is configured to blink an audible alarm disable icon on the main display screen at one second intervals when the audible alarm is disabled.

In an exemplary embodiment, while the main display screen is displayed, system 8000 software is configured to clear the highest priority alarm when reset button 8050 is touched and released within two seconds.

In an exemplary embodiment, while the main display screen is displayed, system 8000 software is configured to toggle the audible alarm flag when reset button 8050 is touched for two seconds or longer.

In an exemplary embodiment, while the main display screen is displayed, system 8000 software is configured to toggle the display unit of measure flag when enter button 8154 is touched and released within two seconds.

In an exemplary embodiment, while the main display screen is displayed, system 8000 software is configured to move to an option select screen when the enter button is touched for two seconds or longer.

In an exemplary embodiment, while the main display screen is displayed, system 8000 software is configured to cause the backlight intensity to increase by 10% when down arrow button 8148 is touched and released.

In an exemplary embodiment, while the main display screen is displayed, system 8000 software is configured not to cause the backlight intensity to increase above 100%.

In an exemplary embodiment, while the main display screen is displayed, system 8000 software is configured to cause the backlight intensity to decrease by 10% when down arrow button 8148 is touched and released.

In an exemplary embodiment, while the main display screen is displayed, system 8000 software is configured not to cause the backlight intensity to decrease below 0%.

In an exemplary embodiment, while the main display screen is displayed, system 8000 software is configured to cause the display contrast to increase by 10% when left arrow button 8150 is touched and released.

In an exemplary embodiment, while the main display screen is displayed, system 8000 software is configured not to increase the display contrast above 100%.

In an exemplary embodiment, while the main display screen is displayed, system 8000 software is configured to cause the display contrast to decrease by 10% when right arrow button 8152 is touched and released within two seconds.

In an exemplary embodiment, while the main display screen is displayed, system 8000 software is configured not to decrease the LCD Contrast below 0%.

In an exemplary embodiment, while the main display screen is displayed, system 8000 software is configured to graph display screen 8166 when right arrow button 8152 is touched for two seconds or longer.

In an exemplary embodiment, while the main display screen is displayed, system 8000 software is configured to move to a temperature sensor setup display screen when enter button 8154 and reset button 8050 are touched simultaneously for two seconds or longer.

Option Select Screen

In an exemplary embodiment, ABTT monitoring system 8000 includes an option selection screen. The option select screen is configured to display an option for selecting the temperature sensor setup screen.

In an exemplary embodiment, the option select screen is configured to display an option for selecting a clear patient data screen.

In an exemplary embodiment, the option select screen is configured to display an option for selecting a low limit alarm edit screen.

In an exemplary embodiment, the option select screen is configured to display an option for selecting a high limit alarm edit screen.

In an exemplary embodiment, the option select screen is configured to display an option for selecting an audible alarm level screen.

In an exemplary embodiment, the option select screen is configured to display an option for selecting a backlight timer edit screen.

In an exemplary embodiment, while in the option select screen, system 8000 software is configured to move to the main display screen when reset button 8154 is touched and released.

In an exemplary embodiment, while in the option select screen, system 8000 software is configured to move to the currently selected option when enter button 8154 is touched and released.

In an exemplary embodiment, while in the option select screen, system 8000 software is configured to display move the currently selected option up one when up arrow button 8146 is touched and released.

In an exemplary embodiment, while in the option select screen, system 8000 software is configured to move the currently selection option to the bottom-most option when up arrow button 8146 is touched and released when the top-most option is currently selected.

In an exemplary embodiment, while in the option select screen, system 8000 software configured to move the currently selected option down one when down arrow button 8148 is touched and released.

In an exemplary embodiment, while in the option select screen, system 8000 software is configured to move the currently selected option to the top-most option when down arrow button 8148 is touched and released and the bottom-most option is currently selected.

Temperature Sensor Setup Screen

In an exemplary embodiment, the System 8000 software is configured to include a temperature sensor setup screen.

In an exemplary embodiment, the temperature sensor setup screen is configured to display numerically the most recent patient or subject temperature.

In an exemplary embodiment, the temperature sensor setup screen is configured to display continuously the most recent patient or subject temperature date.

In an exemplary embodiment, the temperature sensor setup screen is configured to display "PS" for patient or subject temperature data with a value of PROBE_SHORTED.

In an exemplary embodiment, the temperature sensor setup screen is configured to display "NP" for patient or subject temperature data with a value of PROBE_OPEN.

In an exemplary embodiment, the temperature sensor setup screen is configured to display "Ur" for patient or temperature data with a value of PROBE_LOW.

In an exemplary embodiment, the temperature sensor setup screen is configured to display "Or" for patient or subject temperature data with a value of PROBE_HIGH.

In an exemplary embodiment, the temperature sensor setup screen is configured to blink the most recent temperature data once per second to show it is being updated.

In an exemplary embodiment, the temperature sensor setup screen is configured to display graphically the most recent patient temperature on the main display screen as a numerical value.

In an exemplary embodiment, the temperature sensor setup screen is configured to display patient or subject temperature in the currently selected unit of measure.

In an exemplary embodiment, while in the temperature sensor setup screen, system 8000 software is configured to move to a clear patient data screen when reset button is touched and released.

In an exemplary embodiment, while in the temperature sensor setup screen, system 8000 software is configured to move to the main display screen when the enter button is touched and released.

Clear Patient Data Screen

As described herein, an exemplary embodiment system 8000 software is configured to include a clear patient data screen. This feature is important for patient privacy. In an exemplary embodiment, to initiate the clear patient data screen, an authorizing identification or ID may need to be entered. In another exemplary embodiment, a patient or subject identification or ID may need entered, either in addition to an authorizing identification, or in place of the authorizing identification.

In an exemplary embodiment, the clear patient data screen is configured to display the phrase "Clear Patient Data? Reset=Yes, Enter=No." While in the clear patient data screen, system 8000 software is configured to clear stored patient data when reset button 8050 is touched and released, after which the patient data cleared screen is configured to display the phrase "Patient Data Cleared." While in the clear patient data screen, system 8000 software is configured to move to the patient data cleared screen when reset button is touched and released.

In an exemplary embodiment, while the clear patient data screen is displayed the system 8000 software is configured to move to the main display screen when enter button 8154 is touched and released.

While the patient data screen is displayed, system 8000 software is configured to move to the main display screen after a five second interval. Furthermore, the system 8000 software is configured to move or transition from the patient data cleared screen to the main display screen if any button on ABTT system display 8001 is touched.

Low Limit Alarm Edit Screen

As yet another options screen, in an exemplary embodiment, system 8000 software is configured to provide a low limit alarm edit screen.

The low limit alarm edit screen is configured to show the current value of the low limit alarm on entry into the low limit alarm edit screen, and the value displayed is configured to be in the selected display units of measure.

The low limit alarm edit screen is configured to display the value of the low limit alarm in the currently selected display units of measure.

While in the low limit alarm edit screen, system 8000 software is configured to increment the edited low limit alarm by 0.1 degree when up arrow button 8146 is touched and released.

While in the low limit alarm edit screen, system 8000 software is configured not to increment the edited low limit alarm above 38.0 degrees Celsius or above 100.4 degrees Fahrenheit.

While in the low limit alarm edit screen, system 8000 software is configured to decrement the edited low limit alarm by 0.1 degrees when down arrow button 8148 is touched and released.

While in the low limit alarm edit screen, system 8000 software is configured not to decrement the edited low limit alarm below 29.0 degrees Celsius or below 84.2 degrees Fahrenheit.

While in the low limit alarm edit screen, system 8000 software is configured to set the low limit alarm to the edited low limit alarm value when enter button 8154 is touched and released.

The system 8000 software is configured to move from the low limit alarm edit screen to the option select screen when reset button 8154 is touched for less than two seconds and released while the low limit alarm is equal to the edited low limit alarm.

The system 8000 software is configured to return the edited low limit alarm to its low limit alarm value when reset button 8050 is touched for less than two seconds and released while the low limit alarm is not equal to the edited low limit alarm.

While in the low limit alarm edit screen, the system 8000 software is configured to set the edited low limit alarm to the default value of 34.0 degrees Celsius when reset button 8050 is touched and held for two seconds or more.

While in the low limit alarm edit screen, the system 8000 software is configured to set the edited low limit alarm to the default value of 93.2 degrees Fahrenheit when reset button 8050 is touched and held for two seconds or more.

High Limit Alarm Edit Screen

As yet another options screen, in an exemplary embodiment, system 8000 software is configured to provide a high limit alarm edit screen.

The high limit alarm edit screen is configured to show the current value of the high limit alarm on entry into the high limit alarm edit screen, and the value displayed is configured to be in the selected display units of measure.

The high limit alarm edit screen is configured to display the value of the high limit alarm in the currently selected display units of measure.

While in the high limit alarm edit screen, system 8000 software is configured to increment the edited high limit alarm by 0.1 degree when up arrow button 8146 is touched and released.

While in the high limit alarm edit screen, system 8000 software is configured not to increment the edited high limit alarm above 40.0 degrees Celsius or above 104.0 degrees Fahrenheit.

While in the high limit alarm edit screen, system 8000 software is configured to decrement the edited high limit alarm by 0.1 degrees when down arrow button 8148 is touched and released.

While in the high limit alarm edit screen, system 8000 software is configured not to decrement the edited high limit alarm below 35.0 degrees Celsius or below 95.0 degrees Fahrenheit.

While in the high limit alarm edit screen, system 8000 software is configured to set the high limit alarm to the edited high limit alarm value when enter button 8154 is touched and released.

The system 8000 software is configured to move from the high limit alarm edit screen to the option select screen when reset button 8154 is touched for less than two seconds and released while the high limit alarm is equal to the edited high limit alarm.

The system 8000 software is configured to return the edited high limit alarm to its high limit alarm value when reset button 8050 is touched for less than two seconds and released while the high limit alarm is not equal to the edited high limit alarm.

While in the high limit alarm edit screen, the system 8000 software is configured to set the edited high limit alarm to the default value of 38.5 degrees Celsius when reset button 8050 is touched and held for two seconds or more.

While in the high limit alarm edit screen, the system 8000 software is configured to set the edited high limit alarm to the default value of 101.3 degrees Fahrenheit when reset button 8050 is touched and held for two seconds or more.

Audible Alarm Level Edit Screen

In an exemplary embodiment, yet another of the options screens is the audible alarm level edit screen. Upon entry to the audible alarm level edit screen, system 8000 software is configured to display on the audible alarm level edit screen the current audible alarm level in percent of maximum.

While in the audible alarm level edit screen, system 8000 software is configured to increment the edited audible alarm level by 5% when the up arrow button 8146 is touched and released.

While in the audible alarm level edit screen, system 8000 software is configured not to increment the edited audible alarm level above 100%.

While in the audible alarm level edit screen, system 8000 software is configured to decrement the edited audible alarm level by 5% when down arrow button 8148 is touched and released.

While in the audible alarm level edit screen, system 8000 software is configured not to decrement the edited audible alarm level below 10%.

While in the audible alarm level edit screen, system 8000 software is configured to set the audible alarm level to the edited audible alarm level when enter button 8154 is touched and released.

While in the audible alarm level edit screen, system 8000 software is configured to move to the option select screen when reset button 8050 is touched for less than two seconds and released while the audible alarm level is equal to the edited audible alarm level.

While in the audible alarm level edit screen, system 8000 software is configured to set the edited audible alarm level to the audible alarm level when reset button is touched for less than two seconds and released while the audible alarm level is not equal to the edited audible alarm level.

While in the audible alarm level edit screen, system 8000 software is configured to set the edited audible alarm level to the default value of 50% when reset button 8050 is touched and held for two seconds or more.

Backlight Timer Edit Screen

In an exemplary embodiment, yet another of the options screens is the backlight timer edit screen. While in the backlight timer edit screen, system 8000 software is configured to set the edited backlight timer to the default value of 3 seconds when reset button 8050 is touched and held for two seconds or more.

While in the backlight timer edit screen, system 8000 software is configured so that upon entry the current value of the backlight timer is displayed.

While in the backlight timer edit screen, system 8000 software is configured to increment the edited backlight timer by 1 second when up arrow button 8146 is touched and released.

While in the backlight timer edit screen, system 8000 software is configured not to increment the edited backlight timer above 60 seconds.

While in the backlight timer edit screen, system 8000 software is configured to decrement the edited backlight timer by 1 second when down arrow button 8148 is touched and released.

While in the backlight timer edit screen, system 8000 software is configured not to decrement the edited backlight timer below 0 seconds.

While in the backlight timer edit screen, system 8000 software is configured to set the backlight timer to the edited backlight timer value when enter button 8154 is touched and released.

While in the backlight timer edit screen, system 8000 software is configured to move from the backlight timer edit screen to the Option Select Screen when reset button 8050 is touched for less than two seconds and released while the backlight timer is equal to the edited backlight timer.

While in the backlight timer edit screen, system 8000 software is configured to return the edited backlight timer to its currently saved value when reset button 8050 is touched for less than two seconds and released while the backlight timer is not equal to the edited backlight timer.

While in the backlight timer edit screen, system 8000 software is configured to set the edited backlight timer to the default value of 3 seconds when reset button 8050 is touched and held for two seconds or more.

Graphing Display

Figure 14:
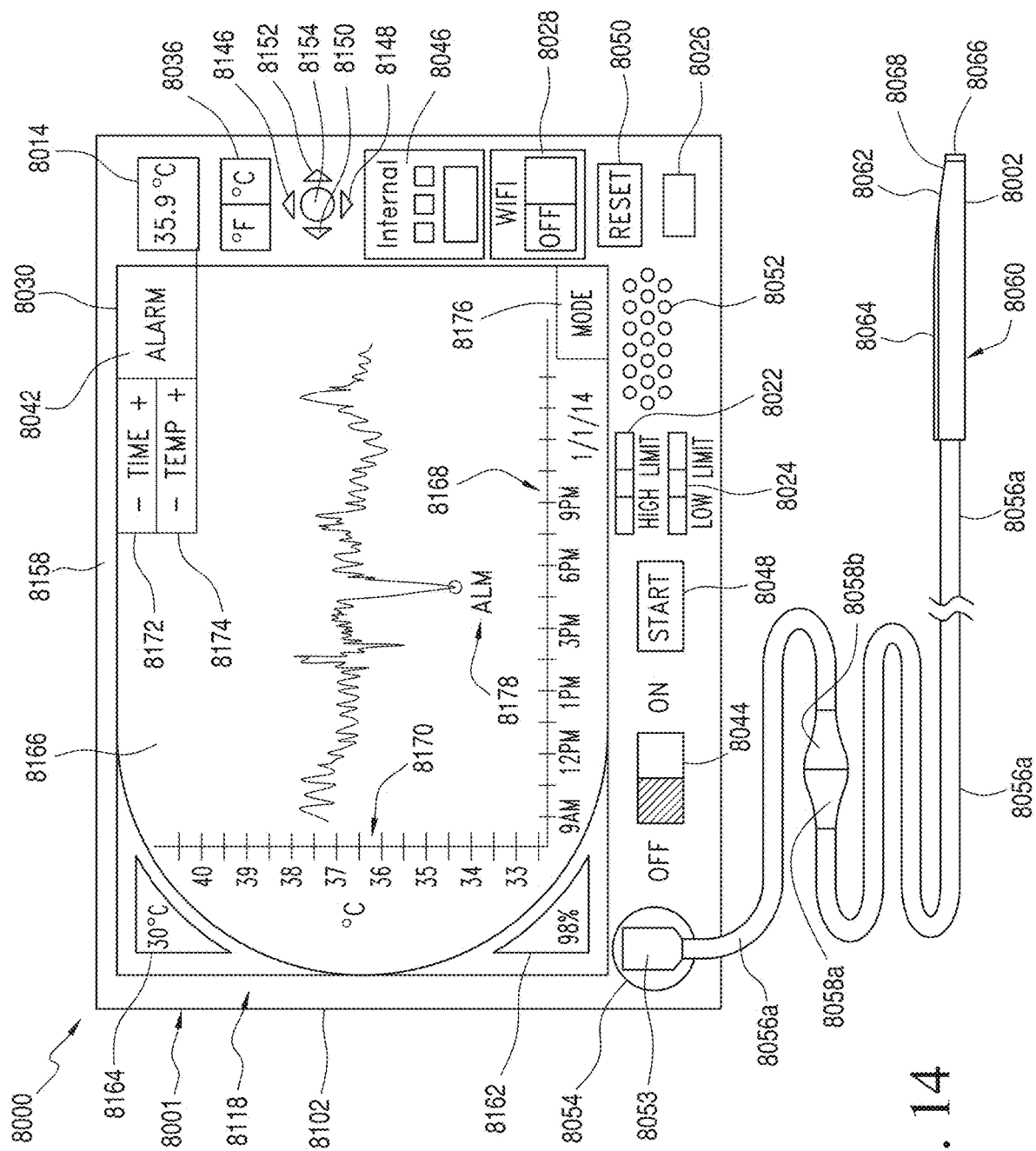
FIG. 14 shows the ABTT monitoring system of FIG. 1 in a graphing mode in accordance with an exemplary embodiment of the present disclosure.

As previously described, and shown in FIG. 14, an exemplary embodiment ABTT monitoring system 8000 in accordance with the present disclosure includes graphing display 8166.

Upon entry into graphing display 8166, system 8000 software is configured to display the previous four hours of patient or subject temperature, if available.

While in graphing display 8166, system 8000 software is configured to display current patient or subject temperature data along with the highest and lowest temperature in what may be described as a high-low graph.

While in graphing display 8166, system 8000 software is configured to display four data points in each entry of the high-low graph.

While in graphing display 8166, in an exemplary embodiment system 8000 software is configured to display graph start time relative to current time for the currently displayed graph.

While in graphing display 8166, system 8000 software is configured to display graph stop time relative to current time for the currently displayed graph.

While in graphing display 8166, system 8000 software is configured to move the currently displayed graph four hours later when right arrow button 8152 is touched and release.

While in graphing display 8166, system 8000 software is configured to move the currently displayed graph to the most recent four hours when enter button 8154 is touched and released.

While in graphing display 8166, system 8000 software is configured to move to the main display screen when reset button 8050 is touched and released.

Display Illumination

As discussed herein, in an exemplary embodiment display 8118 and 8014 are configured to include lighting to improve the readability of those displays. Such lighting may be from backlighting, side lighting, front lighting, etc. For the sake of simplicity and convenience, all such display lighting is described as backlighting herein, though it should be understood that the term backlighting covers any type of display lighting, unless otherwise noted.

Exemplary embodiment backlighting is configured to operate at the currently selected contrast.

Exemplary embodiment backlighting is configured to be off when backlight level is zero.

Exemplary embodiment backlighting is configured to operate at the selected or set backlight level while active.

Exemplary embodiment backlighting is configured to be continuously active in any display screen except the main display screen. This configuration is possible because all screens except the main display screen are kept on for a limited period.

Exemplary embodiment backlighting is configured to operate as follows in the Main Display Screen: backlighting is continuously active in the main display screen while the backlight timer value is zero; when any button is touched in the main display screen the backlight will be activated for backlight timer time; and when the temperature display is updated backlight will be active for backlight timer time while the backlight timer time is less than 15 seconds.

ABTT Monitoring System and ISM Operation

The operation of ABTT monitoring system 8000 and ISM 8136 may have many different exemplary modes and conditions. The operations described herein are examples of the typical operations of ABTT monitoring system 8000 and ISM 8136, with differences between the systems identified as needed.

Initializing

For ABTT monitoring system 8000, simply move ON/OFF switch 8044 from the OFF position to the ON position. ABTT monitoring system 8000 will initialize, and predetermined limits will be uploaded to system unit controller 8112 from non-transitory memory 8114. Typically, ABTT monitoring system 8000 will initialize or begin operation in a default state, which includes Wi-Fi off, interval set to zero or off, and thus temperature readings will be continuous, and units of measure set to degrees Celsius for the digital display. In the exemplary embodiment shown in FIG. 1, units switch 8036 controls the units of digital display 8014 and dial gauge 8010. However, in another embodiment, digital display 8014 may alternate between degrees Celsius and degrees Fahrenheit continuously, or two digital displays showing both temperatures may be provided. Furthermore, dial gauge 8010 may provide two units simultaneously rather than the single units shown in FIG. 1.

To initiate ISM 8136, connect USB port 8053 of ISM 8136 to a port of external computer 8130. Follow the "Found New Hardware" instructions presented on display 8138 of external computer 8130. Interface module 8136 will show up in the device manager of external computer 8130 as an Interface Module, which in the exemplary embodiment is named the Abreu ABTT 3.1.

Double click the Abreu 3.1 icon on the desktop to start the program. Attach any of the temperature sensors disclosed herein, such as temperature sensor 8002, 8004, 8006, or 8008, to ISM 8136. Computer display 8138 will display the temperature of the probe.

For both ABTT monitoring system 8000 and ISM 8136, a tone proportional to temperature will help the operator locate the SMO site of the ABTT, with a higher temperature indicated by a higher pitch tone (e.g., see Table 2). The tone can be disabled by un-checking the "Sound" box provided on display 8138 of computer 8130. Alarm limits can be set by clicking on the "arrow" buttons (not shown) provided on computer display 8138 that mimic the functionality of high limit switch 8022 and low limit switch 8024. Alert warning sounds can be turned off by un-checking the "Alerts" box.

The "up" and "down" arrows allow changing the alarm set points. If the program is re-started or is reset, these settings will revert to the default setting of 34.0° C. and 38.5° C., which are also the default setting for ABTT monitoring system 8000. The temperature will be displayed digitally in the upper right of display 8138 unless an error condition exist, in which case a code will indicate the error, such as codes "NC," "NP," "PS," "Ur," or "Or," previously described herein in conjunction with digital display 8014 of ABTT monitoring system 8000.

Readings from ISM 8136 presented on display 8138 are provided frequently, at least two per second, as are readings on the various temperatures displayed on ABTT system display 8001. The rapid rate of readings enables the operator to best place the temperature probe as quickly as possible on SMO site. A tone mode is entered by depressing the "Sound" box. The displayed patient temperature will update rapidly, allowing the operator to reposition the sensor for the optimum reading, with the highest reading yielding the highest pitch. As the temperature of the sensor rises above the lower limit, a continuous tone proportional to temperature will be heard emanating from the computer. This sound feedback will help the operator easily locate the desired contact position for the sensor. Table 2 shows the correlation between temperature and sound frequency. While it is typical for the ABTT terminus to be higher temperature than surrounding skin, under certain conditions, the ABTT terminus may be cooler than surrounding skin temperature. A trained operator will recognize this situation immediately because the sound from temperature of the surrounding skin will be higher pitch than the ABTT location, which will be lower. It should be understood that the audio correlation disclosed herein associated with the temperature levels can be used with another biological parameter, in which the level of the parameter is associated with a particular audio frequency, said parameters including, but not limited to, heart rate, blood pressure, respiratory rate, oxygen levels, oximetry, blood gases, and analytes such as glucose and the like.

Once the ABTT has been located, and displayed temperature values on either ABTT system display 8001 or display 8138 no longer fluctuate, the sensor has stabilized and the displayed temperature is the measured temperature. Depending on the thermistor being used, e.g., thermistor 8066, 8074, 8086, or 8098, the response time may vary. The greater the mass of the sensor, the longer the response time since thermal equilibrium must be established with the environment, either ambient, the ABTT, or elsewhere.

Figure 12:
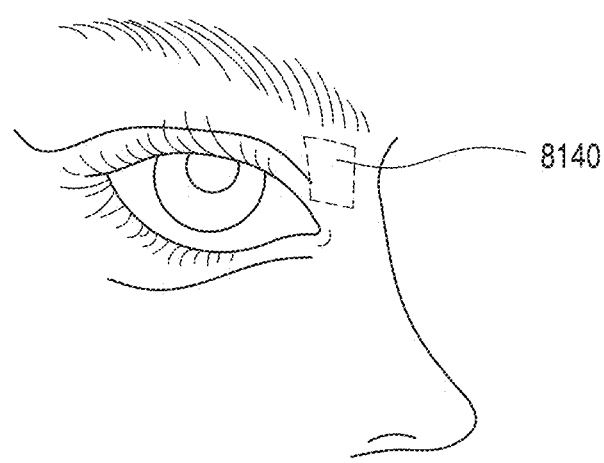
FIG. 12 shows a stylized human face with the location of the ABTT identified.

As shown in FIG. 12, the location depicted by dark round spot 8140 is the approximate location of the SMO ABTT site. Placing a sensor, such as temperature sensor 8004, as shown in FIG. 13, will provide a temperature signal that is tied directly to the hypothalamus area of the human brain, which may be presented on a display, such as digital display 8014, display 8118 of ABTT monitoring system 8000, or display 8138 of external computer 8130. With proper training and practice, the ABTT may be located and temperature stabilized within 5 to 60 seconds.

TABLE 2

Correlation between Temperature and Frequency

| Temp | Freq (Hz) |
|---|---|
| <30 | 100 |
| 30 | 150 |
| 30.1 | 200 |
| 30.2 | 250 |
| 30.3 | 300 |
| 30.4 | 350 |
| 30.5 | 400 |
| 30.6 | 450 |
| 30.7 | 500 |
| 30.8 | 550 |
| 30.9 | 600 |
| 31 | 650 |
| 31.1 | 700 |
| 31.2 | 750 |
| 31.3 | 800 |
| 31.4 | 850 |
| 31.5 | 900 |
| 31.6 | 950 |
| 31.7 | 1000 |
| 31.8 | 1050 |
| 31.9 | 1100 |
| 32 | 1150 |
| 32.1 | 1200 |
| 32.2 | 1250 |
| 32.3 | 1300 |
| 32.4 | 1350 |
| 32.5 | 1400 |
| 32.6 | 1450 |
| 32.7 | 1500 |
| 32.8 | 1550 |
| 32.9 | 1600 |
| 33 | 1650 |
| 33.1 | 1700 |
| 33.2 | 1750 |
| 33.3 | 1800 |
| 33.4 | 1850 |
| 33.5 | 1900 |
| 33.6 | 1950 |
| 33.7 | 2000 |
| 33.8 | 2050 |
| 33.9 | 2100 |
| 34 | 2150 |
| 34.1 | 2200 |

TABLE 2-continued

Correlation between Temperature and Frequency

| Temp | Freq (Hz) |
|---|---|
| 34.2 | 2250 |
| 34.3 | 2300 |
| 34.4 | 2350 |
| 34.5 | 2400 |
| 34.6 | 2450 |
| 34.7 | 2500 |
| 34.8 | 2550 |
| 34.9 | 2600 |
| 35 | 2650 |
| 35.1 | 2700 |
| 35.2 | 2750 |
| 35.3 | 2800 |
| 35.4 | 2850 |
| 35.5 | 2900 |
| 35.6 | 2950 |
| 35.7 | 3000 |
| 35.8 | 3050 |
| 35.9 | 3100 |
| 36 | 3150 |
| 36.1 | 3200 |
| 36.2 | 3250 |
| 36.3 | 3300 |
| 36.4 | 3350 |
| 36.5 | 3400 |
| 36.6 | 3450 |
| 36.7 | 3500 |
| 36.8 | 3550 |
| 36.9 | 3600 |
| 37 | 3650 |
| 37.1 | 3700 |
| 37.2 | 3750 |
| 37.3 | 3800 |
| 37.4 | 3850 |
| 37.5 | 3900 |
| 37.6 | 3950 |
| 37.7 | 4000 |
| 37.8 | 4050 |
| 37.9 | 4100 |
| 38 | 4150 |
| 38.1 | 4200 |
| 38.2 | 4250 |
| 38.3 | 4300 |
| 38.4 | 4350 |
| 38.5 | 4400 |
| 38.6 | 4450 |
| 38.7 | 4500 |
| 38.8 | 4550 |
| 38.9 | 4600 |
| 39 | 4650 |
| 39.1 | 4700 |
| 39.2 | 4750 |
| 39.3 | 4800 |
| 39.4 | 4850 |
| 39.5 | 4900 |
| 39.6 | 4950 |
| 39.7 | 5000 |
| 39.8 | 5050 |
| 39.9 | 5100 |
| 40 | 5150 |
| 40.1 | 5200 |
| 40.2 | 5250 |
| 40.3 | 5300 |
| 40.4 | 5350 |
| 40.5 | 5400 |
| 40.6 | 5450 |
| 40.7 | 5500 |
| 40.8 | 5550 |
| 40.9 | 5600 |
| 41 | 5650 |
| 41.1 | 5700 |
| 41.2 | 5750 |
| 41.3 | 5800 |
| 41.4 | 5850 |
| 41.5 | 5900 |
| 41.6 | 5950 |
| 41.7 | 6000 |

TABLE 2-continued

Correlation between Temperature and Frequency

| Temp | Freq (Hz) |
|---|---|
| 41.8 | 6050 |
| 41.9 | 6100 |
| 42 | 6150 |
| 42.1 | 6200 |
| 42.2 | 6250 |
| 42.3 | 6300 |
| 42.4 | 6350 |
| 42.5 | 6400 |
| 42.6 | 6450 |
| 42.7 | 6500 |
| 42.8 | 6550 |
| 42.9 | 6600 |
| 43 | 6650 |
| 43.1-45 | 6700 |

ABTT Locating Systems
Temperature Sensor Operations

As previously noted herein, temperature sensor 8004 is configured to be a one-use or disposable temperature sensor or probe. Temperature sensor 8004 may come with an adhesive layer 8142, which may be protected by a cover. After locating the SMO site, remove the cover of adhesive layer 8142 and press adhesive layer 8142 against the patient's forehead in the approximate orientation shown in FIG. 13. As previously described herein, finger 8072 may be flexible to accommodate adjustments to the position of thermistor 8074 to accommodate individual differences between subjects. Finger 8072 requires only moderate or mild pressure to adjust before attaching temperature sensor 8004 to a subject's forehead to optimize the angle with which the thermistor's adhesive layer 8142 contacts the subject's skin. A foam layer may be positioned directly between adhesive layer 8142 and face 8078 of temperature sensor 8004, and the foam layer improves compliance of adhesive layer 8142 to the variations in the forehead of a subject. It is recommended that temperature sensor 8004 be replaced every 24 to 36 hours and the skin of the forehead cleaned because the presence of skin oils may weaken the adhesion or adherence of adhesive layer 8142 to the skin, and allow finger 8072 to pull loose or move.

Longitudinally extending temperature sensors, such as temperature sensors 8002 and 8006, shown in FIGS. 1, 4, and 5, may be used with a thin disposable plastic coverlet (not shown) to permit temperature sensors 8002 and 8006 to be reusable with reduced requirements for sterilization. The coverlet should be replaced with each use as a matter of routine clinical procedures. It should be understood that assemblies that do not include an adhesive surface can be used, such as the frame of eyeglasses, specialized frames, nose clips, head bands, and the like Stopping Operations To cease operation of ABTT monitoring system 8000, ON/OFF switch 8044 may be moved from the ON position to the OFF position. For operation with external computer 8130, a displayed "STOP" or "OFF" button may be presented and selected, either by mouse 8128, touch, if display 8138 of external computer 8130 is provided with a touch screen, by a shortcut key (not shown), or through other devices or configurations.

Firmware Description

Once system 8000 initialization has been completed, system 8000 firmware operates entirely in an infinite loop. No interrupts are used or enabled. The mail loop waits for input from the UART or for calibration pin to be pulled low. The mail loop also checks for and corrects UART RX overflow errors. If the calibration input is pulled low new calibration constants are obtained from A/D converter inputs and stored in EEPROM. If a valid command is read from the UART, the firmware executes the corresponding command. Commands include sampling A/D converter inputs, printing version information, and retrieving calibration constants. Each time the A/D converter is sampled at a high level, the firmware computes the average of a predetermined number of successive temperature readings, which in an exemplary embodiment may be 16 successive measurements with the A/D converter. Thermistor drive voltages are disabled until a command is given to measure one of the inputs. Once the measurement is complete (the predetermined number of individual measurements, e.g., 16 individual measurements, plus a short delay) temperature sensor or thermistor drive voltage is once again disabled.

ABTT monitoring system 8000 uses a common port for power, which is 5.0V DC. Following are electrical features of ABTT monitoring system 8000 in an exemplary embodiment.

The maximum patient leakage current is 27 micro-amps.
The maximum patient leakage current is 32 micro-amps.
The maximum patient leakage current is 28 micro-amps.
Patient auxiliary current measurement would require a double fault assumption, therefore it is not applicable.
The maximum touch current of the temperature sensor is so minute it is insignificant (less than 3 micro-amps).
ABTT monitoring system 8000 does not use a protective earth connection.

In addition to protective circuitry design, the means of patient protection are two coats of electrical insulation on the thermistor. The thermistor is soldered to silver/copper wires, then a thin layer of insulation is applied to the thermistor and the soldered connections. In final assembly, the thermistor is attached to the finger, pen, or applique (the longitudinal body of the temperature sensor) and a thick layer of appropriate adhesive is placed over the thermistor, providing voltage isolation.

In an exemplary embodiment, a temperature sensor is connected directly to a personal computer, which then functions as the power supply.

In an exemplary embodiment, the working voltage of the thermistor is 3.3V DC.

The air clearance for MOOP is around the screws which hold the box together, which creates a static distance if the device were deformed or movement of parts.

The screws in ABTT monitoring system 8000 have been isolated with and air gap around them.

Regardless of whether a personal computer serves as the controller or ABTT monitoring system 8000, if a temperature sensor is detached from the PC or ABTT monitoring system 8000, and then reattached, operation of the system continues automatically.

Medical Grade Household Appliances

Healthcare care costs are rapidly increasing and the ability to have an at home medical monitoring devices are onerous. Furthermore, as described in U.S. Pat. No. 7,187,960 to Applicant, Applicant has conquered what may the last frontier for automation of patient monitoring. With the exception of temperature, all other vital signs can currently be monitored continuously, noninvasively, and automatically. Now, with the discovery of the Abreu Brain Thermal Tunnel (ABTT), described herein, all vital signs can be monitored continuously and noninvasively. For a person to buy all the currently available biological monitoring devices, e.g., EKG, EEG, blood pressure, heart rate, etc., would be very expensive. Therefore, the vast majority of the population is not able to take advantage of such medical advances. The inventions of the present disclosure provide a heretofore unrealized opportunity to provide an affordable biological parameter monitoring system for home use. The present discloses describes new household appliances and household electronics designed for continuous and noninvasive monitoring of biological parameters, referred herein as Medical Grade Household Appliances and Electronics (MGHAE). Therefore, when people buy appliances in the future, they may also be receiving a medical device or devices or a medical system or systems. The present disclosure provides new appliances with medical grade configuration and medical grade circuitry, electronics, and ports. Nowadays, a variety of household appliances and electronics have electronic circuitry, ports, and displays which sit idle and have no medical function. The present disclosure maximizes and optimizes the use of such displays, circuitry, memory, and ports by creating medical grade devices while allowing standard features and function of the household device to function in a regular or normal manner. More importantly, the features of the present disclosure allow people to monitor their biological parameters while at home or at work by being connected to a MGHAE of the present disclosure. The monitoring systems disclosed herein for monitoring temperature and its associated electronics, interfaces, and specialized electrical isolation are designed for and can be used for the implementation of the MGHAE.

Many times patients make doctor's appointments, travel to the physician's office, and possibly exposed themselves to diseases, only to find out that their biological parameter profiles are normal. An exemplary embodiment of the present disclosure includes the disclosure of a medical grade data portal to access a medical grade module connected to standard electronic and displays of Household Appliances and Household Electronics (HAHE), wherein medical parameters are able to be logged and displayed. Unnecessary travel to a hospital or doctor's office and exposure to others could be minimized, and the onset of possible disease conditions could be caught before developing complications. Preventive medicine in the very best sense would become a reality since people who need to buy a HAHE, for example a television, will at the same buy a medical device for monitoring biological parameters without the cost, complexity, and large size that characterizes standard medical devices of the prior art.

Telephone or internet connections would provide a path by which the biological parameters measured could be transferred to a health care professional qualified to read and analyze the biological parameters. The special medical grade interface of the present disclosure includes, by way of illustration, in a television-set, allows said television-set at home to display and store the value of any biological parameter and to display, for example, a temperature profile of a person having a bout of influenza. This disease pattern caused by the influenza can be overlaid on the subject's baseline temperature. This baseline temperature, with the features described in the present disclosure, can be acquired effortlessly when the user is watching a television program. A person can be watching a television program while a heart rate waveform, electrocardiogram waveform, or a temperature level is simultaneously displayed (and recorded) in a similar manner as stock ticker symbols and numbers or news headlines displayed on the bottom portion of a television screen by an A/D converter broadcasting network. The difference is that the number for the stock displayed is generated by the television network, while in the present disclosure, the biological parameter number displayed is generated by the television electronic circuitry itself based on the data received from the medical monitoring device through the Medical Grade Module (MGM). Moreover, the interface module is able to display digital numbers representing the level of concern. Appropriate instructions are displayed and the phone number(s) that might be desired for further information are displayed, such as drug names, pharmacy names and locations, doctor's names, laboratories, hospitals, and any other information relevant to the biological signal being received. The signal from MGHAE 8414 can be conveyed to numerous providers and locations that are related to the information being received from medical monitoring device 8416, so if high blood pressure is identified during monitoring, a doctor can be contacted and the information on blood pressure is automatically transmitted.

It is understood that any household appliance or household electronic device are within the scope of the present disclosure. By way of illustration, but not of limitation, a stove having a display and the medical grade port and medical grade module of the present disclosure provides monitoring of biological parameters while a subject is cooking or waiting for food to cook. In this exemplary illustration, the medical grade port is connected to a blood pressure measuring system adapted to work in connection with the medical grade port, which is used to monitor the subject's blood pressure continuously while waiting the food to cook.

Creation of specific systems and sub-systems as described in the present disclosure enables common household appliances and electronics to be turned into medical grade monitoring devices. The range of appliances may include, but is not limited to, a television, camera, stove, washing machine, dryer, refrigerator, microwave oven, computer, cell phone, watch, eyeglasses, music player, video game, telephone, electronic thermometer, and any other device having the electronics, reporting, and input means required for the functions described herein. Any device that has a reporting system, preferably a visual and audio system, is within the scope and can be enabled for medical monitoring. Moreover, the ability of household appliances and electronics manufacturers to offer a medical grade diagnostic to customers will create a new generation of household appliances and electronics with diagnostic and therapeutic capabilities.

The inventions of the present disclosure have several advantages. First, the inventions of the present disclosure will preferably harness power that is present in a variety of household appliance and electronic devices, including but not limited to: computers, television, refrigerators, microwave ovens, radios, thermostats, air conditioners, clocks, cell phones, or telephones. Second, the inventions of the present disclosure are typically low cost and easily adaptable into a variety of household devices. Third, the inventions of the present disclosure include communication between medical monitoring or measuring devices and household devices with a microcontroller or processor circuitry. Fourth, the inventions of the present disclosure use universal medical cables available in the medical industry to allow a variety of biologic monitoring devices to be coupled to household electronics and appliances.

In addition to medical systems communicating by wire, MGHAE 8414 includes communication via wireless transmission as well. In this alternative exemplary embodiment, the household and electronics appliances include a wireless transmitter or transceiver.

In another exemplary embodiment of the system, MGHAE 8414 includes a payment system in which the manufacturers of household appliances or electronics will have the ability to charge the user a fee for use of the monitoring system.

The inventions of the current disclosure allows users to bring a device, such as a cell phone that received the information captured by MGHAE 8414 to their medical professional to have their vital signs reviewed. Alternatively, connection of MGHAE 8414 to the internet or via a cellular network allows a patient to transmit vital signs or other measured information through a network or the internet. The stream of information has a stamp with the original signal with the identification of the household appliance or electronics sending the information.

A benefit of the inventions of the current disclosure is to have the ability to have full medical monitoring in the comfort of your home. Such monitoring saves money on gas, insurance, time, and the environment. This monitoring will also allow for decreased absenteeism at work and increased productivity. By way of illustration, medical grade computers, allows medical monitoring at work (while working on a desk). Thus, the work environment will provide the ability to monitor vital signs continuously while people are at work. By way of another illustration, medical grade television sets allow medical monitoring at home, for example, while watching television. Thus, the home environment provides the ability to monitor vital signs continuously while people are at home. By way of yet another illustration, example, or embodiment, medical grade video game sets allow medical monitoring at home while playing video games. Thus, the entertainment environment will provide the ability to monitor vital signs continuously while people play. By way of yet another illustration, example, or embodiment, medical grade washing machines allow medical monitoring at home while doing household chores. Life expectancy can be increased be improved, cost-effective monitoring. Physical fitness can also be monitored by using MGM 8422 in exercise machines according to the various principles of this disclosure.

MGHAE 8414 of the current disclosure also includes electronics and software to enable monitoring and treating of various diseases. In addition, MGHAE 8414 can include an alarm for values or wave forms that fall outside a pattern of normality (ex: EKG, heart rate, oximetry, oxygen, blood gas, blood pressure, eye pressure, etc.).

By including a second port on the medical grade appliance (TV, Internet connected data logger, etc.), various device manufacturers will have an opportunity to communicate with the host. As used herein, host is a device that receives and processes signal received from medical sensors. The host device is configured so that the manufacturer is able to communicate with the device, while biological information is captured and stored in the host device, for example, a television, in a separate location that is inaccessible to the manufacturer. The primary port that would normally be used by the appliance manufacturer for service, diagnostics, etc., would remain in a default mode dedicated to the manufacturer's communication protocols and use. When the second port is connected to a medical device (temperature, heart rate, blood pressure, etc.), that device uploads to the appliance its ID and how it intends to communicate with the appliance's main port. Alternatively, the medical grade port communicates with the main port, or yet the main port is combined with the medical grade port into one single port.

Inventions of the present disclosure allow medical devices from different manufacturers to communicate and use the display, recording abilities, alarm modes, etc., of the host household appliance, such as, by way of illustration or example, a refrigerator, washing machine, video game or television, without the worry of altering, disrupting, or interfering with the operation of the host household appliance. To preserve the household function intact, such as television settings, stove settings, camera settings, computer settings, and the like, only certain commands or types of data necessary to effect permitted actions are allowed, thereby protecting the internal settings and programmed functions of the host, namely the HAHE, which may be, by way of illustration, a television. It should be understood that those new MGHAE can be constructed as a separate physical device, such as the interface module disclosed herein for monitoring temperature with ABTT Monitoring System 8000, or, alternatively, the medical grade module and system can be integrated into household appliances. In this exemplary embodiment, the appliance manufacturer only allows certain commands or types of data necessary to effect permitted actions (protecting the internal settings and programmed functions of the host). MGHAE 8414 of the present disclosure includes a medical monitoring device and a control system in the host household appliance, with said control system preferably controlling the medical monitoring device.

An exemplary embodiment with a second port allows creation of security and a degree of standardization between various types of input devices. A "hub" allows several different instruments to be connected at the same time, sharing the appliance on a time basis.

As an example, the user may wish to do a thermal scan and send it to his/her doctor. If the appliance is a TV, when the scan is performed, the current "program" is minimized, the temperature scan is displayed and sent to the doctor's office for analysis.

Any medical device, or any device measuring a biologic parameter can be used. By way of illustration, but not of limitation, the present disclosure includes a thermographic device for thermal mapping of the ABTT for identifying an abnormal condition in the body, or by using a thermal sensor as disclosed herein. In the example of a computerized infrared scanner, if the image detects an abnormal condition, that information on abnormal condition is displayed or reported by visual or audio means in the MGHAE, using the display and speakers that are already part of the regular household appliance, but now are transformed into a medical alert reporting system. In the example that uses continuous thermal sensing, the acquired curves are compared to curves that were stored in the memory of household appliances. These acquired curves, for instance when the subject is watching television, can be compared to the subject's baseline pattern, or compared to predetermined patterns that indicator disease or an abnormal condition, or a change in physiological condition, such as ovulation. The standard controller or processor in the MGHAE is adapted to identify an abnormal pattern and alert the user or subject. With the present disclosure, a television, such as a smart TV for example, is adapted to become medical grade for coupling with the medical grade module of the present disclosure and a subject can thereby see and record the biological data being capture. By way of illustration or example, even a digital photo camera that includes electronics and memory can receive biological signals and operate in a similar manner as described for standard household appliances. Although the illustration hereinabove used a temperature sensor and temperature profile stored in the non-transitory memory of the MGHAE, it should be understood that any device measuring a biological signal can be used, such as measuring blood pressure, heart rate, oxygen and oximetry, glucose, and the like, and any device measuring any medical parameter such as EKG (electrocardiogram), electroencephalogram (EEG), and the like.

This portion of the present disclosure includes disclosure of a medical grade household electronic and appliances for monitoring biologic parameters using a medical grade module and a medical grade port, including continuous display of the data being monitored in the household appliance. However, it should be understood that a single measurement or intermittent measurements of biological signals are within the scope of this inventions. By way of illustration, if an altered glucose level (or fever) is identified, that single number can be reported by the MGHAE, using the same processing means, reported means, and stored values. In this embodiment, for example, the stored value in the memory of the MGHAE would be an abnormal glucose level. Hence, by way of illustration, if a level of glucose higher than 150 mg/dl is identified, that higher level is reported by visual and audio means of the MGHAE.

It should be understood that any medical measuring device can be continuously operatively coupled to the MGHAE. In accordance with other embodiments of the present disclosure, in which standard medical devices (including blood pressure measuring device, thermometers, blood glucose measuring devices and the like) are operatively coupled by wired or wireless means to standard household appliances (such as television, computer, cell phones, watches, eyeglasses, refrigerators, microwave ovens, stoves, washing machine, air conditioner, and any household appliance that has any reporting apparatus, including audio or visual). By way of illustration, the subject measures his/her blood pressure (or glucose level), but the subject is not watching television during the measurement and is away from the television. The data collected during the measurement is transmitted to all enabled household appliances. Once the subject turns the television on, for example, the collected data is displayed. If the measurement identified abnormal levels, the medical grade module turns on the television to display the abnormal value. Likewise, the display of a microwave oven, instead of displaying the time or cook settings, uses the LED or a numerical display to display the abnormal value. In the vast majority of cases, complications in patients occur due to lack of compliance with taking medications, and inventions in accordance with the teachings of this disclosure provide a system and device to inform and warn the user about the abnormal levels. Further, the devices and systems of the present disclosure prompt or urge the user or patient to take medications for correcting such abnormal levels; for example, taking a blood pressure medication, antibiotic, or insulin. It should be understood that standard appliances can also display the medication to be taken, said medication information being stored in non-transitory memory of the standard household appliance. It is also understood that the MGHAE can also display the medication to be taken, said medication information being stored in the non-transitory memory of the MGHAE.

Figure 61:
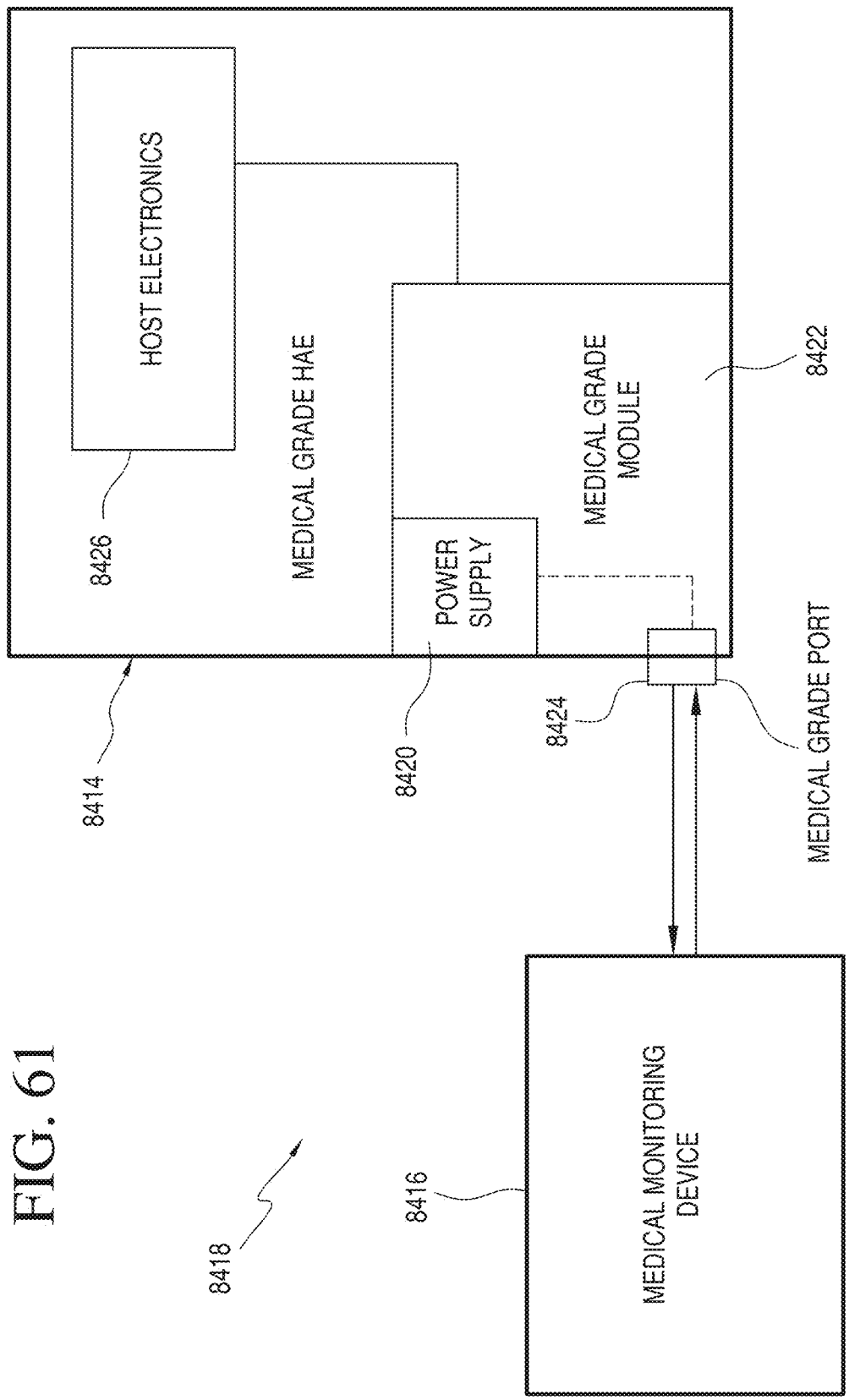
FIG. 61 is a block diagram showing a Medical Grade Household Appliances and Electronics (MGHAE) System, which is an MGHAE electrically connected with a medical monitoring device, in accordance with an exemplary embodiment of the present disclosure.

FIG. 61 shows a block diagram of an MGHAE 8414 electrically connected with a medical monitoring device 8416, which is referred herein as an MGHAE System, generally indicated at 8418. The figure shows medical monitoring device 8416 being connected to a power supply 8420 in MGHAE 8414, and the output of medical monitoring device 8416 is transmitted to a medical grade module (MGM) 8422 via a medical grade port 8424. MGHAE 8414 includes MGM 8422 for receiving, processing, and transmitting output to the electronics of the host 8426. Host herein refers to the standard systems, electronics, and features that characterize a household appliance and electronics that function as described in the present disclosure, by way of illustration, the host being a television.

Figure 57:
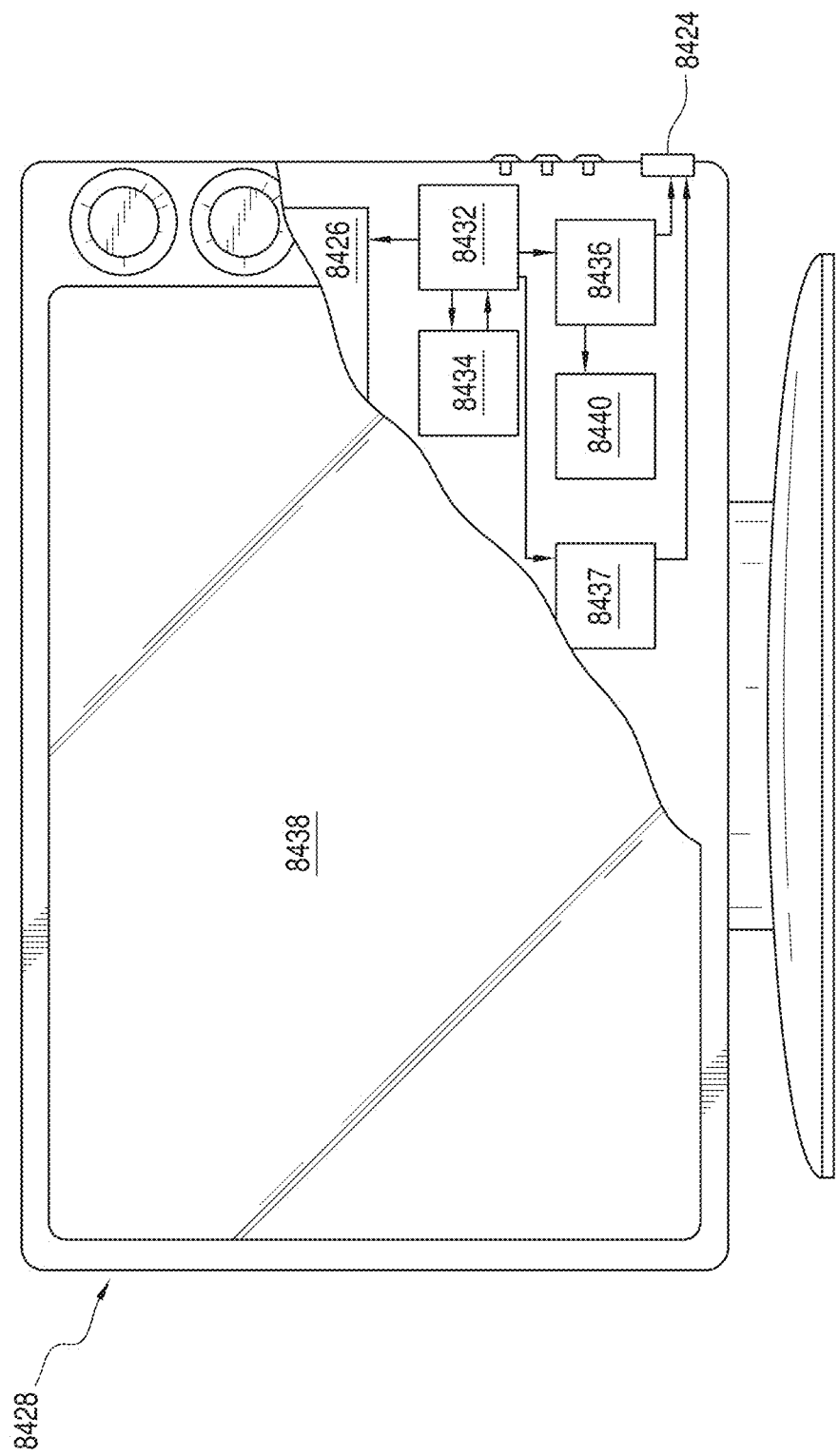
FIG. 57 is a view of a medical grade television with a portion removed to display a block diagram of certain internal features of the medical grade television in accordance with an exemplary embodiment of the present disclosure.

Medical monitoring device 8416 includes, but it is not limited to, measurement of any biological parameter such as blood pressure, eye pressure, heart rate, temperature, oxygen, blood gas, chemical compounds, drugs, analytes, glucose, oxygen saturation (oximetry), blood components, and device for sensing, detecting, or measuring any biological parameter including physical parameters and chemical parameters. Medical monitoring device 8416 provides an output preferably after MGHAE 8414 provides power for medical monitoring device 8416. The setting of medical monitoring device 8416 is then done according to a computer program installed in MGHAE 8414, with a user interface that utilizes a display (not shown) of the host for displaying a control panel for medical monitoring device 8416. Using controls located in MGHAE 8414, medical monitoring device 8416 is activated. MGM 8422 of MGHAE 8414 has processing circuitry adapted to control medical monitoring device 8416, and operation of medical monitoring device 8416 is made from the processing area of MGM 8422. For example, when using a medical grade television 8428, shown in FIG. 57, a control panel (not shown) of television 8428 (for volume, brightness, color, etc.) is activated to perform operations related to medical monitoring when a connector for medical monitoring device 8416 is connected into the medical grade port 8424. The connection of medical monitoring device 8416 into port 8424 of television 8428 activates a program in MGM 8422 to change the settings of the control panel of television 8428 to set up medical monitoring device 8416. Once medical monitoring device 8416 is set up and monitoring starts, the program of MGM 8422 instructs the control panel of television 8428 to return to its standard function. As shown in FIG. 57, MGM 8422, which is incorporated into television 8428, in an exemplary embodiment of the present disclosure, includes a processor 8432, memory 8434, A/D converter 8436, and specialized medical grade port (medical grade port) 8424 for receiving input signals from medical monitoring device 8416. MGM 8422 connects to host electronics 8426 and a host display 8438 of television 8428 for transmission and displaying of data received from medical monitoring device 8416. The signal processing of MGM 8422 includes processing by processor 8432, which receives the data via the medical grade port 8424 from medical monitoring device 8416, and converts the signal via the A/D converter 8436. MGM 8422 includes an isolation circuit 8440 to avoid the risk of electrical hazards.

In another embodiment, the remote control (not shown) of television 8428 functions as the control panel for medical monitoring device 8416. The biological data is then displayed on the display of the host device, referred herein as host display, i.e., the display of MGHAE 8418, which is, for example, the display screen 8438 of television set 8428 in the exemplary embodiment of FIG. 57. Processing and electronics of the host device, referred herein as host electronics 8426, are used for further analysis of the biological data being collected. In order to fulfill criteria required for regulatory approval (such as FDA) MGM 8422 includes specialized features and parts. In an exemplary embodiment, MGM 8422 includes isolation circuitry 8440 to avoid the risk of electrical hazards when medical monitoring device 8416 is connected to MGHAE 8414 and MGHAE 8414 is connected to a standard electrical outlet.

In an exemplary embodiment, medical grade port 8424 is a bi-directional multi-pin port that allows analog as well as digital information to pass between the medical device (e.g., medical monitoring device 8416) and the appliance's internal module adapted to be coupled to a medical monitoring device. It should be understood that MGHAE 8414 can be adapted for connections with standard medical devices produced by a variety of medical device manufacturers. All pins of medical grade port 8424 of MGHAE 8414 are electrically isolated, providing ground and shock protection to users, following ISO 60601 and UL standards. By allocating a certain number of input pins of medical grade port 8424 for analog measurements, some medical instruments (e.g., medical monitoring device 8416), through the present disclosure, can be made available at a lower cost by not requiring a power supply or amplification. In an exemplary embodiment, the host portion of MGHAE 8414, which may also be described as the appliance portion, includes an internal A-to-D converter, such as A/D converter 8436, which has a programmable gain "front end" and allows various analog sensors to be directly monitored. Some of the pins output a variable voltage to control or program the medical instrument (e.g., medical monitoring device 8416), represented as a digital to analog conversion provided by a D/A converter 8437 included as part of MGHAE 8414.

Medical grade port 8424 in accordance with an exemplary embodiment of the present disclosure supports standard RS-232c serial (0-5 volt) communications as well as USB and several industrial protocols. Digital pins in the connector are programmable as inputs or outputs, depending on the device (medical monitoring device 8416) connected. Some of the pins of medical grade port 8424 provide power to the external device (3.3 volts, 5 volts, etc.) eliminating the need for batteries and their disposal.

Figure 58:
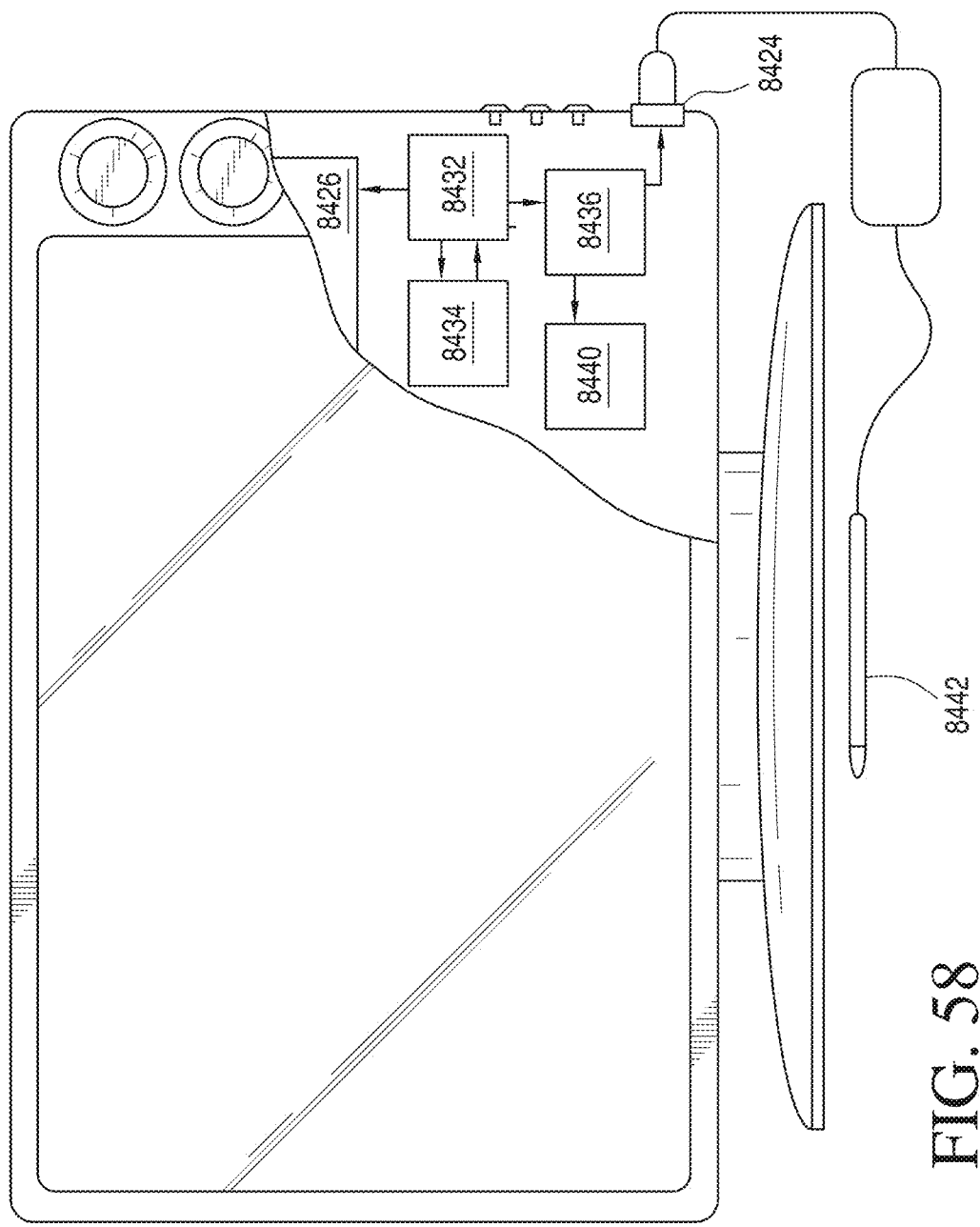
FIG. 58 is a view of the medical grade television of FIG. 57 with a medical monitoring device attached to it in accordance with an exemplary embodiment of the present disclosure.

An example of an instrument that could take advantage of the analog aspect of medical grade port 8424 of this disclosure is Abreu BTT temperature sensor or probe 8442 (wearable continuous sensor or quick read contact "pen"), as shown in FIG. 58. Temperature sensor or probe 8442 does not require any circuitry, other than a thermistor and the wires to connect to the thermistor, taking full advantage of the appliance's (i.e., MGHAE 8414) internal electronic module (host electronics 8426 of the electronic host), allowing temperature sensor 8442 to be very inexpensive and even disposable, reducing the risk or preventing cross contamination with other members of the family.

There are an increasing number of "smart sensors" that operate at very low power (voltage and current) that perform signal processing internally and that transmit data digitally, when requested, over just one signal line. An example of one such sensor is an infrared temperature sensor that enables non-contact skin temperature measurements and graphing. Two such sensors on a wand (side by side), in accordance to the principle of this disclosure, provide a very inexpensive tool for scanning.

In another embodiment, inexpensive integrated circuit pressure transducers, such as the pressure transducers manufactured by Motorola, directly connect to the analog pins in medical port 8424 of the present disclosure, enabling inexpensive pressure and force gauges to be part of the home medical "tool" box (grip strength, scales, lung vital capacity, FEV (forced expiratory volume), etc.).

In another embodiment, the information collected through medical port 8424 from these various instruments is formatted within host electronics 8426 of the appliance and re-transmitted (encrypted) through the appliance's USB port to a computer for further analysis, storage, display, or transmission over the internet as an encrypted data file. However, it should be understood that in some embodiments of the present disclosure that MGHAE 8414 includes in its MGM 8422 a processor and memory adapted for analyzing and storing medical data received via medical grade port 8424, and for communicating said medical data for displaying on a display of MGHAE 8414, such as for example display screen 8438 of television set 8428.

In addition, in another exemplary embodiment, the data/pictures stored in MGM 8422 are transferred from MGM 8422 into a conventional memory stick or flash card (not shown), which can then be brought with the patient to the doctor's office or hospital.

In another embodiment, a medical enabled bedside clock radio is connected to medical monitoring device 8416, for example a continuous measuring Abreu BTT temperature probe in any of the exemplary embodiments described herein, and cause the alarm/radio to turn on when certain "fever" or "chill" set points are exceeded. The same temperature information is transmitted to a clock in the parents' room, which can be enabled to display their child's temperature. In this exemplary embodiment, the clock radio includes a wireless transmitter coupled to a second clock radio. It is understood that any device having a clock and alarm, such as a cell phone, is within the scope of the disclosure. In the embodiment in which MGHAE 8414 is represented by a cell phone, the cellphone includes MGM 8422 and medical grade port 8424, with said cell phone being connected to medical monitoring device 8416 and using its alarm function to activate the warning based on a certain predetermined level of the parameter measured, for example, a certain level of blood pressure, glucose, heart rate, insulin, drug levels, oxygen, oximetry, respiratory rate, and the like.

The ability to utilize programmable, internal, computerized circuitry within an appliance that would normally be in the home for medical monitoring purposes has tremendous impact on all aspects of home care for the elderly, for individuals with medical conditions that would otherwise require continuous monitoring, and in other situations when continuous medical monitoring is desirable but not possible. Almost every nursing home supplies a television in each patient's room, with each television connected by cable to a central point. If each television were medically enabled, as described in the present disclosure, every patient room would have instant patient monitoring capability with no additional wiring required in the facility. In addition, MGHAE 8414 already occupies space to perform an appliance function, such as television, computing, etc., and transforming an appliance requires no additional space on a shelf, on the floor, or on a wall to provide its medical monitoring function.

Software can be easily installed in MGHAE 8414 via medical grade port 8424, to guide the operation of MGM 8422 and to transmit the input received from medical monitoring device 8416 to, for example, processor or controller 8432 and display 8438 for analysis and/or display of data.

Figure 62:
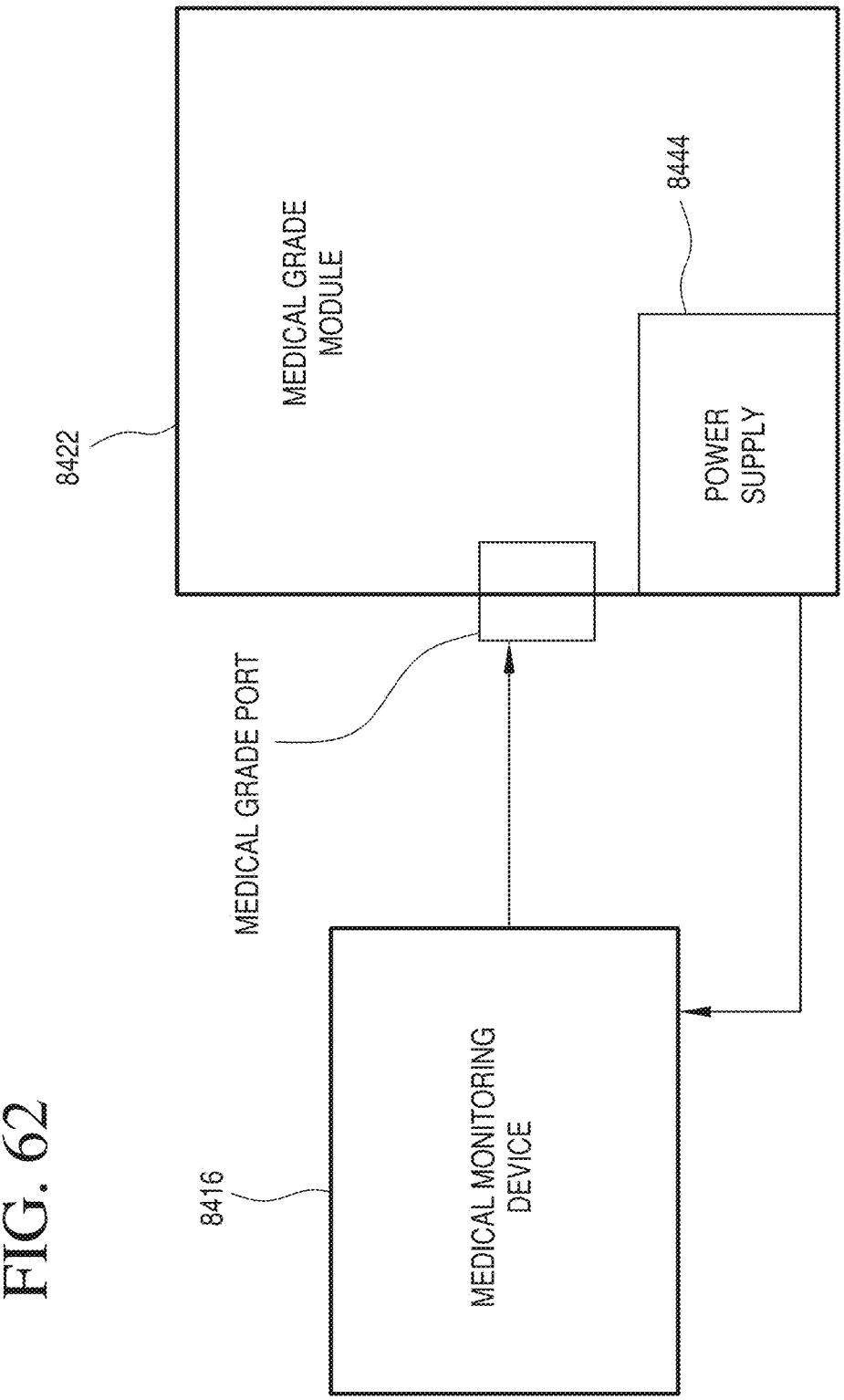
FIG. 62 is a block diagram showing input received from a medical grade module (MGM) and power to medical monitoring device 8416 can be provided by power source derived from MGHAE 8414 connected to an outlet or by batteries housed in MGHAE 8414 but outside of MGM 8422, in accordance with an exemplary embodiment of the present disclosure.

In another exemplary embodiment, as seen in FIG. 62, medical monitoring device 8416 can be controlled by input received from MGM 8422 and power to medical monitoring device 8416 can be provided by a power source or supply 8444 in MGM 8422, by power derived from MGHAE 8414 connected to a conventional electrical outlet, or by batteries housed in MGHAE 8414 but outside of MGM 8422.

The household appliances and household electronics, in accordance with the present disclosure, are configured for a single or multiple data input from a single or multiple MMD's, which are directly connected to MGM 8422 of the HAHE via a medical grade port, thereby allowing the HAHE to store, analyze, and display the biological data. The present disclosure thereby provides a MGHAE, for example a television set, that processes, stores, and displays various types of biological data using one single MGHAE, for example a television set.

Figure 60:
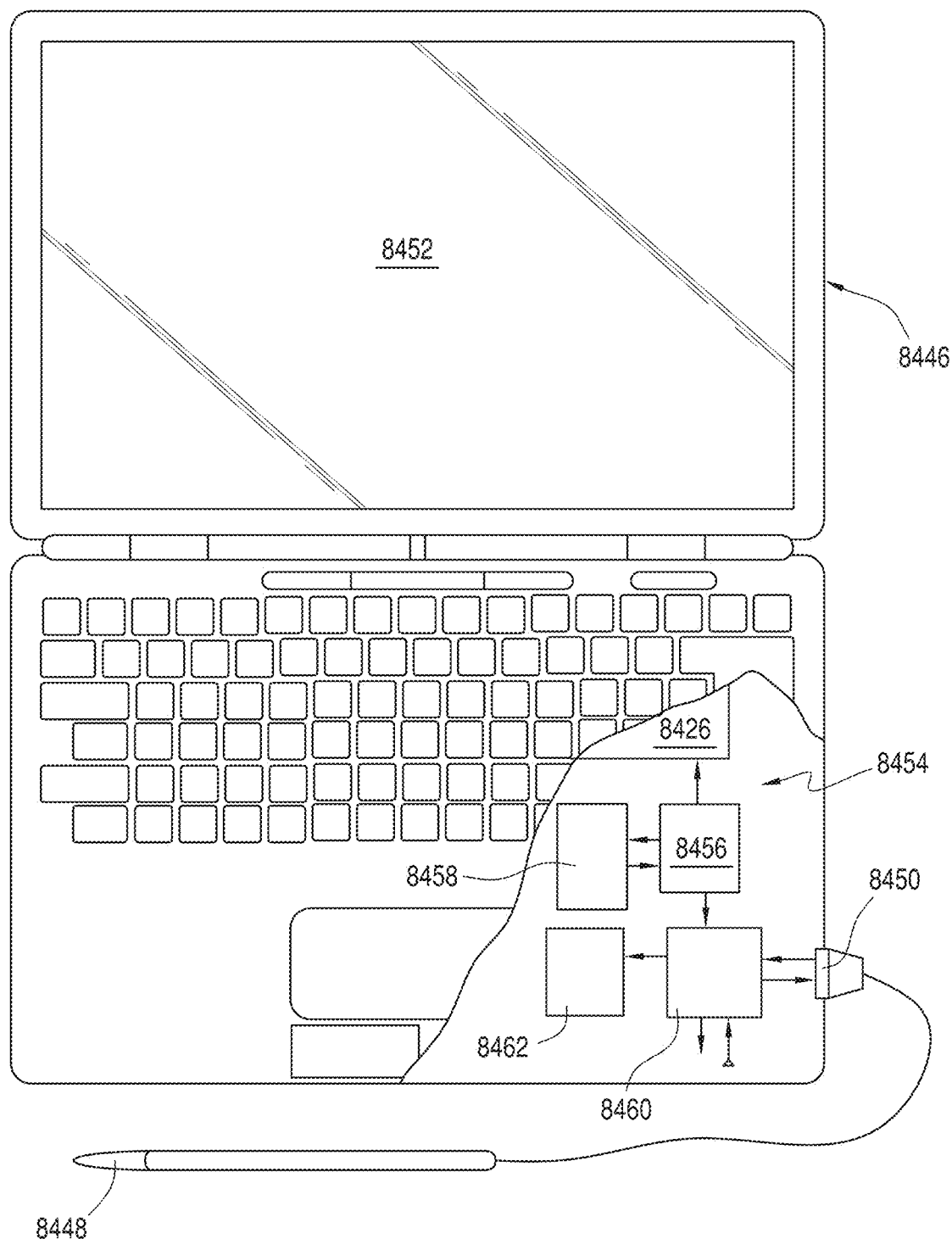
FIG. 60 is a diagram of a medical grade computer with a medical monitoring device attached to it in accordance with an exemplary embodiment of the present disclosure.

In an exemplary embodiment for measuring temperature using the Abreu ABTT system, shown in FIG. 60, which preferably requires proper placement of the probe on the ABTT site (the skin adjacent to or on the ABTT terminus), a medical monitoring device 8448, illustrated herein as the Abreu Brain Temperature Tunnel (ABTT) monitoring device, is connected to a medical grade port 8450 of an MGHAE, illustrated herein as computer 8446. ABTT software installed in the computer 8446 controls medical monitoring device 8448, and as soon as medical monitoring device 8448 is connected to computer 8446 through medical grade port 8450, the image corresponding to the ABTT initial screen (as determined by the ABTT software) is displayed on a computer display 8452, temperature reading mode is activated, and power supply from the computer is supplied to medical monitoring device 8448 (this power supply referred to as host power supply). A medical grade module 8454 includes a controller 8456, non-transitory memory 8458, A/D converter 8460, and specialized medical grade port 8450 for receiving input signal from medical monitoring device 8448. Medical grade module 8454 connects to host electronics 8426 and host display 8452 for transmission and displaying of data received from medical monitoring device 8448. The signal processing of medical grade module 8454 includes processing by controller 8456, which receives data via medical grade port 8450 from medical monitoring device 8448, and converts the signal from medical monitoring device 8448 from analog to digital via A/D converter 8460. Medical grade module 8454 isolation circuit 8462 to avoid the risk of electrical hazards to users, subjects, and patients. According to the principles of the present disclosure, the data from medical monitoring device 8448 can be directly inputted into MGHAE 8446, illustrated herein as a computer 8446. In addition, if medical monitoring device 8448 does not have its own power, MGHAE 8446 (e.g. computer 8446) can provide the necessary power via medical grade port 8450.

Figure 59:
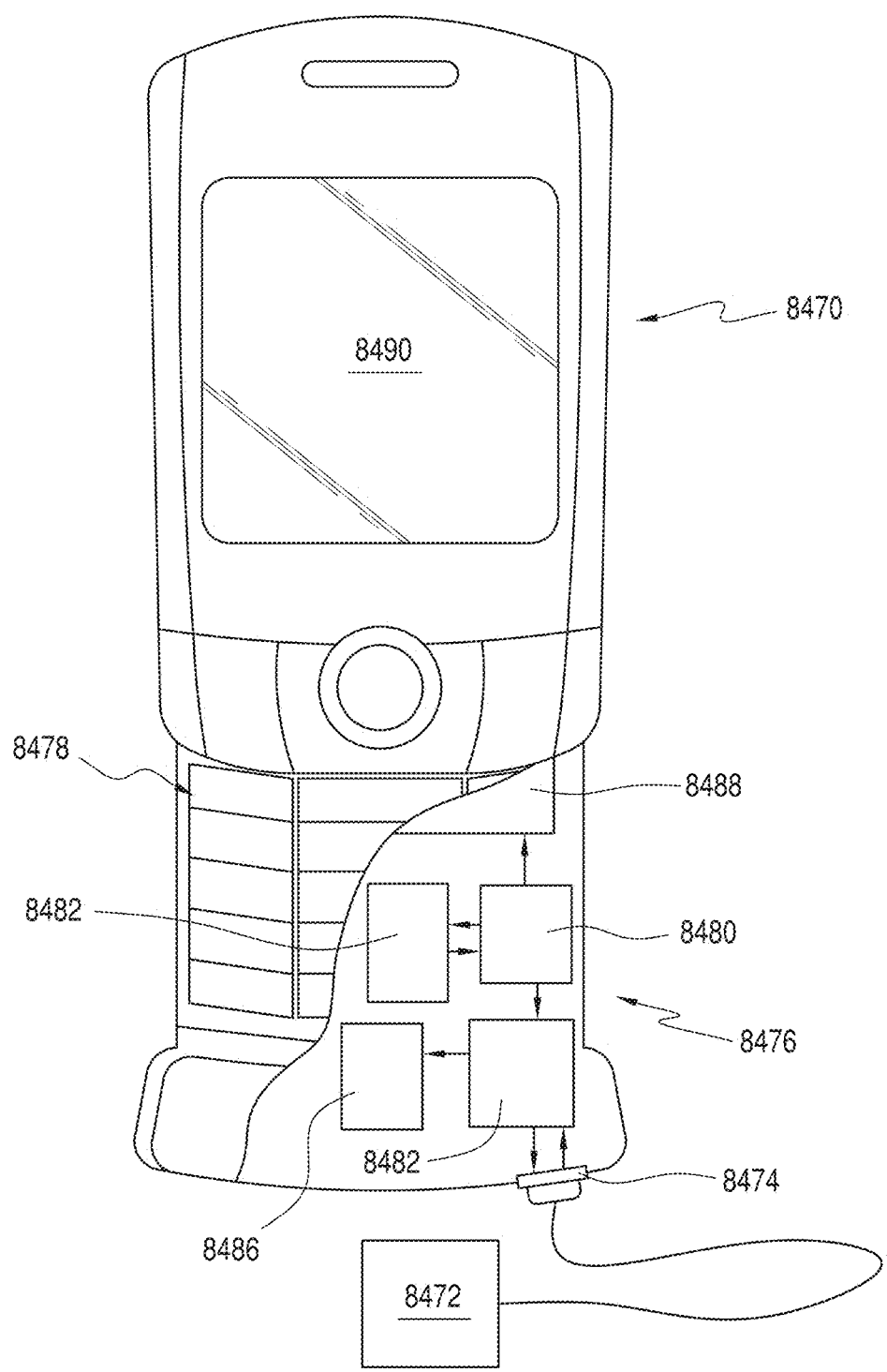
FIG. 59 is a diagram of a medical grade cellular phone with a medical monitoring device attached to it in accordance with an exemplary embodiment of the present disclosure.

In another exemplary embodiment, shown in FIG. 59, an MGHAE 8470, illustrated herein as a medical grade phone or cellular phone 8470, is coupled to a medical monitoring device 8472, illustrated herein as a heart rate monitor 8472. Medical grade phone 8470 includes a medical grade port 8474 and a medical grade module 8476. Using medical grade port 8474, signal transmission from medical monitoring device 8472 is achieved by direct connection with medical grade port 8474. The data represented herein as a wave form corresponding to a cardiac frequency is displayed on the phone screen, and different alarm settings corresponding to fast or slow heart rate can be set up using a phone key pad 8478. Medical grade module 8476 includes a controller 8480, non-transitory memory 8482, A/D converter 8482, and an isolation circuit 8486, connected to medical monitoring device 8472 by way of specialized medical grade port 8474 for receiving input signals from medical monitoring device 8472. Medical grade module 8476 connects to host electronics 8488 and host display 8490 for transmission and displaying of data received from medical monitoring device 8472. The signal processing of medical grade module 8476 includes processing by controller 8480, which receives data via medical grade port 8474 from medical monitoring device 8472, and converts the signal via the A/D converter 8482. Medical grade module 8476 includes isolation circuit 8486 to avoid the risk of electrical hazards. Thus, according to the present disclosure, medical monitoring devices can be made quite inexpensive since a phone's key pad 8478 (or control panel of a camera or remote control of a television) can be used as key pads or control panel of a medical device. Thus, the cost of key pads and control panels needed are eliminated, thereby allowing a medical monitoring device, such as medical monitoring device 8472, to be quite inexpensive. Furthermore, screens are already included in most phones and cellular phones. Additionally, display screens can be quite expensive, thus, by using other host screens, such as display 8490, the screen of a television, the screen of a computer, the screen of a camera, and the like, the cost of a screen for medical monitoring device 8472 is eliminated, thus further and greatly reducing the cost of medical monitoring device 8472. By medical grade port 8472 having proper safety features for isolation and other hazards, patient safety is assured.

Moreover, since medical grade module 8476 includes controller 8480, A/D converter 8482, and non-transitory memory 8482, all of those components which are currently present in a variety of biological monitoring devices and measurement systems are eliminated from said devices and systems, thereby reducing cost of the medical devices since one HAHE can be used to monitor a series of medical monitoring devices, and there is no need for additional screens, processors, memory, converters, and the like. The present disclosure provides the most cost-effective medical device since the medical device only include a sensor, a wire, and a connector to connect to the medical grade port, and/or a wireless transmitter.

In an exemplary embodiment, the primary port that would normally be used by the appliance manufacturer for service, diagnostics, etc., would remain in a default mode dedicated to the manufacturer's communication protocols and use. When a second, medical grade, port is connected to a medical device that measures temperature, heart rate, blood pressure, etc., the medical device loads its ID to the appliance and how it intends to communicate with the appliance's main port.

Generally, the output signal of most temperature sensors is analog. However, some temperature sensors include an integral A/D conversion, and the output may be input directly into a controller without conversion, providing a highly accurate measurement signal and eliminating the need for an A/D converter. However, this input needs to be on connector pins that connect directly to the controller rather than pins normally used for A/D conversion to reduce the chance that the signal is erroneously read if the temperature sensor or other medical monitoring device with a digital output is attached to a device with an A/D converter.

Figure 64:
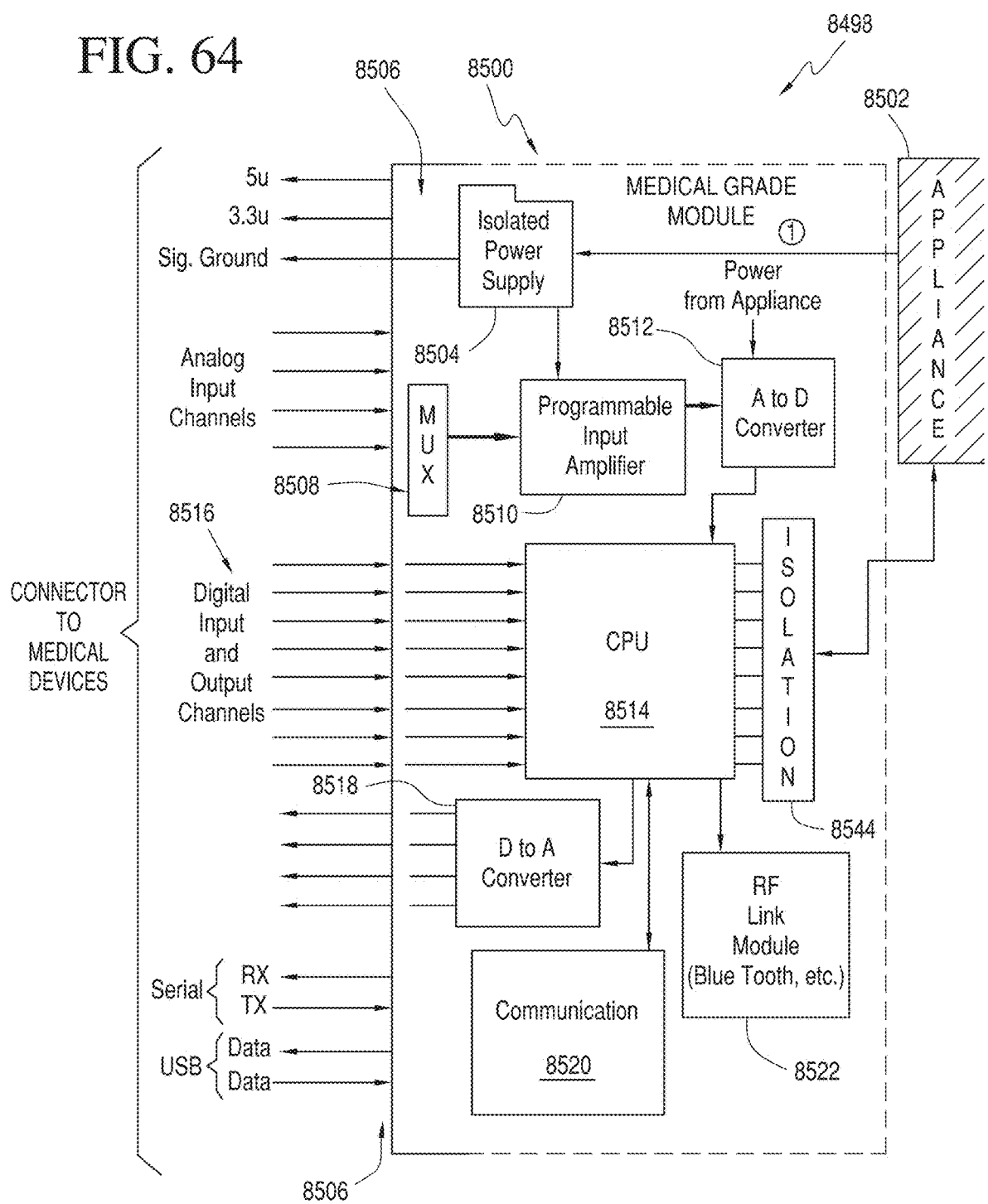
FIG. 64 is a block diagram showing a configuration of the medical grade module (MGM) internal to a medical enabled appliance, in accordance with an exemplary embodiment of the present disclosure.

FIG. 64 displays another exemplary embodiment MGHAE 8498 of the present disclosure, showing a configuration of medical grade module 8500 internal to a medical enabled electronic device or household appliance 8502. In an exemplary embodiment, medical grade module 8500 includes a power supply 8504 that is powered by household electronic device or appliance 8502 and totally isolates all the circuitry within medical grade module 8500 and any medical device connected to it by means of a medical grade port 8506. Analog inputs to medical grade module 8500 are routed through a multiplexer 8508 to a programmable amplifier 8510 to an A/D converter 8512 analog to digital converter (D). Programmable amplifier 8510 allows most sensors to be directly connected without the need for additional circuitry within the medical device itself. The digital output of A/D converter 8512 is directly connected to a controller 8514. In another exemplary embodiment, controller 8514 may include an A/D converter, and thus a separate A/D converter is not needed.

Digital data lines 8516 going to medical grade port 8506, which are usually in groups of 8 or 16 lines, are programmable as inputs or outputs as the situation may require for MGHAE 8498 acting as a diagnostic (input) or therapeutic (output) device.

In another exemplary embodiment, 8514 also controls a digital to analog (D/A) converter 8518 providing programmable voltage levels to an external medical device, allowing control of some sensors or therapy equipment without the need for additional circuitry within the connected sensor, therapy equipment, or other medical device.

Figure 63:
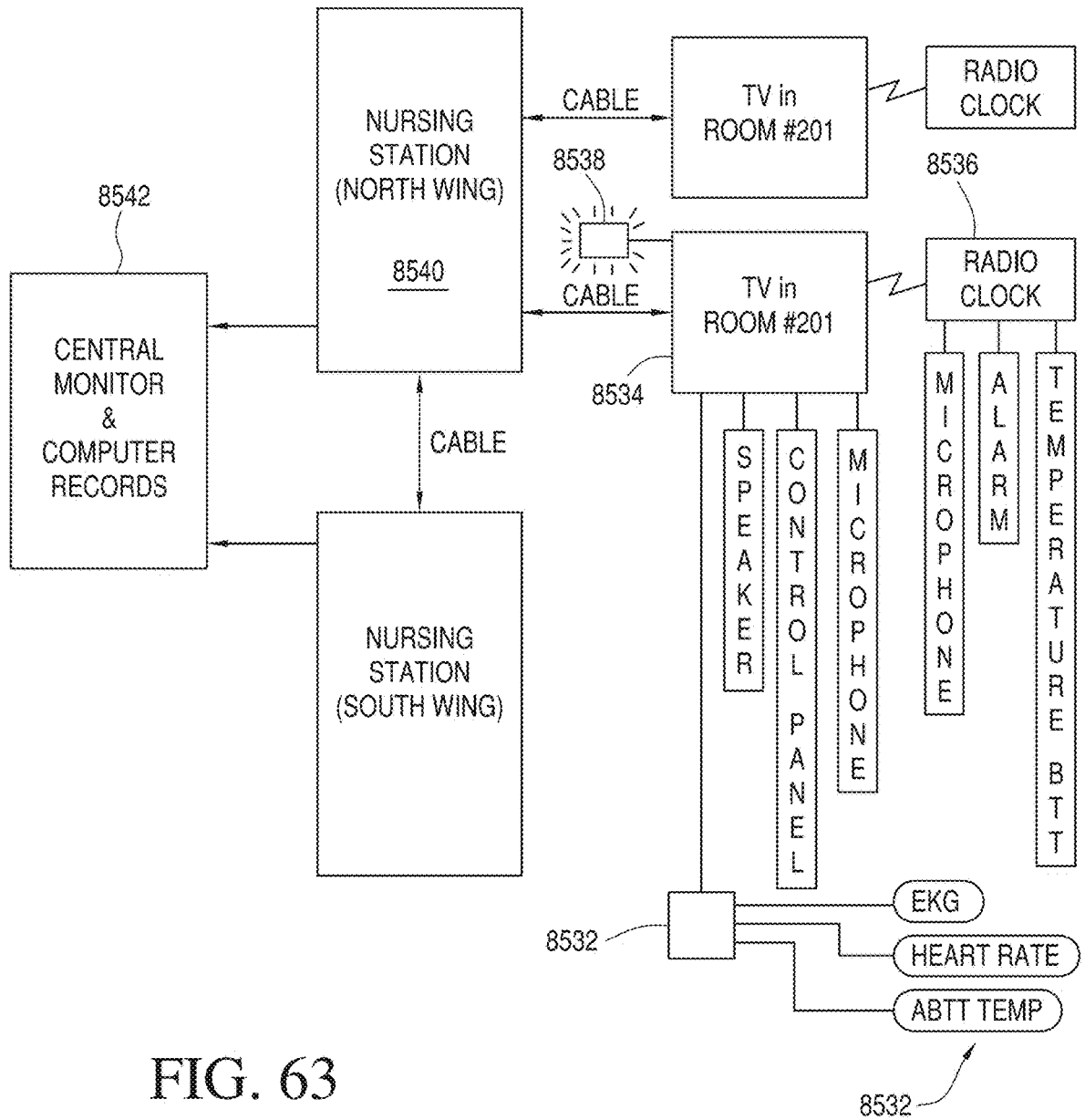
FIG. 63 is a block diagram showing an MGHAE System used in a hospital or nursing home, in accordance with an exemplary embodiment of the present disclosure.

A communication section or unit 8520 has the necessary components and wires to communicate directly with "smart" devices containing microprocessors using standard serial, USB, RS-232, or other protocols. An RF link, unit, or module 8522 includes hardware for wireless communication to a device or a series of devices in close proximity, with close proximity being at least feet, but could be tens of feet. Several different standards exist for intelligent "polling" and control of multiple RF linked transceivers that all interact with each other and can "pass" information packets from one to another to reach all those involved in a necessary task; i.e., the linked RF transceivers form an ad hoc local network. The present disclosure uses a saltatory transmission, in a similar manner as nerves impulses hop along axons. As shown in FIG. 63, this configuration allows medical grade module 8500 to receive information wirelessly from an ABTT probe, such as those disclosed herein, or other medical sensor 8530 by way of a medical grade port 8532.

Medical grade module 8500, which may be positioned in a television or MGHAE 8534 in a patient's room, displays the temperature on television 8534 or a clock radio 8536, and turns on a wirelessly connected alert light 8538 outside a patient's or subject's door, which sends it "down the line" to a nurse's station 8540. In an exemplary embodiment, a network of appliances and electronics is disclosed: Smart appliances, which include a medical grade module such as medical grade module 8500, the medical grade module further including wireless transmitters, circuitry, and controllers programmed for sequential transmission of a signal, when receiving a signal from a medical device with said signal falling outside a pattern or level of normality, or falling outside a predetermined level for the signal, activates transmission of that signal to the nearest appliance, and to a subsequent appliance until arriving at a central station (e.g., nurse station). These "smart medical grade modules" can be used in any environment and require little power because of their short transmission range.

When medical grade module 8500 is "awakened" by receiving an abnormal signal, medical grade module 8500 transmits that it was "awakened" to all adjacent medical grade modules and appliances containing the proper handshake protocol or encryption enabled communication over a discrete area, such as an entire house, floor of a hospital, wing of a hospital, etc., until finally reaching a central receiving medical grade module 8542, which may be a personal computer, laptop, tablet, or similar device, a server, a desktop computer, or a mainframe, where the identification of MGHAE 8498 that was "awakened" far away from central medical grade module 8452 is decoded and recorded. Furthermore, central medical grade module 8452 may communicate via one or more routes, including internet, cellular networks, Wi-Fi, and landline, to one or medical professionals that a condition exists which may require attention or correction, and in some cases, an emergency condition that requires immediate attention. In practice, medical grade modules may be communicating with medical grade modules that are inches apart to many feet apart.

An illustration will clarify the advantages and innovation of the present disclosure related to the saltatory transmission: a household has a plurality of appliances and electronics disposed in its various areas, inside and outside the house. Those appliances remain unused most of the time. However, these appliances and electronics have a variety of host electronics, transceivers, displays, etc., and the inventions of the present disclosure uses said host electronics, transceivers, display, etc. for reporting or communicating signals (preferably abnormal signals) to each other. For example, a house may have three rooms located in different parts of the house, each of said rooms having a child in it and each child has a medical device monitoring biological parameters. By way of example, one child (with heart problems) has a heart rate monitor, one child (with an infection) has a temperature monitoring device, and one child (with asthma) has an oxygen (or oximetry) monitoring device. The parents are outside working in the back yard away from her children. Once the child with an infection starts to develop fever, the signal is recognized by a processor integral to the medical monitoring device, based on comparison of the received signal with predetermined values for normality stored in non-transitory memory, as abnormal. The processor is programmed to recognize the abnormal signal and then to activate a wireless transmitter (in an exemplary embodiment, the transmitter is short range one, but any transmitter can be used—an exemplary transmitter includes a Bluetooth), to transmit the signal to the nearest appliance enabled with a smart medical grade module, such as medical grade module 8500. In an exemplary embodiment, the wireless transmitter is integral to the medical monitoring device, but it may be a separate wireless transmitter.

For example, the child with fever is in room with a medical grade television, which receives a signal from a medical monitoring devices that "awakens" the television with the abnormal signal. Once medical grade module 8500 in the television is awake, controller 8514 transmits a signal via RF link and, if available, communication section 8520 to all medical enabled appliances in range. For example, the television transmits its signal to the next room and "awakens" a video game including a medical grade module, which may also be similar to medical grade module 8500. Once the medical grade module of the video game is "awake," the medical grade module of the video game transmits the signal to an electronic clock in the living room that includes a medical grade module. The medical grade module of the electronic clock in the living room then awakens an enabled microwave in the kitchen. The medical grade module in the microwave then awakens the medical grade module in a central station presently position outside in the back yard, which then flashes a red light, or reports the information via a display. Once the abnormal signal reaches the central station outside, the ID (identification) of the medical monitoring device that was disturbed far away is provided to the central station outside, thereby identifying the child generating the abnormal signal. In an exemplary embodiment, the reporting apparatus includes a red light for the child with fever. If the child with asthma was sending the abnormal signal, then the light activated would be blue, and if the child with heart problems was transmitting the signal, the light activated would be yellow. This differentiation of signals allows the parents to know immediately and precisely which child requires assistance. At night, the central station can be in the parents' room, so if any child during the night has a problem the abnormal signal would be transmitted to the parents' room using all medical grade module enabled appliances and electronics.

Although the present embodiment was described for medical care in a house, the system can have a plurality of applications. For example, a burglary alarm, in which opening a door or window at a certain time of the night awakens other medical grade module enabled appliances that will transmit signals to the central station, possibly indicating a burglary in progress. The same apparatus configuration can apply to an alarm system in a bank, or alarm system in a hospital, and the like. The present embodiment takes advantage of the low price of wireless transmitters (e.g. Bluetooth) and of electrical and electronic appliances already in use to create a precise, efficient, and low cost alarm system. Any electrical devices outside the house can be enabled with a medical grade module and used as part of the sequential alarm system of the invention, including a chain saw, lawn mower, leaf blower, snow blower, weed trimmer, electrical pump, or any other device that either has a battery or is connected to an electrical outlet, so as to power the medical grade module in an embodiment in which the medical grade module does not have its own power supply. Preferably, electrical power is derived from the standard (and already used) connection of the appliance or electrical device to an electric outlet.

Magnetic or optical isolation 8544 would transfer the necessary digital data between medical grade module 8500 and host appliance 8502. Isolation 8544 is a two-way path covering control signals and data to medical grade module 8500 or to/from a medical monitoring device directly.

Figure 67:
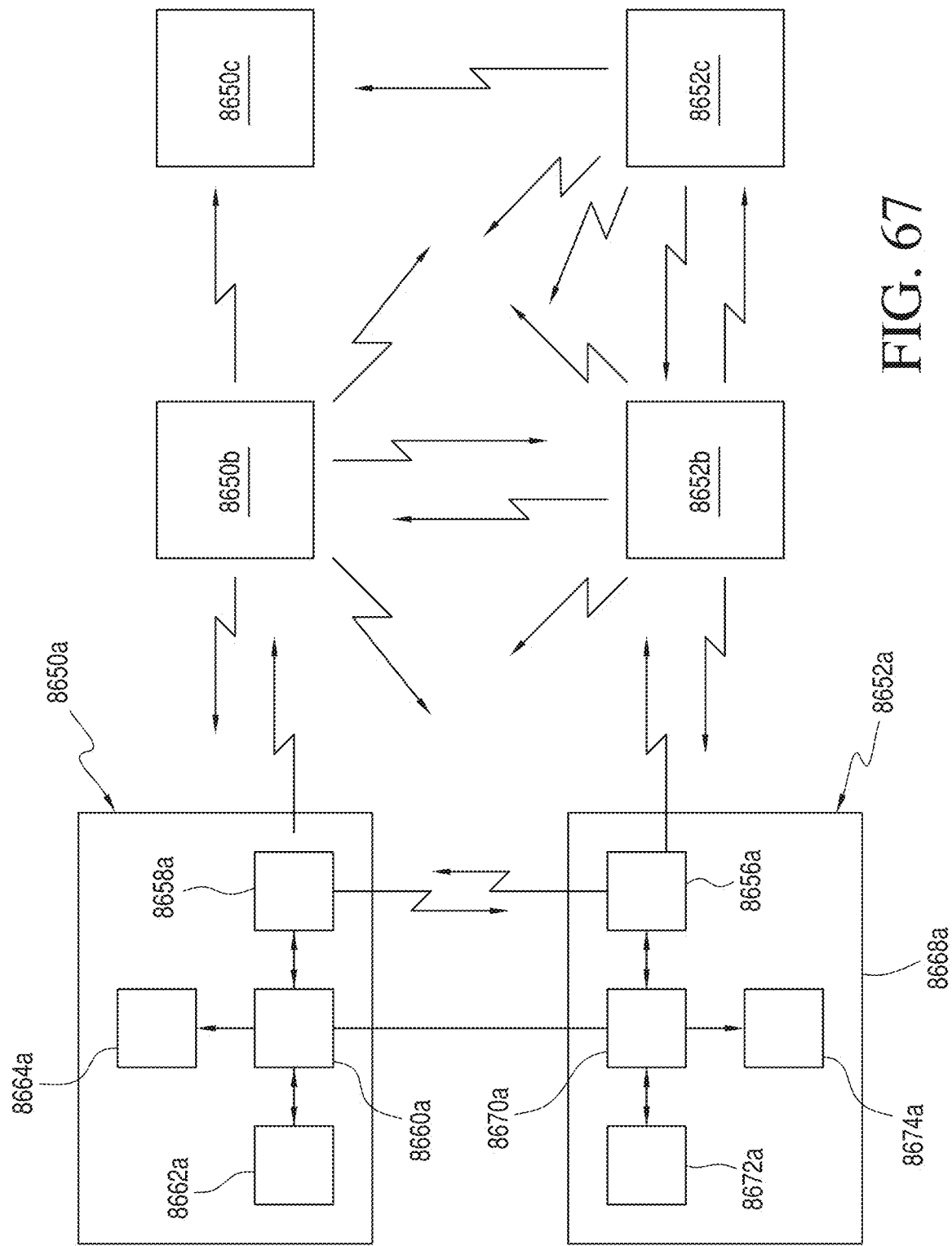
FIG. 67 is a block diagram of an ad hoc network of medical monitoring devices and household appliances in accordance with an exemplary embodiment of the present disclosure.

The MGHAE, also referred herein as Medically-enabled household appliances and electronics (MEHE) include an embodiment, shown in FIG. 67, exemplified as a medically enabled television 8650*a*. Medically enabled television 8650*a* is operatively coupled to a medical device 8652*a*, exemplified herein as a blood pressure (BP) monitor. The majority of medical complications occur as a result of lack of compliance in taking medications, from patients going blind by not taking their anti-glaucoma medications to patients having a stroke by not taking their BP medication. This embodiment is to provide an improved living condition for patients with a medical condition, who might otherwise have a disabling medical event, such as a stroke, as a result of not paying attention to abnormal BP levels.

Applicant has recognized that patients are often diligent about taking certain actions when specifically reminded. For instance, patients will bring their blood pressure measuring device to a doctor's appointment when reminded by someone in the medical professional's office. In many instances, patients measure their blood pressure (BP) and read levels that are high and in some instances alarming. In one exemplary example, a patient X had spent the weekend prior to having a stroke watching television, listening to music, cooking, and working on a computer. Despite high BP levels measured that same weekend, patient X did not take medications for lowering blood pressure, nor did patient X contact a doctor. It appears that patient X was focused on media, information devices, and even cooking, such that patient X "forgot" to address a high BP problem. Unfortunately, patient X suffered a stroke and became permanently disabled. Even more unfortunately, patient X's situation appears to be somewhat common in individuals with potentially life-threatening conditions. Applicant further recognized that this situation appeared even more common among individuals who lived alone.

Figure 77:
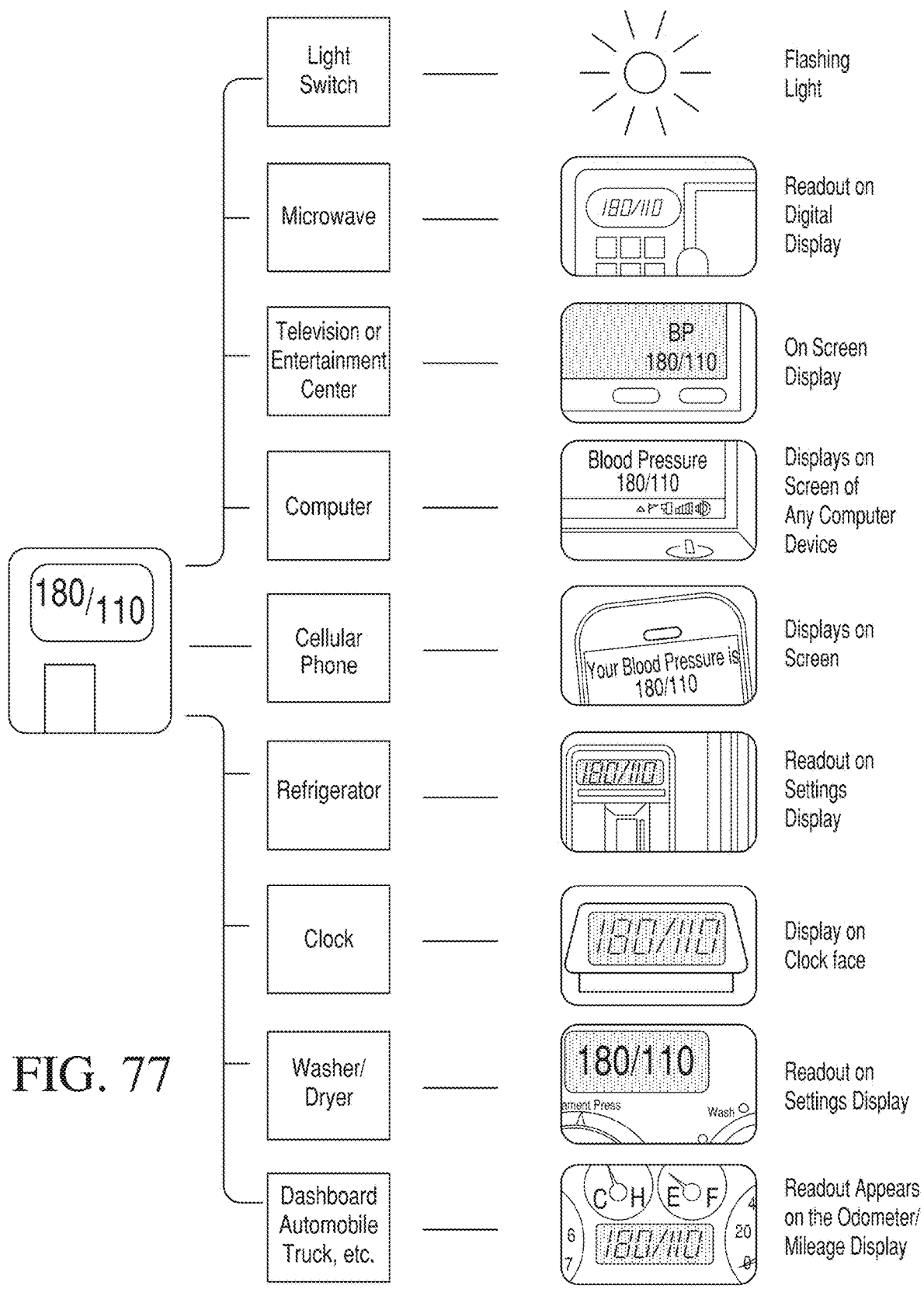
FIG. 77 shows various medically enabled household devices in accordance with an exemplary embodiment of the present disclosure.
Figure 78:
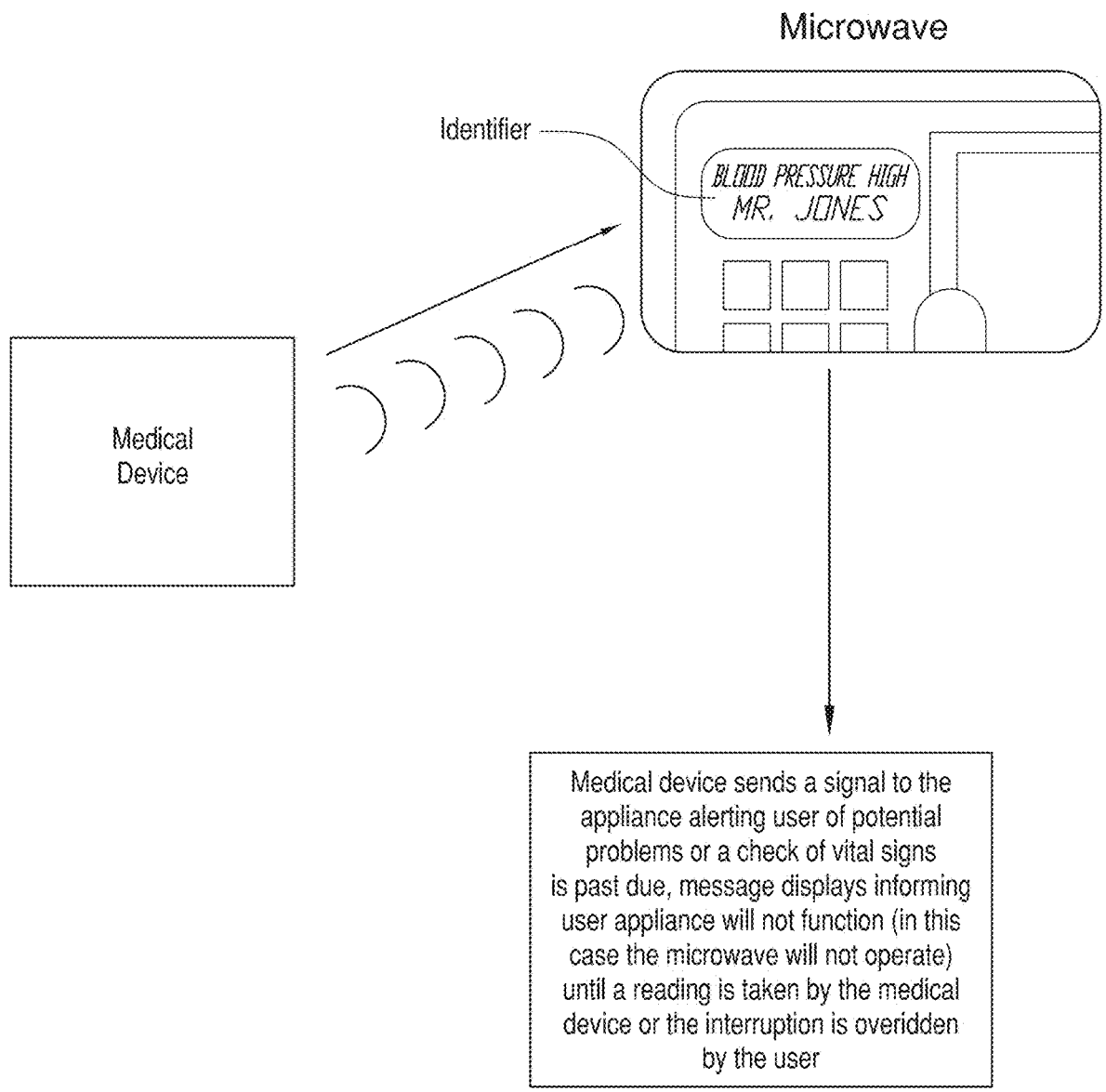
FIG. 78 shows a medically enabled microwave in accordance with an exemplary embodiment of the present disclosure.

Applicant recognized that a uniquely enabled system, such as that shown in FIGS. 67, 77, and 78, in which medical devices 8652*a*-*c* are operatively coupled with electrical and electronic device 8650*a*-*c* reduce the chance of having a preventable medical event from happening by medical devices 8652*a* communicating with electrical and electronic devices 8650*a*-*c* and interfering with their function until the abnormal level measured by one or more medical devices 8652*a*-*c* is corrected in some fashion. Accordingly, FIG. 67 shows medical devices 8652*a*-*c* coupled or connected by a wired connection 8654*a*-*c* or by a near field communication device 8656*a*-*c* to a plurality of household appliances, electrical and electronic devices 8650*a*-*c*, including by way of example, television set 8650*a* including, in an exemplary embodiment, wireless transceiver 8658*a*, a processor 8660*a*, a non-transitory memory 8662*a*, and reporting apparatus 8664*a*. Medical device 8652*a* further includes a medical device housing 8668*a*, wireless transceiver 8656*a*, a controller or processor 8670*a*, a non-transitory memory 8672*a*, and a reporting apparatus 8674*a*, such as audio and visual display. Exemplary appliances and electrical device and electronic devices 8650*a*-*c*, include, by way of illustration, television, refrigerator, microwave oven, stove, lawn mower, weed trimmer, leaf blower, snow blower, clock, washer/dryer machine, radio, video game, computer, cell phone, phone, vehicle dash board, and a light switch, examples of which are shown in FIG. 77 and FIG. 78, and any device that can be actuated and/or the function altered by receiving a signal from medical device(s) 8652*a*-*c*. Exemplary medical devices 8652*a*-*c*, by way of illustration, but not limitation, include thermometer, blood glucose meter, heart rate monitor, blood pressure monitor, and oxygen monitor.

Figure 68:
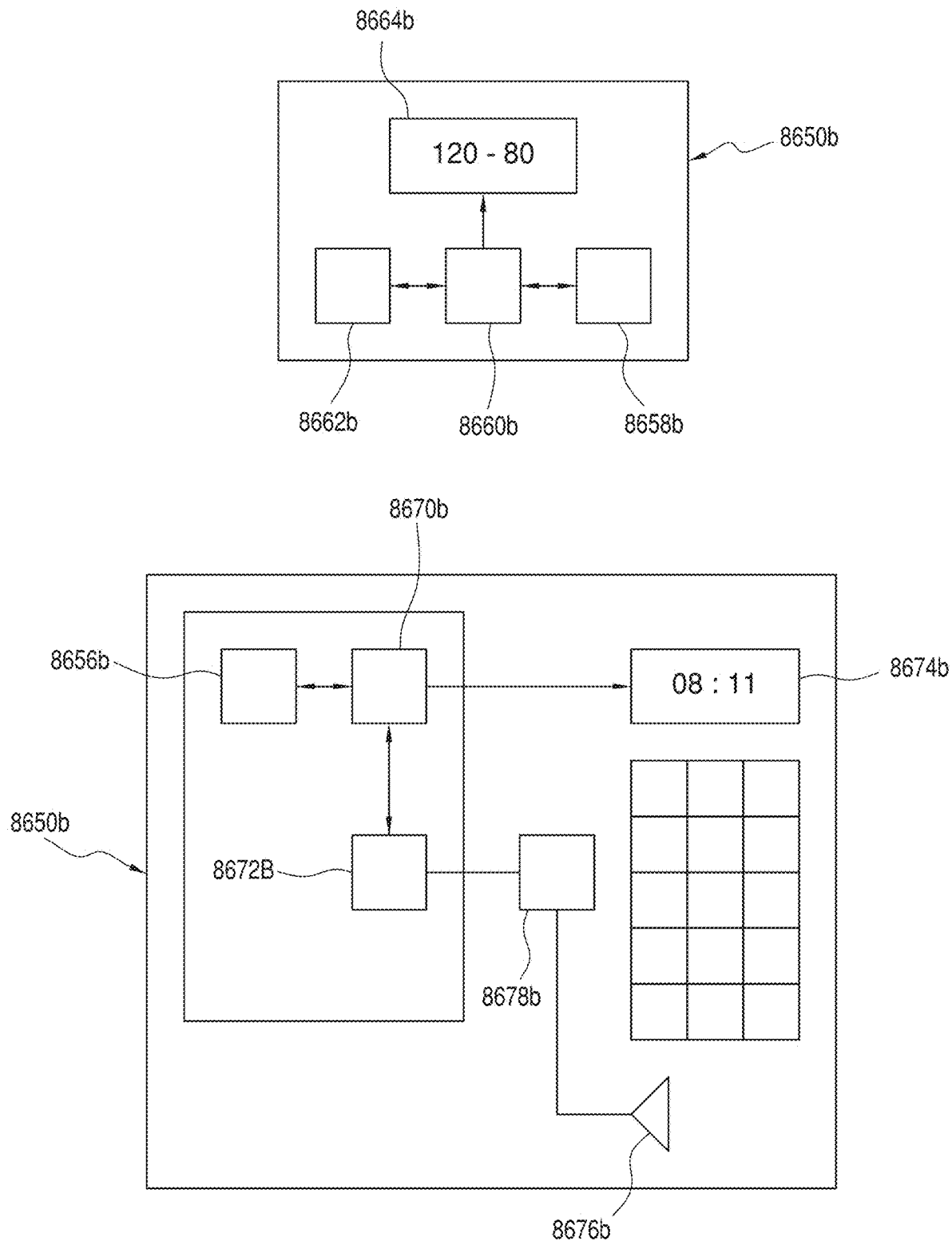
FIG. 68 is an exemplary medical monitoring device and household appliance in accordance with an exemplary embodiment of the present disclosure, with the reporting apparatus of the household device providing a conventional function.
Figure 69:
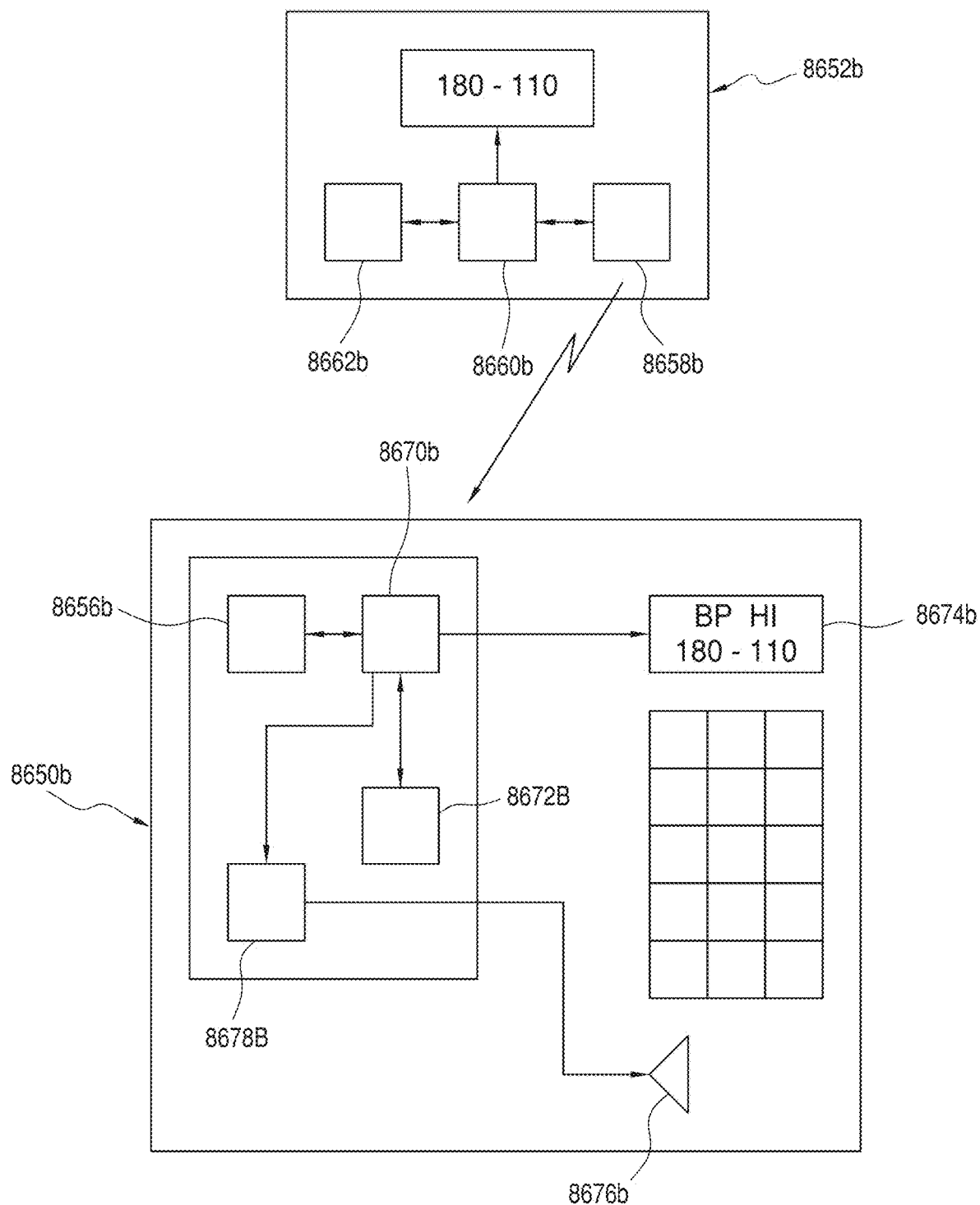
FIG. 69 is the medical monitoring device and household appliance of FIG. 68, with the reporting apparatus of the household device displaying a medical condition from the medical monitoring device.

FIGS. 68 and 69 show exemplary medical device 8652*a* measuring BP coupled with household appliance 8650*b* (illustrated as microwave oven) in two situations. In FIG. 68, medical device 8652*a* registered BP within normal levels, thus controller 8670*a* does not activate wireless transceiver 8658*a* to transmit signal to household appliance 8650*b*, and thus household appliance 8650*b* provides in reporting apparatus 8674*a* customary information, represented by time, e.g., 08:35 AM. In FIG. 69, medical device 8652*a* registered BP outside normal levels, thus processor 8670*a* activates transceiver 8658*a* to transmit signals to household appliance 8650*b*, informing household appliance 8650*b* of the high BP. Controller 8660*b* of appliance 8650*b*, by receiving abnormal BP values, executes a series of functions including executing a program that displays in reporting apparatus 8674*b*, which in the exemplary embodiment of FIG. 68 is a digital display, BP HI, which may alternate with a blood pressure reading, for example, 180-110, depending on the number of digits that digital display 8674*b* is capable of displaying. Furthermore, in an exemplary embodiment, controller 8660*b* causes a delay in the cooking function of the microwave oven 8650*b*. Microwave oven 8650*b* may include an audio amplifier 8678*b* connected to controller 8660*b* and connected to a speaker 8676*b* that delivers an audio alert informing the user that cooking function is delayed to allow the user to take medications for BP. In this manner, appliance 8650*b* is helping the user to take care of his or her health and reminding and motivating the user to take his or her medications. Speaker 8674*b* or display 8674*b* can also display the name of the medication to be taken. If the BP signal transmitted by medical device 8652*b* is at dangerously high levels, the function of appliance 8650*b* may become disabled for a predetermined time to allow the user to take care of his or her health, or the function of appliance 8650*b* remains disabled until controller or processor 8670*b* receives data from medical device 8652*b* consisting with normal BP values (or a reduction of the BP values). Priority in the function of controller or processor 8670*b* is normalization of BP levels, the microwave function is only enabled after dangerously high BP levels are reduced to an acceptable level. A signal from medical device 8652*b* can also be sent to at least one other appliance 8652*c* located remotely, as shown in FIG. 67. Furthermore, all appliances 8650*a-c* provided with the apparatus described hereinabove transmit data to each other as well as all medical devices 8652*a-c*. Similarly, all medical devices 8652*a-c* provided with the apparatus described hereinabove transmit data to each other as well as appliances 8650*a-c*. Thus, appliances 8650*a-c* and medical devices 8652*a-c* form an ad hoc local area network. When output of any one medical device 8652*a-c* is abnormal or unusual, signals are transmitted to all devices in the network and displayed on all devices in the network when they are powered. In an exemplary embodiment, an appliance 8650*a-c* may be powered on to provide an indication of an abnormal output. Also, in-use appliances, such as a television or computer, may have their display overwritten with the abnormal value, and even a flashing alarm display may be provided on the display.

Vehicle Safety System

Figure 65:
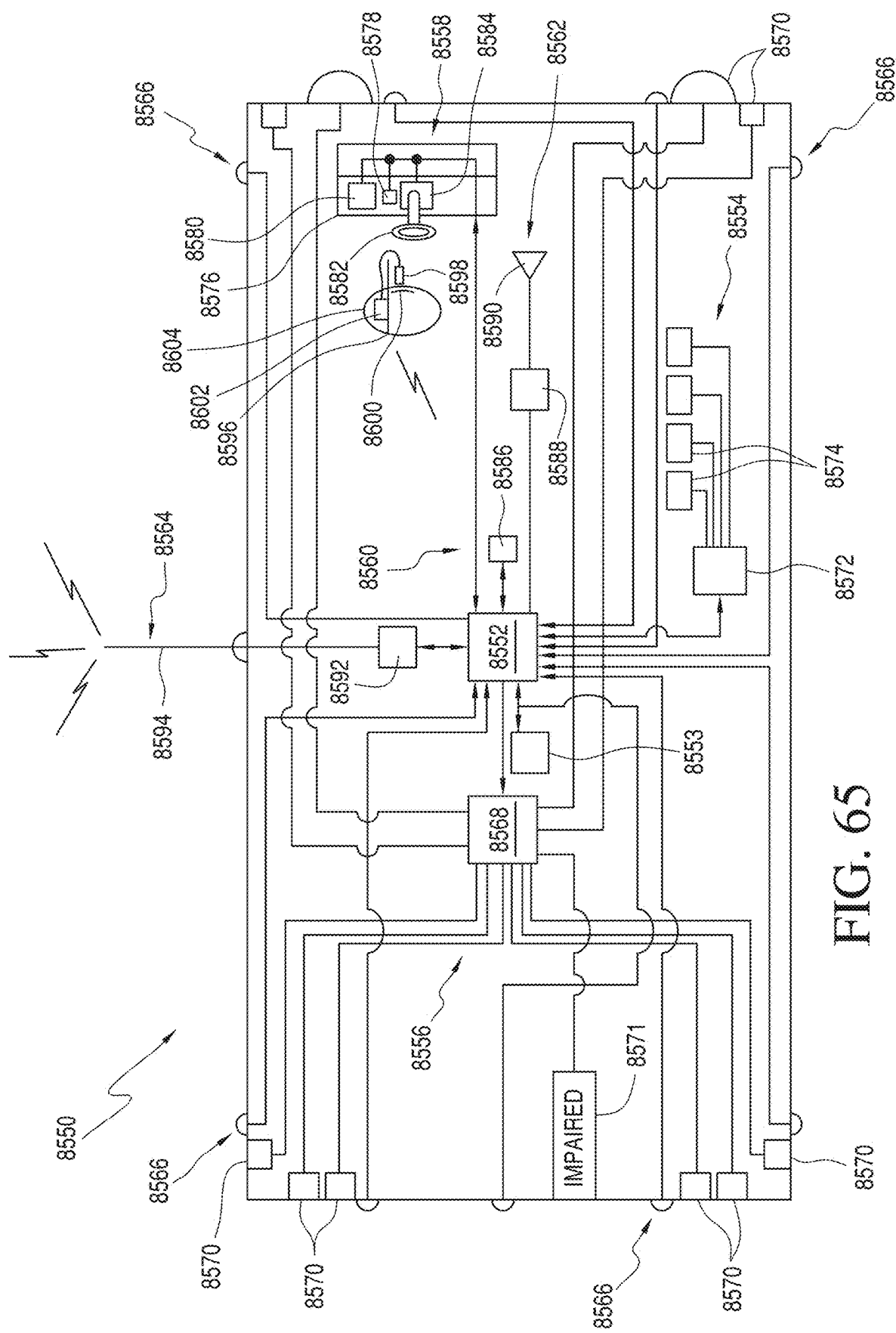
FIG. 65 is a block diagram of a vehicle implementing a safety system in accordance with an exemplary embodiment of the present disclosure.

The capability to measure the temperature of the skin over the ABTT terminus and to analyze that information provides new capabilities for safety in the operation of equipment. Referring to FIG. 65, a vehicle is shown and generally indicated at 8550. Vehicle 8550 incorporates an ABTT temperature sensor driven system that is configured to improve the safe operation of any vehicle by providing ABTT temperature sensor information to a controller, which is able to at least provide warnings to other vehicles in the event of operator incapacity, and may be to take control of vehicle 8550 to bring vehicle 8550 to a stop, to steer vehicle 8550 to a safe location, such as a shoulder. Additionally, the system incorporated in vehicle 8550 may have the ability to call for assistance and provide specific information as to the nature of an operator's incapacity. It should be understood that, besides ABTT monitoring, any other medical device monitoring or measuring of a biological parameter (such as blood pressure, heart rate, oxygen, glucose, temperature and the like) can be used as sensor driving system according to this invention.

In an exemplary embodiment, vehicle 8550 includes a vehicle system controller 8552, which is connected to a braking system 8554, a lighting system 8556, and a vehicle control system 8558. Vehicle 8550 may also include a near-field communication system 8560, a speaker system 8562, an external communication system 8564, and a sensor system 8566.

Vehicle system controller 8552 is connected to a non-transitory memory 8553, which provides information and routines to vehicle system controller 8552.

In an exemplary embodiment, lighting system 8556 includes a lighting system controller 8568, which is connected to a plurality of vehicle lights 8570. As discussed further herein, one or more systems in vehicle 8550 may command lights 8570 to operate. For example, switches may directly command headlights, and turn signals. Actuation of brakes may command brake lights. The request for lights may go directly to lighting system controller 8568, or may go to vehicle controller 8552, which sends control signals to lighting system controller 8568.

In an exemplary embodiment, braking system 8554 includes a braking system controller 8572, which is connected to vehicle system controller 8552 and a plurality of individual brakes 8574. Braking system controller 8572 controls the amount of braking provided by each one of the plurality of individual brakes 8574, each of which is positioned close to one of vehicle 8550 wheels (not shown). Braking commands by an operator may be routed to vehicle system controller 8552, which then routes the braking command to braking system controller 8572, or, in another exemplary embodiment, braking commands are directed from a brake pedal or other brake actuator (not shown) directly to brake controller 8572.

In an exemplary embodiment, vehicle control system 8558 includes the controls the operator uses to operate the vehicle. Operator controls are typically positioned on or near a dashboard 8576. Controls included in control system 8558 may include an override switch 8578, a display 8580, a steering column and wheel 8582, and a steering control unit 8584. Steering control unit 8584 may be commanded by movement of steering column and wheel 8582, or it may be controlled by vehicle system controller 8552, as described further herein. Display 8580 provides operator alerts on dashboard 8576. Other types of operator controls exist. However, such controls are not discussed in this disclosure.

In an exemplary embodiment, near field communication system 8560 may include one or more system elements, such as a near field transceiver 8586, which is connected to and communicates with vehicle system controller 8552. Near field communication system 8560 may be, for example, a Bluetooth connection.

In an exemplary embodiment, speaker system 8562 may include an amplifier 8588, which may be connected to vehicle system controller 8552, and at least one speaker 8590, which is connected to amplifier 8588. Sound signals may be directed into vehicle system controller 8552, which then directs the sounds signals to amplifier 8588, or vehicle system controller 8552 may generate sound signals, which are provided to amplifier 8588 and, ultimately, speaker 8590.

In an exemplary embodiment, external communication system 8564 includes a transceiver 8592 and an antenna 8594. External communication system 8564 may be a system that communicates with a remote location for emergency communication, roadside assistance, etc.

An operator 8596 of vehicle 8550 has an ABTT temperature sensor 8598 positioned to measure the temperature of the skin over the ABTT terminus 8600. ABTT temperature sensor 8598 is connected to a battery and a near field transceiver or transmitter 8602. The battery to power ABTT temperature sensor 8598 and the transceiver that connects ABTT temperature sensor 8598 to near field communication system 8560 may be located in many different places, such as a hat 8604, eyeglass frame (not shown), headband (not shown), or other locations.

Figure 66:
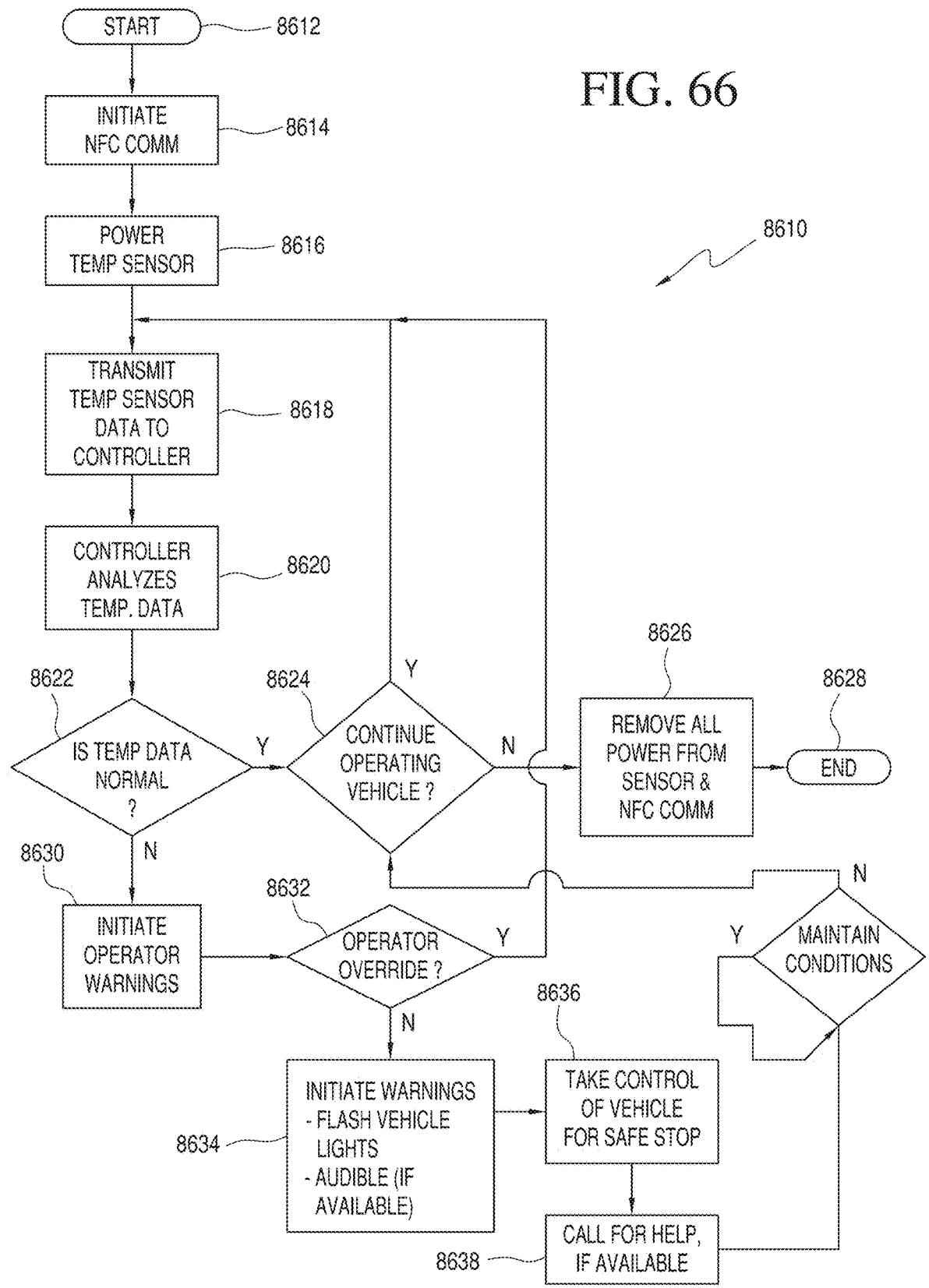
FIG. 66 is a process flow chart showing an exemplary process of the present disclosure that may be used with the vehicle of FIG. 65.

A safety function of vehicle 8550 is described with respect to FIG. 66, which shows an incapacitated operator safety system process, generally indicated at 8610, in accordance with an exemplary embodiment of the present disclosure. Safety system process 8610 begins with a start process 8612. In start process 8612, vehicle 8550 is started, and systems of vehicle 8550 are powered, such as vehicle control system 8558, braking system 8554, etc. Certain portions of vehicle 8550 may clear registers, upload programs, and data from non-transitory memory 8568, etc. Once start process 8612 is complete, control passes to an initiate near field communications (NFC) process 8614.

In NFC process 8614, NFC system 8560 is powered, and NFC system 8560 determines the presence of operating NFC devices that have been properly connected to NFC system 8560. One such NFC device is transceiver or transmitter 8602, which is connected to ABTT temperature sensor 8598, which is positioned to measure the temperature of the skin over ABTT terminus 8600. If transceiver 8602 is operating, NFC system 8560 will initiate communications with transceiver 8602. Once communication is established with transceiver 8602, control passes from NFC process 8614 to a power temperature sensor process 8616.

ABTT temperature sensor 8598 may be powered by a switch located on ABTT temperature sensor 8598, or on battery and transceiver 8602, or elsewhere. In an exemplary embodiment, transceiver 8602 may contain electronics to automatically power ABTT temperature sensor 8598 once communication with a controller enabled to receive temperature data has been established. In an exemplary embodiment, ABTT temperature sensor 8598 is powered only while receiving temperature data, and remains off at other times. In another exemplary embodiment, ABTT temperature sensor 8598 may be powered by a battery pack located in hat 8604. In yet another exemplary embodiment, ABTT temperature sensor 8598 may be powered by vehicle 8550, which may be accomplished by a connection to a power outlet of vehicle 8550 or through other apparatus. Once power has been provided to ABTT temperature sensor 8598, control passes from power temperature sensor process 8616 to a transmit data process 8618.

In transmit data process 8618, ABTT temperature sensor 8598 reads temperature, which is presumably the temperature of ABTT terminus 8600, and sends a signal representing the temperature data to transceiver or transmitter 8602. The data from ABTT temperature sensor 8598 is analog. This analog data may be converted to digital data by an A/D converter located in proximity to or contained as a part of transceiver 8602. Alternatively, the analog temperature signal may be provided to transceiver 8602 for transmission. Transceiver 8602 transmits the temperature data to vehicle near field transceiver 8586. Near field transceiver 8586 transmits a signal to vehicle system controller 8552 that represents the temperature measured by ABTT temperature sensor 8598. Control then passes from transmit data process 8618 to a data analysis process 8620.

In an exemplary embodiment, data analysis process 8620 is performed in vehicle system controller 8552. However, data analysis process 8620 may be performed in a controller (not shown) specifically configured to process temperature data. In another exemplary embodiment, temperature data may be transmitted to a portable controller (not shown) specifically configured to process temperature data, and data transmission is from the portable controller to vehicle system controller 8552.

Data analysis process 8620 performs several functions. First, data analysis process performs a validity check on the temperature data. This validity check determines whether the temperature data is measuring the temperature of ABTT terminus 8600. If the temperature data is not valid, in an exemplary embodiment, vehicle system controller 8552 provides a visual alert to operator 8596 via vehicle display 8580, an audible alert to operator 8596 via speaker 8590, or other types of alerts that may include seat vibrations, steering wheel shakers, cell phone ringing alerts, etc. Failure to properly measure temperature may be because ABTT temperature sensor 8598 is not operating properly, because it is misaligned with ABTT terminus 8600, because it is malfunctioning, because insufficient power, improper communications, or for other reasons. If the temperature is not valid, it will be considered a not normal condition for other safety system 8610 processes.

If the temperature data is valid, data analysis process 8620 analyzes the temperature data for at least one condition of operator 8596. Once such condition may be a drowsiness or sleepiness condition, such as that described in connection with FIGS. 16 and 17. If vehicle 8550 is configured to perform spectrum analysis, data analysis process 8620 may perform a frequency analysis, such as that shown in FIGS. 21 and 22. If the temperature analysis predicts, because temperature at BTT terminus 8600 is predictive of impending events, or indicates that operator 8596 is about to become impaired due to a condition, which may be a medical condition or sleep, or is currently impaired, then the result of data analysis process 8620 is a not normal temperature condition. Once the temperature data has been analyzed, control passes to a normal temperature data decision process 8622.

In normal temperature data decision process 8622, a process path is chosen based on whether temperature data is valid and normal or whether the temperature data is not normal. A not normal condition may be indicated because the temperature data is invalid or because the temperature data indicates an operator 8596 impaired condition. If the temperature data is valid and normal, control passes from normal temperature data decision process 8622 to continue operating vehicle decision process 8624.

In continue operating vehicle decision process 8624, safety system process determines whether operation of vehicle 8550 is continuing. Such decision may be made on the basis of continued operation of various vehicles systems, such as a combustion system (not shown), an ignition key (not shown) position, or other indicators of continued vehicle operation. If operation of vehicle 8550 is continuing, control passes from continue operating vehicle decision process 8624 to transmit data process, and safety system process 8610 continues as previously described herein. If operation of vehicle 8550 is ceasing, control passes from continue operating vehicle decision process 8624 to a remove power process 8626.

In remove power process 8626, power to ABTT temperature sensor 8598 is removed, power to transceiver or transmitter 8602 is removed, and various vehicle systems are powered down as operation of vehicle 8550 ends. During this process, certain data, potentially including temperature data from ABBT temperature sensor 8598, may be stored in non-transitory memory 8568 to be used the next time vehicle 8550 is operated. It should be apparent that multiple operators may use vehicle 8550, and each ABTT temperature sensor 8598 may be associated with a specific individual, or an individual ABTT temperature sensor 8598 may be associated with a specific operator via a vehicle input (not shown). Thus, temperature data may be stored in non-transitory memory to establish a baseline for current measurements. Once power has been removed from vehicle systems that are associated with operation of vehicle 8550, control passes from remove power process 8626 to an end process 8628, which ends safety system process 8610.

Returning to normal temperature data decision process 8622, if the temperature data is not valid or normal, control passes to an initiate operator warnings process 8630. In initiate operator warnings 8630, in an exemplary embodiment, display 8580 may provide an indicator or warning that temperature data is not valid, indicates an impending impairment condition, such as sleep or a medical condition, or indicates that an impairment condition is occurring. In another exemplary embodiment, an audible warning may be provided by speaker system 8562. Such audible warnings may be tones, warbles, alarms, etc., or may be an audible warning, for example: "Temperature data invalid," "Impairment condition imminent," or "Driver Impaired." Once one or more operator warnings have been initiated, control passes from normal temperature data decision process 8622 to an operator override decision process 8632.

In operator override decision process 8632, operator 8596 has an opportunity to override any further action by safety system process 8610 by providing an input to vehicle system controller 8552. In an exemplary embodiment, such input may be by way of a switch, such as override switch 8578. In other exemplary embodiments, inputs may be via a touch screen on a display, such as display 8580, via voice command, via gesture, or other via other apparatus that reduces or prevents inadvertent override commands. Reducing the chance of inadvertent override commands may including placing override switch 8578 behind a protective shield that is required to be lifted, by biasing override switch 8578 into an off position, requiring the bias to be moved to actuate override switch 8578. For purposes of continued operation and in an exemplary embodiment, operator override decision process 8632 may automatically consider an invalid temperature data condition as an automatic operator override. If operator 8596 selects override, or if temperature data is invalid, control passes from operator override decision process 8632 to transmit data process 8618, and operation of safety system process 8610 continues as previously described.

If operator 8596 does not indicate or select override of initiated warnings, and if temperature data indicates an impending impairment condition or active impairment condition, control passes from operator override decision process 8632 to an initiate vehicle warnings process 8634. The function of initiate vehicle warnings process 8634 is to warn drivers around vehicle 8550 that the operator of vehicle 8550 is suffering from an impairment condition, which may be sleep, medical, or other impairment condition that may be detected by ABTT temperature sensor 8598. In exemplary embodiments, such warnings may be flashing of one or more external lights 8570, including flashing in specific patterns, flashing of special "impairment" lights 8570 located in non-traditional locations, such as the sides of vehicle 8550, along the doors of vehicle 8550, or in other locations. In an exemplary embodiment, vehicle lights 8570 may include a new type of lighting for vehicles comprising a medical alert light, which, when activated, indicates medical emergency and risk of accident by the driver being incapacitated. These lights may include a new set of lights in vehicles, such as two rear lights and two front lights that flash only in medical emergencies. In another exemplary embodiment, conventional vehicle lights 8570 could be activated in a strobe (high frequency) level to alert other drivers and people. In yet another exemplary embodiment, a sign 8571 indicating "impaired," "medical," or other word or symbol, such as a red cross or caduceus may be present in a location visible at least from one of a back, front, or side of vehicle 8550. In another exemplary embodiment, impaired or medical light 8571 may be present on the top of vehicle 8550, providing for rapid identification of vehicle 8550 from the air by helicopters or airplanes responding to an emergency request.

In another exemplary embodiment, warnings may be audible external to vehicle 8550, such as sounding of a car horn or speakers warning of an impaired operator. Such audible warnings may be a specific pattern of tones or sounds that may be adopted to indicate impaired operator. External vehicle warnings will continue at least until vehicle 8550 is turned off, though such warnings may require a reset specifically to stop external vehicle warnings, such as by actuating override switch 8578. Once vehicle warning(s) have been initiated, control passes from initiate vehicle warnings process 8634 to a control vehicle process 8636.

In control vehicle process 8636, controller 8552 takes control of vehicle 8550 to the extent that controller 8552 is enabled to bring vehicle 8550 to a controlled stop in the safest manner possible. In an exemplary embodiment, such control may be actuating braking system 8572 to activate individual brakes 8574. In an exemplary embodiment, such braking is configured to be a rapid stop, but not an emergency stop where brakes are locked up and tires screech, because such a stop risks a rear end collision in the presence of another vehicle behind vehicle 8550. In another exemplary embodiment, controller 8552 may be enabled to control steering wheel 8582 via steering control unit 8584, such that controller 8552, by receiving inputs from sensor system 8566, is able to steer vehicle 8550 onto a shoulder or side of a road out of traffic, and then provide braking to vehicle 8550. Once control vehicle process 8636 is complete control passes to a call for help process 8638.

In call for help process 8638, if vehicle 8550 is configured with an external communication system 8564, vehicle system controller 8552 will initiate a call for help via antenna 8594. Alternatively, vehicle 8550 may be coupled to a cell phone (not shown) of operator 8596, and thus the cell phone becomes part of external communication system 8564, and the cell phone can initiate a call for help under the command of vehicle system controller 8552.

Though safety system process 8610 shows call for help process 8638 occurring after external vehicle warnings are initiated and after controller 8552 has taken control of vehicle 8550, if vehicle 8550 is configured to permit controller 8552 to have such control, call for help process 8638 may occur while initiate vehicle warnings process 8634 and control vehicle process 8636 are in process to enable the fastest emergency response possible to the condition of operator 8596.

Once call for help process 8638 is complete, safety system process 8610 has performed all the functions enabled in vehicle 8550 that permit warning other vehicle operators, controlling vehicle 8550 to a stop, or moving vehicle 8550 to the side of the road and then stopping vehicle 8550, and calling for help. Control then passes to a maintain conditions decision process 8640.

In maintain conditions decision process 8640, vehicle system controller 8552 will maintain vehicle 8550 in a stopped condition with external warnings continued until either fuel and battery power are depleted, until vehicle 8550 is turned off, or until override switch 8578 is actuated. If any condition exists that indicate maintaining warnings, maintain conditions decision process 8640 will loop back on itself. If a power off or fuel and battery power depleted condition occurs, or if the condition that led to warnings and control has been overridden or reset, control may return to any previous point in safety system process 8610. In an exemplary embodiment, control passes from maintain conditions decision process 8640 to continue operating vehicle decision process 8624, and operation of vehicle safety process 8610 continues as previously described.

ABTT Monitoring

While this disclosure provides significant information regarding apparatus for measuring the temperature at the skin adjacent to, over, or on the brain thermal tunnel or ABTT, ultimately the value and benefit of ABTT measurements is for monitoring, diagnosis, and treatment of patients or subjects. In the following paragraphs are exemplary embodiments of applications of ABTT measurements, which may be made by the apparatus disclosed herein or by other apparatus appropriately configured to locate and measure the skin at the ABTT terminus.

Sleep Studies and Diagnosis

As described herein, measures of body core temperature may not reflect brain temperature and, certainly, are not suited for detecting rapid changes in brain temperature. Use of an embedded hypothalamic probe in sheep has identified changes in hypothalamic temperature disproportionate to those of intracarotid and rectal probes. Applicant has established that a surface sensor placed on the skin of the SMO and eyelid overlying a "brain thermal tunnel" (ABTT), to the cavernous sinus constitutes an effective means for continuous noninvasive assessment of intracranial brain temperature. Applicant tested whether ABTT monitoring via a surface probe on the skin at the ABTT terminus (e.g., see FIG. 12) during sleep would identify characteristic sleeping brain patterns including sleep onset, arousal during sleep, and awakening.

Over 200 patients and healthy subjects participated in the studies. By way of illustration, equally calibrated temperature sensors were placed or positioned on the SMO skin of six subjects. Five of the subjects also had a temperature sensor positioned on the skin over the temporal artery of the forehead. The sixth subject had a rectal thermometer probe positioned to measure rectal temperature. Simultaneous readings in degrees Celsius were obtained at intervals ranging from 15 to 60 sec during sleep in a persistently dark room. All subjects urinated at least once during the study period to measure arousal or awakening; urination was into a urinal to avoid ambulation). Temperature increases and decreases were quantified during sleep onset, arousal from sleep, and awakening from sleep.

Figure 16:
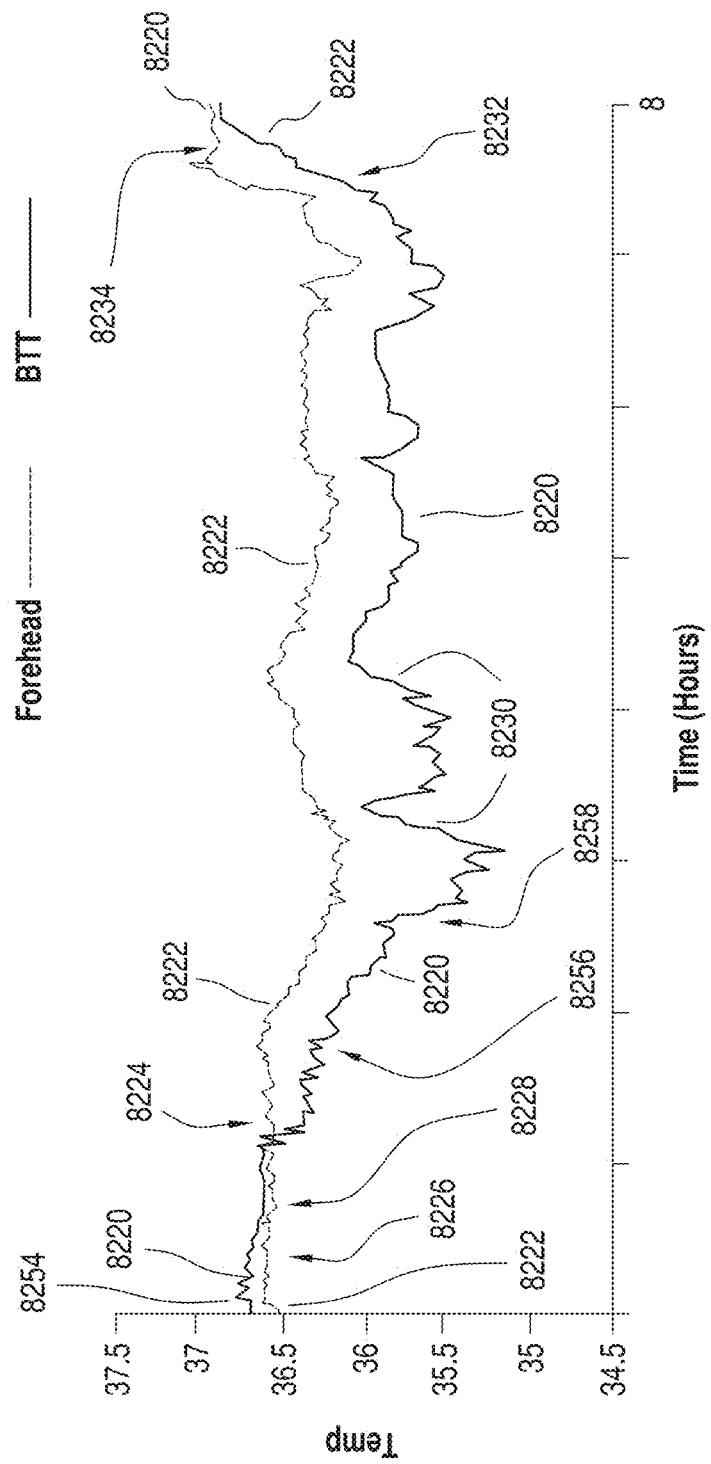
FIG. 16 is a graph showing a relationship between temperatures measured on the skin of a forehead and at the ABTT terminus during a sleep cycle of the same subject.

The results of testing show consistency with the decrease in metabolism that accompanies sleep. Referring to FIG. 16, which shows ABTT temperature 8220 and forehead temperature 8222 for a first test subject, ABTT temperature 8220 decreases at sleep onset 8224 by 1.60±0.2° C. The decrease in forehead temperature 8222 was of lesser magnitude at 0.42±0.09° C., with a p-value<0.000001 vs. ABTT, indicating a very strong presumption of significance. Further, changes in forehead temperature 8222 appeared to be delayed in comparison to ABTT temperature 8220 response. An unexpected result was that even though ABTT temperature 8220 was initially higher than forehead temperature 8222 at initial temperature 8226 in FIG. 16, ABTT temperature 8220 decreased to a lower level with sleep progression; each subject had a first ABTT/forehead temperature crossing 8228, distinguishing forehead skin surface from brain temperature. During episodes of sleep arousal 8230 and upon awakening 8232, ABTT temperature 8220 increased by 0.92±0.29° C. and 1.26±0.37° C., respectively. The corresponding increases in forehead temperature 8222 were delayed and were of lesser magnitude at 0.19±0.15° C., with a p-value<0.00001, and 0.38±0.36° C., with a p-value=0.018. Upon awakening, there was a second ABTT/forehead temperature crossing 8234 as ABTT temperature 8220 became higher than forehead temperature 8222.

Referring to FIGS. 17A-F, and 70, which show graphs corresponding to thermal delineation using the ABTT site, standard invasive and surface methods for temperature monitoring, and a Sleep Optimization System. As shown herein, measures of body core temperature may not reflect brain temperature and certainly are not suited for detecting rapid changes in brain temperature. FIGS. 17A-F shows graphs of ABTT monitoring (FIGS. 17A-C), monitoring using standard invasive rectal probes (FIG.17D), invasive tympanic probes (FIG. 17E), and surface (forehead skin, FIG. 17F) temperature monitoring using equally calibrated temperature sensors. The results of testing revealed thermal aspects not yet recognized in the current body of knowledge because of the lack of noninvasive continuously brain temperature measurement as provided by the current disclosure. Lack of apparatus to measure brain temperature noninvasively and continuously prevented acquisition of brain temperature signals in an undisturbed manner and continuous manner 24 hours a day, 7 days a week, as shown herein. In sharp contrast to the noninvasive capability to measure brain temperature as provided by the ABTT terminus, prior art has relied on invasive means that is distant from the brain, such as rectum, bladder, esophagus, and ear canal. Due to the high risk, including fatal events, monitoring of brain tissue temperature is not possible, except in rare situations, and those methods require using aggressive and painful methods. However, the ABTT apparatus and methods described herein capture signals from an open window to the brain's thermal milieu, which is also a window to brain function and brain activity, as described herein, and allow brain thermal monitoring in a noninvasive and undisturbed manner.

Figure 17A:
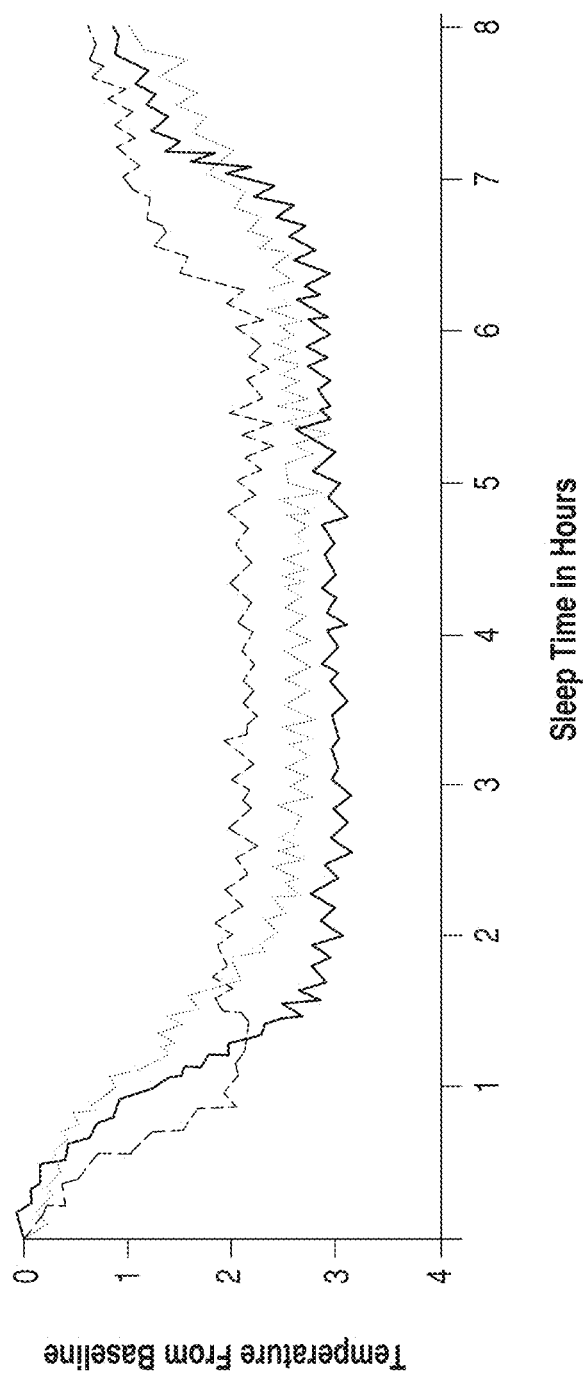
Figure 17B:
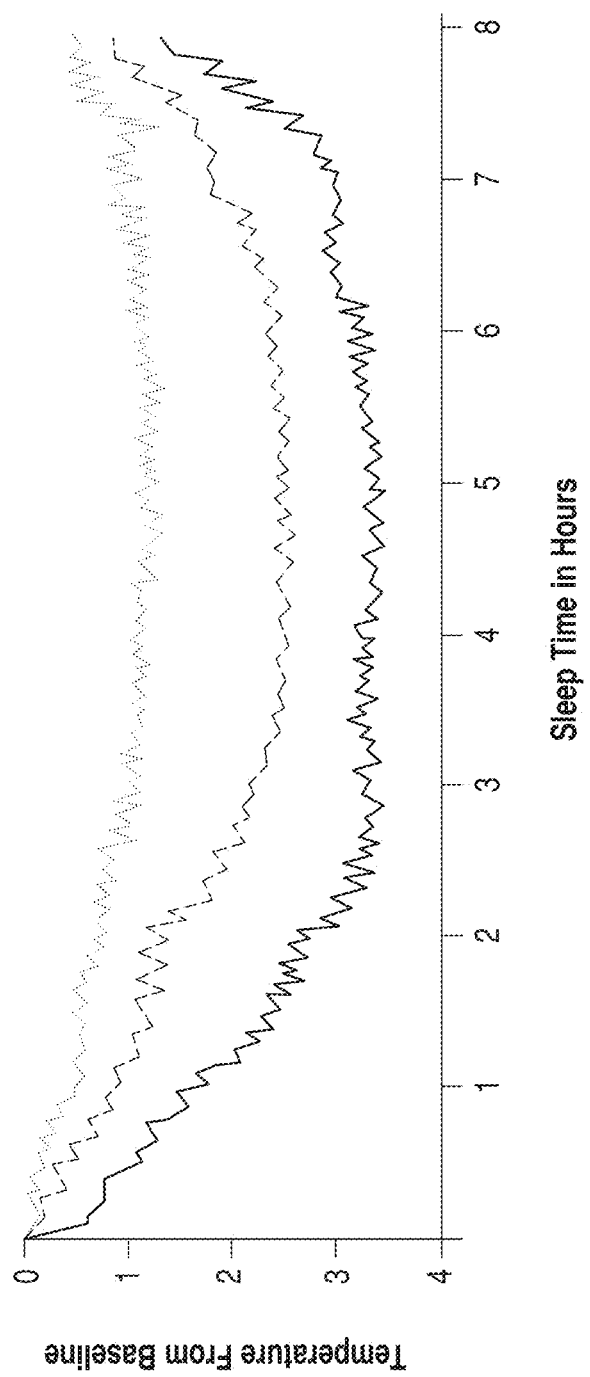
Figure 17C:
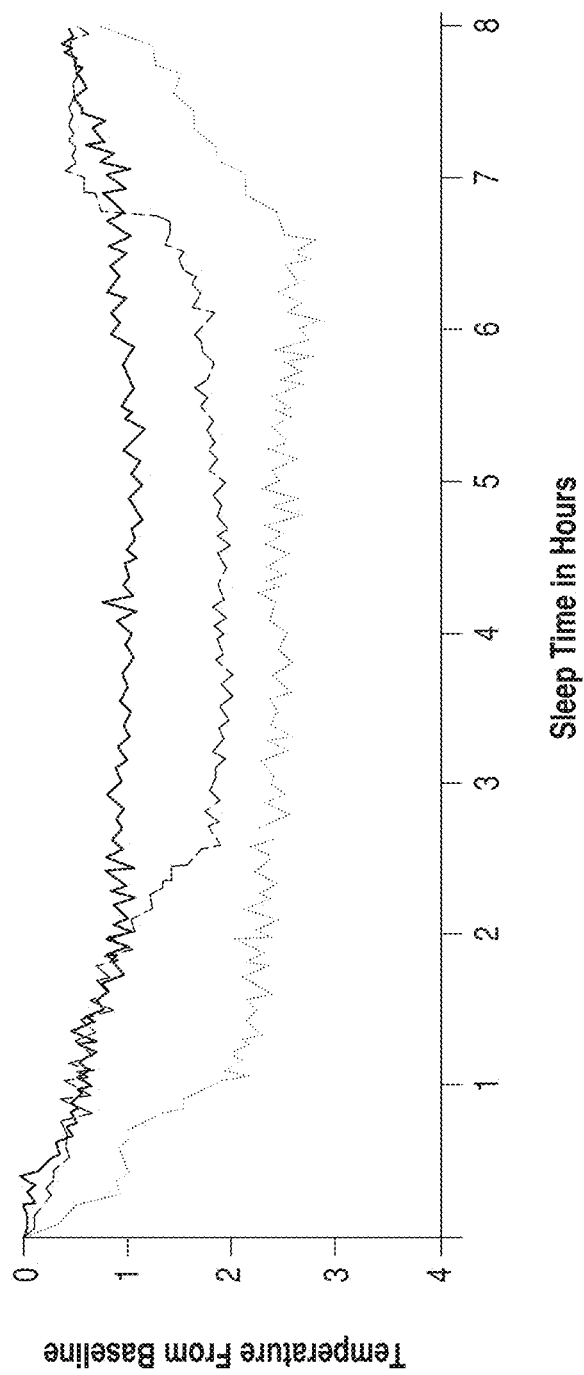
Figure 17F:
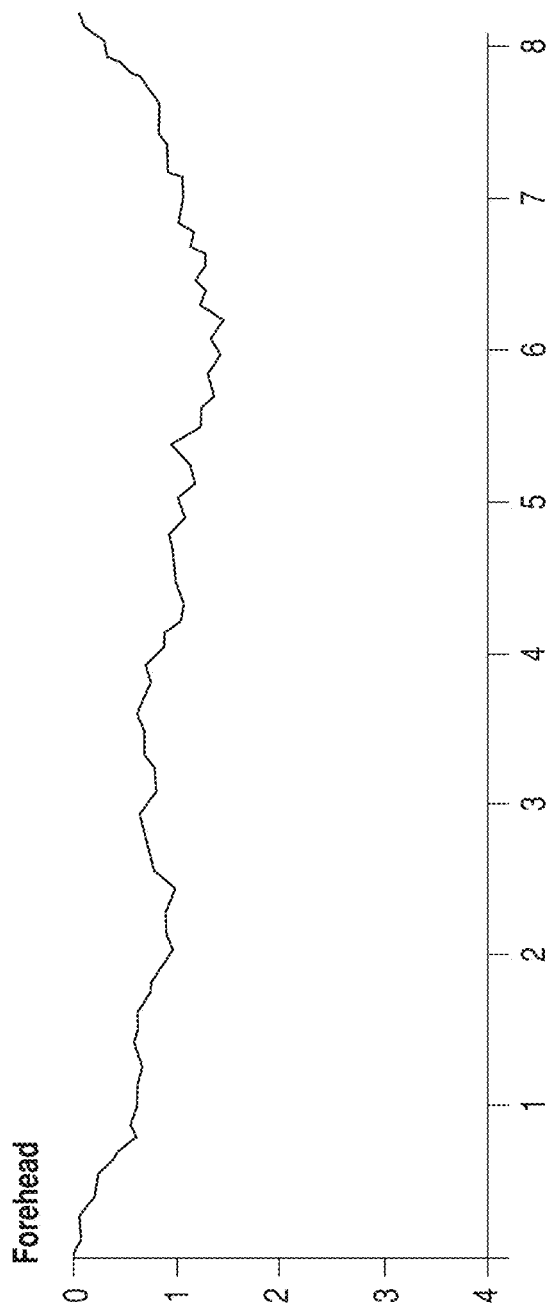

Monitoring at the ABTT terminus site with the apparatus disclosed herein revealed brain thermal information during sleep that was previously unknown, including the level of temperature, thermal patterns, thermal signatures, and thermal gradients. ABTT temperature monitoring, in accordance with this invention, was performed in two hundred subject and patients during sleep. Eighteen normal patterns were identified, and of those eighteen patterns, nine patterns showed the highest consistency of measurements (FIGS. 17 A-C) for both the reduction of temperature at sleep onset and the time required to achieved thermal level for sleep. Blood analysis for immunity activity, including velocity of leucocyte migration, showed that the nine patterns identified herein have optimized immunity, thus being less susceptible to development of diseases, including infection and cancer. Patients showing these nine patterns also showed minimal sleep fragmentation and unwanted motion during sleep. ABTT temperature monitoring showed consistent brain temperature decrease in all subjects. The brain temperature reduction occurring with sleep onset may reflect reduced brain metabolism. The range of temperature drop from baseline, as shown in FIGS. 17A-C, ranges from approximately 0.8° C. to 2.9° C., and the time to reach the lowest brain temperature from time zero ranges from 59 min to 180 min. The consistency with the decrease in brain metabolism that accompanies sleep was reflected only in ABTT temperature monitoring. In contrast, temperature measurement at locations other than the ABTT terminus, with invasive (rectal and tympanic) and surface temperature (forehead), did not reveal the reduction in brain temperature nor the thermal patterns shown in FIGS. 17D-F. Contrarily, ABTT temperature monitoring consistently characterized the drop in temperature, as shown in FIGS. 17 A-C.

Figure 70:
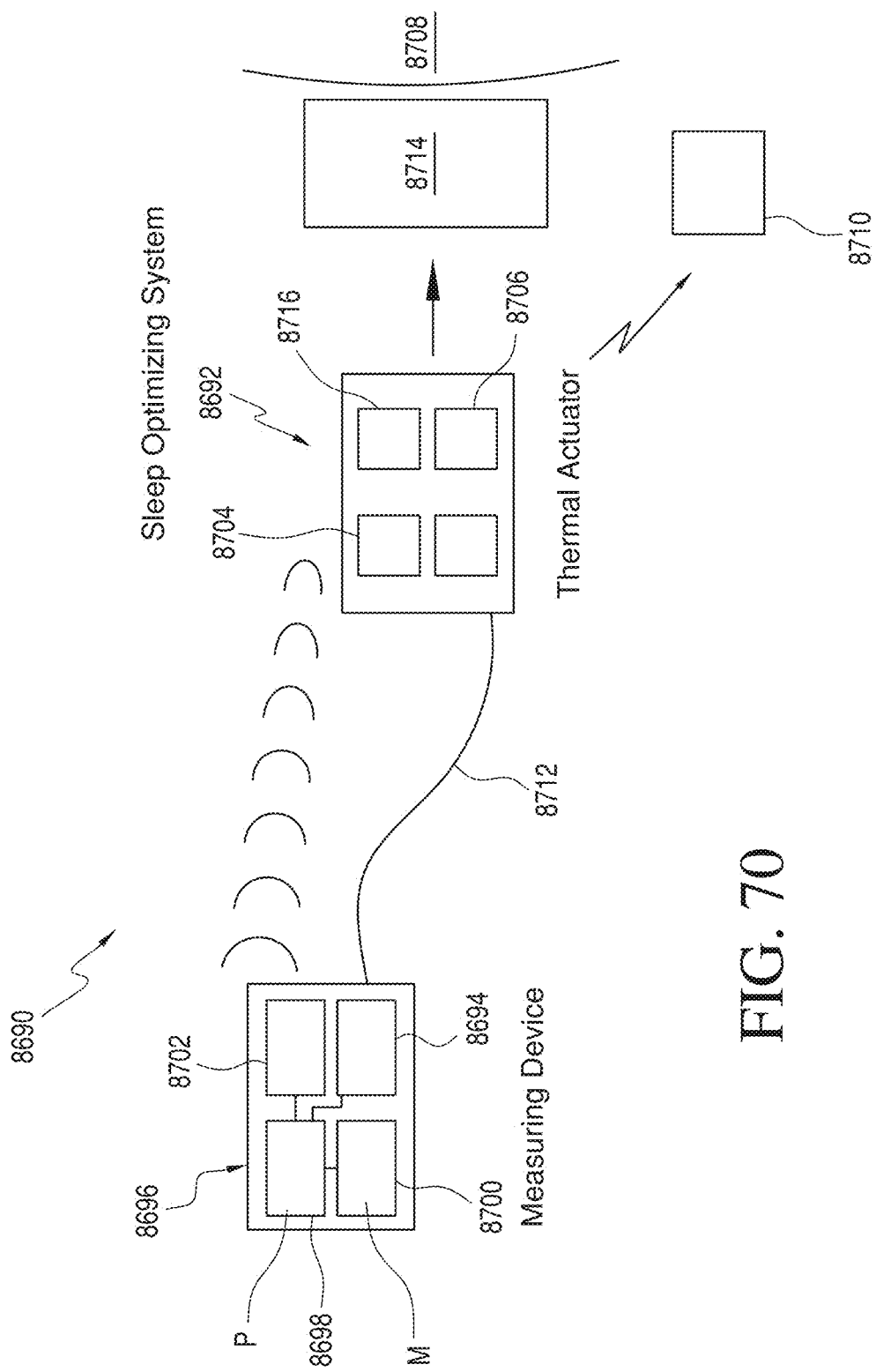
FIG. 70 is a sleep optimizing system in accordance with an exemplary embodiment of the present disclosure.

By identifying ideal thermal patterns for sleep for optimizing immune function and reduction of sleep fragmentation, the present disclosure provides another embodiment that includes a method, apparatus and system for optimizing sleep (referred herein as a Sleep Optimization System, SOS), shown in FIG. 70 and generally indicated at 8690. Accordingly, SOS 8690 includes a temperature monitoring system (such as ABTT temperature monitoring system or any other temperature monitoring system), and external thermal actuators 8692 to adjust the temperature of the brain to match the ideal thermal patterns revealed herein. Thermal actuators 8692 modify brain temperature and/or body temperature. Exemplary thermal actuators include contact actuators such as a thermal mattress, a thermal blanket, a thermal pillow, thermal clothing, thermal apparel, and the like. Contact actuators are configured to have parts adapted for generating a thermal input to increase or decrease the temperature (to warm-up or cool) the body part in contact with said contact actuators. Exemplary non-contact thermal actuators include air conditioners, external heaters, fans, nasal cooling sprays, infrared light, and the like, said non-contact thermal actuators being adapted for generating a thermal input to increase or decrease the temperature (to warm-up or cool) the body (and brain). Another exemplary thermal actuator includes actuators that act on the ABTT terminus site, said thermal actuators being adapted for generating a thermal input to increase or decrease the temperature of the BTT (or ABTT) terminus site (to warm-up or cool the site), and consequently the temperature of the brain. Yet another thermal actuator may include invasive means with injection of cold or blood fluids inside the body (or in the vasculature). In one exemplary embodiment at least one thermal actuator 8692 or a series of contact and non-contact thermal actuators provide a thermal input, said input causing an increase or decrease in the body (brain) temperature, said input being adapted to match the ideal curve patterns disclosed herein, such as to cause a decrease of brain temperature ranging from 0.8° C. to 2.9° C., within a time period ranging from 59 min to 180 min. Accordingly, if during sleep brain temperature escapes from this optimal thermal pattern, at least one thermal actuator 8692 is activated so as to cause the brain temperature to adjust in order to match an ideal thermal pattern. In accordance with an exemplary embodiment of the present disclosure, the brain temperature signal is captured by thermal sensor 8694 of temperature monitoring system 8696, said signal being processed by a controller or processor 8698 included as a part of thermal sensor 8694. Thermal sensor 8694 further includes a non-transitory memory 8700 connected to controller 8698. Non-transitory memory 8700 contains the ideal thermal sleep patterns disclosed herein.

Once the thermal sleep pattern as measured by temperature monitoring system 8696 starts to depart from the ideal thermal sleep pattern, the thermal signal is recognized by controller 8698 (based on comparison of the received signal with predetermined values for ideal sleep stored in non-transitory memory 8700). Controller 8698 is configured to recognize the abnormal temperature signal and then to activate a wireless transmitter 8702 included as a part of temperature monitoring system 8696. In an exemplary embodiment, wireless transmitter 8702 is a near field communication transmitter with a relatively short range, such as Bluetooth or Wi-Fi. Wireless transmitter 8702 transmits a temperature signal to a wireless receiver 8704 of thermal actuator 8692. Thermal actuator 8692 is chosen based on the need to cool or warm a subject to achieve an ideal sleep pattern. Thermal actuator 8692 includes a controller 8706. Controller 8706 is configured to identify the need to heat or cool a body 8708. If body 8708 needs cooled rather than heated, controller 8706, in an exemplary embodiment controller 8706 communicates with a cooling system 8710 to provide cooling to body 8708. Thus, controller 8706 is able to command heating or cooling to best match the temperature curve slope of the ABTT terminus characterizing an ideal sleep pattern. Although the description hereinabove uses a wireless system for transmission, it should be understood that a wired connection can be used, and in an exemplary embodiment, a wire or cable 8712 of thermal actuator 8692 is connected to the temperature monitoring system 8698. On the other hand, if controller 8706 identifies a need for warming up the brain, then, for example, a contact thermal device 8714 such as thermal blanket is activated. Ideal sleep patterns include a decrease in brain temperature ranging from 0.8° C. to 2.9° C. from a baseline temperature, within a time period ranging from 59 minutes to 180 minutes, where baseline is the waking temperature at time zero. Ten preferred sleep temperature patterns include: (i) temperature drop of 2.0° C. within 59 min; (ii) temperature drop of 2.7° C. within 101 min; (iii) temperature drop of 2.1° C. within 150 min; (iv) temperature drop of 2.1° C. within 180 min; (v) temperature drop of 1.9° C. within 75 min; (vi) temperature drop of 2.8° C. within 135 min; (vii) temperature drop of 1.1° C. within 139 min; (viii) temperature drop of 0.8° C. within 100 min; (ix) temperature drop of 1.4° C. within 170 min; and (ix) temperature drop of 1.2° C. within 121 min (not in graph).

SOS System 8690 of the present disclosure includes controller 8698 in temperature monitoring apparatus 8696. Controller 8698 is configured to include instructions for the operation of temperature monitoring system 8696 and is operatively coupled to non-transitory memory 8700 and wireless transmitter 8702. In the embodiment of FIG. 70, controller 8698 is also connected by wire or cable 8712 for wired communication.

Controller 8698 is configured to compare an acquired thermal pattern and slope to thermal patterns stored in the non-transitory memory 8700. Furthermore, controller 8698 is configured to identify an acquired thermal sleep pattern that departs from an ideal pattern stored in non-transitory memory 8700. If an abnormal pattern is detected, then controller 8698 activates wireless transmitter 8702 to send a signal to a thermal actuator 8714 or a cooling system 8710, as described herein. Thermal actuator 8692 includes a wireless receiver 8704, which is coupled to thermal actuator controller 8706. Controller 8706 adjusts thermal output up or down based on temperature data (thermal curve) received from temperature monitoring device or system 8696.

In an exemplary embodiment, a method of controlling the temperature of a body 8708 during sleep may include the following steps: (1) measuring temperature of the ABTT terminus (preferably at 1 Hz); (2) identifying a thermal sleep pattern (such as slope of the curve and/or the velocity of temperature drop) every 1 minute or less (or preferably every 30 seconds or less); it should be that any frequency of measurement ranging from every 10 minutes to every 1 second is within the scope of the disclosure, but the preferred embodiment uses the most frequent measurements possible; (3) although this next step is optional, controller 8698 may be configured to predict the final thermal pattern based on the slope acquired; in step (4) controller 8698 compares the acquired slope or thermal pattern with the predetermined ideal thermal pattern stored in non-transitory memory 8700; if in the next step (5) controller 8698 identifies a departure from ideal sleep pattern, then in next step (6) wireless transmitter 8702 of temperature monitoring system 8696 is actuated, with a signal transmitted to thermal actuator 8692; and (7) thermal actuator 8692 is configured to determine the amount of thermal adjustment needed to achieve ideal thermal sleep pattern (disclosed herein) by delivering, by way of illustration, heat, via a device such as contact thermal device 8714, or cold, such as by cooling system 8710, to body 8708 of a subject.

Figure 17G:
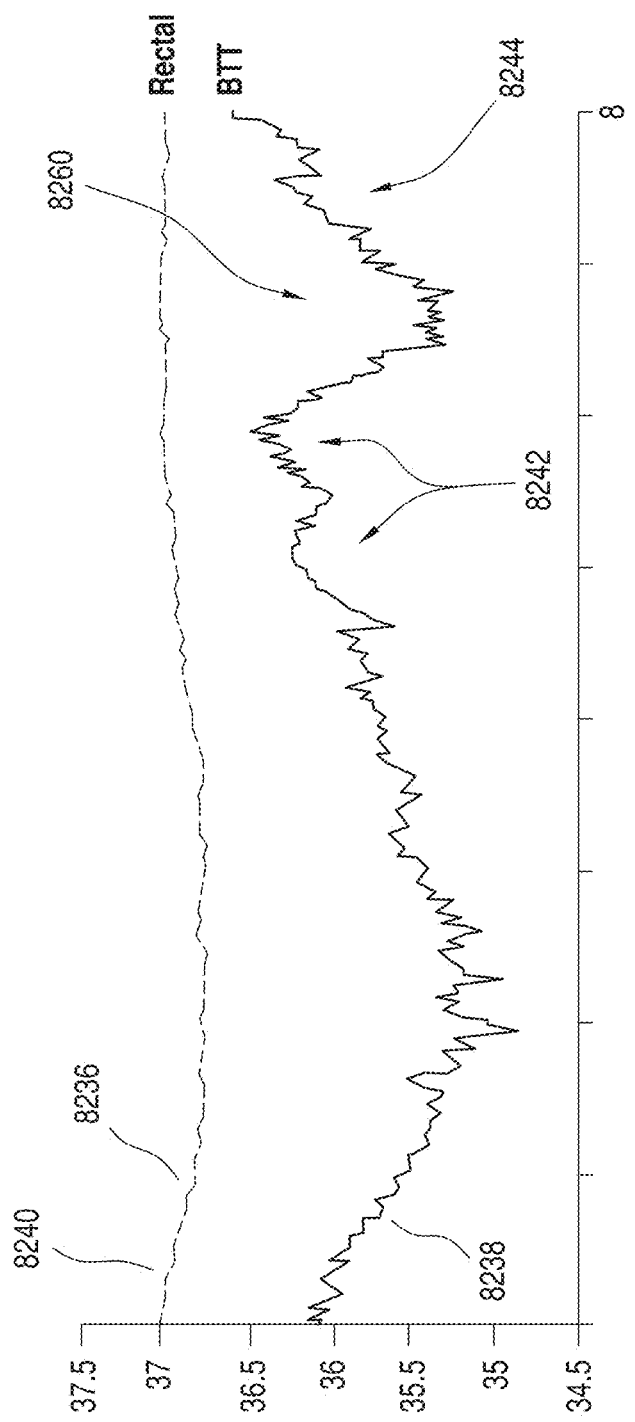

What is clear from FIG. 17g is that while rectal temperature appeared to have some correlation to passing into a state of sleep, rectal temperatures were not predictive of arousal from sleep, and a subsequent sleep interval 8260 after sleep arousal 8242 and awakening from sleep 8244 appeared to have a negligible effect on rectal temperature. Thus, rectal temperature is a weak indicator of sleep and wakefulness, but provides no information with respect to sleep arousal and awakening.

In contrast to forehead temperature 8222 and rectal temperature 8236, ABTT temperature 8220 and 8238 very precisely detected changes in brain metabolism associated with sleep onset 8224 and 8240, sleep arousal 8230 and 8242, and awakening 8232 and 8244. The ability to monitor sleep cycles in this manner provides a new and hitherto unknown capability to diagnose normal disturbed sleep cycle patterns. Furthermore, with ABTT temperature analysis, a new diagnostic tool is presented to analyze insomnia, catatonia, and coma, and determine whether recovery and treatment are possible and effective. Furthermore, because intensity of sleep is monitored, ABTT temperature analysis leads to effective assessment of depth of anesthesia, intra-operative awareness, intensity of anesthesia-induced coma, and normal progression of recovery from anesthesia. Perhaps even more importantly, ABTT temperature analysis is capable of determining when a brain is under critical stress indicative of a pre-death condition, which is currently not possible with conventional temperature measurement apparatus and methods.

Stated more clearly, measurement of the skin temperature at the ABTT terminus can predict when a patient or subject is moving from an awakened state to a pre-sleep condition by: (1) identifying an awake condition ABTT temperature 8254; (2) identifying a pre-sleep or drowsy condition by a sustained decline 8256 in ABTT temperature 8220 of at least 0.5° C.; and (3) identifying onset of a sleep condition by a precipitous decline 8258 in ABTT temperature 8220 of at least 0.2° C. in a period of approximately one minute. Further, an arousal condition 8230 during sleep can be predicted by monitoring ABTT temperature 8220 for a precipitous increase during arousal condition 8230 of at least 0.2° C. in a period of approximately one minute. Further yet, an awakening condition 8232 can be predicted by monitoring ABTT temperature 8232 for an increase in ABTT temperature of at least 0.7° C. from a minimum temperature recorded during a sleep cycle in a period of five minutes or less. The dramatic improvement in the present system and apparatus is that such predictions of sleep progression are made in advance of even the patient or subject knowing that they are become aroused or awake. Indeed, the patient or subject may be completely unaware of an aroused state, but by monitoring an ABTT temperature, such conditions may be more than recognized, they may be accurately predicted.

The consequence of predicting arousal and awakening are significant in a variety of circumstances. When a patient is under anesthesia, for example, an arousal state corresponds to inadequate anesthesia. Furthermore, an awakening state during a medical procedure, which rarely happens, can readily be predicted by identifying an awakening condition 8232 from ABTT temperature 8220, and applying additional anesthetic to restore a patient to a sleep condition.

Additionally, the ability to sense drowsiness has implications for maintaining an awakened state. For example, if a drowsy state is identified by sustained decline 8256, a device, such as a loud tone, a mechanical vibration, or the like, can restore a subject to a full awakened condition before sleep occurs. Broadly, because changes in the ABTT temperature precedes the actual onset of a drowsiness, sleep, arousal, and awakening, these conditions may be used to predict the actual condition and the impending condition may be prevented, if such is desirable in a specific environment.

It should be noted that current determination of sleep condition in sleep studies requires positioning of sensors in a plurality of locations on a patient, each sensor connected by a wire that is non-conducive to sleep and non-conducive to sustained sleep. Furthermore, such sensors can be invasive, sometimes requiring shaving of skin in multiple locations. Still further, diagnosticians often do not know the patient is awake until the patient is actually awake, in contrast to ABTT temperature, which begins generating heat in the brain to provide a sort of "firing up" of brain systems in anticipation of being awake. Similarly, heat is generated in the ABTT as part of arousal, though less than is needed for waking, because the needs of body systems is less than for waking. Thus, the benefits of ABTT temperature monitoring for sleep in any environment is more accurate than conventional techniques, is predictive, and is minimally invasive, replacing hordes of wires and sensors in some circumstances.

Figure 71:
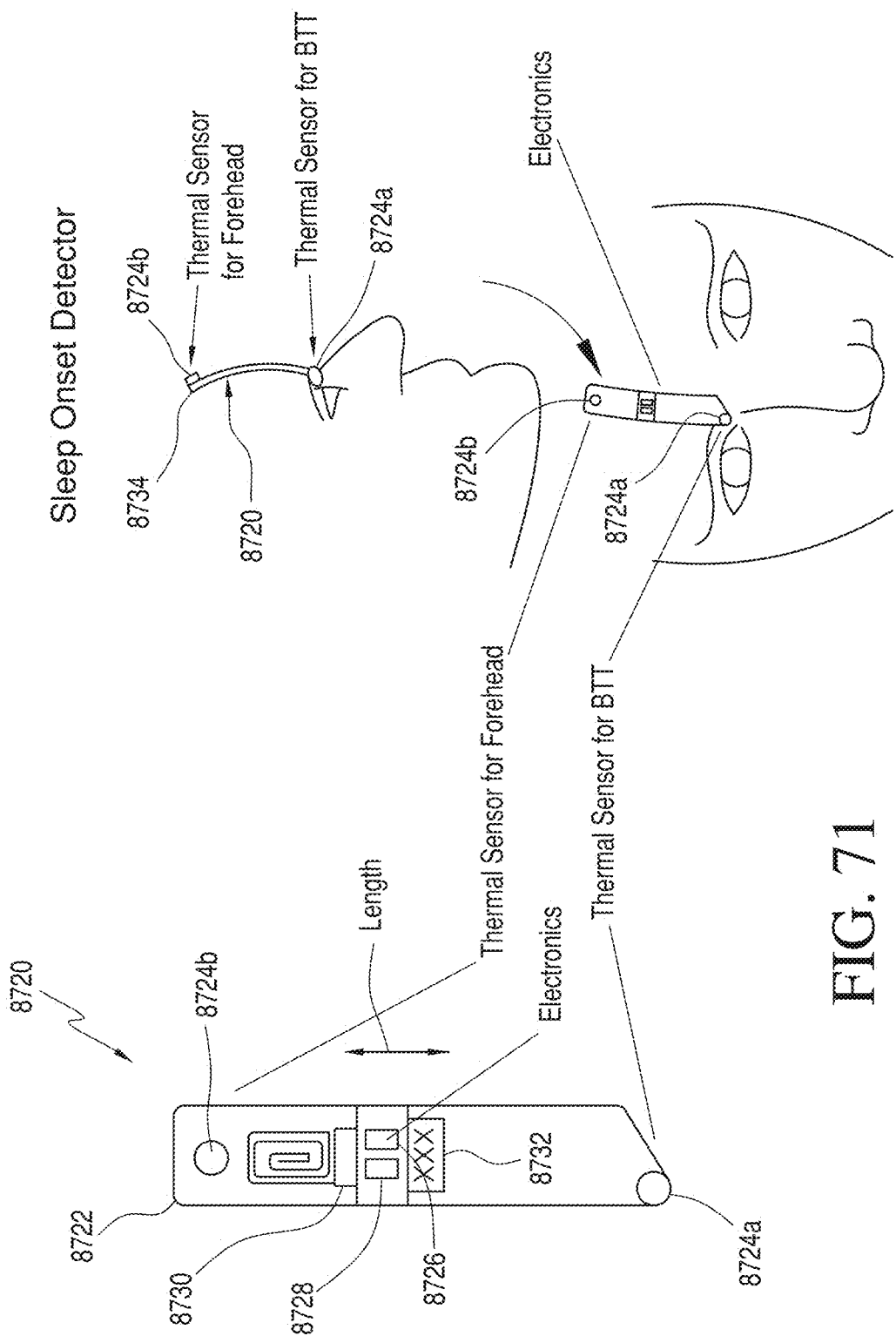
FIG. 71 is a sleep onset detector in accordance with an exemplary embodiment of the present disclosure.

FIG. 71 shows a sleep onset detector 8720 that includes a housing 8722 containing a pair of temperature sensors 8724a and 8724b, a controller 8726, a non-transitory memory 8728, a transmitter 8730, and a reporting apparatus 8732. Temperature sensors 8724a and 8724b are operatively coupled to controller 8726. Controller 8726 is configured to identify when temperature of sensor 8724a becomes lower than the temperature of sensor 8724b. As shown in the graphs of FIGS. 16 and 17A-G, when the temperature of the ABTT terminus measured by temperature sensor 8724a becomes lower than the temperature of the forehead measured by temperature sensor 8724b, sleep onset is indicated. A sleep onset detector and method in accordance with an exemplary embodiment of the present disclosure includes the following steps: (1) positioning one thermal sensor 8724a at the ABTT terminus site and a second temperature sensor at another skin surface location away from the ABTT terminus site, such as the forehead; (2) measuring temperature simultaneously at the ABTT terminus site and at the second skin surface site; (3) comparing temperature levels from both sites; (4) identifying the moment in which temperature at the ABTT terminus site is lower than temperature at surface skin site; and an optional step (5), reporting by visual, audio, vibration means, and the like the moment that inversion occur (i.e., when the ABTT terminus site has lower temperature).

The last step can be used when the sleep onset detector is used to alert the user about sleep onset, such as when driving, operating machinery, and for any other situation that the user needs to remain awake. In situations in which the user does not need to be awakened or alerted, sleep onset detector 8720 does not activate reporting apparatus 8732, and in this case, sleep onset detector 8720 is used to identify abnormal sleep patterns, disease patterns, or changes in physiology such as ovulation. Sleep onset detector 8720 can include an adhesive surface 8734, and has a length of at least 1 inch to position one sensor over the ABTT and the second sensor on the forehead skin. Although a second sensor adapted to measure temperature on the forehead is described, it should be understood that a second sensor measuring temperature in any body cavity (such as mouth, rectum, bladder, esophagus) or on any surface of the face (such as cheek, mouth, and the like), surface of the head and neck (such as retro-auricular and the like), or surface of the body (e.g., chest, shoulder, arm, hands and the like) can be used, and such a temperature measurement for comparison is in accordance with the scope of this invention. It should also be understood that although an adhesive-based embodiment of sleep onset detector 8720 is described, any other temperature detector containing at least two thermal sensors can be used to measure the temperature of the ABTT terminus site and other skin location, and are within the scope of this disclosure. Exemplary embodiments of sleep onset detector 8720 include: One physical unit 8720 as shown in FIG. 71, in which the at least two thermal sensors 8724a and 8724b are contained on or in a single physical unit, support structure, or housing 8722. In other exemplary embodiments, the support structure may include a clip, specialized eyeglasses and frames, head mounted gear, and the like, all of which are adapted to position one sensor at the ABTT and a second sensor outside the ABTT. In another exemplary embodiment, which is not shown, at least one thermal sensor is contained in one unit, and a second thermal sensor is contained I a separate unit. The two units may be connected by wire or a wireless transmitter. At least one of the two units includes a controller, non-transitory memory, and a reporting apparatus.

Validity of ABTT Monitoring

As previously described herein, monitoring core brain temperatures is beneficial for understanding brain reaction in a surgical environment. Recent surgical care improvement program (SCIP) criteria include attempting to maintain perioperative core temperature at >36° C. One of the most difficult aspects of complying with such guidelines is the limitation of current means of thermometry. Invasive monitoring is restricted to limited settings, i.e., rectal, forehead, oral, and armpit, and may not be readily transferred between settings. Besides being limited by the difference to actual core temperature, skin monitoring is distorted by anesthesia and changes in room or ambient temperature. As described herein, Applicant has unexpectedly found through significant research and testing that the superior medial orbit, or SMO, and medial eyelid area, typically sustains the highest temperature on the body surface, absent ambient temperatures higher than SMO, and measures core temperature without need for an offset or correction factor. As described herein, the SMO site overlies the brain thermal tunnel or ABTT, an insulated pathway between the SMO and the perihypothalamic region located in a central portion of the brain. Applicant undertook significant research to understand the consistency of ABTT terminus temperature readings in the context of two potentially disruptive settings: patients or subjects exposed to an operating room environment after induction of anesthesia, and cattle exposed to extremes of temperature. Applicant unexpectedly found through research and testing that monitoring skin temperature over the brain thermal tunnel was unaffected by changes in ambient temperature in humans undergoing surgery and cattle exposed to extremes of temperature.

ABTT adhesive thermal or temperature sensors were placed on the skin of the SMO of ten cardiac patients during median sternotomy prior to cardiopulmonary bypass. Simultaneous measurements were obtained of the temperature of the Pulmonary Artery (PA) and ABTT 8140 after insertion of a PA catheter and 40 minutes later, during which interval the patient was exposed to an operating room temperature of approximately 13° C.

Additionally, the similarity of ABTT 8140 temperature to the standard measure of core temperature in animals and the impact of changes in ambient temperature were assessed in four cattle at two-hour intervals in a climate-controlled chamber while chamber temperature was changed between 20° C. and 36° C. over the course of 140 hours.

The results of the patient data indicate that, at the onset of PA catheter measurements, the average PA-ABTT temperature difference was 0.08±0.12° C. At 40 minutes, the mean PA-ABTT temperature difference was 0.16±0.13° C. In other words, averaged ABTT temperature is measurably as well as statistically indistinguishable from pulmonary artery temperature.

Figure 18:
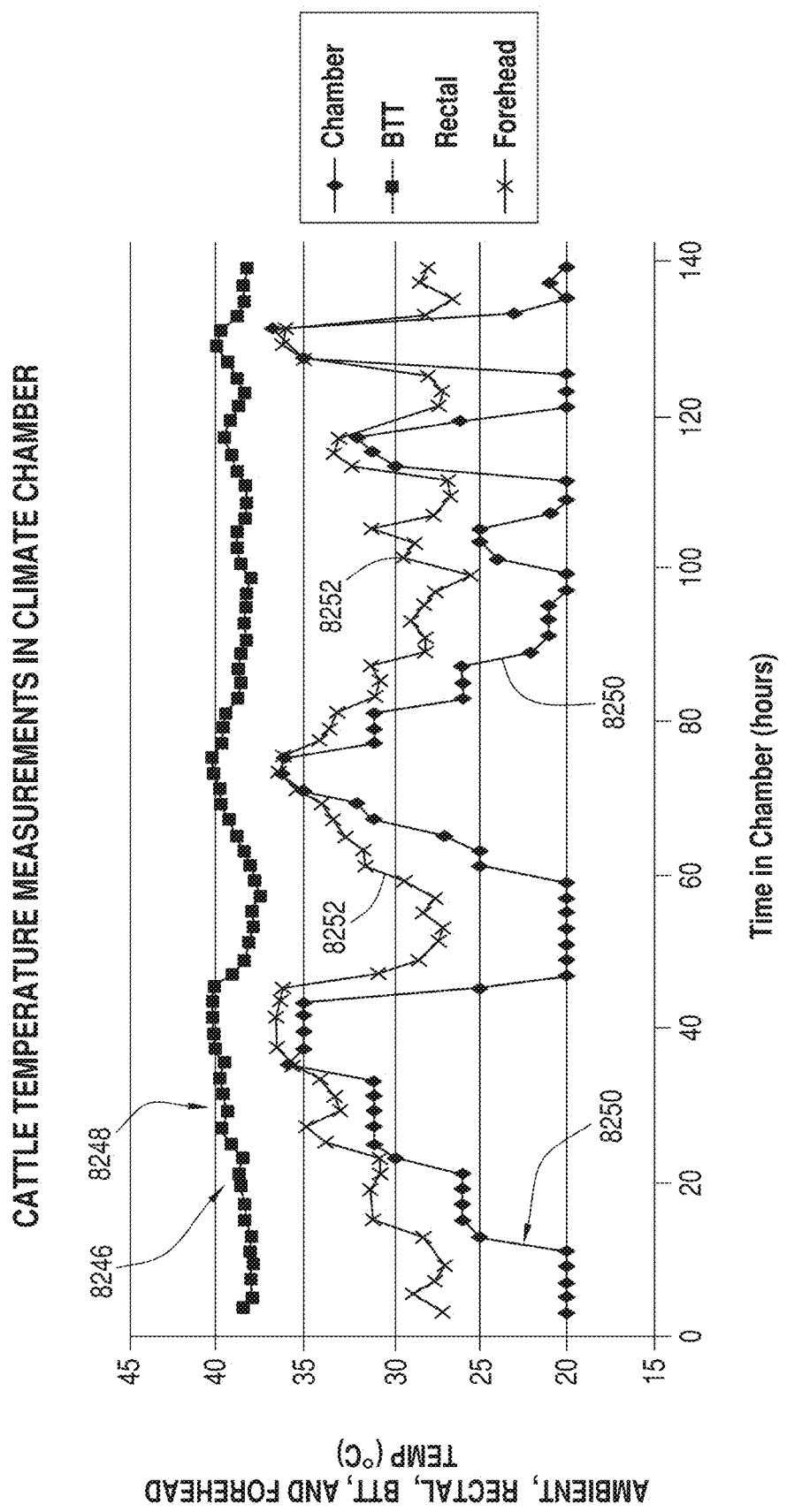
FIG. 18 is a graph showing ambient temperature and the temperatures collected from various locations on cattle in a climate chamber.

Referring to FIG. 18, the findings in cattle indicate ABTT temperature 8246 and rectal temperature 8248 readings were relatively closely clustered together throughout a 140 hour testing period, with mean values of 38.89±0.7° C. and 38.92±0.6° C., respectively and an overall ABTT-Rectal temperature difference of −0.03° C. In other words, cow rectal temperatures tracked cow brain temperature closely, which is different from human subjects. In contrast, cow forehead temperature 8252 was directly affected by room or ambient temperature 8250, often diverging from core temperatures; with an ABTT-forehead (ABTT minus forehead) temperature average of 8° C.

The data in FIG. 18 indicate that ABTT temperature provides an accurate measure of core temperature (as reflected by PA temperature in humans and rectal temperature in cattle) and that the measurement is not influenced appreciably by changes in ambient temperature. This similarity is in contrast to other surface sites. For example, forehead temperatures in cattle readily reflected ambient cooling and warming. Thus, ABTT terminus temperature measurements appear to provide a useful noninvasive location for measuring core temperature in operative and the non-operative anesthesia settings as well as in animal populations.

ABTT Monitoring During Heart Bypass Surgery

As described herein, the measurements of skin temperature at the ABTT terminus provides multiple advantages in a variety of settings. One such type of setting is one in which the brain is at increased risk for hyperthermic injury, ranging from patients undergoing hypothermic cardiac bypass (hCPB) to cerebral protection for active athletes and soldiers in a warm environment. Extreme changes in core temperature can result in a severe reduction and ultimately cessation of metabolic functions. Such extreme changes in core temperature are the case when hypothermia or hyperthermia occurs. These thermal disturbances can be life-threatening if not diagnosed or properly treated.

As described herein, with the discovery of the ABTT core body temperature can be monitored continuously and non-invasively. Measurements of temperature on the skin over, adjacent to, or on the ABTT terminus with a surface sensor on the superomedial orbit correlate highly with established core readings during steady states, as described herein. Thus, the ABTT may be beneficially used to measure the temperature of patients during cardiopulmonary bypass and the temperature of athletes, workers in any adverse temperature environment, and soldiers during exercise by identifying brain temperature instead of core temperature.

As described herein, measurements of skin temperature over, adjacent to, or on the brain thermal tunnel or ABTT with a surface sensor on the superomedial orbit and eyelid correlate highly with established core readings during steady states. Of potential value is measuring the core temperature during medical procedures, such as surgery.

Applicant has shown that a thermal sensor on the skin of the superomedial orbit and eyelid, overlying the brain thermal tunnel, provides reliable assessment of core temperature during steady state conditions in healthy volunteers and patients under anesthesia. Ongoing anatomical studies indicate that ABTT anatomy enables a surface monitor to be in virtual continuum with an insulated passage to the cavernous sinus; and Applicant has proven that ABTT is reflective of intracranial and brain temperature. We therefore applied a thermal sensor to the skin overlying the ABTT during hypothermic cardiopulmonary bypass (hCPB) and compared it to changes in core blood.

Figure 19:
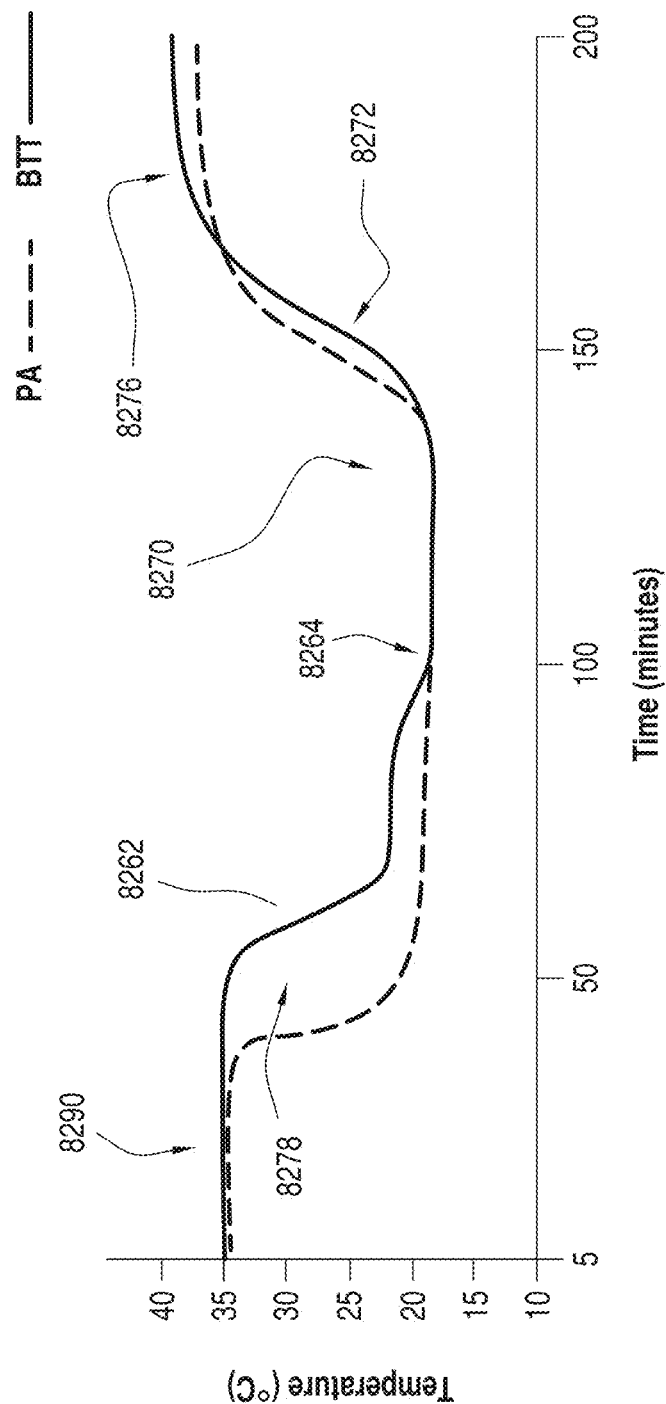
FIG. 19 is a graph of temperature measured on the skin adjacent to, over, or on the ABTT terminus and at the pulmonary artery during of a single subject during cooling of the subject.

In a research study, a ABTT thermal sensor at the end of a plastic wing anchored by adhesive to the forehead, similar to temperature sensor 8002 (see FIGS. 2 and 3), was placed on the skin between the edge of the right upper eyelid and the eyebrow adjacent to, on, or over the superior aspect of the medial canthus. Referring to FIG. 19, simultaneous measurements of ABTT terminus temperature 8262 and pulmonary artery (PA) temperature 8264, were made in ten patients undergoing hCPB. Simultaneous measurements were also made of esophageal temperature, bladder temperature, oxygenator inflow temperature, and oxygenator outflow temperature, but are not provided in FIG. 19 to minimize confusion in the graph and because the measurements at these locations did not reflect brain temperature.

During pre-bypass phase 8290, it was confirmed that the mean ABTT temperature (34.9±0.4° C.) was similar to pulmonary artery temperature (PA, 35.1±0.5° C.) and esophageal temperature (34.8±0.5° C.—not shown). Applicant compared the relationship of ABTT temperature 8262 to these measures of core as well to oxygenator inflow (not shown) and oxygenator outflow (not shown) after onset of bypass and at their respective troughs.

The results in FIG. 19 show changes in ABTT temperature 8262 and PA temperature 8264, for a single subject pre-bypass 8290, during cooling, and during rewarming 8274. As described herein, pre-bypass 8290 ABTT 8262 was similar to other measures of core body temperature. During initial cooling 8278, ABTT terminus temperature 8262 cooled more slowly than core temperature. At 5 min, the mean temperature was 16.3±6.0° C. for oxygenator inflow, 26.4±3.2° C. for oxygenator outflow, 25.7±3.5° C. for PA 8264, and 29.4±3.2° C. for esophageal (not shown), but was still 31.0±2.1° C. for ABTT, with a statistical significant of p<0.001 by ANOVA analysis. The respective troughs of the BTT temperature, the PA temperature, and the esophageal temperature were 23.5° C., 21.0° C., and 21° C., respectively.

These studies suggest that although the skin at the ABTT terminus provided readings comparable to established measures of core temperature under steady-state and slowly changing conditions, it evidenced decoupling from core temperatures during cooling for hCPB. This research highlights the potential to overestimate the speed at which cooling provides brain protection.

The results show that during hCPB, in a period 8270 prior to rewarming, ABTT terminus temperature 8262 cooled to a slightly lesser degree hCPB than PA temperature 8264, esophageal temperature (not shown in FIG. 19), oxygenator inflow temperature (not shown in FIG. 19), and oxygenator outflow temperature (not shown in FIG. 19). During an initial rewarming period 8272, ABTT temperature 8262 lagged behind all other temperature sources. However, at a time 8274 when oxygenator outflow temperature (not shown in FIG. 19) reached 36° C., ABTT terminus temperature 8262 consistently exceeded the temperature from all other sources. ABTT terminus temperature 8262 exceeded PA temperature 8264, which is currently considered the standard for temperature measurements during hCPB, in all 10 subjects. Respective peaks were 38.2±0.8° C. and 37.4±0.7° C. at the end of rewarming 8276, with a statistical significance of p=0.0002 by a paired t-test.

These studies indicate that the greater ABTT temperature 8262 measured towards the end of rewarming 8276 is evidence that ABTT temperature is uniquely sensitive to brain metabolism and may constitute a noninvasive measure of brain temperature that is vital to prevent hyperthermia-induced and/or hyperthermia-exacerbated neurocognitive injury in this context.

Furthermore, during the initial cooling period 8278, measured ABTT temperature 8262 was substantially higher than PA temperature 8264, which has significant implications for proper cooling of patients during certain medical procedure. Therapeutic hypothermia is believed to reduce the risk of brain tissue injury due to the lack of blood flow by decreasing oxygen demand in the brain, reducing production of neurotransmitters, and reducing free radicals. Currently, PA temperature 8264 is used as an indicator of brain temperature. However, as shown in FIG. 19, it is apparent that temperature of PA 8264 is lower than ABTT terminus temperature 8262 by 5° C. or more. If a particular medical procedure requires a particular brain temperature, it is apparent from FIG. 19 that the only reliable indicator of brain temperature is ABTT terminus temperature 8262.

Accordingly, the ability to measure temperature of the ABTT terminus during a medical procedure leads to an improved ability to establish proper therapeutic hypothermia and/or hyperthermia and to prevent tissue destroying hyperthermia and life-threatening hypothermia. More specifically, such a procedure may be accomplished in an exemplary embodiment by a temperature modifying apparatus that includes (1) positioning a temperature sensor on the skin adjacent to, over, or on the ABTT terminus; (2) applying cooling or heating to a patient or subject; and (3) when the ABTT terminus indicates brain temperature has reached a predetermined target level, change from a temperature modifying (either increasing or decreasing) operation to a temperature maintenance operation. To specifically provide appropriate warming or re-warming from a cooled condition using an existing or properly positioned ABTT terminus temperature sensor, (1) remove any remaining cooling apparatus; (2) begin rewarming protocol; (3) monitor brain temperature response by monitoring the slope of ABTT temperature increase during initial warming; (4) when the ABTT temperature reaches a first predetermined target warming temperature, which in an exemplary embodiment may be 35° C., begin reducing warming procedures; (5) when the ABTT temperature reaches a second predetermined target warming temperature, which in an exemplary embodiment may be 36.5° C., cease all warming procedures; and (6) if ABTT temperature moves into a hyperthermic temperature range, which in an exemplary embodiment may be above 37.0° C., reintroduce cooling protocol to reduce or prevent neural damage due to hyperthermia; (7) otherwise, cease all warming and cooling protocols.

An exemplary embodiment of therapeutic hyperthermia may be accomplished through a similar technique, by (1) positioning a temperature sensor to measure the temperature of the skin adjacent to, over, or on the ABTT terminus; (2) begin a hyperthermia warming protocol; (3) monitor brain temperature response by monitoring the slope of ABTT temperature increase during initial warming; (4) when the ABTT temperature reaches a first predetermined target warming temperature, begin reducing warming procedures; (5) when the ABTT temperature reaches a second predetermined target warming temperature, cease warming protocol and, if appropriate, change to an elevated temperature maintenance protocol; and (6) if ABTT temperature moves beyond the target temperature, cease warming protocols and introduce gradual cooling to the body trunk.

It should be noted that the target temperatures for therapeutic hyperthermia or hypothermia varies based on the purpose of the treatment. Furthermore, because conventional temperature measurements are unreliable, target temperatures may need to be adjusted, and can be adjusted, given the ability to accurately measure brain temperature at the ABTT terminus. Further yet, all temperatures that are "normal" or "baseline" should be for a particular subject or patient, given the normal variation of temperatures for humans. Thus, any changes in temperature are not absolute, but are tailored to the normal temperature of an individual.

Once therapeutic hyperthermia is completed, cooling of the patient or subject to normal temperatures may occur. Because therapeutic hyperthermia provides relatively small temperature elevation, ambient temperature is normally sufficient to return the patient to a normal temperature. Continuous monitoring of the ABTT terminus is important during cooling to normal temperature to prevent the brain for compensating for cooling by generating heat through shivering or other techniques. It is generally accepted procedure to incorporate an anti-shiver mechanism in therapeutic hypothermia. Such mechanism may be, for example, one or more drugs for suppressing a shiver response. However, shivering may also be limited by heating extremities (hands and feet) while cooling the body trunk. Generally, exemplary cooling is accomplished by (1) positioning a temperature sensor to measure the temperature of the skin adjacent to, over, or on the ABTT terminus; (2) provide an ambient temperature no greater than approximately 27° C., and no less than approximately 19° C.; (3) depending on the reaction of the ABTT temperature in response to cooling, it may be necessary to slow the rate of cooling by adding insulation or a slight amount of heating to the patient; and (4) once a ABTT target temperature is reached, which in an exemplary embodiment is approximately between 37.5° C. and 38.0° C., reduce the rate of cooling and begin to change to a temperature maintenance protocol.

Figure 76:
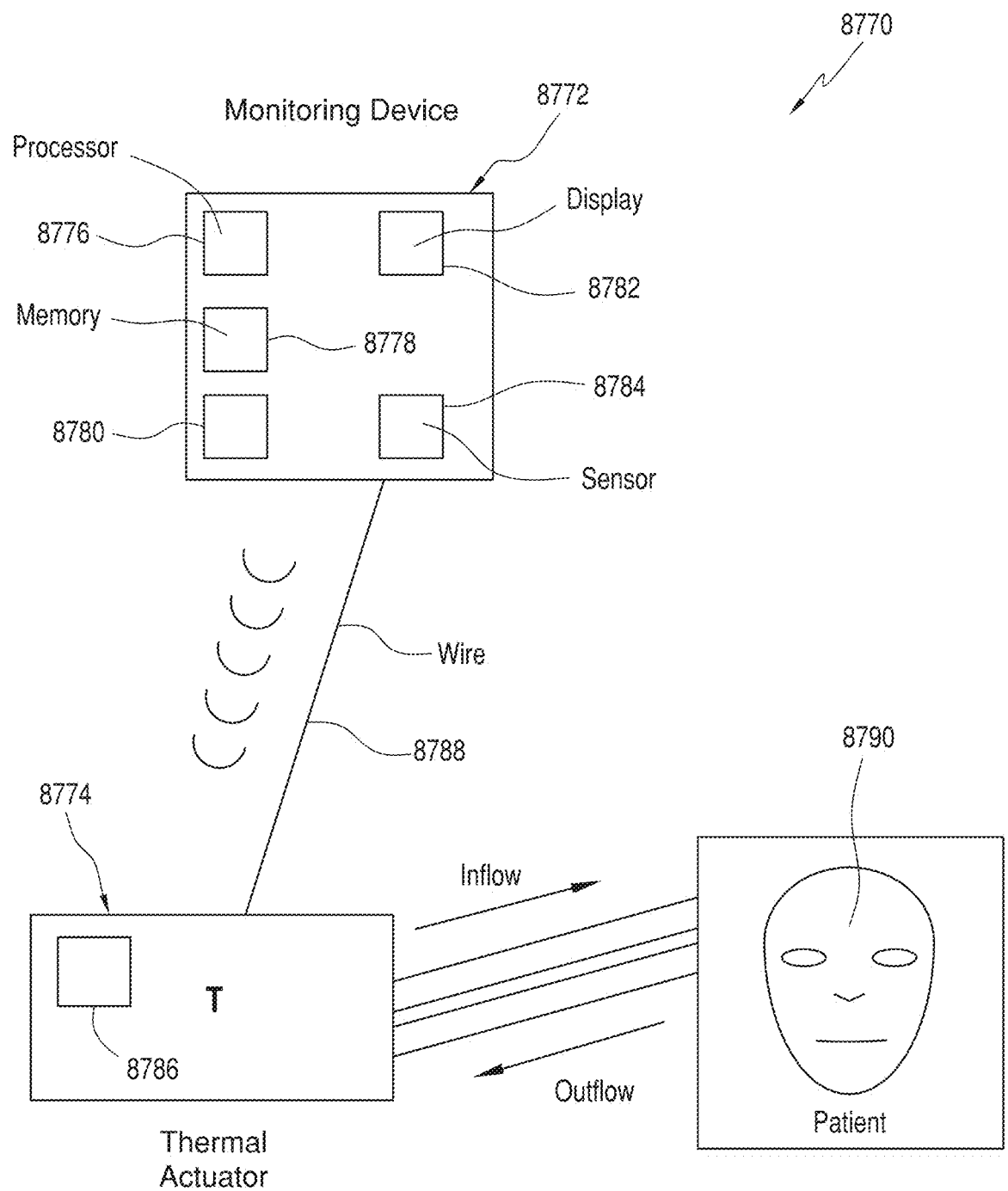
FIG. 76 shows an automated warming-cooling system in accordance with an exemplary embodiment of the present disclosure.

Currently the level of temperature of the blood (or fluid) being delivered to the patient, called inflow, is chosen in a random manner because there is no way to know what the temperature of blood should be to accomplish cerebral cooling. Likewise, currently there is no method to predict exactly the duration of infusion of cold blood (or duration of inflow). By measuring the temperature of the skin on, over, or adjacent the ABTT terminus in over 200 patients undergoing surgery, Applicant has identified the thermal pattern that provides answers to both of those questions: (a) temperature level of the blood (or fluid) being infused (i.e., inflow temperature), and (b) duration of time delivering fluid (i.e., time of inflow). In accordance with the principles of the present disclosure, as shown in FIG. 76, an automated warming-cooling system is disclosed and generally indicated at 8770.

Automated warming-cooling system 8770 includes a temperature measuring device 8772 and a thermal actuator 8774, which in an exemplary embodiment may be an oxygenator or bypass machine. In the exemplary embodiment of FIG. 76, temperature measuring device 8772 includes a controller or processor 8776, a non-transitory memory 8778, a wireless transceiver 8780, a reporting apparatus 8782, which may be a display, and a temperature sensor 8784. In an exemplary embodiment, temperature measuring device 8772 may be connected to thermal actuator 8774 by a wire 8788 or wirelessly, for example by way of wireless transceiver 8780 located in temperature measuring device 8772 and a wireless transceiver 8786 included in thermal actuator 8774.

Controller 8776 is configured to calculate the temperature of flow or inflow, the inflow temperature being presented on reporting apparatus 8782 of temperature measuring device 8772. In the embodiment of FIG. 76, temperature is measured at ABTT terminus site 8790, and the inflow temperature is based on the baseline temperature of the skin on, over, or adjacent the ABTT terminus, i.e., the ABTT terminus site, but not temperature of any other part of the body. It should be understood that though it is within the scope of this disclosure to use other sites, outside the ABTT site and the eyelid, to identify the temperature of inflow fluid and duration of inflow, the apparatus and methods of this invention to determine temperature of fluid (inflow fluid) and duration of inflow can be used with measurements done in other parts of the body, such as other skin surface sites, and invasively (bladder, blood, esophagus, ear, rectal, nose, and the like), but those sites and methods outside the ABTT are not preferred because they do not provide an accurate representation of brain temperature, as described herein.

Baseline temperature at the ABTT site provides the basis for determining the temperature of inflow fluid, said inflow fluid temperature being 15° C. lower than the ABTT terminus baseline temperature, and more preferably in the range 15° C. and 25° C. lower than the ABTT terminus baseline temperature, and yet more preferably 25° C. lower than ABTT terminus baseline temperature, when ABTT terminus baseline temperature is within levels between 35° C. and 37° C. Likewise, when there is a predetermined drop in temperature from the baseline, inflow should cease since the duration of inflow and temperature of the inflow fluid will reach the brain cooling effect, which is predicted by the apparatus 8770, said prediction based on the temperature drop from baseline and slope of the curve corresponding to the drop of temperature, said controller or processor 8776 being adapted to continuously identify change in the temperature measured and compare to the baseline temperature stored in non-transitory memory 8778.

When controller 8776 identifies a temperature drop in the range of 10° C. to 18° C. at the ABTT terminus site compared to baseline, and more preferably a temperature drop in the range of 13° C. and 16° C. at the ABTT terminus site compared to baseline, controller 8776 activates a stop mechanism at the thermal actuator or oxygenator 8774, so as to stop inflow of cold fluid.

Likewise, controller 8776 is configured to perform a similar function for warming. When there is a predetermined increase in temperature from the ABTT terminus baseline, inflow of warm fluid should cease since the duration of inflow and temperature of the inflow fluid will reach the desired brain warming effect, which is predicted by automated heating-cooling system 8770, said prediction based on the increase of temperature from ABTT terminus temperature baseline and slope of the curve corresponding to the increase of temperature, controller 8776 being adapted or configured to continuously identify change in temperature measured and compare to the baseline temperature stored in non-transitory memory. When controller 8776 identifies a temperature increase between 4° C. and 11° C. at the ABTT site compared to baseline, and yet more preferably a temperature increase between 6° C. and 9° C. at the ABTT site compared to baseline temperature, controller 8776 is configured to actuate a stop mechanism at thermal actuator or warming machine 8774, so as to stop inflow (or heat transfer for warming using any other device), and thereby prevent damage due to brain overheating, also called hyperthermia.

It should be understood that the ABTT terminus baseline can be the initial temperature of the patient, but other baselines can be used, such as the no-flow phase of cardiac bypass surgery, the no-flow baseline being used by controller 8776 being configured to use the no-flow baseline to control heating or cooling of blood inflow. Alternatively, the ABTT terminus baseline is the lowest temperature achieved prior to executing the warming function by controller 8776.

Thermal actuator 8774 includes any device or article of manufacturing that can warm or cool a body, by contact or non-contact means, and by way of illustration, any warming or cooling system that delivers air or fluid to the body and any article of manufacturing that can exchange temperature with the body by contact through warming or cooling any part of the body.

Therapeutic hypothermia and hyperthermia may provide significant benefit in the treatment of certain diseases and conditions. However, such therapies also present a risk of brain damage. The accurate and fast measurement of brain temperature at the skin on the ABTT terminus and characterization of slope that exceeds a predetermined slope pattern, as disclosed herein, reduces the risk of such therapies to the brain by "listening" to the brain. It should be apparent from the foregoing description that the use of non-invasive ABTT terminus temperature measurements during therapeutic hypothermia and therapeutic hyperthermia is a significant improvement over conventional approaches to measuring analogs for brain temperature.

ABTT Monitoring During Exercise

Figure 20:
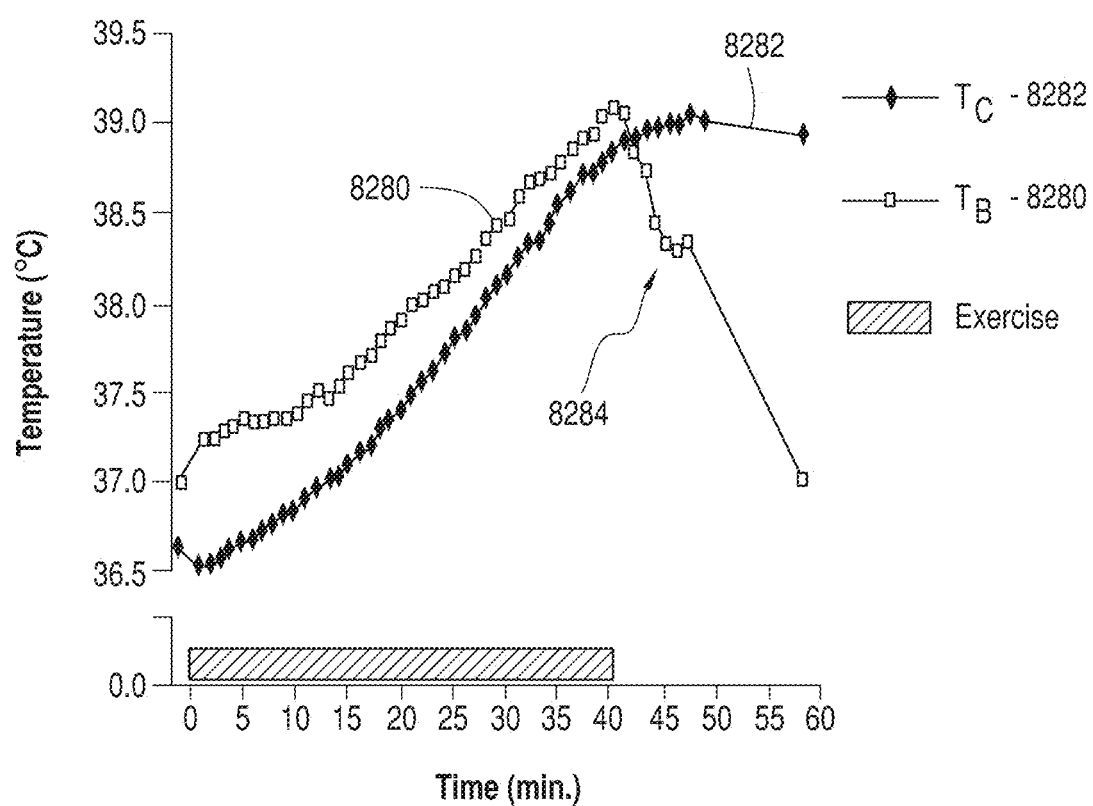
FIG. 20 is a graph of temperature measured on the skin adjacent to, over or on the ABTT terminus and the body core temperature during and after an exercise interval.

As yet another embodiment of the present disclosure, research was conducted on volunteers during exercise. As shown in FIG. 20, ABTT temperature 8280 was measured at the skin of the ABTT terminus while core temperature 8282 was measured with a thermal capsule ingested approximately six hours prior to exercise. The subject exercised vigorously in a heated chamber for approximately 40 minutes. During the entire exercise interval, ABTT temperature 8280 was higher than core temperature 8282. When the ABTT temperature reached approximately 39° C., exercise was halted and the subject was moved to a cool environment. The reaction of the ABTT was immediate and profound. While core temperature 8282 in post exercise period 8284 remained above 39° C., ABTT temperature 8280 plummeted from above 39.0° C. to a near nominal normal temperature of 37.0° C. in approximately 20 minutes. This result is significant because it provides a perfectly reliable measure of excessive brain temperature during exercise, which leads to a safe, simple, and effective way to prevent heat stroke by monitoring ABTT temperature during exercise. Furthermore, by measuring the rate of ABTT increase during exercise, individual subjects may be identified for a propensity to sustain thermal injury and heat stroke.

Accordingly, a first exemplary embodiment thermal injury susceptibility may be measured by a brain temperature response function (BTRF) during exercise in any environment, but most particularly an environment with an elevated temperature. The BTRF is broadly a change in brain temperature in response to any stimulus, either external or internal. In an exemplary embodiment, such a measurement of BTRF may include (1) providing an environment with an elevated temperature, for example, 35° C.; (2) establish a nominal ABTT temperature condition prior to exercise or entry in the heated environment; (3) place the subject in the heated environment; (4) measure the BTRF in the heated environment; (5) initiate exercise activities if appropriate to the subject and the initial BTRF response; and (6) cease all activities when the subject's BTRF reaches a predetermined temperature, for example 39.0° C. and place the subject into an environment with a temperature approximately nominal room temperature. Be wary of cooling the patient too rapidly, which may generate an adverse effect by causing the body to believe it is becoming excessively cool, causing shivering or other adverse reactions. Measurement of the ABTT temperature must be maintained throughout the process. The BTRF determines the ability of the subject to function in an environment with an elevated temperature without permanent injury. It should be understood that the BTRF can be used in other applications, including, but not limited to, surgery as described herein in which a patient is cooled and warmed, or any other procedure for cooling or warming the body and brain.

As a second exemplary embodiment, such monitoring may be accomplished during exercise in a non-heated environment to monitor brain temperature and keep such temperature from reaching damaging levels. In an exemplary embodiment, such a measurement of BTRF may include (1) establish a nominal ABTT temperature condition prior to exercise; (2) initiate exercise activities appropriate to the subject and the initial BTRF response; and (3) cease all activities when the subject's BTRF reaches a predetermined temperature, for example 39.0° C., or if the slope of the BTRF exceeds a predetermined slope, for example, a BTRF slope steeper or greater than approximately 0.07° C./minute, and place the subject into an environment with a temperature approximately nominal room temperature. As before, be wary of cooling the patient too rapidly, which may generate an adverse effect by causing the body to believe it is becoming excessively cool, causing shivering or other adverse reactions. Measurement of the ABTT temperature must be maintained throughout the process. In this particular case, the function of the BTRF is to assure that exercising is performed in a thermal regime that is non-damaging to the brain. For example, obese individual moving heavy objects continuously even in relatively cool weather may see a BTRF that exceeds a dangerous level, leading to an adverse systematic response, including coma, heart attack, and, in the most extreme cases, death. However, measurement of ABTT temperature permits calculation of a BTRF, and ultimately an acceptable or safe BTRF for any individual.

Frequency Analysis of ABTT Temperature Signals

While the various embodiments of measuring the ABTT temperature and graphing that temperature in a BTRF provides many advantages over conventional temperature measurements, particularly when coupled with specific situations, including surgery, anesthesia, exercise, sleep, etc., an entirely unexpected result occurred in a frequency analysis of the temperature at the skin of the ABTT terminus.

In the prior art, thermoregulation has not been assessed by changes in body temperature because of the inability to measure brain temperature; instead, investigators relied, and still rely, on changes in cardiovascular signals. The development of temperature sensors and monitoring equipment described herein that enabled capturing of thermal signals at a rate faster than thermal band frequencies enabled assessment of thermal variability, and thereby enabled assessment of the nonlinear dynamics of thermoregulation. ABTT technology is applicable to a unique, hitherto unknown system for measuring the health of individuals.

In an ongoing series of studies, Applicant employed ABTT sensors that recorded temperature as frequently as q15sec at the forehead, rectum, and at the skin of the ABTT terminus. As described herein, the results of the ABTT temperature sensor showed the greatest time variability, suggesting plasticity of the thermoregulatory system that is not appreciated by monitoring at a site remote from the hypothalamus, e.g., the rectum. FIG. 20 illustrates the spectral pattern of the ABTT temperature signal of FIG. 17 in the frequency domain. It demonstrates oscillatory power in the range encompassing the thermoregulatory band described above.

It has been noted that, despite the potential utility of assessing temperature variations to predict morbidity, all too often temperature is viewed as a dichotomous variable (fever/no fever). The present findings open new avenues of research with respect to thermal and thermodynamic phenomena. The assessment of temperature as disclosed herein enables better understanding of thermoregulatory control during health, as well as disease, and during normothermia as well as hypothermia, hyperthermia and fever. To this end, Applicant connected a spectrum analyzer 8177 to BTT system display 8001. More specifically, controller 8112 provided temperature data to spectrum analyzer 8177. The present data were collected at 15 sec. Greater spectral resolution will be attainable with new probes that sample as rapidly as 1 Hz.

Figure 21:
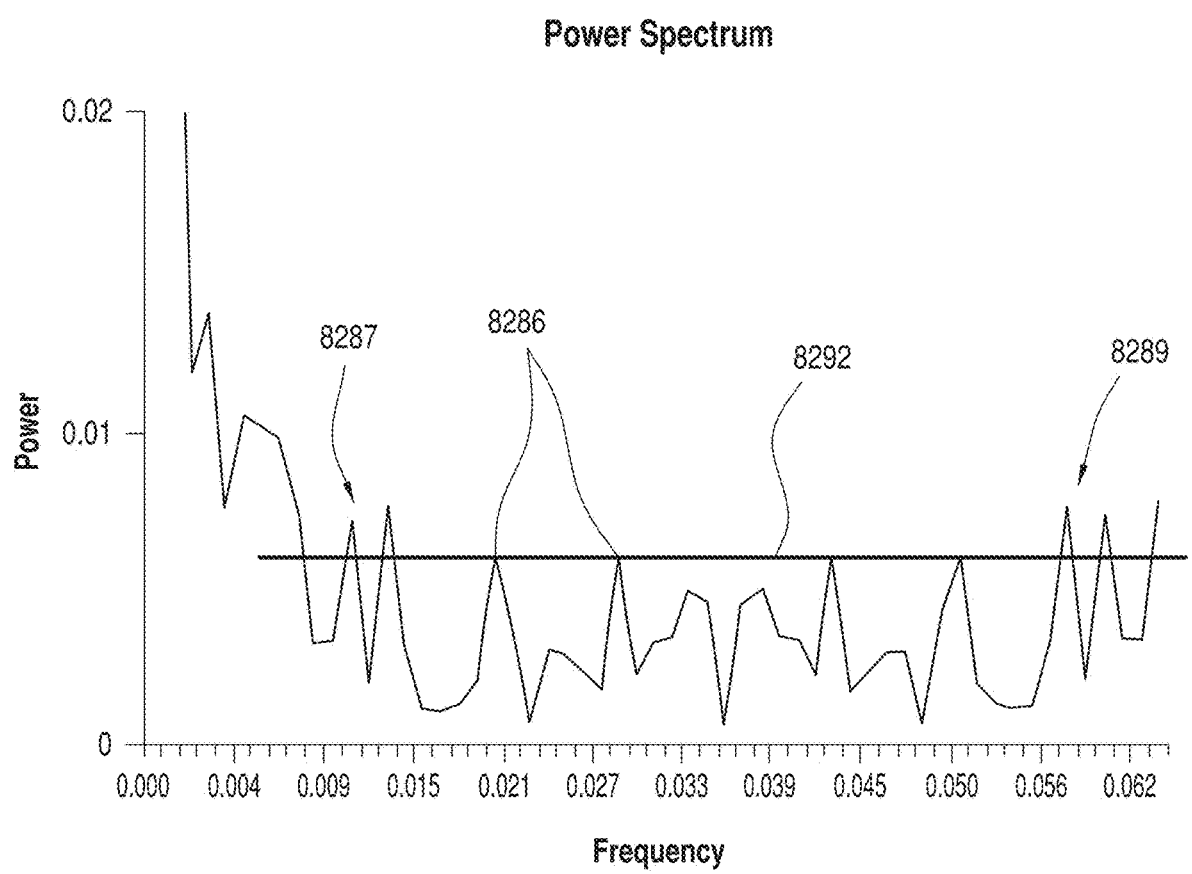
FIG. 21 is a graph of frequency response of the ABTT temperatures shown in FIG. 17.

FIG. 21 includes at least two characteristics representative of a healthy individual. First, peaks 8286, both positive and negative, having the greatest power across the spectrum are distributed as intervals that suggest harmonics, and greatest power at the frequency of 0.01 Hz. Further, it appears that there are two or more harmonics overlaid upon each other. The second characteristic is that the peaks across the central portion of the spectrum are generally the same amplitude, creating a line 8292 having a slope that is near zero.

Figure 22:
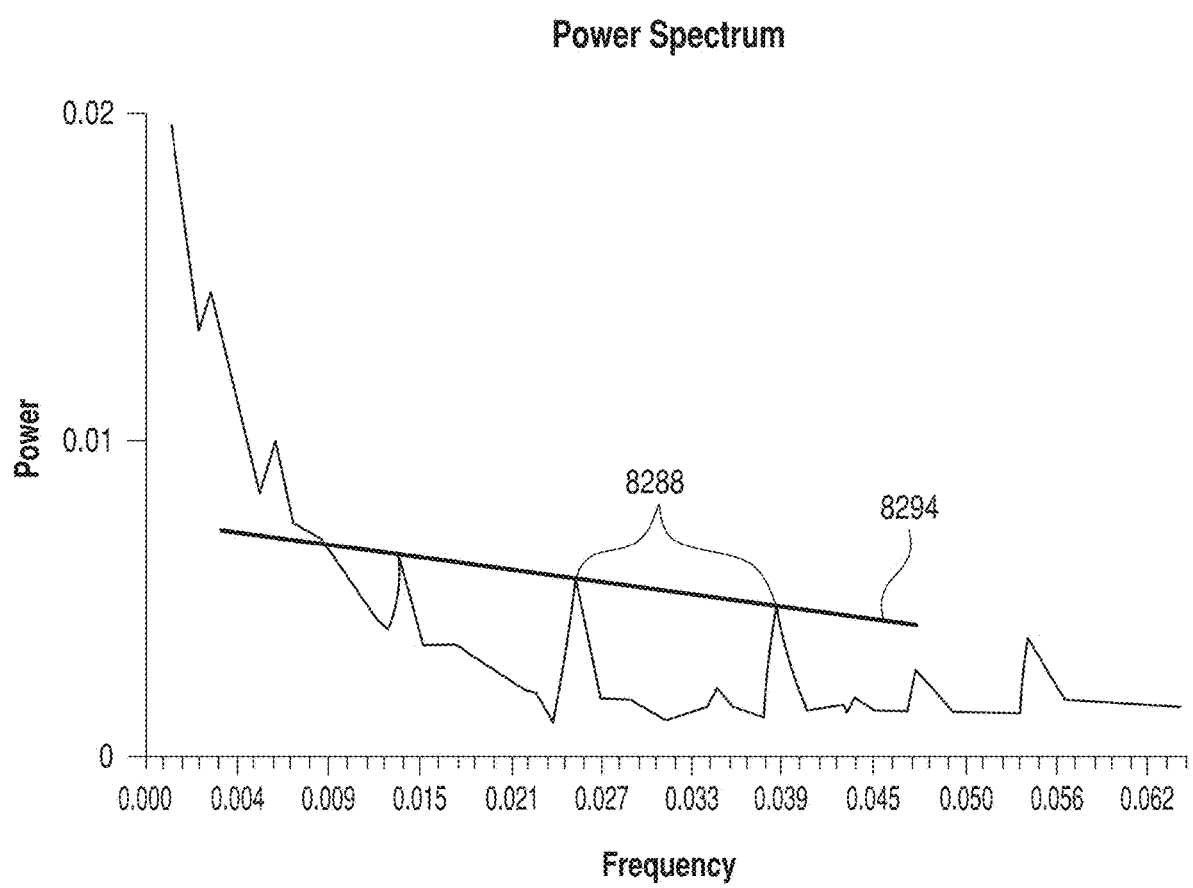
FIG. 22 is a graph of frequency response of ABTT temperatures similar to FIG. 21, showing the ABTT temperature frequency response of an ill subject.

FIG. 22 is in comparison to FIG. 21, and shows the power spectrum of a sick individual. Two things are immediately apparent. First, peaks 8288 in FIG. 22 are spaced further apart than the peaks in FIG. 21. In an exemplary embodiment, Applicant has determined through research and experimentation that the best measurements of frequency are with a subject's own baseline. However, any spacing of peaks greater than 0.007 Hz is indicative of a medical condition, with spacing of peaks greater than 0.008 Hz indicative of a potentially serious medical condition. Spacing greater than 0.008 Hz is indicative of a very serious, and potentially life-threatening, medical condition requiring immediate treatment. Second, the power of the higher frequency components is lower in amplitude than the lower frequency elements, and a line 8292 drawn through the center peaks 8288 is markedly tilted, slanted, or sloped with respect to the horizontal axis. Indeed, applicant has found that when a line, such as line 8294, is drawn through the central peaks of the spectral analysis, the more line 8294 deviates from the horizontal, the more ill the patient or subject is. In an exemplary embodiment, a slope of 0.03/Hz (power per frequency) or more equates to a medical condition of a patient requiring medical treatment. The non-horizontal slope and increased spacing are indications of a defective temperature regulation mechanism in the brain core, which may be due to disease or a medical condition. Further, the lower power at the higher frequencies is an indication that even the current capability of the temperature regulation mechanism is suffering. It should be apparent from FIG. 21 that an exemplary range for measuring frequency peaks is in a range 0.015 to 0.050 Hz.

Additionally, the symmetry of peaks 8287 and 8289 located at the left or low frequency end of line 8292 and the right or high frequency end of line 8292 also relate to the health of an individual, with nearly perfect symmetry indicative of a healthy individual, and asymmetric peaks, either by frequency position or amplitude, is indicative of a less healthy person, or, when the peaks begin deviating from each other, a person with a medical condition. Such condition should be suspected when peaks 8287 and 8289 are asymmetric by 5% or more, and such condition is likely when peaks 8287 and 8289 are asymmetric by 10% or more.

Accordingly, a diagnostic system enabled by frequency analysis is enabled by ABTT temperature measurement. In an exemplary embodiment, the system includes: (1) monitoring ABTT temperature with the fastest temperature sensor available for a time interval, for example, an hour; (2) converted the received temperatures to a frequency response through a spectrum or frequency analyzer 8177; (3) determine the mean interval between peaks and the slope of the peaks across the central portion of the frequency spectrum. If the mean interval between peaks is more than a predetermined amount greater than the mean interval between peaks for a healthy individual of a similar age, for example, 10%, or more than 0.007 Hz, then a medical condition or disease could be at work and further diagnosis may warranted. Similarly, if the slope of the peaks deviates from a horizontal line by a predetermined amount, such as a slope greater than −0.03 power/Hz, a disease or medical condition should be suspected.

It should be understood that an exemplary embodiment of the apparatus described herein includes a controller or processor, a non-transitory memory, and a reporting apparatus, such as a display, audible or written output, etc. The controller is operatively coupled to the non-transitory memory, and the controller is configured to analyze data captured by an ABTT temperature sensor and to compare the analyzed data to pre-determined information, such as, by way of example, temperature levels, temperature variation in a certain time, slopes, and the like, stored in non-transitory memory. The controller is configured to compare the acquired and analyzed temperature data with the data stored in non-transitory memory, and when there is an identified analytical match, i.e., the data matches predetermined ratios or percentages or predetermined profiles, the reporting apparatus reports, displays, signals, prints out, or otherwise provides notification of the identified match.

Apparatus for Locating the ABTT

Applicant has determined, through experimentation, that finding the precise location of the skin location overlying the ABTT terminus can be accomplished relatively quickly with a properly training and experienced individual. However, in some circumstances it may be difficult to locate the location of the ABTT terminus rapidly. For example, during an emergency, dim light conditions, and other circumstances, it may be challenging to find the skin location of the ABTT terminus. Accordingly, Applicant has developed various apparatuses to improve the ability to find the skin location of the ABTT terminus.

Scanning the Skin of the ABTT Terminus

When using any of temperature sensors 8002, 8004, 8006, or 8008, typically the sensor will be moved back and forth over the skin in the area of the ABTT terminus. When locating the ABTT terminus in typical room temperature conditions, the temperature scans provide temperature outputs that appear similar to those presented in FIG. 23, which shows a stylized representation of a scan of the skin over the ABTT terminus. The temperature skins appear similar to a "bull's eye" or target, with the center having the hottest temperature, except when the skin temperature around the ABTT terminus is higher than the skin at the ABTT terminus, when the skin temperature at the ABTT terminus is much lower than the temperature of the surrounding skin. As can be understood, by viewing the temperature readout on display 8118 or digital display 8014 while moving a temperature sensor back and forth in the area of the ABTT terminus, a peak temperature, either positive or negative, can be found in the area of the ABTT terminus.

Figure 25:
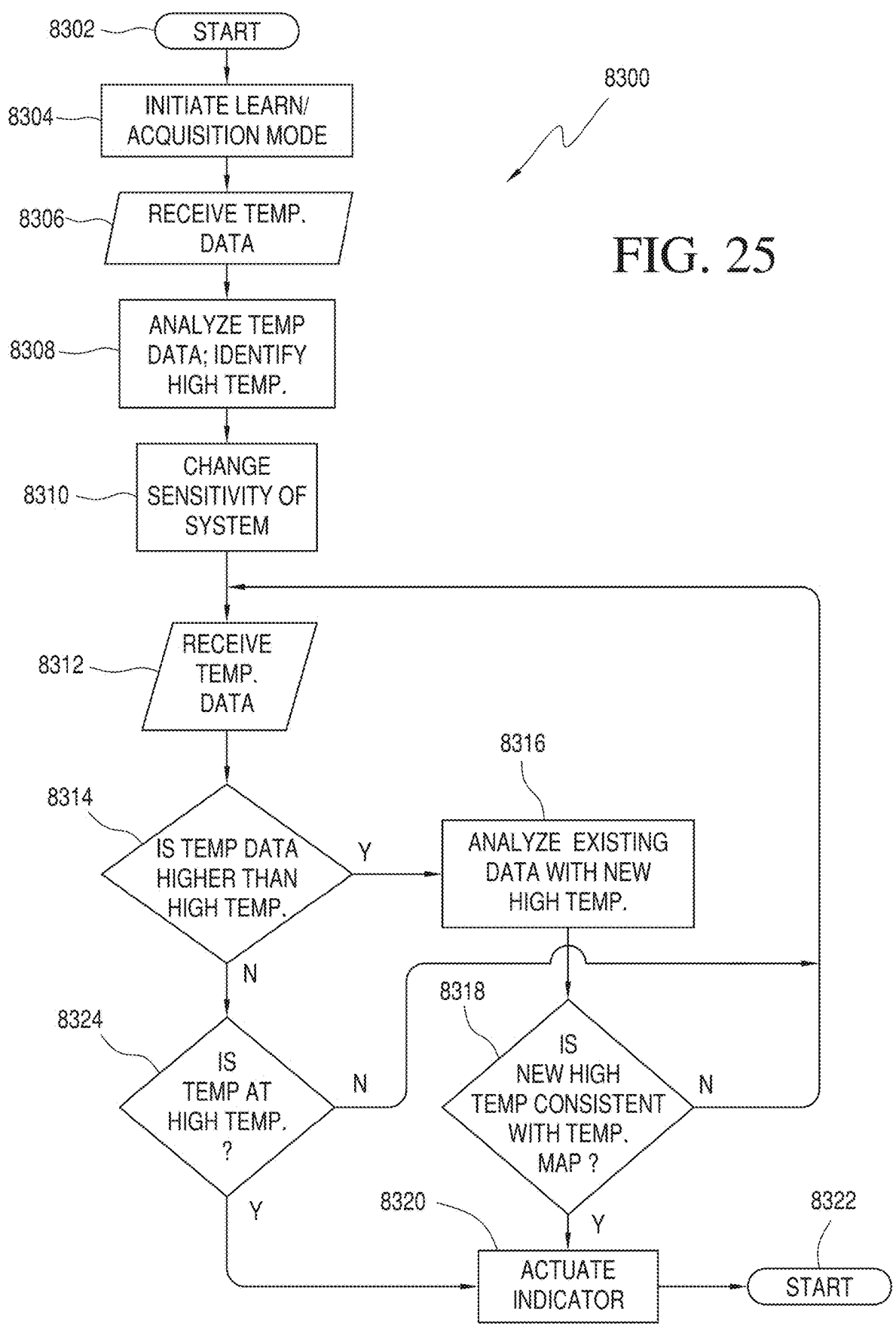
FIG. 25 is a process flow chart representing a process for locating the ABTT terminus in accordance with an exemplary embodiment of the present disclosure.

As described hereinabove, under certain circumstances, it may be challenging to locate the center of the ABTT terminus. FIG. 25 shows an ABTT terminus location process 8300 representing a process for locating the ABTT terminus by using a temperature sensor such as temperature sensor 8002, 8004, 8006, or 8008, in conjunction with a controller of ABTT monitoring system 8000, such as system unit controller 8112.

ABTT terminus location process 8300 begins with a start process 8302, where registers may be reset to zero, any predetermined values may be loaded, and other initializations may occur. Once start process 8302 is complete, control passes from start process 8302 to an initiate learn/acquisition mode process 8304.

In initiate learn/acquisition mode process 8304, ABTT monitoring system 8000 provides power to a temperature sensor and prepares to acquire data from the temperature sensor. ABTT monitoring system 8000 may perform other activities in initiate learn/acquisition mode process 8304, such as uploading from non-transitory memory 8114 a program to analyze temperature data, setting aside memory to store temperature data in non-transitory memory 8114, etc. Once initiate learn/acquisition mode process 8304 is complete, control passes to a receive temperature data process 8306.

In temperature data process 8306, ABTT monitoring system 8000 receives a plurality of data points that represent the temperature of the skin in the area adjacent to, over, or on the ABTT terminus. The temperature data is stored in memory in ABTT monitoring system 8000, which may be non-transitory memory 8114. Once a plurality of data points have been received, control passes from temperature data process 8306 to an analyze temperature data process 8308.

Figure 23:
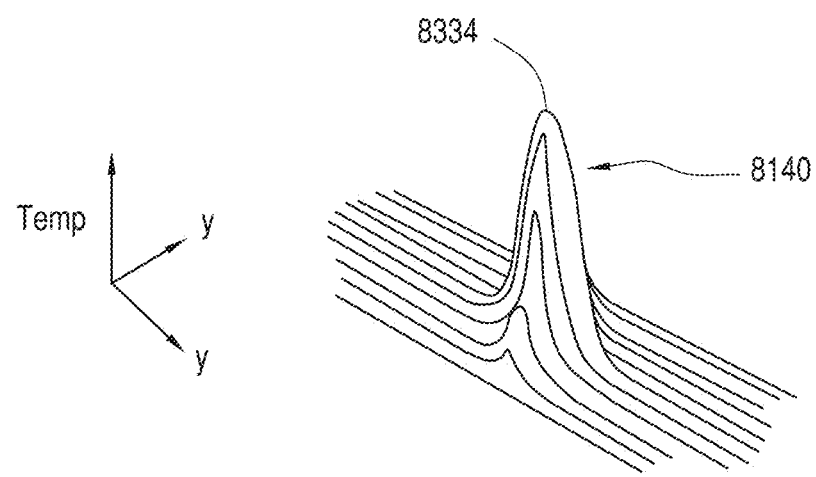
FIG. 23 is a stylized representation of the scan of the skin over the ABTT terminus.

In analyze temperature data process 8308, a virtual representation of the temperatures of the ABTT terminus is created, which may appear similar to the three-dimensional graph of FIG. 23. It should be evident from FIG. 23 that the X and Y-axes represent positions around the area of the ABTT terminus, and the Z axis is temperature. As part of the creation of the three-dimensional representation of the temperature of the ABTT terminus, a peak temperature is either found by direct measurement or calculated from the acquired data. Part of the analysis process is a smoothing of the temperature data and best-curve fits in both the X and Y directions. Once a representation of the temperature profile around the ABTT terminus is determined, control passes from analyze temperature data process 8308 to a change sensitivity of ABTT system process 8310.

Figure 24:
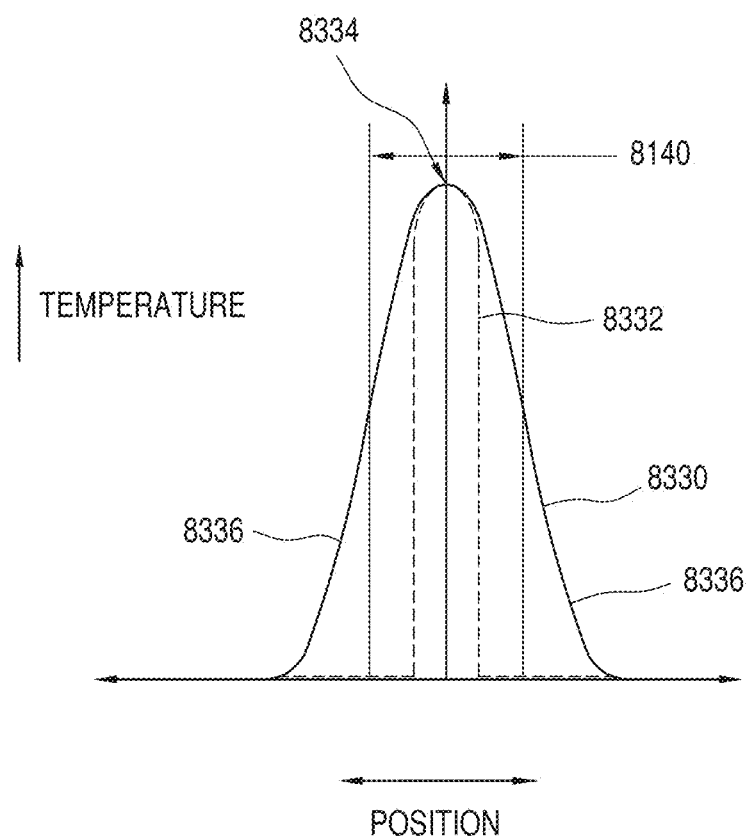
FIG. 24 is a graph of two temperature sensor sensitivities in accordance with an exemplary embodiment of the present disclosure.

In change sensitivity process 8310, the sensitivity of the ABTT monitoring system 8000 is changed from standard, approximately linear sensitivity, where all temperatures are read, to a cutoff sensitivity, wherein temperatures below a certain value are no longer considered in locating the position of the ABTT terminus. Such change in sensitivity behaves functionally in a manner similar to that shown in FIG. 24. A first temperature curve 8330 represents the temperature of the skin, beginning in an area away from ABTT terminus 8140 (see also FIG. 12). As ABTT terminus 8140 is approached, skin temperature rises rapidly to a peak 8334 representing the brain temperature, if the center of the ABTT terminus 8140 is reached. Once ABTT monitoring system 8000 has identified peak temperature 8334 of ABTT terminus 8140, ABTT monitoring system 8000 may modify the sensitivity of the electronics of ABTT system display 8001 so that a temperature based on peak temperature 8334 is set as a cutoff temperature. Such change in sensitivity may occur in amplifier 8108, if present, in A/D converter 8110, or in system unit controller 8112. Alternatively, such cutoff may be performed by software located in system unit controller 8112. In an exemplary embodiment, if the cutoff temperature is 90% of peak temperature 8334, then no temperatures below 90% are measured, which is shown as a second temperature curve 8332.

The function of change sensitivity process 8310 is aid a user in finding the location of ABTT terminus 8140. Once a user has scanned the area of ABTT terminus 8140 in learn/acquisition mode process 8304, and once ABTT monitoring system 8000 has identified peak or high temperature 8334, in analyze temperature process 8308, the need is for ABTT monitoring system 8000 to tell the user where peak or high temperature 8334 is located. A coronal temperature 8336 surrounds ABTT terminus 8140, and the coronal temperature may make it hard to find peak temperature 8334. By reducing the sensitivity of ABTT monitoring system 8000 in change sensitivity process 8310, using peak temperature 8334 as a basis, the search area is greatly reduced, making the center of ABTT terminus 8140 easier to location. Once the sensitivity of ABTT monitoring system 8000 has been modified, control passes to a receive temperature data process 8312.

In receive temperature data process 8312, temperature data from a temperature sensor is received by ABTT system display 8001, where the temperature data is analyzed. Once the temperature data has been received and analyzed, control passes to a high temperature decision process 8314.

In high temperature decision process 8314, ABTT terminus location process 8300 determines whether the received temperature data is higher than the current high temperature identified in analyze temperature data process 8308. If the received temperature data is higher or greater than the current high temperature, control passes from high temperature decision process 8314 to an analyze existing data process 8316.

In analyze existing data process 8316, any existing temperature curve is analyzed in view of the newly received temperature data. ABTT terminus location process 8300 may determine that the higher temperature appears, by analysis, to be the actual high temperature. Alternatively, ABTT terminus location process 8300 may determine that the temperature curve data indicates a higher temperature may be available. Once the newly received temperature data is analyzed, control passes from analyze existing data process 8316 to a temperature consistency decision process 8318.

In temperature consistency decision process 8318, based on the analysis provided by analyze existing temperature data process 8316, ABTT terminus location process 8300 decides whether the newly received high temperature is consistent with the existing temperature map as a peak temperature of the ABTT terminus. If the newly received data appears to be consistent with the temperature map, control passes from temperature consistency decision process 8318 to an actuate indicator process 8320, which an indicator of ABTT monitoring system 8000 is actuated to indicate the ABTT terminus high temperature has been located. Such indicators may include tones, flashing displays, and/or other visual, vibrational, or audio indications on ABTT system display 8001. Alternatively, an indication may be provided on the temperature sensor. In an exemplary embodiment, LED's 8088 shown in FIG. 5 may be flashed or blinked to indicate the peak temperature of ABTT terminus 8140 has been reached. Other lights, audio, vibrational indicators may be actuated when provided in other exemplary embodiments. Once actuate indicator process 8320 has actuated one or more indicators, control passes from actuate indicator process 8320 to an end process 8322, where ABTT terminus location process 8300 stops operation and passes control back to a calling program or other process of ABTT monitoring system 8000.

Returning to temperature consistency decision process 8318, if the new high temperature is not consistent with the current temperature map, control is passed from temperature consistency decision process 8318 to received temperature data process 8312, and ABTT terminus location process 8300 functions as previously described.

Returning to high temperature decision process 8314, if the temperature data is not higher than the high temperature, control passes from high temperature decision process 8314 to a high temperature located decision process 8324. In high temperature located decision process 8324, ABTT terminus location process 8300 decides whether the current temperature data is at or near the identified high temperature. In an exemplary embodiment, if the temperature data is within 0.2 degrees Celsius of the peak temperature, ABTT monitoring system 8000 may consider the current temperature data to be close enough to peak ABTT temperature 8334 to consider the present temperature to be the peak, in which case, control passes from high temperature located decision process 8324 to actuate indicator process 8320, which functions as previously described. Alternatively, control passes from high temperature located decision process 8324 to receive temperature data process 8312, where ABTT terminus location process 8300 functions as previously described.

While ABTT terminus location process 8300 appears to be lengthy process, in practice, the learn/acquisition mode generally occurs within 5 to 30 seconds, and locating the ABTT peak temperature typically occurs in another 5 to 30 seconds. Thus, the entire process, from start to finding the peak ABTT terminus temperature, occurs in approximately 10 to 15 seconds, but may vary between 10 to 60 seconds.

Figure 26:
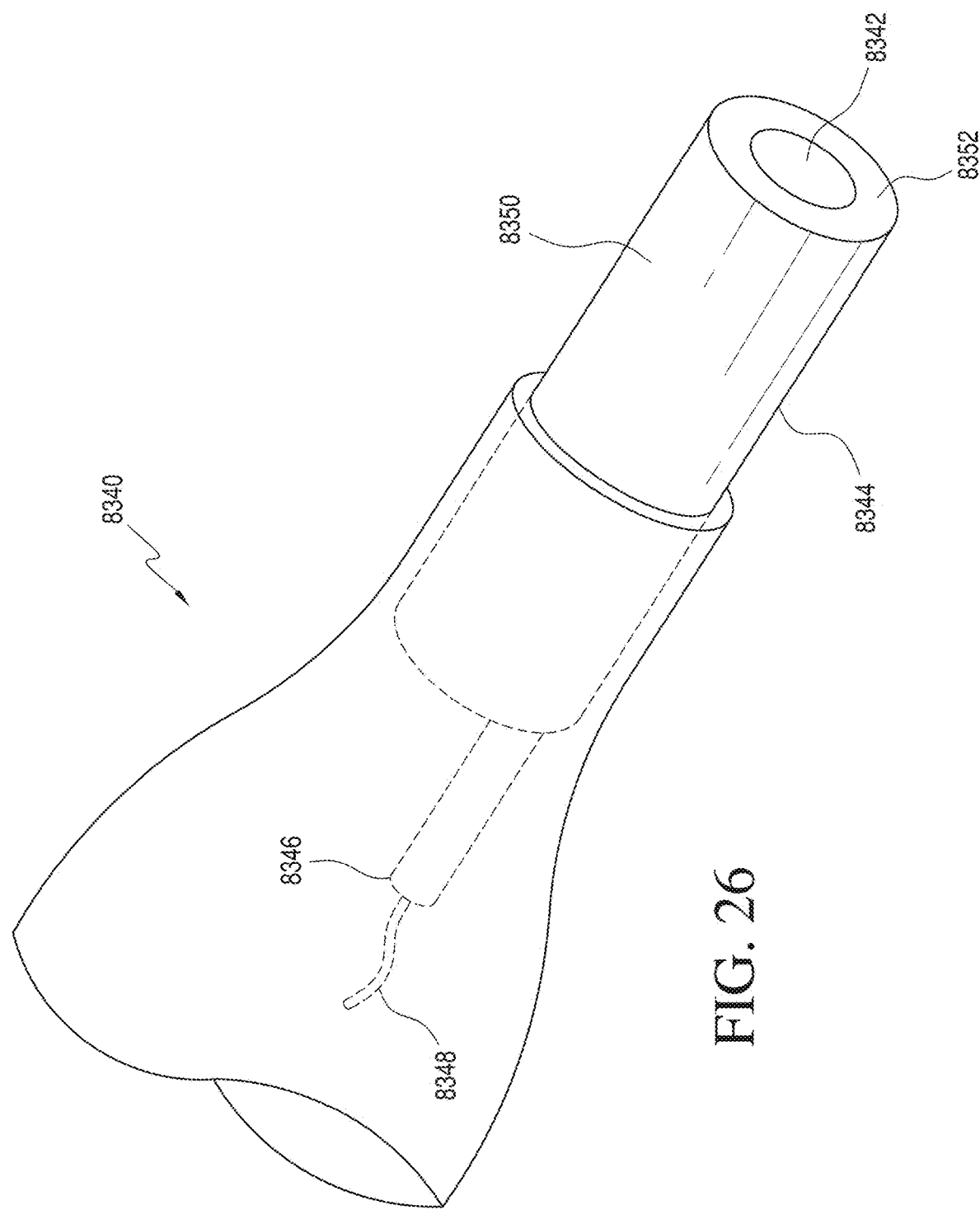
FIG. 26 is a portion of a temperature sensor including an integral indicator in accordance with an exemplary embodiment of the present disclosure.

Indicators on temperature sensors, such as LED's 8088 shown in FIG. 5, have been described herein as a possible apparatus for informing a user that peak ABTT temperature has been located. Another exemplary embodiment indicator is shown in FIG. 26, which shows a portion of a temperature sensor, generally indicated at 8340. Temperature sensor 8340 includes a thermistor 8342, surrounded by a plastic or glass annulus or tube 8344, and a light 8346, which may be an LED. The outer surface 8350 of annulus 8344 may be roughened to be translucent rather than transparent. When ABTT monitoring system 8000 determines that an indicator needs to be actuated, a signal may be transmitted via a wire or cable 8348 to light 8346, which illuminates. The light output from light 8346 travels along annulus 8344, illuminating annulus 8344 and outer surface 8350. As the light from light 8346 passes through an end surface 8352 of annulus 8344, it provides illumination of surfaces, such as skin adjacent to, over, or on the ABTT terminus, which can make it easier to locate the ABTT terminus.

Figure 27:
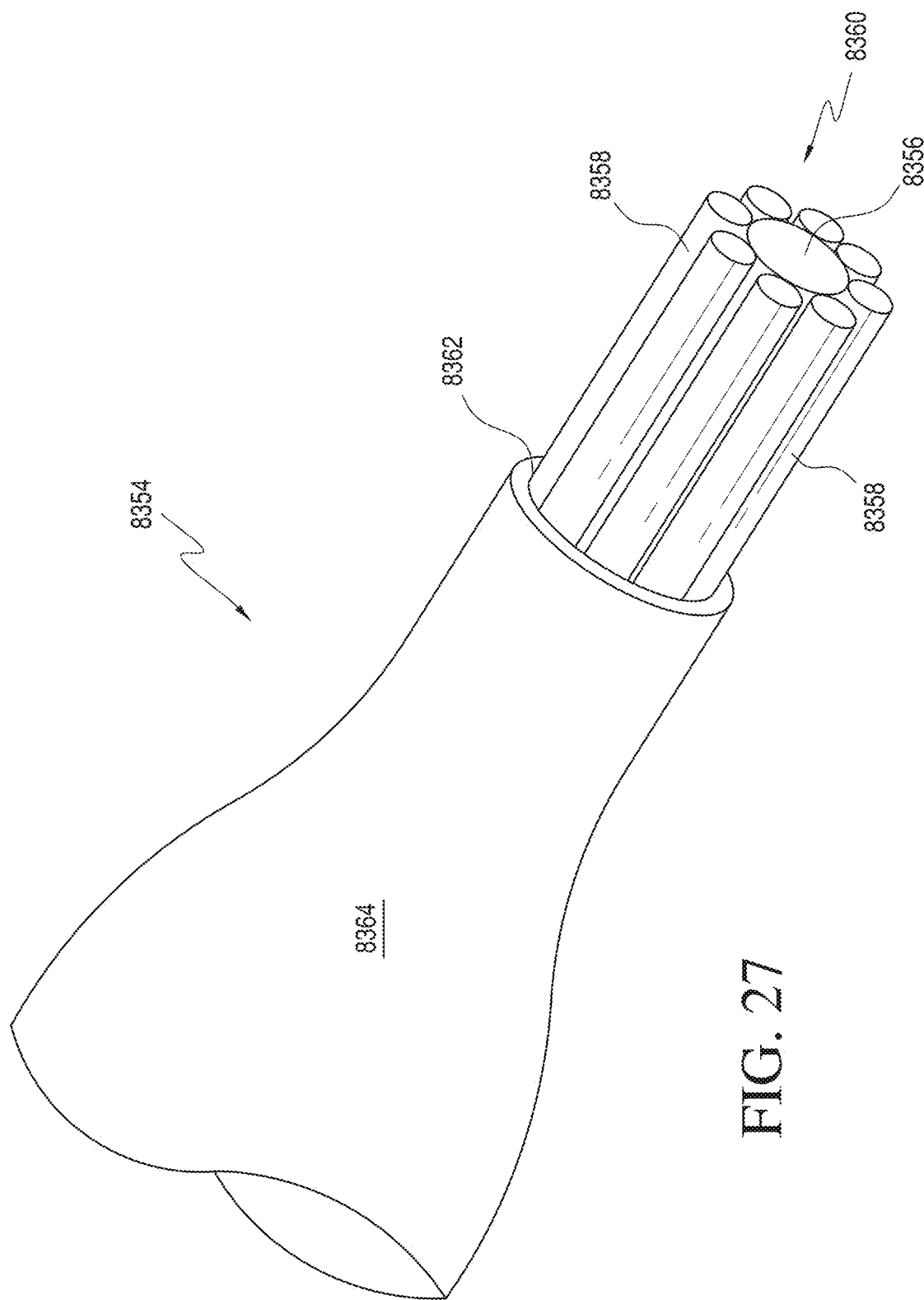
FIG. 27 is a portion of a temperature sensor including a plurality of thermistors in accordance with an exemplary embodiment of the present disclosure.

Another exemplary temperature sensor that provides a different apparatus for detecting the center of the ABTT terminus is shown in FIG. 27 and generally indicted at 8354. Temperature sensor 8354 includes a main thermistor 8356 and a plurality of smaller thermistors 8358 arranged symmetrically about main thermistor 8356, to form a thermistor array 8360. It should be understood that other thermal sensors, such as non-contact sensors, including thermopiles, can be disposed in the configuration disclosed herein or in an array arrangement, and are within the scope of this disclosure. As thermistor array 8360 passes over the ABTT terminus, ABTT monitoring system is able to identify the direction of the hottest temperatures by which thermistors 8358 encounter the highest temperature. When peak temperature 8334 is positioned near the center of thermistor array 8360, each of the smaller thermistors 8358 will indicate approximately the same temperature, indicating that thermistor array 8360 is located over the center of the ABTT terminus. While temperature sensor 8354 provides an efficient way to locate the ABTT terminus, it is relatively expensive to produce because of the number of thermistors required, and positioning smaller thermistors 8358 and holding them in place while an adhesive 8362 and sleeve 8364 are positioned about the assembly.

Figure 28:
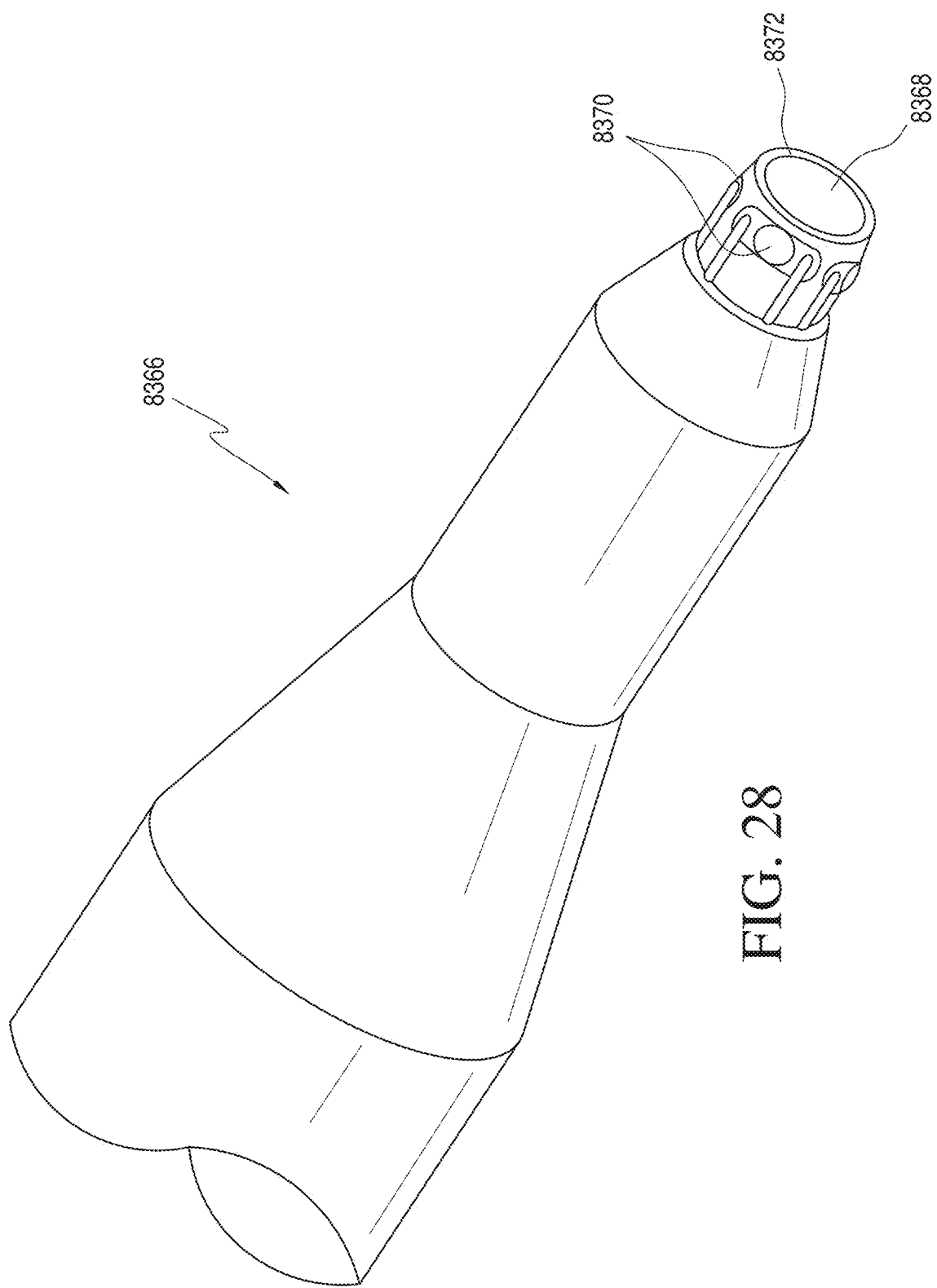
FIG. 28 is a portion of a temperature sensor including a plurality of indicators in accordance with an exemplary embodiment of the present disclosure.
Figure 29:
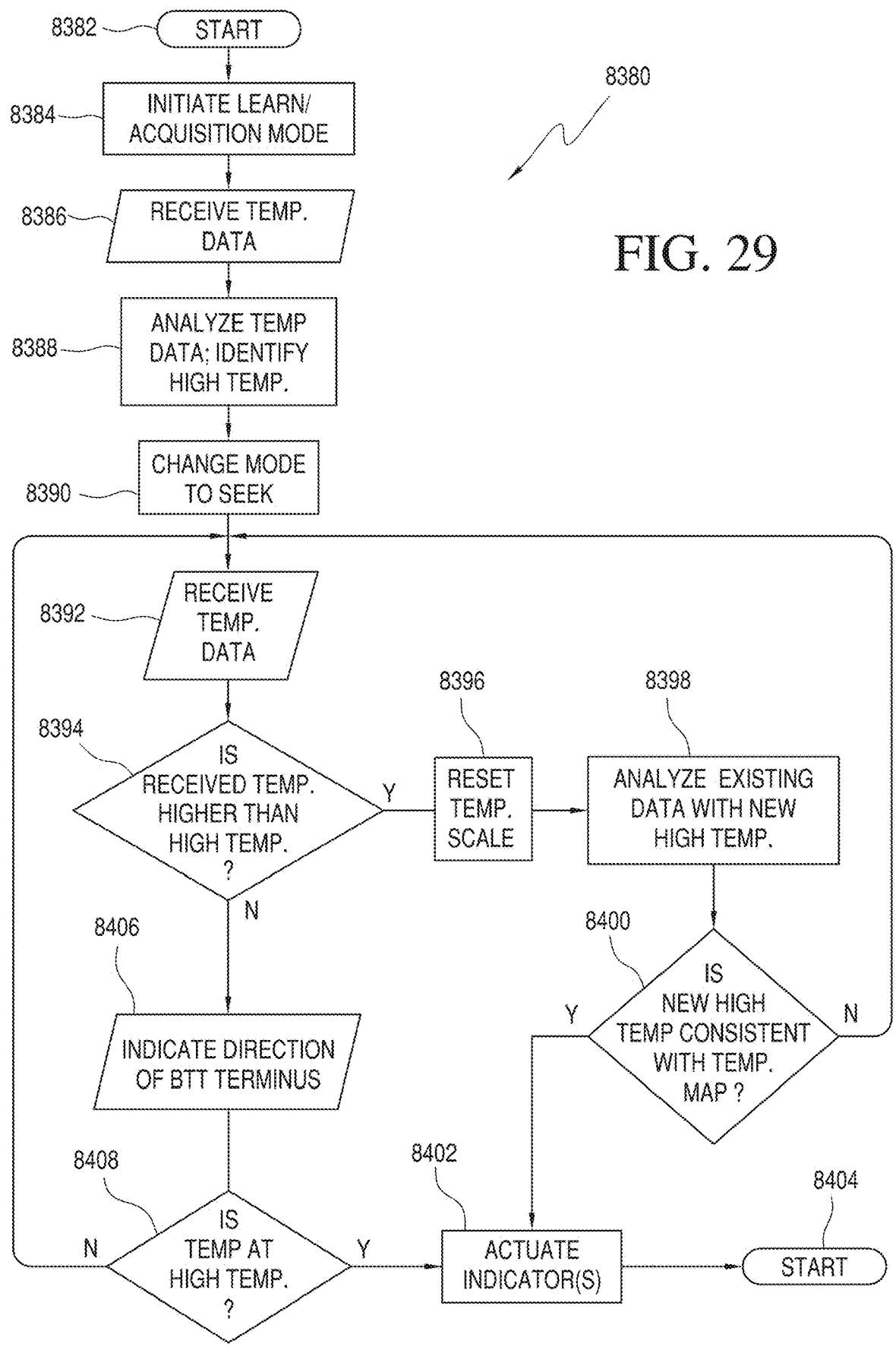
FIG. 29 is a process flow chart representing a process for locating the ABTT terminus in accordance with an exemplary embodiment of the present disclosure.
Figure 35:
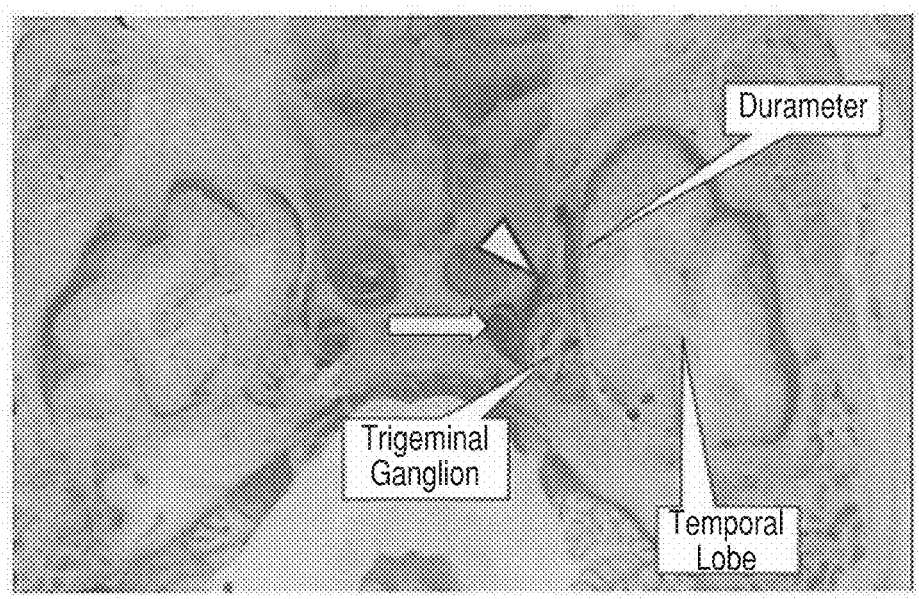
FIG. 35 is an axial cut of a human cranium at the CS level showing the internal carotid artery (ICA), trigeminal ganglion, and the close relationship of the CS-temporal lobe.

Another exemplary embodiment temperature sensor is shown in FIG. 28 and generally indicated at 8366. Temperature sensor 8366 includes a thermistor 8368 and a plurality of small lights 8370, which may be LED's. A temperature insulating sleeve 8372 may be positioned between thermistor 8368 and LED's 8370. An ABTT acquisition process, generally indicated at 8380, which makes use of temperature sensor 8366 is described in FIG. 29. It should be understood that other thermal sensors, such as non-contact sensors, including thermopiles, can be disposed in the configurations disclosed herein and are within the scope of this disclosure.

ABTT acquisition process 8380 begins with a start process 8382, where registers may be reset to zero, any predetermined values may be loaded, and other initializations may occur. Once start process 8382 is complete, control passes from start process 8382 to an initiate learn/acquisition mode process 8384.

In initiate learn/acquisition mode process 8384, ABTT monitoring system 8000 provides power to temperature sensor 8366 and prepares to acquire data from temperature sensor 8366. ABTT monitoring system 8000 may perform other activities in initiate learn/acquisition mode process 8384, such as uploading from non-transitory memory 8114 a program to analyze temperature data, setting aside memory to store temperature data in non-transitory memory 8114, etc. Once initiate learn/acquisition mode process 8384 is complete, control passes to a receive temperature data process 8386.

In temperature data process 8386, ABTT monitoring system 8000 receives a plurality of data points that represent the temperature of the skin in the area adjacent to, over, or on the ABTT terminus. The temperature data is stored in memory in ABTT monitoring system 8000, which may be non-transitory memory 8114. Once a plurality of data points have been received, control passes from temperature data process 8386 to an analyze temperature data process 8388.

In analyze temperature data process 8388, a virtual representation of the temperatures of the ABTT terminus is created in ABTT monitoring system 8000, which may appear similar to the three-dimensional graph of FIG. 23. It should be evident from FIG. 23 that the X and Y-axes represent positions around the area of the ABTT terminus, and the Z axis is temperature. As part of the creation of the three-dimensional representation of the temperature of the ABTT terminus, a peak temperature is either found by direct measurement or calculated from the acquired data. Part of the analysis process is a smoothing of the temperature data and best-curve fits in both the X and Y directions. Once a representation of the temperature profile around the ABTT terminus is determined, control passes from analyze temperature data process 8388 to a change mode to seek process 8390.

In changing the mode of ABTT monitoring system 8000 from the learn mode, which system 8000 may indicate to a user by a tone, a display indication, a temperature sensor indication, such as flashing LED's 8370, or by other techniques or apparatus, to the seek mode, system 8000 is indicating to the user that system 8000 has sufficient data to identify and find the approximate center of the ABTT terminus. More specifically, system 8000 is indicating that it is able to find the peak, or near peak, temperature of the ABTT terminus. Once the mode of ABTT monitoring system 8000 changes to the seek mode, and advises the user that the mode has changed, control passes from change mode to seek process 8390 to a receive temperature data process 8392.

In receive temperature data process 8392, temperature data from temperature sensor 8366 is received by ABTT system display 8001, where the temperature data is analyzed. Once the temperature data has been received and analyzed, control passes to a high temperature decision process 8394.

In high temperature decision process 8394, ABTT terminus location process 8300 determines whether the received temperature data is higher than the current high temperature identified in analyze temperature data process 8308. If the received temperature data is higher or greater than the current high temperature, control passes from high temperature decision process 8394 to a reset temperature scale process 8396.

In reset temperature scale process 8396, the peak temperature is used to reset the temperature scale based on the new high temperature. In other words, the previous high temperature is replace by the new high temperature, after which control passes from reset temperature scale process 8396 to an analyze existing data process 8398.

In analyze existing data process 8398, any existing temperature curve is analyzed in view of the newly received temperature data. ABTT acquisition process 8380 may determine that the higher temperature appears, by analysis, to be the actual high temperature. Alternatively, ABTT terminus location process 8380 may determine that the temperature curve data indicates a higher temperature may be available. Once the newly received temperature data is analyzed, control passes from analyze existing data process 8398 to a temperature consistency decision process 8400.

In temperature consistency decision process 8400, based on the analysis provided by analyze existing temperature data process 8398, ABTT terminus location process 8380 decides whether the newly received high temperature is consistent with the existing temperature map as a peak temperature of the ABTT terminus. If the newly received data appears to be consistent with the temperature map, control passes from temperature consistency decision process 8400 to an actuate indicator process 8402, where all LED's 8370 are actuated to indicate that the ABTT terminus high temperature has been located. In addition to LED's 8370 being actuated, other indicators may be actuated, including tones, flashing displays, and/or other visual indications on ABTT system display 8001. Once actuate indicator process 8402 has actuated at least LED's 8370, control passes from actuate indicator process 8402 to an end process 8404, where ABTT terminus location process 8380 stops operation and passes control back to a calling program or other process of ABTT monitoring system 8000.

Returning to temperature consistency decision process 8400, if the new high temperature is not consistent with the current temperature map, control is passed from temperature consistency decision process 8400 to receive temperature data process 8392, and ABTT terminus location process 8380 functions as previously described.

Returning to high temperature decision process 8394, if the temperature data is not higher than the high temperature, control passes from high temperature decision process 8394 to an indicate direction of ABTT process 8406. In indicate direction of ABTT process 8406, LED's or lights 8370 that point along a direction where the ABTT terminus should be are illuminated. While ABTT monitoring system is able to determine the line along which the ABTT should be located, it is unable to indicate definitively which of the two possible directions temperature sensor 8366 should be moved to be in a direction that is toward the ABTT terminus. However, a user can easily determine the proper direction by visual inspection and/or moving temperature sensor 8366 in the indicated direction during the next back and forth movement or scan of temperature sensor 8366. Once the direction of the ABTT terminus is indicated, control passes from indicate ABTT direction process 8406 to a high temperature decision process 8408.

In high temperature decision process 8408. In high temperature decision process 8408, ABTT terminus location process 8380 decides whether the current temperature data is at or near the identified high temperature. In an exemplary embodiment, if the temperature data is within 0.2 degrees Celsius of the peak temperature, ABTT monitoring system 8000 may consider the current temperature data to be close enough to peak ABTT temperature 8334 to consider the present temperature to be the peak, in which case, control passes from high temperature decision process 8408 to actuate indicator process 8402, which functions as previously described. Alternatively, control passes from high temperature decision process 8408 to receive temperature data process 8392, where ABTT terminus location process 8380 functions as previously described.

While it appears that process 8406 and 8402 may yield confusing information, with two lights going on, followed by four lights when the ABTT terminus is located, in practice the two lights are kept illuminated until new information changes the direction of motion needed for the temperature sensor, so the movement of the temperature sensor toward the ABTT terminus until all lights illuminate is readily perceived as being natural.

Furthermore, the aforementioned process if very fast in comparison to most processes used to find ABTT terminus 8140. In actual use, ABTT terminus 8140 may be identified within seconds using temperature sensor 8366 and ABTT acquisition process 8380. A properly trained operator or user is typically able to find the ABTT terminus according to the system and method of this embodiment in no more than 15 seconds, and often in much less time.

Bovine Heat Stress

It has been well documented that hot climate can strongly affect animal bioenergetics, with negative effects on livestock performance and welfare. High temperatures and acute heat loads on the homoeothermic animal depress feeding intake and affect animal performance like growth, milk and meat production as well as fertility. Capturing early animal responses to environmental challenges is very crucial to the livestock managers for adopting the right husbandry practices to reduce losses during hot weather or for defining threshold limits for the animal to cope with the environment. Moreover, mild infection when associated with high baseline temperature of an animal can have serious adverse events not only causing loss of productivity but also actual loss of life.

Body temperature is a key parameter for monitoring animal physiological, health and welfare status. Animal stressors, such as heat loads, infections, parasites and metabolic diseases, or physiological processes, such as lactation and estrus, can alter body thermoregulation, and knowledge of body temperature variation pattern may help to improve livestock husbandry. For many clinical, pathological, or physiological uses, brain temperature (BrT) seems to be more sensitive to change in the animal status than any core temperature (CrT) in the body. Several studies comparing invasive brain monitoring (BrT) with invasive CrT were performed at different organs or sites of human body. However, little information is available for livestock. In sharp contrast, the ABTT temperature measuring systems of the present disclosure measures brain temperature non-invasively and allows a noninvasive way to assess thermoregulatory responses while serving as an index of hypothalamic temperature, which plays a vital role in regulating feeding intake, endocrine and immunologic functions. However, rectal temperature (RcT) is the most common clinical measure of CrT in cattle because invasive measurement of brain temperature is not possible outside research settings. BrT, carotid arterial blood temperature (CtT), and RcT in conscious sheep exposed to 40° C., 22° C. and 5° C. has been measured. The observed values of RcT were consistently higher than CtT and BrT, for all exposures. Applicant confirmed higher rectal temperature than brain temperature, noting that temperature levels causing brain injury as yet unknown were identified by the inventions of the present disclosure.

Figure 72:
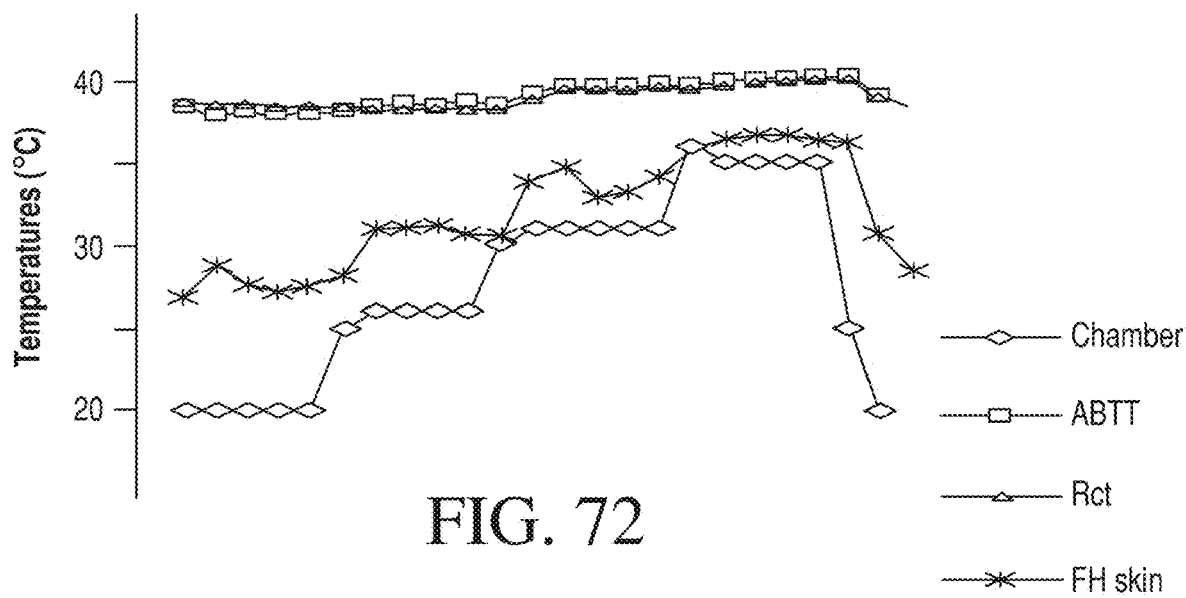
FIG. 72 shows representative temperature curves of a subject during sleep.
Figure 73:
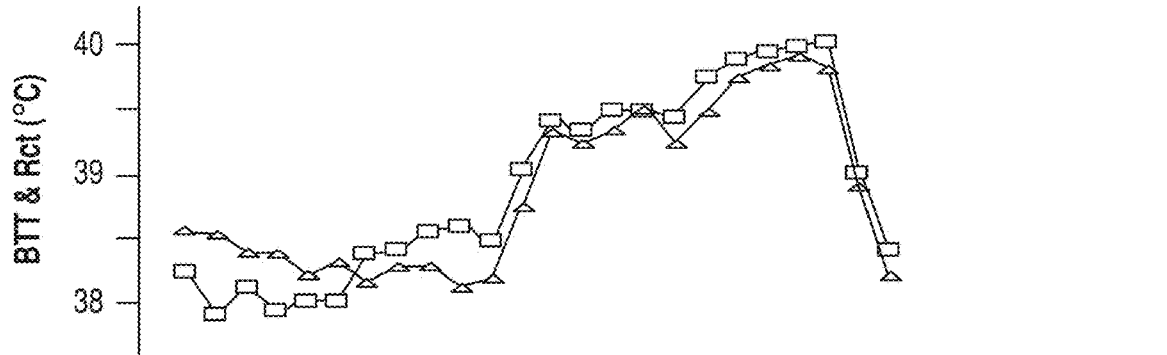
FIG. 73 shows further representative temperature curves of the subject of FIG. 72.
Figure 74:
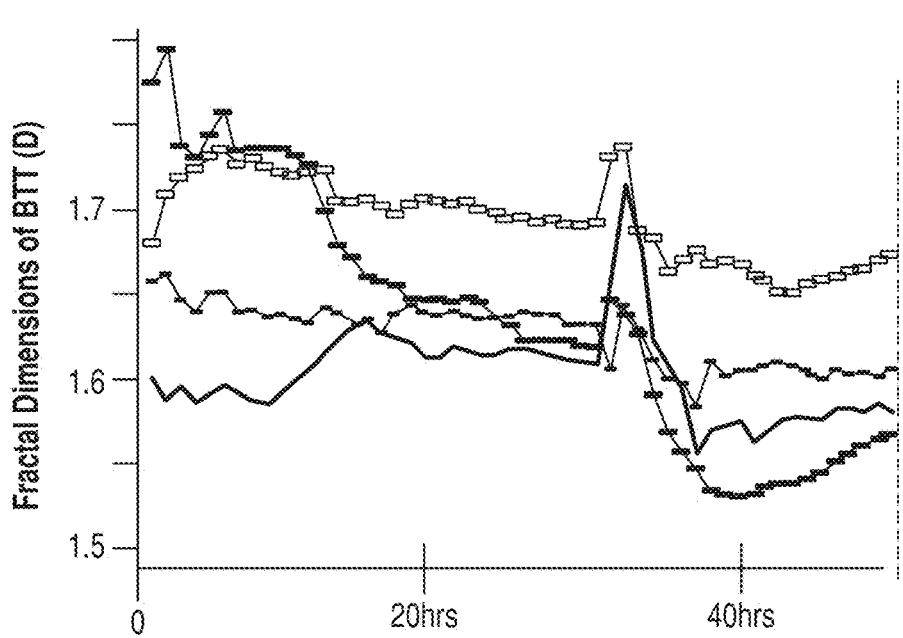
FIG. 74 shows further representative temperature curves of the subject of FIGS. 72 and 73.

The bovine experiments herein disclosed showed that intracranial (ABTT) measurements respond to thermally induced stress more rapidly and to a greater degree than core (Rectal). ABTT not only provided continuous (at 0.75 Hz) monitoring of temperature but also of temperature variations. Adhesive patches and sensors described by the Applicant in previous patent applications were used in the studies. FIGS. 72-74 show ABTT and Rectal crossing. FIG. 72 shows mean ABTT, Rectal (Rct), Forehead (FH) and chamber temperatures every 2-hours for first 50 hours of the experiment (total number of hours inside the climate chamber was 144 hours as shown in FIG. 72). FIG. 73 ABTT and Rct on a customized y-axis, which reveals ABTT and Rct crossing upon chamber warming. Beyond temperature of crossing, ABTT exceeded Rct at all points during this session. FIG. 74 delineates fractal dimensions [D] of ABTT monitoring, with precipitous declines in D for each animal at chamber temperature≥31° C. This sign of thermally induced stress, [mild (D<1.6) in three cattle, slight (D<1.7)] in one] was associated with disproportionate rise in ABTT readings noted in FIG. 73. During each thermal challenge in each bovine, the fractal dimension (D) of continuous ABTT readings changed dramatically, indicative of waxing and waning stress. FIGS. 72-74 relate the change in D (FIG. 74) to ABTT vs Rectal differences (FIG. 73) and changes in chamber temperature (FIG. 72) during the first 50-hr session. As occurred throughout the series of stresses, D declined precipitously in response to the pronounced and rapid increase (to level equal or higher than 31° C.) of chamber temperature, indicating a stress-induced decline in entropy that forebode cerebral injury if environmental conditions (e.g., chamber warming) were allowed to worsen. Concurrent viewing of FIGS. 72-74 reveals that, near the time of the thermal stress-induced decline in D, ABTT and Rectal readings crossed, indicative of brain/core discordance induced by heat-stress. Consistent with the persistent decline in D, ABTT remained greater than Rectal during subsequent chamber cooling and associated decline in bovine temperature for the next several readings. These findings indicated protracted cerebral disturbance and associated cerebral metabolic activity after the external warming challenge is removed (of great relevance in the prevention and therapy of heat injury); and they eliminated potential artefact—ABTT would not remain above rectal if ABTT were distorted by exposure to cool air. The ability of BTT to detect such variations in brain temperature was supported by several other trials of animals and humans. The study showed that there are two critical levels for heat stress in bovine (confirmed by fractal analysis), which is the point of crossing where ABTT temperature became higher than rectal (38.3° C. or higher), and at the point of maximum decline in D (39.2° C. or higher), which are objects of the present disclosure.

Figure 75:
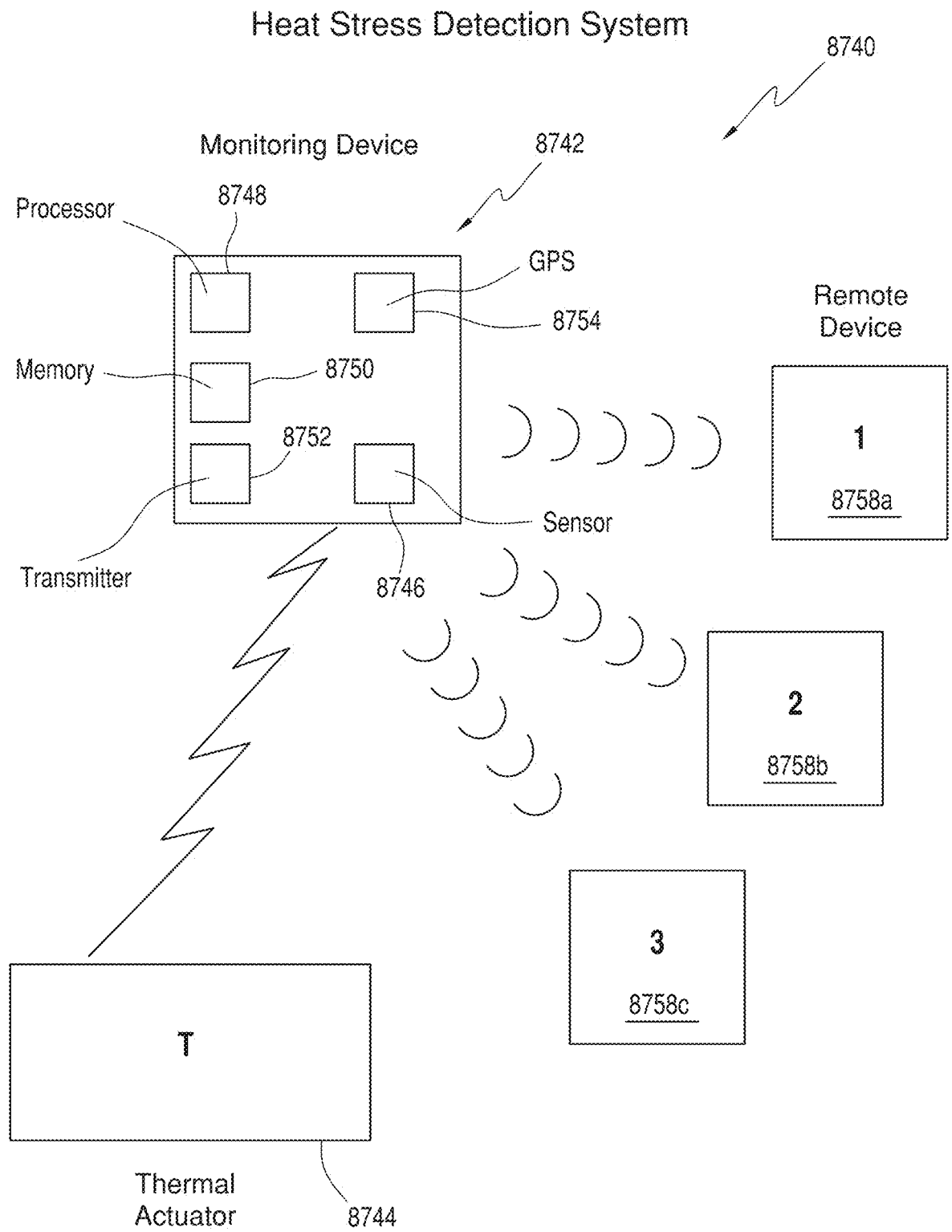
FIG. 75 shows a heat stress detection system in accordance with an exemplary embodiment of the present disclosure.

By identifying herein the thermal and fractal patterns using ABTT temperature monitoring, the present disclosure provides a method, apparatus, and system for Brain Heat Stress Detection, shown in FIG. 75. Accordingly, the brain heat stress detection system 8740 includes a temperature monitoring device (such as ABTT Monitoring System or any other temperature monitoring system) 8742, and external thermal actuator 8744*a*. Temperature monitoring device 8742 includes temperature sensor 8746, controller 8748, non-transitory memory 8750, transmitter 8752, GPS 8754, and reporting apparatus 8756. Thermal actuator 8744 alters temperature around the animal or on the animal to modify the temperature of the brain to avoid heat stress.

Once the thermal profile acquired by temperature sensor 8746 starts to depart from a safe thermal profile, or when certain critical levels of brain temperature are identified, the signal is recognized by controller 8748, based on comparison of the received signal with predetermined values for critical temperate values or unsafe thermal patterns stored in non-transitory memory 8750. Controller 8748 is configured to recognize the abnormal signal and then to activate wireless transmitter 8752, which in an exemplary embodiment may be a short-range transmitter. Exemplary transmitters include a Bluetooth, Wi-Fi, cell phone, or radio waves, to transmit the signal to wireless receivers 8758*a-c* remotely located to inform a farmer about the health of the animals and risk of heat stress. Once an abnormal signal is identified, controller 8748 couples a signal from GPS 8754 in order to identify the location of the animal at risk. Once a signal is transmitted to a remote station 8758*a-c*, and GPS 8754 informs processor 8748 of location, processor 8748 is configured to execute a program to activate a nearby thermal actuator 8744, exemplified herein as a spray to spray cold water in the area where the animal is located.

Once temperature sensor 8746 measures temperature reaching high risk levels for heat stress exemplified herein by temperature equal to or higher than 38.3° C., controller 8748 is configured to transmit a signal to one or more remote receivers 8758*a-c*, warning a foreman or farmer. Once temperature sensor 8746 measures temperature reaching critical levels, exemplified herein by temperature equal to or higher than 39.2° C., controller 8748 is configured to transmit a signal to a plurality of remote receivers such as receiver 8758a, warning the owner, receiver 8758b, warning the veterinarian, and receiver 8758c, warning the foreman.

A method using the described apparatus includes the following steps: (1) measuring temperature (preferably at the ABTT site in animals); (2) identifying temperature level and thermal pattern (such as slope of the curve and/or the velocity of temperature increase) every 1 minute or less (or preferably every 30 seconds or less); it should be understood that any frequency of measurement ranging from every 10 minutes to every 1 second is within the scope of the disclosure, but the most frequent measurements possible is preferred; (3) although this next step is optional, controller 8748 may be configured to predict the final thermal pattern based on the slope acquired; in step (4) controller 8748 is configured to compare the acquired slope (or thermal pattern) or temperature level with a predetermined safe thermal pattern or temperature threshold (e.g., 38.3° C. or 39.2° C. stored in non-transitory memory 8750; if in the next step (5) controller 8748 identifies a departure from a safe thermal pattern or temperature level, then in next step (6) controller 8748 acquires a location signal from GPS 8754 and pairs the signal from GPS 8754 with the temperature level signal; and in next step (7) activates wireless transmitter 8752 to transmit a signal package (temperature level plus location) to at least one remote receiver 8758a-c; an optional step (8) includes controller 8748 actuating at least one thermal actuator 8744.

While various embodiments of the disclosure have been shown and described, it is understood that these embodiments are not limited thereto. The embodiments may be changed, modified, and further applied by those skilled in the art. Therefore, these embodiments are not limited to the detail shown and described previously herein, but also include all such changes and modifications. It should also be understood that any part of series of parts of any embodiment can be used in another embodiment, and all of those combinations are within the scope of the disclosure.

I claim:

1. A system for modifying a core temperature of a human over a period of time comprising:
    a temperature sensor positioned in contact with the skin of the human on, over, or adjacent the human's brain thermal tunnel terminus, said temperature sensor measuring a temperature of the human at or adjacent the human's brain thermal tunnel terminus over the period of time and generating a plurality of temperature signals over the period of time therefrom;
    a temperature modifying apparatus comprising an oxygenator or a warming machine positioned in physical communication with the human to modify the core temperature of the human;
    at least one of an alarm and a display; and
    a controller configured to receive said plurality of temperature signals generated by said temperature sensor over the period of time, said controller determines a first temperature representative of a baseline core temperature of the human measured at a first time, said controller determines when a second temperature that is at least 0.5 degrees Celsius different from the first temperature is measured at a second time, and said controller transmits a signal to at least one of said alarm and said display to present an indication that the second temperature has been reached; and
    said controller further configured to actuate one of said oxygenator, an inflow temperature of said oxygenator being at least 15 degrees Celsius lower than a human's brain thermal tunnel terminus baseline temperature, or said warming machine based on said second temperature, and operating said warming machine until a temperature increase at the human's brain thermal tunnel terminus is in a range between 4 degrees Celsius and 11 degree Celsius as compared to the human's brain thermal tunnel terminus baseline temperature is measured.

2. The system of claim 1, wherein said oxygenator reduces the core temperature of the human.

3. The system of claim 1, wherein said warming machine elevates the core temperature of the human.

4. A system for reducing a core temperature of a human over a period of time comprising:
    a temperature sensor positioned in contact with the skin of the human on, over, or adjacent the human's brain thermal tunnel terminus, said temperature sensor measuring a temperature of the human at or adjacent the human's brain thermal tunnel terminus over the period of time and generating a plurality of temperature signals over the period of time therefrom;
    a cooling apparatus comprising an oxygenator positioned in physical communication with the human to reduce the core temperature of the human;
    at least one of an alarm and a display; and
    a controller configured to receive said plurality of temperature signals generated by said temperature sensor over the period of time, said controller determines a first temperature representative of an uncooled core temperature of the human measured at a first time, said controller determines when a second temperature that is at least 0.5 degrees Celsius less than the first temperature is measured at a second time, and said controller transmits, a signal to at least one of said alarm and said display to present an indication that the second temperature has been reached; and
    said controller further configured to actuate said oxygenator once said second temperature has been reached, an inflow temperature of said oxygenator being at least 15 degrees Celsius lower than a human's brain thermal tunnel terminus baseline temperature.

5. The system of claim 4, wherein the controller is configured to determine when a third temperature representative of a core temperature of the human below a predetermined lower limit and to transmit a further signal to actuate at least one of the alarm and the display.

6. The system of claim 5, wherein said predetermined lower limit of the third temperature is less than or equal to 35 degrees Celsius.

7. The system of claim 4, wherein an anti-shiver mechanism is provided to the human prior to initiating a reduction of the core temperature of the human.

8. The system of claim 7, wherein said anti-shiver mechanism is heat applied to one or more extremity.

* * * * *